(12) United States Patent
Lagu et al.

(10) Patent No.: US 7,452,997 B2
(45) Date of Patent: Nov. 18, 2008

(54) TETRAHYDRO-INDAZOLE CANNABINOID MODULATORS

(75) Inventors: Bharat Lagu, Hillsborough, NJ (US); Fina Liotta, Westfield, NJ (US); Meng Pan, Neshanic Station, NJ (US); Michael P. Wachter, Bloomsbury, NJ (US); Mingde Xia Xia, Belle Mead, NJ (US)

(73) Assignee: Janssen Pharmaceutica, N.V., Beerse (BE)

( * ) Notice: Subject to any disclaimer, the term of this patent is extended or adjusted under 35 U.S.C. 154(b) by 169 days.

(21) Appl. No.: 11/087,943

(22) Filed: Mar. 23, 2005

(65) Prior Publication Data
US 2005/0228034 A1 Oct. 13, 2005

Related U.S. Application Data

(60) Provisional application No. 60/555,890, filed on Mar. 24, 2004.

(51) Int. Cl.
*C07D 211/32* (2006.01)
*C07D 231/54* (2006.01)
*C07D 411/12* (2006.01)

(52) U.S. Cl. ............... 546/199; 548/360.1; 544/140
(58) Field of Classification Search ............ 548/360.1; 546/199; 544/140
See application file for complete search history.

(56) References Cited

U.S. PATENT DOCUMENTS

| 3,895,026 | A |   | 7/1975 | Palazzo et al. |
| 4,851,425 | A |   | 7/1989 | Smith |
| 4,861,777 | A | * | 8/1989 | Okada et al. ............ 514/234.5 |
| 5,532,237 | A | * | 7/1996 | Gallant et al. ........... 514/235.2 |
| 6,410,533 | B1 |   | 6/2002 | Hirth et al. |
| 7,230,024 | B2 | * | 6/2007 | Carpino et al. ............. 514/406 |

FOREIGN PATENT DOCUMENTS

| EP | 0 307 801 | 3/1989 |
| JP | 06 306053 | 11/1994 |
| WO | WO 01/58869 | 8/2001 |
| WO | WO 03/035005 | 5/2003 |
| WO | WO 03/087037 | 10/2003 |

OTHER PUBLICATIONS

Stoit et al., Chem. Pharm. Bull. 50 (8) 1109-1113 (2002).*
Cardia, M.C. et al., "New cycloalkylpyrazoles as potential cyclooxygenase inhibitors", Rome, IT, vol. 53, pp. 698-708, 1998.
Cardia, M.C. et al., "Synthesis of new arylidencycloalkylpyrazoles fo potential biological interest", Journal of Heterocyclic Chemistry, Provo, US, vol. 40, pp. 309-315, 2003.
Croce, P.D. et al., "A Convenient Syntehsis of Indazoles", Syntehsis, Thieme, Stuttgart, DE, pp. 982-983, 1984.
Fusco, Raffaello et al., "Enamines. V. Syntehsis of 1-arylpyrazoles", Gazzetta Chimica Italiana, vol. 91, pp. 1233-1249, 1961.
Henke, B.R., et al., "Optimization of 2-(1H-indazol-3-ylmethyl)-1, 5-benzodiazepines as potent, orally active CCK-A agonists", Journal of Medicinal Chemistry, Washington, US, vol. 40, No. 17, pp. 2706-2725, 1997.
Massaroli, Giangiacomo et al., "Preparation of 3-substituted 1-aryl-4,5-cyclomethylenepyrazoles", Bollettino Chimico Farmceutico, vol. 107, No. 10, pp. 613-628, 1968.
Nagakura, Mashahiko et al., "Syntheses and antiinflammatory actions fo 4,5,6,7-tetrahydroindazole-5- carboxylic acids", Journal of Medicinal Chemistry, vol. 22, No. 1, pp. 48-52, 1979.
Ruccia, Michele et al., "Conversion of tetrahydroindoxazenes to tetrahydroindazoles", Gazzetta Chmica Italiana, vol. 97, No. 10, pp. 1494-1506, 1967.

* cited by examiner

*Primary Examiner*—Kamal Saeed
*Assistant Examiner*—Robert Havlin
(74) *Attorney, Agent, or Firm*—Thomas Dodd

(57) ABSTRACT

This invention is directed to a tetrahydro-indazole cannabinoid modulator compound of formula I:

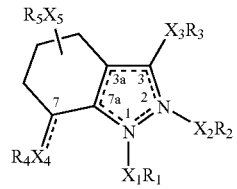

and a method for use in treating, ameliorating or preventing a cannabinoid receptor mediated syndrome, disorder or disease.

4 Claims, No Drawings

TETRAHYDRO-INDAZOLE CANNABINOID MODULATORS

CROSS REFERENCE TO RELATED APPLICATIONS

This present application claims benefit of U.S. Provisional Patent Application Ser. No. 60/555,890, filed Mar. 24, 2004, which is incorporated herein by reference in its entirety and for all purposes.

FIELD OF THE INVENTION

This invention is directed to tetrahydro-indazole cannabinoid (CB) modulator compounds and a method for use in treating, ameliorating or preventing a cannabinoid receptor mediated syndrome, disorder or disease.

BACKGROUND OF THE INVENTION

Before the discovery of the cannabinoid CB1 and CB2 receptors, the term cannabinoid was used to describe the biologically active components of *cannabis sativa*, the most abundant of which are delta-9-tetrahydrocannabinol (THC) and cannabidiol.

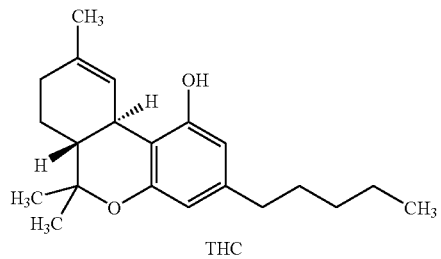

THC

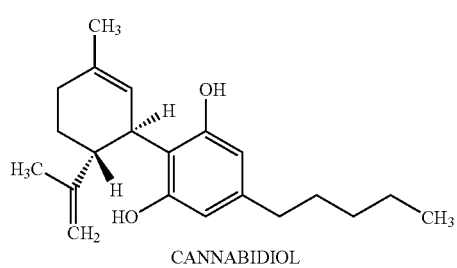

CANNABIDIOL

THC is a moderately potent partial agonist of the CB1 and CB2 receptors and is considered the "classical cannabinoid," a term now used to refer to other analogues and derivatives that are structurally related to the tricyclic dibenzopyran THC core. The term "nonclassical cannabinoid" refers to cannabinoid agonists structurally related to cannabidiol.

Pharmacological investigations have concentrated on selective CB receptor modulators of the pyrazole structural class, which include SR 141716A (the monohydrochloride salt of SR 141716) and SR 144528. SR 141716A was the first potent and selective CB1 receptor antagonist.

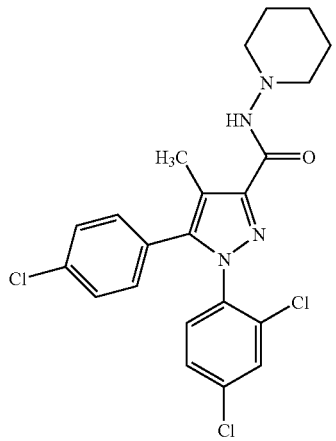

SR 141716

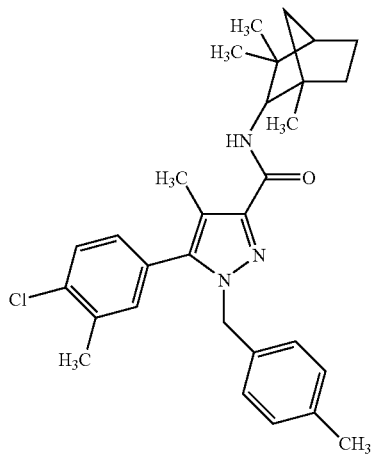

SR 144528

Pyrazole cannabinoid modulators are one among the many different structural classes which have aided the development of CB pharmacology, have helped to determine the biological effects mediated by the cannabinoid receptors, will lead to further refinement of current compounds and will be a source of new chemical classes in the future.

Certain compounds (including SR 141716, SR 144528 and the like) that were originally classified as selective antagonists are now considered to act as "inverse agonists" rather than pure antagonists. Inverse agonists have the ability to decrease the constitutive level of receptor activation in the absence of an agonist instead of only blocking the activation induced by agonist binding at the receptor. The constitutive activity of CB receptors has important implications since there is a level of continuous signaling by both CB1 and CB2 even in the absence of an agonist. For example, SR 141716A increases CB1 protein levels and sensitizes cells toward agonist action, thus indicating that inverse agonists may be another class of ligands used to modulate the endocannabinoid system and the downstream signaling pathways activated by CB receptors.

Advances in the synthesis of CB and cannabimimetic ligands have furthered the development of receptor pharmacology and provided evidence for the existence of additional cannabinoid receptor sub-types. However, there remains an ongoing need for the identification and development of CB1 or CB2 receptor cannabinoid modulators for the treatment of a variety of CB receptor modulated syndromes, disorders and diseases.

DETAILED DESCRIPTION OF THE INVENTION

This invention is directed to a compound of formula I:

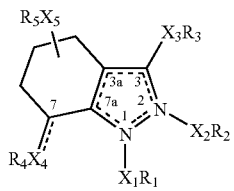

wherein
the dashed lines between positions 2-3 and positions 3a-7a in formula I represent locations for two double bonds present when $X_1R_1$ is present;
the dashed lines between positions 3-3a and positions 7a-1 in formula I represent locations for two double bonds present when $X_2R_2$ is present;
the dashed line between positions 7 and $X_4R_4$ in formula I represents the location for a double bond;
$X_1$ is absent, or is lower alkylene;
$X_2$ is absent, or is lower alkylene;
wherein only one of $X_1R_1$ and $X_2R_2$ are present;
$X_3$ is absent, or is lower alkylene, lower alkylidene or —NH—;
when the dashed line between positions 7 and $X_4R_4$ is absent, $X_4$ is absent, or is lower alkylene;
when the dashed line between positions 7 and $X_4R_4$ is present, $X_4$ is absent;
$X_5$ is absent, or is lower alkylene;
$R_1$ is selected from the group consisting of aryl, $C_3$-$C_{12}$ cycloalkyl, or heterocyclyl, any of which are optionally substituted at one or more positions by halogen, lower alkyl, hydroxy or lower alkoxy;
$R_2$ is selected from the group consisting of aryl, $C_3$-$C_{12}$ cycloalkyl, or heterocyclyl, any of which are optionally substituted at one or more positions by halogen, lower alkyl, hydroxy or lower alkoxy;
$R_3$ is

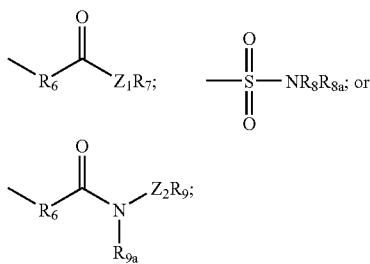

when the dashed line between positions 7 and $X_4R_4$ is absent, $R_4$ is hydrogen; hydroxy; lower alkyl; lower alkoxy; halogen; aryl optionally substituted at one or more positions by hydroxy, lower alkyl, lower alkoxy or halogen; heterocyclyl optionally substituted at one or more positions by hydroxy, lower alkyl, lower alkoxy or halogen; or $C_3$-$C_{12}$ cycloalkyl optionally substituted at one or more positions by hydroxy, lower alkyl, lower alkoxy or halogen;
when the dashed line between positions 7 and $X_4R_4$ is present, $R_4$ is CH-aryl wherein aryl is optionally substituted at one or more positions by hydroxy, lower alkyl, lower alkoxy or halogen; or CH-heterocyclyl wherein heterocyclyl is optionally substituted at one or more positions by hydroxy, lower alkyl, lower alkoxy or halogen;
$R_5$ is hydrogen; hydroxy; lower alkyl; lower alkoxy; hydroxy-lower alkylene-; carboxy; alkoxycarbonyl; aryloxycarbonyl; aryl-alkoxycarbonyl; $NHR_{10}$; —C(O)$NR_{11}R_{11a}$; —O—C(O)—$R_{12}$; oxo; or —C(O)$R_{13}$;
$R_6$ is absent, or is —CH($R_{6a}$)—;
$R_{6a}$ is hydrogen; lower alkyl; or aryl optionally substituted by one or more of halogen, hydroxy, lower alkoxy, carboxy or alkoxycarbonyl;
$R_7$ is lower alkoxy; aryl optionally substituted by one or more hydroxy, halogen, lower alkyl, carboxy, alkoxycarbonyl, lower alkoxy, hydroxy-alkylene-, —NH($R_{6a}$), aryloxy, arylalkoxy, or aryl-lower alkylene-; $C_3$-$C_{12}$ cycloalkyl optionally substituted by one or more hydroxy, halogen, lower alkyl, lower alkyl-aminocarbonyl, carboxy, alkoxycarbonyl, lower alkoxy, lower alkoxy-lower alkylene-, hydroxy-alkylene-, aryloxy, arylalkoxy, arylalkoxy-lower alkylene- optionally substituted on aryl by one or more hydroxy, halogen or lower alkyl; or aryl-lower alkylene-; heterocyclyl optionally substituted by one or more hydroxy, halogen, lower alkyl, carboxy, alkoxycarbonyl, lower alkoxy, lower alkoxy-lower alkylene-, hydroxy-alkylene-, aryloxy or arylalkoxy;
$R_8$, $R_{8a}$, $R_9$ and $R_{9a}$ are each individually hydrogen; lower alkyl; —$NHR_{15}$; aryl optionally substituted by one or more hydroxy, halogen, —NH($R_{6a}$), —$SO_2$—NH($R_{6a}$), lower alkyl, carboxy, alkoxycarbonyl, lower alkoxy, hydroxy-alkylene-, aryloxy or arylalkoxy; $C_3$-$C_{12}$ cycloalkyl optionally substituted by one or more hydroxy, halogen, amino, lower alkyl, carboxy, alkoxycarbonyl, lower alkoxy, hydroxy-alkylene-, aryloxy, arylalkoxy, or lower alkylene; or heterocyclyl optionally substituted by one or more hydroxy, halogen, amino, lower alkyl, carboxy, alkoxycarbonyl, lower alkoxy, hydroxy-alkylene-, aryloxy or arylalkoxy;
$R_{10}$ is hydrogen, $C_1$-$C_{10}$ alkoxycarbonyl optionally substituted at one or more positions by hydroxy, halogen or aryl; —C(O)$CF_3$; —$SO_2$—$NR_{14}R_{14a}$; —C(O)-heterocyclyl optionally substituted at one or more positions by hydroxy, halogen or aryl; —C(O)$NR_{14}R_{14a}$; —$SO_2$-aryl; —$SO_2R_{14}$; or $SO_2NR_{14}R_{14a}$;
$R_{11}$, $R_{11a}$, $R_{12}$, $R_{13}$, $R_{14}$ and $R_{14a}$ and $R_{15}$ are each individually hydrogen; $C_1$-$C_{10}$ alkyl; heterocyclyl; $C_3$-$C_{12}$ cycloalkyl; or aryl optionally substituted by lower alkyl, hydroxy, alkoxy, halogen —$SO_2$—N($R_{6a}$)$_2$, heterocyclyl or aryl-lower alkylene-;
$Z_1$ is absent; —NH—; or is lower alkylene optionally substituted at one or more positions by halogen, hydroxy, lower alkoxy, carboxy or lower alkoxycarbonyl;
$Z_2$ is absent; or is lower alkylene optionally substituted at one or more positions by aryl, cycloalkyl, halogen, hydroxy, lower alkyl, lower alkoxy, carboxy, alkoxycarbonyl or aryl;

or a pharmaceutically acceptable salt, isomer, prodrug, metabolite or polymorph thereof.
An example of the present invention is a compound of formula (I) wherein $X_1$ is absent, or is lower alkylene, and $R_1$ is $C_3$-$C_{12}$ cycloalkyl; or aryl optionally substituted at one or more positions by lower alkyl, lower alkoxy or halogen.

An example of the present invention is a compound of formula (I) wherein the dashed line between positions 7 and $X_4R_4$ is absent; $X_4$ is absent, or is lower alkylene; and, $R_4$ is hydrogen; hydroxy; lower alkyl; lower alkoxy; halogen; aryl optionally substituted at one or more positions by lower alkoxy or halogen; heterocyclyl optionally substituted at one or more positions by halogen; or $C_3$-$C_8$ cycloalkyl.

An example of the present invention is a compound of formula (I) wherein the dashed line between positions 7 and $X_4R_4$ is absent; $X_4$ is absent; and, $R_4$ is hydrogen.

An example of the present invention is a compound of formula (I) wherein $R_3$ is —$R_6C(O)NHZ_2R_9$; $R_6$ is absent; $Z_2$ is absent; or is lower alkylene optionally substituted by lower alkyl, lower alkoxy, carboxy, lower alkoxycarbonyl, hydroxy or halogen; and, $R_9$ is aryl optionally substituted by one or more hydroxy, halogen, —NH($R_{6a}$), —$SO_2$—NH($R_{6a}$), lower alkyl, lower alkoxy or arylalkoxy; $C_5$-$C_{12}$ cycloalkyl optionally substituted at one or more positions by lower alkyl, lower alkoxy, hydroxy, amino, halogen or lower alkoxycarbonyl; or heterocyclyl.

An example of the present invention is a compound of formula (I) wherein $R_3$ is —$R_6C(O)Z_1R_7$; $R_6$ is absent; and, $R_7$ is lower alkoxy; aryl optionally substituted by one or more hydroxy, lower alkoxy, —NH($R_{6a}$) or arylalkoxy; $C_3$-$C_{12}$ cycloalkyl optionally substituted by one or more lower alkyl, lower alkyl-aminocarbonyl, carboxy, alkoxycarbonyl, lower alkoxy-lower alkylene-, hydroxy-alkylene-, arylalkoxy-lower alkylene- optionally substituted on aryl by one or more halogen; or heterocyclyl optionally substituted by one or more lower alkyl, alkoxycarbonyl or lower alkoxy-lower alkylene-.

An example of the present invention is a compound of formula (I) wherein $X_3$ is lower alkylidene; $R_3$ is —$SO_2NHR_8$; and, $R_8$ is aryl or $C_5$-$C_{12}$ cycloalkyl.

An example of the present invention is a compound of formula (I) wherein $X_2$ is absent, or is lower alkylene; and, $R_2$ is $C_3$-$C_{12}$ cycloalkyl; or aryl optionally substituted at one or more positions by lower alkyl, lower alkoxy or halogen.

An example of the present invention is a compound of formula (I) wherein the dashed line between positions 7 and $X_4R_4$ is present, $X_4$ is absent; and, $R_4$ is CH-aryl wherein aryl is optionally substituted at one or more positions by hydroxy, lower alkyl, lower alkoxy or halogen; or CH-heterocyclyl wherein heterocyclyl is optionally substituted at one or more positions by hydroxy, lower alkyl, lower alkoxy or halogen.

An example of the present invention is a compound of formula (I) wherein the dashed line between positions 7 and $X_4R_4$ is present, $X_4$ is absent; and, $R_4$ is CH-aryl wherein aryl is optionally substituted at one or more positions by lower alkyl, lower alkoxy or halogen; or CH-heterocyclyl, wherein heterocyclyl is optionally substituted at one or more positions by lower alkyl, lower alkoxy or halogen.

An example of the present invention is a compound of formula (I) wherein the dashed line between positions 7 and $X_4R_4$ is present, $X_4$ is absent; and, $R_4$ is CH-phenyl, CH-thienyl or CH-furyl, wherein phenyl, thienyl or furyl is each optionally substituted at one or more positions by lower alkyl, lower alkoxy or halogen.

An example of the present invention is a compound of formula (I) wherein $X_5$ is absent; and, $R_5$ is hydrogen; hydroxy; lower alkyl; hydroxy-lower alkylene-; carboxy; lower alkoxycarbonyl; aryl-alkoxycarbonyl; $NHR_{10}$; —C(O)$NR_{11}R_{11a}$; —O—C(O)—$R_{12}$; or oxo.

An example of the present invention is a compound of formula (I) wherein $R_{10}$ is hydrogen; $C_1$-$C_{10}$ alkoxycarbonyl; —C(O)$CF_3$; —C(O)-heterocyclyl; —C(O)$NR_{14}R_{14a}$; or —$SO_2NR_{14}R_{14a}$; and wherein $R_{11}$, $R_{11a}$, $R_{12}$, $R_{14}$ and $R_{14a}$ are each individually hydrogen; $C_1$-$C_{10}$ alkyl; or aryl optionally substituted by lower alkyl, heterocyclyl or aryl-lower alkylene-.

An example of the present invention is a compound of formula (Ia)

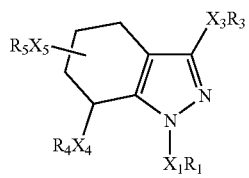

wherein $X_1R_1$, $X_3R_3$, $X_4R_4$ and $X_5R_5$ are dependently selected from

| Cpd | $X_1R_1$ | $X_3R_3$ | $X_5R_5$ | $X_4R_4$ |
|---|---|---|---|---|
| 1 | phenyl | C(O)NH-1,3,3-$(CH_3)_3$-bicyclo[2.2.1]hept-2-yl | H | H |
| 2 | (4-$OCH_3$)-phenyl | C(O)NHN[($CH_2CH_3$)(2-$OCH_3$-phenyl)] | H | H |
| 3 | (4-$OCH_3$)-phenyl | C(O)NHCH($CO_2CH_3$)$CH_2$—(3-$OCH_2$-phenyl)phenyl | H | H |
| 5 | (4-$OCH_3$)-phenyl | C(O)NHCH($CO_2CH_3$)$CH_2$—(4-OH)phenyl | H | H |
| 7 | (4-$OCH_3$)-phenyl | C(O)N H($CH_2$)$_2$—(4-$NH_2$)phenyl | H | H |
| 9 | (4-$OCH_3$)-phenyl | C(O)NH-1,3,3-$(CH_3)_3$-bicyclo[2.2.1]hept-2-yl | H | H |
| 10 | (4-F)phenyl | C(O)NH-1,3,3-$(CH_3)_3$-bicyclo[2.2.1]hept-2-yl | H | H |
| 11 | (4-$CH_3$)-phenyl | C(O)NH-1,3,3-$(CH_3)_3$-bicyclo[2.2.1]hept-2-yl | H | H |

-continued

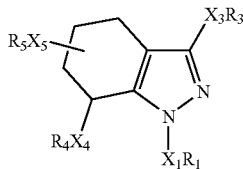

wherein $X_1R_1$, $X_3R_3$,
$X_4R_4$ and $X_5R_5$ are dependently selected from

| Cpd | $X_1R_1$ | $X_3R_3$ | $X_5R_5$ | $X_4R_4$ |
|---|---|---|---|---|
| 12 | (4-Cl)-phenyl | C(O)NH-1,3,3-$(CH_3)_3$-bicyclo[2.2.1]hept-2-yl | H | H |
| 13 | (4-F)phenyl | C(O)NH-1,3,3-$(CH_3)_3$-bicyclo[2.2.1]hept-2-yl | H | $CH_3$ |
| 14 | (4-F)phenyl | C(O)NH$CH_2$-6,6-$(CH_3)$2-bicyclo[3.1.1]hept-2-yl | H | H |
| 15 | (4-F)phenyl | C(O)NH-cyclooctyl | H | H |
| 16 | (2-F)phenyl | C(O)NH-1,3,3-$(CH_3)_3$-bicyclo[2.2.1]hept-2-yl | H | H |
| 17 | (2-F)phenyl | C(O)NH$CH_2$-6,6-$(CH_3)_2$-bicyclo[3.1.1]hept-2-yl | H | H |
| 18 | (3-F)phenyl | C(O)NH-1,3,3-$(CH_3)_3$-bicyclo[2.2.1]hept-2-yl | H | H |
| 19 | (3-F)phenyl | C(O)NH$CH_2$-6,6-$(CH_3)_2$-bicyclo[3.1.1]hept-2-yl | H | H |
| 20 | (4-F)phenyl | C(O)NH-bicyclo[2.2.1]hept-2-yl | H | H |
| 21 | (4-F)phenyl | C(O)NH-1,7,7-$(CH_3)_3$-bicyclo[2.2.1]hept-2-yl | H | H |
| 22 | (4-F)phenyl | C(O)NHCH($CH_3$)-adamantan-2-yl | H | H |
| 23 | (4-F)phenyl | C(O)NH-3-$CO_2CH_2CH_3$-bicyclo[2.2.1]hept-2-yl | H | H |
| 24 | (4-F)phenyl | C(O)NH-1,3,3-$(CH_3)_3$-bicyclo[2.2.1]hept-2-yl | H | cyclohexyl |
| 25 | cyclohexyl | C(O)NH-1,7,7-$(CH_3)_3$-bicyclo[2.2.1]hept-2-yl | H | H |
| 26 | cyclohexyl | C(O)NHCH($CH_3$)-adamantan-1-yl | H | H |
| 27 | cycloheptyl | C(O)NH-(2R)-1,3,3-$(CH_3)_3$-bicyclo[2.2.1]hept-2-yl | H | H |
| 28 | cyclohexyl | C(O)NH-2-$CO_2CH_2CH_3$-bicyclo[2.2.1]hept-3-yl | H | H |
| 29 | $CH_2$-phenyl | C(O)NHNH(cyclohexyl) | H | H |
| 30 | (4-F)phenyl | C(O)NHNH(cyclohexyl) | H | H |
| 31 | cyclohexyl | C(O)NHNH(cyclohexyl) | H | H |
| 32 | cyclohexyl | C(O)NH$CH_2$-adamantan-1-yl | H | H |
| 33 | (4-F)phenyl | C(O)NH-(1S,2R)-2-$CO_2CH_2CH_3$-cyclohexyl | H | H |
| 34 | (4-F)phenyl | C(O)NH-(1R,2R)-2-$CO_2CH_2CH_3$-cyclohexyl | H | H |
| 35 | (4-F)phenyl | C(O)NH-azepan-1-yl | H | H |
| 36 | cyclohexyl | C(O)NH-(1S,2R)-2-$CO_2CH_2CH_3$-cyclohexyl | H | H |
| 37 | cyclohexyl | C(O)NH-azepan-1-yl | H | H |
| 38 | $CH_2$-phenyl | C(O)NH-(1S*,2R*)-2-$CO_2CH_2CH_3$-cyclohexyl | H | H |
| 39 | $CH_2$-phenyl | C(O)NHCH($CH_3$)-adamantan-1-yl | H | H |
| 40 | cyclohexyl | C(O)NH-2-$CH_2OH$-bicyclo[2.2.1]hept-3-yl | H | H |
| 41 | $CH_2$-phenyl | C(O)NH-azepan-1-yl | H | H |
| 43 | $CH_2$-phenyl | C(O)NH-2-$CO_2CH_2CH_3$-bicyclo[2.2.1]hept-3-yl | H | H |
| 44 | cyclohexyl | C(O)NH-adamantan-1-yl | H | H |
| 45 | cyclohexyl | C(O)NH-adamantan-2-yl | H | H |
| 46 | cyclohexyl | C(O)NH-8-$CH_3$-8-aza-bicyclo[3.2.1]oct-3-yl | H | H |
| 47 | cyclohexyl | C(O)NH-2-$CH_2OH$-bicyclo[2.2.1]hept-3-yl | H | H |
| 48 | cyclohexyl | C(O)NH-(1R*,2S*)-2-$CH_2OH$-cyclohexyl | H | H |
| 49 | cyclohexyl | C(O)NH-(1R*,2R*)-2-$CH_2OH$-cyclohexyl | H | H |
| 50 | cyclohexyl | $(CH_2)_2$C(O)NH-1,3,3-$(CH_3)_3$-bicyclo[2.2.1]hept-2-yl | H | H |
| 51 | cyclohexyl | $(CH_2)_2$C(O)NH-(1R*,2R*)-2-$CH_2OH$-cyclohexyl | H | H |
| 52 | cyclohexyl | $(CH_2)_2$C(O)NH-(2S,3R)-2-$CH_2OH$-bicyclo[2.2.1]hept-3-yl | H | H |
| 53 | cyclohexyl | $(CH_2)_2$C(O)NHCH($CH_3$)-adamantan-1-yl | H | H |
| 54 | cyclohexyl | $(CH_2)_2$C(O)NH-(2S,3R)-2-$CO_2CH_2CH_3$-bicyclo[2.2.1]hept-3-yl | H | H |
| 55 | cyclohexyl | C(O)NH-3-$CO_2CH_2CH_3$-5,6,7,8-tetrahydro-4H-cyclohepta(b)thien-2-yl | H | H |

-continued

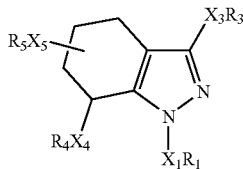

wherein $X_1R_1$, $X_3R_3$, $X_4R_4$ and $X_5R_5$ are dependently selected from

| Cpd | $X_1R_1$ | $X_3R_3$ | $X_5R_5$ | $X_4R_4$ |
|---|---|---|---|---|
| 56 | cyclohexyl | C(O)NH-3-CO$_2$CH$_2$CH$_3$-5,6-dihydro-4H-cyclopenta(b)thien-2-yl | H | H |
| 57 | cyclohexyl | C(O)NH-2-CO$_2$CH$_2$CH$_3$-cyclopent-1-en-1-yl | H | H |
| 58 | cyclohexyl | C(O)NH-(1R,2S)-2-CO$_2$CH$_2$CH$_3$-cyclopentyl | H | H |
| 59 | cyclohexyl | C(O)NH-(1S,2S)-2-CO$_2$CH$_2$CH$_3$-cyclohexyl | H | H |
| 60 | cyclohexyl | C(O)NH-(1S*,2R*)-2-CH$_2$OH-cyclohexyl | H | Cl |
| 61 | cyclohexyl | C(O)NH-(1S*,2R*)-2-CO$_2$CH$_2$CH$_3$-cyclopentyl | H | Cl |
| 62 | cyclohexyl | C(O)NH-adamantan-2-yl | H | Cl |
| 63 | cyclohexyl | C(O)NH-(2S*,3R*)-2-CO$_2$CH$_2$CH$_3$-bicyclo[2.2.1]hept-3-yl | H | Cl |
| 64 | cyclohexyl | C(O)NHCH(CH$_3$)-adamantan-1-yl | H | Cl |
| 65 | cyclohexyl | CH$_2$C(CH$_3$)$_2$C(O)NHCH(CH$_3$)-adamantan-1-yl | H | H |
| 66 | cyclohexyl | CH$_2$C(CH$_3$)$_2$C(O)NH-adamantan-2-yl | H | H |
| 67 | cyclohexyl | C(O)NH-1,3,3-(CH$_3$)$_3$-bicyclo[2.2.1]hept-2-yl | 5-CO$_2$—CH$_2$CH$_3$ | H |
| 68 | cyclohexyl | C(O)NH-adamantan-2-yl | 6-CO$_2$—CH$_2$CH$_3$ | H |
| 69 | cyclohexyl | C(O)NHCH(CH$_3$)-adamantan-1-yl | 6-CO$_2$—CH$_2$CH$_3$ | H |
| 70 | cyclohexyl | C(O)NH-1,3,3-(CH$_3$)$_3$-bicyclo[2.2.1]hept-2-yl | 6-CO$_2$—CH$_2$CH$_3$ | H |
| 71 | cyclohexyl | C(O)NH-adamantan-2-yl | 4-CO$_2$—CH$_2$CH$_3$ | H |
| 72 | cyclohexyl | C(O)NHCH(CH$_3$)-adamantan-1-yl | 4-CO$_2$—CH$_2$CH$_3$ | H |
| 73 | cyclohexyl | C(O)NH-1,3,3-(CH$_3$)$_3$-bicyclo[2.2.1]hept-2-yl | 4-CO$_2$—CH$_2$CH$_3$ | H |
| 74 | cycloheptyl | C(O)NH-1,3,3-(CH$_3$)$_3$-bicyclo[2.2.1]hept-2-yl | H | H |
| 75 | CH$_2$-phenyl | C(O)NHCH(CO$_2$CH$_3$)CH$_2$-(4-OH)phenyl | H | H |
| 76 | CH$_2$-phenyl | C(O)NHCH(CO$_2$H)CH$_2$-(4-OCH$_2$-phenyl)phenyl | H | H |
| 77 | cyclohexyl | C(O)NHCH(CO$_2$CH$_3$)CH$_2$-(4-OH)phenyl | H | H |
| 78 | cyclohexyl | C(O)NHCH(CO$_2$H)CH$_2$-(4-OCH$_2$-phenyl)phenyl | H | H |
| 79 | cyclohexyl | C(O)NH-adamantan-2-yl | 5-CO$_2$CH$_2$-phenyl | H |
| 80 | CH$_2$-phenyl | C(O)NHCH(CO$_2$CH$_3$)CH$_2$—(4-OCH$_2$-phenyl)phenyl | H | H |
| 81 | cyclohexyl | C(O)NHCH(CO$_2$CH$_3$)CH$_2$—(4-OCH$_2$-phenyl)phenyl | H | H |
| 82 | CH$_2$-phenyl | C(O)NHCH(CO$_2$CH$_3$)CH$_2$-(3,4-(OH)$_2$-phenyl) | H | H |
| 83 | CH$_2$-phenyl | C(O)NHCH(CO$_2$CH$_3$)CH$_2$-1H-indol-3-yl | H | H |
| 85 | cyclohexyl | C(O)NH-adamantan-2-yl | 5-NHCO$_2$—C(CH$_3$)$_3$ | H |
| 86 | cyclohexyl | C(O)NH-1,3,3-(CH$_3$)$_3$-bicyclo[2.2.1]hept-2-yl | 5-NHCO$_2$—C(CH$_3$)$_3$ | H |
| 87 | cyclohexyl | C(O)NH-adamantan-2-yl | 5-NHC(O)—CF$_3$ | H |
| 88 | cyclohexyl | C(O)NH-adamantan-2-yl | 5-NH—CO$_2$CH$_3$ | H |
| 89 | cyclohexyl | C(O)NH-adamantan-2-yl | 5-NHC(O)—N(CH$_3$)$_2$ | H |
| 90 | cyclohexyl | C(O)NH-adamantan-2-yl | 5-NHC(O)-morpholin-4-yl | H |
| 92 | cyclohexyl | C(O)NH-1,3,3-(CH$_3$)$_3$-bicyclo[2.2.1]hept-2-yl | 5-NH$_2$ | H |
| 93 | cyclohexyl | C(O)NH-1,3,3-(CH$_3$)$_3$-bicyclo[2.2.1]hept-2-yl | 5-OH | H |

-continued

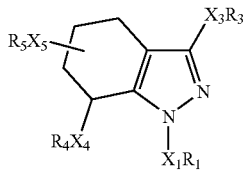

wherein $X_1R_1$, $X_3R_3$,
$X_4R_4$ and $X_5R_5$ are dependently selected from

| Cpd | $X_1R_1$ | $X_3R_3$ | $X_5R_5$ | $X_4R_4$ |
|---|---|---|---|---|
| 94 | cyclohexyl | C(O)NH-1,3,3-(CH$_3$)$_3$-bicyclo[2.2.1]hept-2-yl | 5-OC(O)—CH$_3$ | H |
| 95 | cyclohexyl | C(O)NH-adamantan-2-yl | 5-C(O)NH-[1,2,4]-triazol-4-yl | H |
| 96 | cyclohexyl | C(O)NH-1,3,3-(CH$_3$)$_3$-bicyclo[2.2.1]hept-2-yl | 5-oxo | H |
| 97 | cyclohexyl | C(O)NHCH(CH$_3$)-adamantan-1-yl | 5-oxo | H |
| 98 | cyclohexyl | C(O)NH-adamantan-2-yl | 5-C(CH$_3$)$_3$ | H |
| 99 | cyclohexyl | C(O)NH-1,3,3-(CH$_3$)$_3$-bicyclo[2.2.1]hept-2-yl | 5-C(CH$_3$)$_3$ | H |
| 100 | cyclohexyl | C(O)NHCH(CH$_3$)-adamantan-1-yl | 5-C(CH$_3$)$_3$ | H |
| 101 | cyclohexyl | C(O)NH-octahydro-2,5-methano-pentalen-3a-yl | 5-C(CH$_3$)$_3$ | H |
| 102 | cyclohexyl | C(O)NHCH$_2$-adamantan-1-yl | 5-C(CH$_3$)$_3$ | H |
| 103 | cyclohexyl | C(O)NH-adamantan-2-yl | 5-NHC(O)—N[(CH$_3$)-phenyl] | H |
| 104 | cyclohexyl | C(O)NH-adamantan-2-yl | 5-NH—SO$_2$CH$_3$ | H |
| 105 | cyclohexyl | C(O)NH-adamantan-2-yl | 5-NHSO$_2$—(4-CH$_3$)-phenyl | H |
| 106 | cyclohexyl | C(O)NH-adamantan-2-yl | 5-NHSO$_2$—N(CH$_3$)$_2$ | H |
| 107 | cyclohexyl | C(O)NH-(2S,3R)-2-CH$_2$OCH$_2$CH$_3$-bicyclo[2.2.1]hept-3-yl | H | H |
| 108 | cyclohexyl | C(O)NH-(2S,3R)-2-CH$_2$OCH$_2$-(2-Br-phenyl)-bicyclo[2.2.1]hept-3-yl | H | H |
| 109 | phenyl | C(O)NH-adamantan-2-yl | 5-C(CH$_3$)$_3$ | H |
| 110 | phenyl | C(O)NHCH(CH$_3$)-adamantan-1-yl | 5-C(CH$_3$)$_3$ | H |
| 111 | phenyl | C(O)NH-1,3,3-(CH$_3$)$_3$-bicyclo[2.2.1]hept-2-yl | 5-C(CH$_3$)$_3$ | H |
| 112 | phenyl | C(O)NHCH$_2$-adamantan-1-yl | 5-C(CH$_3$)$_3$ | H |
| 113 | phenyl | C(O)NH-adamantan-1-yl | 5-C(CH$_3$)$_3$ | H |
| 114 | phenyl | C(O)NHCH(CH$_3$)-(1R)-cyclohexyl | 5-C(CH$_3$)$_3$ | H |
| 115 | phenyl | C(O)NH-adamantan-2-yl | 5-CO$_2$—CH$_2$CH$_3$ | H |
| 116 | phenyl | C(O)NHCH(CH$_3$)-adamantan-1-yl | 5-CO$_2$—CH$_2$CH$_3$ | H |
| 117 | phenyl | C(O)NHCH$_2$-adamantan-1-yl | 5-CO$_2$—CH$_2$CH$_3$ | H |
| 118 | phenyl | C(O)NH-adamantan-1-yl | 5-CO$_2$—CH$_2$CH$_3$ | H |
| 119 | CH$_2$-phenyl | C(O)NH-6-CO$_2$CH$_2$CH$_3$-cyclohex-3-en-1-yl | H | H |
| 120 | cyclohexyl | C(O)NH-6-CO$_2$CH$_2$CH$_3$-cyclohex-3-en-1-yl | H | OCH$_3$ |
| 122 | CH$_2$-cyclohexyl | C(O)NH-adamantan-2-yl | H | H |
| 123 | CH$_2$-cyclohexyl | C(O)NHCH(CH$_3$)-adamantan-1-yl | H | H |
| 124 | CH$_2$-cyclohexyl | C(O)NH-(2S,3R)-2-CO$_2$CH$_2$CH$_3$-bicyclo[2.2.1]hept-3-yl | H | H |
| 125 | CH$_2$—(4-CH$_3$)-phenyl | C(O)NH-1,3,3-(CH$_3$)$_3$-bicyclo[2.2.1]hept-2-yl | H | H |
| 126 | CH$_2$-(4-CH$_3$)-phenyl | C(O)NH-2-CO$_2$CH$_2$CH$_3$-bicyclo[2.2.1]hept-3-yl | H | H |
| 127 | CH$_2$-phenyl | C(O)NH-cyclooctyl | H | H |
| 128 | cyclohexyl | C(O)NH-cyclooctyl | H | H |
| 129 | (2,4-Cl$_2$)-phenyl | C(O)NH-1,3,3-(CH$_3$)$_3$-bicyclo[2.2.1]hept-2-yl | H | H |
| 130 | (2,4-Cl$_2$)-phenyl | C(O)NH-(2S,3R)-2-CO$_2$CH$_2$CH$_3$-bicyclo[2.2.1]hept-3-yl | H | H |
| 131 | (2,4-Cl$_2$)-phenyl | C(O)NH-adamantan-2-yl | H | H |

-continued

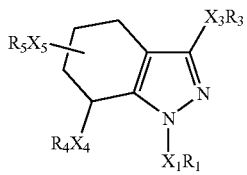

wherein $X_1R_1$, $X_3R_3$,
$X_4R_4$ and $X_5R_5$ are dependently selected from

| Cpd | $X_1R_1$ | $X_3R_3$ | $X_5R_5$ | $X_4R_4$ |
|---|---|---|---|---|
| 132 | cyclohexyl | C(O)NHCH(CH$_3$)-adamantan-1-yl | 5-CO$_2$—CH$_2$CH$_3$ | H |
| 133 | cyclohexyl | C(O)NHCH(CH$_3$)-adamantan-1-yl | 5-CO$_2$H | H |
| 134 | (2,4-Cl$_2$)-phenyl | C(O)NH-azepan-1-yl | H | H |
| 135 | CH$_2$-phenyl | C(O)NHCH$_2$-adamantan-1-yl | H | H |
| 136 | CH$_2$-phenyl | C(O)NH-adamantan-2-yl | H | H |
| 137 | cyclohexyl | C(O)NH-3-CO$_2$CH$_2$CH$_3$-bicyclo[2.2.1]hept-2-yl | 5-CO$_2$—CH$_2$CH$_3$ | H |
| 138 | cyclohexyl | C(O)NH-3-CH$_2$OH-bicyclo[2.2.1]hept-2-yl | 5-CO$_2$H | H |
| 139 | (2,4-Cl$_2$)-phenyl | C(O)NH-adamantan-1-yl | H | H |
| 141 | (2,4-Cl$_2$)-phenyl | C(O)NHCH$_2$-adamantan-1-yl | H | H |
| 143 | cyclohexyl | C(O)NHCH(CH$_3$)-adamantan-1-yl | 5-CH$_2$OH | H |
| 144 | (4-F)phenyl | C(O)NH-1,3,3-(CH$_3$)$_3$-bicyclo-2.2.1]hept-2-yl | H | phenyl |
| 145 | (4-F)phenyl | C(O)NHCH$_2$-adamantan-1-yl | H | phenyl |
| 146 | (4-F)phenyl | C(O)NHCH(CH$_3$)-adamantan-1-yl | H | phenyl |
| 147 | (4-F)phenyl | C(O)NH-(2S,3R)-2-CO$_2$CH$_2$CH$_3$-bicyclo[2.2.1]hept-3-yl | H | phenyl |
| 148 | CH$_2$-phenyl | C(O)NHCH(CH$_3$)-adamantan-1-yl | 5-CO$_2$—CH$_2$CH$_3$ | H |
| 149 | CH$_2$-phenyl | C(O)NH-1,3,3-(CH$_3$)$_3$-bicyclo[2.2.1]hept-2-yl | 5-CO$_2$—CH$_2$CH$_3$ | H |
| 150 | (4-F)phenyl | C(O)NH-adamantan-1-yl | H | (CH$_2$)$_2$-phenyl |
| 151 | (4-F)phenyl | C(O)NH-1,3,3-(CH$_3$)$_3$-bicyclo[2.2.1]hept-2-yl | H | (CH$_2$)$_2$-phenyl |
| 152 | (4-F)phenyl | C(O)NHCH$_2$-adamantan-1-yl | H | (CH$_2$)$_2$-phenyl |
| 153 | (4-F)phenyl | C(O)NHCH(CH$_3$)-adamantan-1-yl | H | (CH$_2$)$_2$-phenyl |
| 154 | (4-F)phenyl | C(O)NH-(2S,3R)-2-CO$_2$CH$_2$CH$_3$-bicyclo[2.2.1]hept-3-yl | H | (CH$_2$)$_2$-phenyl |
| 155 | CH$_2$-phenyl | C(O)NH-1,3,3-(CH$_3$)$_3$-bicyclo[2.2.1]hept-2-yl | 5-CO$_2$H | H |
| 156 | CH$_2$-phenyl | C(O)NHCH$_2$-adamantan-1-yl | 6-CO$_2$—CH$_2$CH$_3$ | H |
| 157 | CH$_2$-phenyl | C(O)NH-octahydro-2,5-methano-pentalen-3a-yl | 6-CO$_2$—CH$_2$CH$_3$ | H |
| 158 | CH$_2$-phenyl | C(O)NH-adamantan-2-yl | 4-CO$_2$—CH$_2$CH$_3$ | H |
| 159 | CH$_2$-phenyl | C(O)NHCH$_2$-adamantan-1-yl | 4-CO$_2$—CH$_2$CH$_3$ | H |
| 160 | pyridin-2-yl | C(O)NH-1,3,3-(CH$_3$)$_3$-bicyclo[2.2.1]hept-2-yl | H | H |
| 161 | cyclohexyl | C(O)NHCH(CH$_3$)-adamantan-1-yl | H | OCH$_3$ |
| 162 | cyclohexyl | C(O)NH-adamantan-2-yl | H | OCH$_3$ |
| 163 | cyclohexyl | C(O)NHCH(CH$_3$)-adamantan-1-yl | H | OH |
| 164 | cyclohexyl | C(O)NH-(2S*,3R*)-2-CO$_2$CH$_2$CH$_3$-bicyclo[2.2.1]hept-3-yl | H | OH |
| 165 | (4-F)phenyl | C(O)NH-adamantan-1-yl | H | phenyl |
| 166 | CH$_2$-phenyl | C(O)NHCH(CH$_3$)-adamantan-1-yl | 5-CO$_2$H | H |
| 167 | CH$_2$-phenyl | C(O)NH-(2R*,3S*)-2-C(O)NHCH$_2$CH$_3$-bicyclo[2.2.1]hept-3-yl | H | H |
| 168 | cyclohexyl | C(O)NH-1,3,3-(CH$_3$)$_3$-bicyclo[2.2.1]hept-2-yl | 5-CO$_2$H | H |
| 169 | cycloheptyl | C(O)NH-1,3,3-(CH$_3$)$_3$-bicyclo[2.2.1]hept-2-yl | 5-CO$_2$CH$_3$ | H |
| 170 | cyclohexyl | C(O)NH-1,3,3-(CH$_3$)$_3$-bicyclo[2.2.1]hept-2-yl | 5-C(O)—NH$_2$ | H |
| 171 | CH$_2$-phenyl | C(O)NH-1-CO$_2$CH$_2$CH$_3$-piperidin-4-yl | H | H |
| 172 | (4-F)phenyl | C(O)NH-1-CO$_2$H-cyclohexyl | H | H |

-continued

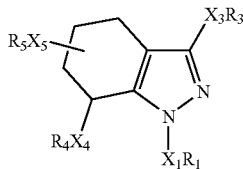

wherein $X_1R_1$, $X_3R_3$, $X_4R_4$ and $X_5R_5$ are dependently selected from

| Cpd | $X_1R_1$ | $X_3R_3$ | $X_5R_5$ | $X_4R_4$ |
|---|---|---|---|---|
| 173 | cyclohexyl | C(O)NHCH$_2$-pyridin-3-yl | H | H |
| 174 | CH$_2$-phenyl | C(O)NH(CH$_2$)$_2$-morpholin-4-yl | H | H |
| 175 | CH$_2$-phenyl | C(O)NH(CH$_2$)$_2$-morpholin-4-ium | H | H |
| 176 | cyclohexyl | C(O)NHCH$_2$C(O)-(4-OCH$_3$)phenyl | H | H |
| 177 | cyclohexyl | C(O)NHCH$_2$C(O)-(4-Br)phenyl | H | H |
| 178 | cyclohexyl | NHC(O)naphthalen-2-yl | H | H |
| 179 | cyclohexyl | NHC(O)adamantan-1-yl | H | H |
| 180 | cyclohexyl | NHC(O)cyclohexyl | H | H |
| 181 | cyclohexyl | NHC(O)naphthalen-1-yl | H | H |
| 182 | cyclohexyl | NHC(O)NH-adamantan-1-yl | H | H |
| 183 | cyclohexyl | C(O)NH-1,2,3,4-tetrahydro-naphthalen-1-yl | H | H |
| 184 | cyclohexyl | C(O)NHCH(CH$_3$)-cyclohexyl | H | H |
| 185 | cyclohexyl | C(O)NHCH$_2$CH(OH)-cyclohexyl | H | H |
| 186 | cyclohexyl | NHC(O)phenyl | H | H |
| 187 | cyclohexyl | C(O)NHCH$_2$C(O)-cyclohexyl | H | H |
| 188 | cyclohexyl | C(O)NHCH$_2$C(O)-phenyl | H | H |
| 189 | CH$_2$-phenyl | C(O)NHCH$_2$-cyclohexyl | H | H |
| 191 | (4-F)phenyl | C(O)NH-(2S*,3R*)-2-CO$_2$CH$_2$CH$_3$-bicyclo[2.2.1]hept-3-yl | H | CH$_2$CH$_3$ |
| 192 | (4-F)phenyl | C(O)NH-1,3,3-(CH$_3$)$_3$-bicyclo[2.2.1]hept-2-yl | H | CH$_2$CH$_3$ |
| 193 | cyclohexyl | C(O)NHCH(CH$_3$)-cyclopentyl | H | H |
| 194 | CH$_2$-phenyl | C(O)NH-1,3,3-(CH$_3$)$_3$-bicyclo[2.2.1]hept-2-yl | H | H |
| 195 | cyclohexyl | C(O)NHCH—(R—CH$_3$)-cyclohexyl | H | H |
| 196 | cyclohexyl | C(O)NHCH—(S—CH$_3$)-phenyl | H | H |
| 197 | cyclohexyl | C(O)NHCH—(R—CH$_3$)-phenyl | H | H |
| 198 | CH$_2$-phenyl | C(O)NHCH—(R—CH$_3$)-cyclohexyl | H | H |
| 199 | CH$_2$-phenyl | C(O)NHCH—(R—CH$_3$)-phenyl | H | H |
| 200 | CH$_2$-phenyl | C(O)NHCH—(S—CH$_3$)-phenyl | H | H |
| 201 | CH$_2$-phenyl | C(O)NHCH—(S—CH$_3$)-cyclohexyl | H | H |
| 202 | (4-F)phenyl | C(O)NH-(2S)-1,3,3-(CH$_3$)$_3$-bicyclo[2.2.1]hept-2-yl | H | H |
| 203 | cyclohexyl | C(O)N[(CH$_2$CH$_3$)[CH(R—CH$_3$)cyclohexyl]] | H | H |
| 204 | cyclohexyl | C(O)NHCH—(R—CH$_2$CH$_3$)-phenyl | H | H |
| 205 | cyclohexyl | NHC(O)NH-1,3,3-(CH$_3$)$_3$-bicyclo[2.2.1]hept-2-yl | H | H |
| 206 | CH$_2$-phenyl | C(O)NH-(2R*,3S*)-2-CO$_2$CH$_2$CH$_3$-bicyclo[2.2.1]hept-5-en-3-yl | H | H |
| 207 | cyclohexyl | C(O)NH-(2S*)-1,3,3-(CH$_3$)$_3$-bicyclo[2.2.1]hept-2-yl | H | H |
| 208 | cyclohexyl | C(O)NH-adamantan-2-yl | 5S*—CO$_2$—CH$_2$CH$_3$ | H |
| 209 | cyclohexyl | C(O)NH-adamantan-2-yl | 5R*—CO$_2$—CH$_2$CH$_3$ | H |
| 210 | CH$_2$-phenyl | C(O)NH-adamantan-2-yl | 5S*—CO$_2$—CH$_2$CH$_3$ | H |
| 211 | CH$_2$-phenyl | C(O)NH-adamantan-2-yl | 5R*—CO$_2$—CH$_2$CH$_3$ | H |
| 212 | cyclohexyl | C(O)NHCH—(R*—CH$_3$)-adamantan-1-yl | H | H |
| 213 | cyclohexyl | C(O)NHCH—(S*—CH$_3$)-adamantan-1-yl | H | H |
| 214 | cyclohexyl | C(O)NHCH(CH$_3$)-adamantan-1-yl | 5R*—CO$_2$—CH$_2$CH$_3$ | H |
| 215 | cyclohexyl | C(O)NHCH(CH$_3$)-adamantan-1-yl | 5S*—CO$_2$—CH$_2$CH$_3$ | H |
| 216 | cyclohexyl | C(O)NH-(2S*,3S*)-2-CH$_3$-6,6-(CH$_3$)$_2$-bicyclo[3.1.1]hept-3-yl | H | H |
| 217 | CH$_2$-phenyl | C(O)NH-(2R*)-1,3,3-(CH$_3$)$_3$-bicyclo[2.2.1]hept-2-yl | H | H |
| 218 | cyclohexyl | C(O)NH-adamantan-2-yl | 5S*—CO$_2$—CH$_3$ | H |
| 219 | cyclohexyl | C(O)NH-adamantan-2-yl | 5R*—CO$_2$—CH$_3$ | H |

-continued

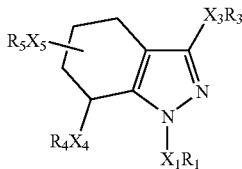

wherein X₁R₁, X₃R₃,
X₄R₄ and X₅R₅ are dependently selected from

| Cpd | X₁R₁ | X₃R₃ | X₅R₅ | X₄R₄ |
|---|---|---|---|---|
| 220 | phenyl | C(O)NH-1,3,3-(CH$_3$)$_3$-bicyclo[2.2.1]hept-2-yl | 5R*-CO$_2$—CH$_2$CH$_3$ | H |
| 222 | cyclohexyl | C(O)NH-adamantan-2-yl | 5-CO$_2$—CH$_2$CH$_3$ | H |
| 223 | cyclohexyl | C(O)NH-adamantan-2-yl | 5-CO$_2$H | H |
| 224 | cyclohexyl | C(O)NHCH(CH$_3$)-adamantan-1-yl | 5-C(O)NH$_2$ | H |
| 225 | cyclohexyl | C(O)NH-1-aza-bicyclo[2.2.2]oct-3-yl | H | H |
| 226 | CH$_2$-phenyl | C(O)NH-adamantan-2-yl | 5-CO$_2$—CH$_2$CH$_3$ | H |
| 228 | cyclohexyl | C(O)NH-adamantan-2-yl | 5-C(O)NH—C(CH$_3$)$_2$—CH$_2$—C(CH$_3$)$_3$ | H |
| 229 | cyclohexyl | C(O)NH-piperidin-1-yl | 5-CO$_2$—CH$_2$CH$_3$ | H |
| 230 | CH$_2$-phenyl | C(O)NH-adamantan-2-yl | 6-CO$_2$—CH$_2$CH$_3$ | H |
| 231 | cyclohexyl | C(O)NH-adamantan-2-yl | 5-CO$_2$CH$_3$ | H |
| 232 | cyclohexyl | C(O)NH-adamantan-2-yl | 5-CO$_2$—CH(CH$_3$)$_2$ | H |
| 233 | cyclohexyl | C(O)NH-adamantan-2-yl | 5-CO$_2$—C(CH$_3$)$_3$ | H |
| 234 | cyclohexyl | C(O)NHCH(CH$_2$CH$_3$)-cyclohexyl | H | H |
| 235 | cyclohexyl | C(O)NH-1,3,3-(CH$_3$)$_3$-bicyclo[2.2.1]hept-2-yl | 5-C(O)—N(CH$_3$)$_2$ | H |
| 236 | cyclohexyl | C(O)NH(CH$_2$)$_2$—(2-OCH$_3$)phenyl | H | H |
| 237 | CH$_2$-phenyl | C(O)NH(CH$_2$)$_2$—(2-OCH$_3$)phenyl | H | H |
| 238 | phenyl | C(O)NH(CH$_2$)$_2$—(2-OCH$_3$)phenyl | H | H |
| 239 | CH$_2$-phenyl | C(O)NH-adamantan-2-yl | 5-CO$_2$H | H |
| 240 | cyclohexyl | C(O)NHCH$_2$CH(OH)-(4-Br)phenyl | H | H |
| 241 | cyclohexyl | C(O)NHCH$_2$CH(OH)-(4-OCH$_3$)phenyl | H | H |
| 242 | CH(CH$_3$)-phenyl | C(O)NHCH$_2$-cyclohexyl | H | H |
| 243 | CH(CH$_3$)-phenyl | C(O)NH-adamantan-2-yl | H | H |
| 244 | CH(CH$_3$)-phenyl | C(O)NH-adamantan-1-yl | H | H |
| 245 | cyclohexyl | C(O)NH-2-CH$_3$-cyclohexyl | H | H |
| 246 | cyclohexyl | C(O)NHCH(CH$_3$)-cycloheptyl | H | H |
| 247 | cyclohexyl | C(O)NHCH(CH$_3$)-cyclobutyl | H | H |
| 248 | cyclohexyl | C(O)NHCH(CH$_3$)-(1R,4R)-4-CH$_3$-cyclohexyl | H | H |
| 249 | CH(CH$_3$)-phenyl | C(O)NHCH(CH$_3$)-cyclohexyl | H | H |
| 250 | CH(CH$_3$)-phenyl | C(O)NH-1,3,3-(CH$_3$)$_3$-bicyclo[2.2.1]hept-2-yl | H | H |
| 251 | cyclohexyl | C(O)NH—(R*—CH)(CH$_3$)-cyclohexyl | 5-CO$_2$—CH$_2$CH$_3$ | H |
| 252 | cyclohexyl | C(O)NH-(2R*,3R*)-2-CH$_3$-6,6-(CH$_3$)$_2$-bicyclo[3.1.1]hept-3-yl | H | H |
| 253 | CH$_2$-phenyl | C(O)NHCH(CH$_3$)-phenyl | H | phenyl |
| 254 | CH$_2$-phenyl | C(O)NH-3-CH$_2$OCH$_3$-pyrrolidin-1-yl | H | phenyl |
| 255 | CH$_2$-phenyl | C(O)NH-phenyl | H | phenyl |
| 256 | CH$_2$-phenyl | C(O)NH-CH(CH$_3$)-phenyl | 5-CO$_2$—CH$_2$CH$_3$ | H |
| 257 | cyclohexyl | C(O)NH-CH(CH$_3$)-phenyl | 5-CO$_2$—CH$_2$CH$_3$ | H |
| 258 | (4-F)phenyl | (CH)$_2$—SO$_2$NH—CH(CH$_3$)-phenyl | H | (CH$_2$)$_2$-phenyl |
| 259 | (4-F)phenyl | (CH)$_2$—SO$_2$NH—CH(CH$_3$)-cyclohexyl | H | (CH$_2$)$_2$-phenyl |
| 260 | CH$_2$-phenyl | (CH)$_2$—SO$_2$NH—CH(R—CH$_3$)-phenyl | H | H |
| 261 | CH$_2$-phenyl | (CH)$_2$—SO$_2$NH—CH(S—CH$_3$)-phenyl | H | H |
| 262 | CH$_2$-phenyl | (CH)$_2$—SO$_2$NH—CH(R—CH$_3$)-cyclohexyl | H | H |

-continued

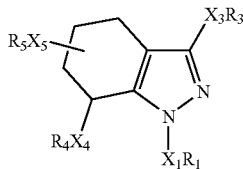

wherein $X_1R_1$, $X_3R_3$, $X_4R_4$ and $X_5R_5$ are dependently selected from

| Cpd | $X_1R_1$ | $X_3R_3$ | $X_5R_5$ | $X_4R_4$ |
|---|---|---|---|---|
| 263 | $CH_2$-phenyl | $(CH)_2$—$SO_2NH$—$CH(S$—$CH_3)$-cyclohexyl | H | H |
| 264 | $CH_2$-phenyl | C(O)NH-1-$CO_2C(CH_3)_3$-piperidin-4-yl | H | H |
| 265 | $CH_2$-phenyl | C(O)NH-1,3,3-$(CH_3)_3$-bicyclo[2.2.1]hept-2-yl | H | phenyl |
| 266 | $CH_2$-phenyl | C(O)NH-piperidin-1-yl | H | phenyl |
| 267 | $CH_2$-phenyl | C(O)NHCH($CH_3$)-cyclohexyl | H | phenyl |
| 268 | $CH_2$-phenyl | C(O)NH-azepan-1-yl | H | phenyl |
| 269 | cyclohexyl | C(O)NH-(1R,2R)-2-$CO_2CH_2CH_3$-cyclohexyl | H | H |
| 272 | $CH_2$-phenyl | C(O)NH-(2R-$CO_2CH_2CH_3$)—(R)-cyclohexyl | H | H |
| 274 | $CH_2$-phenyl | C(O)NH-(2R*,3S*)-2-$CO_2CH_2CH_3$-bicyclo[2.2.1]hept-3-yl | H | H |
| 276 | $CH_2$-phenyl | C(O)NH-(2S,3R)-2-$CO_2CH_2CH_3$-bicyclo[2.2.1]hept-5-en-3-yl | H | H |
| 278 | cyclohexyl | C(O)NH-(2R,3S)-2-$CO_2CH_2CH_3$-bicyclo[2.2.1]hept-3-yl | H | H |
| 279 | cyclohexyl | C(O)NH-(2S,3R)-2-$CO_2CH_2CH_3$-bicyclo[2.2.1]hept-5-en-3-yl | H | H |
| 280 | cyclohexyl | C(O)NH-(2R,3S)-2-$CO_2CH_2CH_3$-bicyclo[2.2.1]hept-5-en-3-yl | H | H |
| 281 | cyclohexyl | $CH_2C(CH_3)_2$C(O)NH-(2S,3R)-2-$CO_2CH_2CH_3$-bicyclo[2.2.1]hept-3-yl | H | H |
| 282 | cyclohexyl | C(O)NH-(2S,3R)-2-$CO,CH_2CH_3$-bicyclo[2.2.1]hept-3-yl | H | $OCH_3$ |
| 283 | (2,4-$Cl_2$)-phenyl | C(O)NHCH($CH_3$)-adamantan-1-yl | H | H |
| 284 | cyclohexyl | C(O)NH—(R*—CH)($CH_3$)-cyclohexyl | 6-$CO_2$—$CH_2CH_3$ | H |
| 285 | cyclohexyl | C(O)NH—(R*—CH)($CH_3$)cyclohexyl | 4-$CO_2$—$CH_2CH_3$ | H |
| 286 | cyclohexyl | C(O)NH—(R*—CH)($CH_3$)cyclohexyl | 5-$NHCO_2$—$C(CH_3)_3$ | H |
| 287 | (2,4-$Cl_2$)-phenyl | C(O)NH-pipendin-1-yl | H | H |
| 288 | cyclohexyl | C(O)NHCH—(R—$CH_3$)-phenyl | 5-$CO_2$—$CH_2CH_3$ | H |
| 289 | $CH_2$-phenyl | C(O)NH—(R—CH)($CH_3$)-cyclohexyl | 5-$CO_2$—$CH_2CH_3$ | H |
| 299 | (4-F)phenyl | C(O)NHNH(cyclooctyl) | H | H |
| 300 | cyclohexyl | C(O)NHNH(cyclooctyl) | H | H |
| 301 | cyclohexyl | C(O)NH-6-$CO_2CH_2CH_3$-cyclohex-3-en-1-yl | H | H |
| 302 | cyclohexyl | C(O)NH-(2S*,3R*)-2-$CH_2OH$-bicyclo[2.2.1]hept-3-yl | H | H |
| 303 | cyclohexyl | C(O)NHCH$_2$-pyridin-4-yl | H | H |
| 304 | cyclohexyl | C(O)NHCH$_2$-cyclohexyl | H | H |
| 305 | $CH_2$-phenyl | $(CH)_2$—C(O)NH—CH(S—$CH_3$)-phenyl | H | H |
| 306 | $CH_2$-phenyl | $(CH)_2$—C(O)NH—CH(R—$CH_3$)-phenyl | H | H |
| 312 | (2,4-$Cl_2$)-phenyl | C(O)NHCH(R—$CH_3$)-phenyl | H | (3-$OCH_3$)-phenyl |
| 313 | (2,4-$Cl_2$)-phenyl | C(O)NHCH(S—$CH_2OH$)-phenyl | H | (3-$OCH_3$)-phenyl |
| 314 | (2,4-$Cl_2$)-phenyl | C(O)NHCH(R—$CH_2OH$)-phenyl | H | (3-$OCH_3$)-phenyl |
| 315 | (2,4-$Cl_2$)-phenyl | C(O)NHCH(R—$CH_2Cl$)-phenyl | H | (3-$OCH_3$)-phenyl |
| 316 | (2,4-$Cl_2$)-phenyl | C(O)NHCH(S—$CH_2Cl$)-phenyl | H | (3-$OCH_3$)-phenyl |
| 317 | (2,4-$F_2$)-phenyl | C(O)NHCH(R—$CH_3$)-phenyl | H | (3-$OCH_3$)-phenyl |
| 318 | (2,4-$F_2$)-phenyl | C(O)NHCH(R—$CH_2OH$)-phenyl | H | (3-$OCH_3$)-phenyl |
| 326 | cyclohexyl | C(O)NH-adamantan-2-yl | 5-C(O)—N($CH_2$—phenyl)$_2$ | H |

-continued

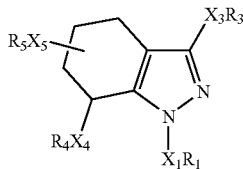

wherein $X_1R_1$, $X_3R_3$, $X_4R_4$ and $X_5R_5$ are dependently selected from

| Cpd | $X_1R_1$ | $X_3R_3$ | $X_5R_5$ | $X_4R_4$ |
|---|---|---|---|---|
| 327 | cyclohexyl | C(O)NH-adamantan-2-yl | 5-C(O)NH—$(CH_2)_2CH_3$ | H |
| 328 | cyclohexyl | C(O)N($CH_3$)CH(R—$CH_3$)cyclohexyl | H | H |
| 329 | cyclohexyl | C(O)N[CH($CH_3$)$_2$]CH(R—$CH_3$)-cyclohexyl | H | H |
| 330 | cyclohexyl | C(O)NHCH($CH_3$)$CH_2$-cyclohexyl | H | H |
| 331 | cyclohexyl | C(O)NHCH(phenyl)-cyclohexyl | H | H |
| 332 | cyclohexyl | $CH_2$CH($CO_2CH_2CH_3$)-(2-$OCH_3$)-phenyl | H | H |
| 333 | cyclohexyl | $CH_2$CH(2-$OCH_3$-phenyl)-C(O)NH-1,3,3-($CH_3$)$_3$-bicyclo[2.2.1]hept-2-yl | H | H |
| 334 | cyclohexyl | NHC(O)NH—CH($CH_3$)-cyclohexyl | H | H |
| 335 | $CH_2$-phenyl | C(O)N($CH_3$)(phenyl) | H | phenyl |
| 336 | cyclohexyl | $NHSO_2$-(4-$CH_3$)phenyl | H | H |
| 337 | $CH_2$-phenyl | NHC(O)NH-adamantan-1-yl | H | H |
| 338 | $CH_2$-phenyl | NHC(O)NH-1,3,3-($CH_3$)$_3$-bicyclo[2.2.1]hept-2-yl | H | H | and pharmaceutically acceptable forms thereof.

An example of the present invention is a compound of formula (Ib)

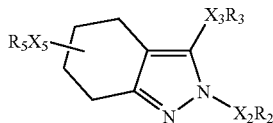

wherein $X_2R_2$, $X_3R_3$ and $X_5R_5$ are dependently selected from

| Cpd | $X_2R_2$ | $X_5R_5$ | $X_3R_3$ |
|---|---|---|---|
| 4 | (4-$OCH_3$)-phenyl | H | C(O)NHCH($CO_2CH_3$)$CH_2$—(4-$OCH_2$-phenyl)phenyl |
| 6 | (4-$OCH_3$)-phenyl | H | C(O)NHCH($CO_2CH_3$)$CH_2$—(4-OH)phenyl |
| 8 | (4-$OCH_3$)-phenyl | H | C(O)NH($CH_2$)$_2$—(4-$NH_2$)phenyl |
| 42 | $CH_2$-phenyl | H | C(O)NH-(2-$CO_2CH_2CH_3$)-bicyclo[2.2.1]hept-3-yl |
| 84 | cyclohexyl | 5-$NHCO_2C(CH_3)_3$ | C(O)NH-adamantan-2-yl |
| 91 | phenyl | 5-$CO_2CH_2CH_3$ | C(O)NH-adamantan-1-yl |
| 121 | (4-$OCH_3$)-phenyl | H | C(O)N—($CH_2CH_3$)—(2-$OCH_3$)phenyl |
| 140 | (2,4-$Cl_2$)-phenyl | H | C(O)NH-adamantan-1-yl |
| 142 | (2,4-$Cl_2$)-phenyl | H | C(O)NH$CH_2$-adamantan-1-yl |
| 190 | cyclohexyl | 5-$CO_2CH_2CH_3$ | C(O)NHCH($CH_3$)-adamantan-1-yl |
| 221 | cyclohexyl | 5-$CO_2CH_2CH_3$ | C(O)NH-adamantan-2-yl |
| 227 | $CH_2$-phenyl | 5-$CO_2CH_2CH_3$ | C(O)NH-octahydro-2,5-methano-pentalen-3a-yl |
| 270 | $CH_2$-phenyl | H | C(O)NH-(1S*,2R*)-2-$CO_2CH_2CH_3$-cyclohexyl |
| 271 | $CH_2$-phenyl | H | C(O)NH—(1S,2S)-2-$CO_2CH_2CH_3$-cyclohexyl |
| 273 | $CH_2$-phenyl | H | C(O)NH—(2R,3S)-2-$CO_2CH_2CH_3$-bicyclo[2.2.1]hept-3-yl |
| 275 | $CH_2$-phenyl | H | C(O)NH—(2S,3R)-2-$CO_2CH_2CH_3$-bicyclo[2.2.1]hept-5-en-3-yl |
| 277 | $CH_2$-phenyl | H | C(O)NH—(2R,3S)-2-$CO_2CH_2CH_3$-bicyclo[2.2.1]hept-5-en-3-yl |
| 322 | phenyl | 5-$CO_2CH_2CH_3$ | C(O)NH-1,3,3-($CH_3$)$_3$-bicyclo[2.2.1]hept-2-yl |
| 323 | phenyl | 5-$CO_2CH_2CH_3$ | C(O)NHCH$_2$-adamantan-1-yl |

-continued

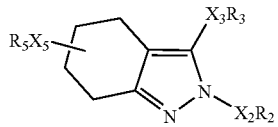

wherein X₂R₂, X₃R₃ and X₅R₅ are dependently selected from

| Cpd | X₂R₂ | X₅R₅ | X₃R₃ |
|---|---|---|---|
| 324 | phenyl | 5-CO$_2$CH$_2$CH$_3$ | C(O)NH-adamantan-2-yl |
| 325 | phenyl | 5-CO$_2$CH$_2$CH$_3$ | C(O)NHCH(CH$_3$)-adamantan-1-yl |

15 and pharmaceutically acceptable forms thereof.

An example of the present invention is a compound of Formula (Ic)

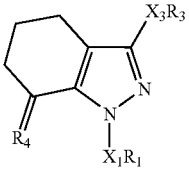

Formula (Ic)

wherein X₁R₁, X₃R₃ and R₄ are dependently selected from

| Cpd | X₁R₁ | R₄ | X₃R₃ |
|---|---|---|---|
| 290 | (2,4-Cl$_2$)phenyl | CH—(4-Cl)phenyl | C(O)NH-piperidin-1-yl |
| 291 | (2,4-Cl$_2$)phenyl | CH—(4-Cl)phenyl | C(O)NH-morpholin-4-yl |
| 292 | (2,4-Cl$_2$)phenyl | CH—(4-Cl)phenyl | C(O)NH—(1S,2R,4R)-1-CH$_3$-3,3-(CH$_3$)$_2$-bicyclo[2.2.1]hept-2-yl |
| 293 | (2,4-Cl$_2$)phenyl | CH—(4-Cl)phenyl | C(O)NH—(R—CH)(CH$_3$)-cyclohexyl |
| 294 | (2,4-Cl$_2$)phenyl | CH—(4-Cl)phenyl | C(O)NH—(S—CH)(CH$_3$)-phenyl |
| 295 | (2,4-Cl$_2$)phenyl | CH—(4-F)phenyl | C(O)NH—(R—CH)(CH$_3$)-cyclohexyl |
| 296 | (2,4-Cl$_2$)phenyl | CH—(4-F)phenyl | C(O)NH—(R—CH)(CH$_3$)-phenyl |
| 297 | (2,4-Cl$_2$)phenyl | CH—(4-F)phenyl | C(O)NH-piperidin-1-yl |
| 298 | (2,4-Cl$_2$)phenyl | CH—(4-F)phenyl | C(O)NH-morpholin-4-yl |
| 307 | (2,4-Cl$_2$)phenyl | CH—(4-Cl)phenyl | C(O)NH—(R—CH)(CH$_3$)-phenyl |
| 308 | (2,4-Cl$_2$)phenyl | CH—(4-F)phenyl | C(O)NH—(S—CH)(CH$_3$)-phenyl |
| 309 | (2,4-Cl$_2$)phenyl | CH—(4-F)phenyl | C(O)NH—(S—CH)(CH$_3$)-cyclohexyl |
| 310 | (2,4-Cl$_2$)phenyl | CH—(4-Cl)phenyl | C(O)NHNH-(4-SO$_2$NH$_2$)phenyl |
| 311 | (2,4-Cl$_2$)phenyl | CH—(4-F)phenyl | C(O)NHNH-pyridin-4-yl |
| 319 | (2,4-Cl$_2$)phenyl | CH—(4-Cl)phenyl | C(O)NHCH$_2$-pyridin-2-yl |
| 320 | (2,4-Cl$_2$)phenyl | CH—(4-Cl)phenyl | C(O)NHCH(CH$_3$)-pyridin-2-yl |
| 321 | (2,4-Cl$_2$)phenyl | CH—(4-Cl)phenyl | C(O)NH—(S—CH)(CH$_3$)-cyclohexyl |
| 339 | (2,4-Cl$_2$)phenyl | CH—(4-F)phenyl | C(O)NH-azepan-1-yl |
| 340 | (2,4-Cl$_2$)phenyl | CH-thien-2-yl | C(O)NH—CH(R—CH$_3$)-phenyl |
| 341 | (2,4-Cl$_2$)phenyl | CH-thien-2-yl | C(O)NH—CH(R—CH$_3$)-cyclohexyl |
| 342 | (2,4-Cl$_2$)phenyl | CH-thien-2-yl | C(O)NH-piperidin-1-yl |
| 343 | (2,4-Cl$_2$)phenyl | CH-thien-2-yl | C(O)NH-azepan-1-yl |
| 344 | (2,4-Cl$_2$)phenyl | CH-thien-2-yl | C(O)NH-2,6-(CH$_3$)$_2$-piperidin-1-yl |
| 345 | (2,4-Cl$_2$)phenyl | CH-thien-2-yl | C(O)NH-pyrrolidin-1-yl |
| 346 | (2,4-Cl$_2$)phenyl | CH-thien-2-yl | C(O)NH-hexahydro-cyclopenta[c]pyrrol-2-yl |
| 347 | (2,4-Cl$_2$)phenyl | CH-thien-3-yl | C(O)NH-piperidin-1-yl |
| 348 | (2,4-Cl$_2$)phenyl | CH-thien-3-yl | C(O)NH-azepan-1-yl |
| 349 | (2,4-Cl$_2$)phenyl | CH-thien-3-yl | C(O)NH-2,6-(CH$_3$)$_2$-piperidin-1-yl |
| 350 | (2,4-Cl$_2$)phenyl | CH-thien-3-yl | C(O)NH-hexahydro-cyclopenta[c]pyrrol-2-yl |
| 351 | (2,4-Cl$_2$)phenyl | CH-thien-3-yl | C(O)NH—CH(R—CH$_3$)-cyclohexyl |
| 352 | (2,4-Cl$_2$)phenyl | CH-thien-3-yl | C(O)NH—CH(S—CH$_3$)-cyclohexyl |
| 353 | (2,4-Cl$_2$)phenyl | CH-thien-3-yl | C(O)NH—CH(R—CH$_3$)-phenyl |
| 354 | (2,4-Cl$_2$)phenyl | CH-thien-3-yl | C(O)NH—CH(S—CH$_3$)-phenyl |
| 355 | (2,4-Cl$_2$)phenyl | CH-thien-3-yl | C(O)NH—(R—CH)(CH$_2$OH)-phenyl |
| 356 | (2,4-Cl$_2$)phenyl | CH-thien-3-yl | C(O)NH—(S—CH)(CH$_2$OH)-phenyl |
| 357 | (2,4-Cl$_2$)phenyl | CH-thien-3-yl | C(O)NH-pyrrolidin-1-yl |

-continued

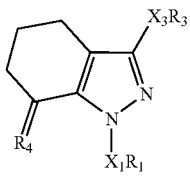

Formula (Ic)

wherein $X_1R_1$, $X_3R_3$ and $R_4$ are dependently selected from

| Cpd | $X_1R_1$ | $R_4$ | $X_3R_3$ |
|---|---|---|---|
| 358 | (2,4-Cl$_2$)phenyl | CH-fur-3-yl | C(O)NH—CH(R—CH$_3$)-phenyl |
| 359 | (2,4-Cl$_2$)phenyl | CH-fur-3-yl | C(O)NH—CH(S—CH$_3$)-phenyl |
| 360 | (2,4-Cl$_2$)phenyl | CH-fur-3-yl | C(O)NH—CH(R—CH$_3$)-cyclohexyl |
| 361 | (2,4-Cl$_2$)phenyl | CH-fur-3-yl | C(O)NH—CH(S—CH$_3$)-cyclohexyl |
| 362 | (2,4-Cl$_2$)phenyl | CH-fur-3-yl | C(O)NH-2,6-(CH$_3$)$_2$-pipendin-1-yl |
| 363 | (2,4-Cl$_2$)phenyl | CH-fur-3-yl | C(O)NH-azepan-1-yl |
| 364 | (2,4-Cl$_2$)phenyl | CH-fur-3-yl | C(O)NH-piperidin-1-yl |
| 365 | (2,4-Cl$_2$)phenyl | CH-fur-3-yl | C(O)NH-hexahydro-cyclopenta[c]pyrrol-2-yl |
| 366 | (2,4-Cl$_2$)phenyl | CH-fur-3-yl | C(O)NH—(R—CH)(CH$_2$OH)-phenyl |
| 367 | (2,4-Cl$_2$)phenyl | CH-fur-3-yl | C(O)NH—(S—CH)(CH$_2$OH)-phenyl |
| 368 | (2,4-Cl$_2$)phenyl | CH-fur-3-yl | C(O)NH-pyrrolidin-1-yl |
| 369 | (2,4-Cl$_2$)phenyl | CH-fur-2-yl | C(O)NH—CH(R—CH$_3$)-cyclohexyl |
| 370 | (2,4-Cl$_2$)phenyl | CH-fur-2-yl | C(O)NH—CH(S—CH$_3$)-cyclohexyl |
| 371 | (2,4-Cl$_2$)phenyl | CH-fur-2-yl | C(O)NH—CH(R—CH$_3$)-phenyl |
| 372 | (2,4-Cl$_2$)phenyl | CH-fur-2-yl | C(O)NH—CH(S—CH$_3$)-phenyl |
| 373 | (2,4-Cl$_2$)phenyl | CH-fur-2-yl | C(O)NH-azepan-1-yl |
| 374 | (2,4-Cl$_2$)phenyl | CH-fur-2-yl | C(O)NH-piperidin-1-yl |
| 375 | (2,4-Cl$_2$)phenyl | CH-fur-2-yl | C(O)NH-2,6-(CH$_3$)$_2$-pipendin-1-yl |
| 376 | (2,4-Cl$_2$)phenyl | CH-fur-2-yl | C(O)NH-hexahydro-cyclopenta[c]pyrrol-2-yl |
| 377 | (2,4-Cl$_2$)phenyl | CH-fur-2-yl | C(O)NH-pyrrolidin-1-yl |
| 378 | (2,4-Cl$_2$)phenyl | CH-fur-2-yl | C(O)NH—(R—CH)(CH$_2$OH)-phenyl |
| 379 | (2,4-Cl$_2$)phenyl | CH-fur-2-yl | C(O)NH—(S—CH)(CH$_2$OH)-phenyl |
| 380 | (2,4-Cl$_2$)phenyl | CH—(4-Br)phenyl | C(O)NH-hexahydro-cyclopenta[c]pyrrol-2-yl |
| 381 | (2,4-Cl$_2$)phenyl | CH—(4-Br)phenyl | C(O)NH—(R—CH)(CH$_3$)-pyndin-2-yl |
| 382 | (2,4-Cl$_2$)phenyl | CH—(4-Br)phenyl | C(O)NH—(R—CH)(CH$_3$)-cyclohexyl |
| 383 | (2,4-Cl$_2$)phenyl | CH—(4-Br)phenyl | C(O)NH—(R—CH)(CH$_3$)-phenyl |
| 384 | (2,4-Cl$_2$)phenyl | CH—(4-Br)phenyl | C(O)NH-piperidin-1-yl |
| 385 | (2,4-Cl$_2$)phenyl | CH—(5-Cl)thien-2-yl | C(O)NH—CH(R—CH$_3$)-cyclohexyl |
| 386 | (2,4-Cl$_2$)phenyl | CH—(5-Cl)thien-2-yl | C(O)NH—CH(R—CH$_3$)-phenyl |
| 387 | (2,4-Cl$_2$)phenyl | CH—(5-Cl)thien-2-yl | C(O)NH-piperidin-1-yl |
| 388 | (2,4-Cl$_2$)phenyl | CH—(5-Cl)thien-2-yl | C(O)NH-azepan-1-yl |
| 389 | (2,4-Cl$_2$)phenyl | CH—(5-Cl)thien-2-yl | C(O)NH-2,6-(CH$_3$)$_2$-piperidin-1-yl |
| 390 | (2,4-Cl$_2$)phenyl | CH—(5-Cl)thien-2-yl | C(O)NH-hexahydro-cyclopenta[c]pyrrol-2-yl |
| 391 | (2,4-Cl$_2$)phenyl | CH—(5-Cl)thien-2-yl | C(O)NH—CH(S-CH$_3$)-cyclohexyl |
| 392 | (2,4-Cl$_2$)phenyl | CH—(5-Cl)thien-2-yl | C(O)NH—CH(S-CH$_3$)-phenyl |
| 393 | (2,4-Cl$_2$)phenyl | CH—(5-Cl)thien-2-yl | C(O)NH-pyrrolidin-1-yl |
| 394 | (2,4-Cl$_2$)phenyl | CH—(5-Br)thien-2-yl | C(O)NH-piperidin-1-yl |
| 395 | (2,4-Cl$_2$)phenyl | CH—(5-Br)thien-2-yl | C(O)NH-azepan-1-yl |
| 396 | (2,4-Cl$_2$)phenyl | CH—(5-Br)fur-2-yl | C(O)NH-hexahydro-cyclopenta[c]pyrrol-2-yl |
| 397 | (2,4-Cl$_2$)phenyl | CH—(5-Br)fur-2-yl | C(O)NH—CH(R—CH$_3$)-phenyl |
| 398 | (2,4-Cl$_2$)phenyl | CH—(5-Br)fur-2-yl | C(O)NH—CH(R—CH$_3$)-cyclohexyl |
| 399 | (2,4-Cl$_2$)phenyl | CH—(3-Br)thien-2-yl | C(O)NH-2,6-(CH$_3$)$_2$-piperidin-1-yl |
| 400 | (2,4-Cl$_2$)phenyl | CH—(4-Br)thien-3-yl | C(O)NH-piperidin-1-yl | and pharmaceutically acceptable forms thereof.

An example of the present invention is a compound selected from:

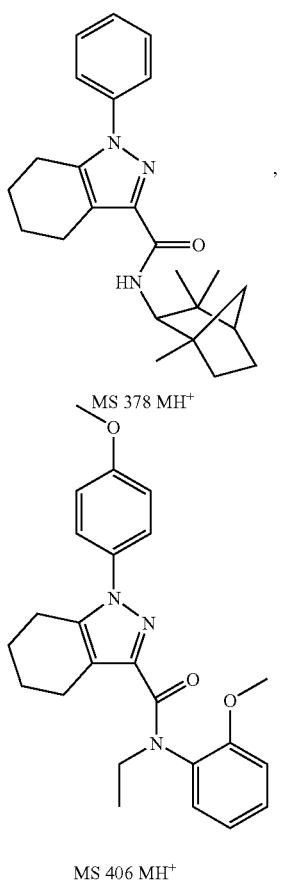
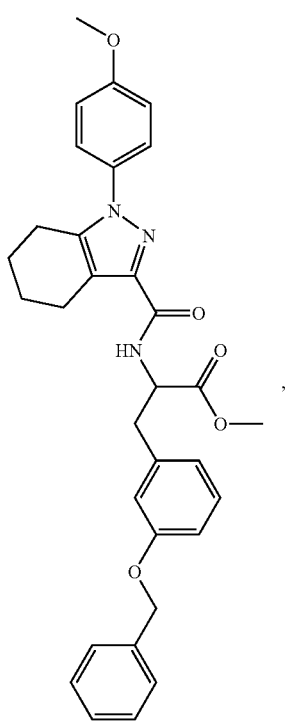
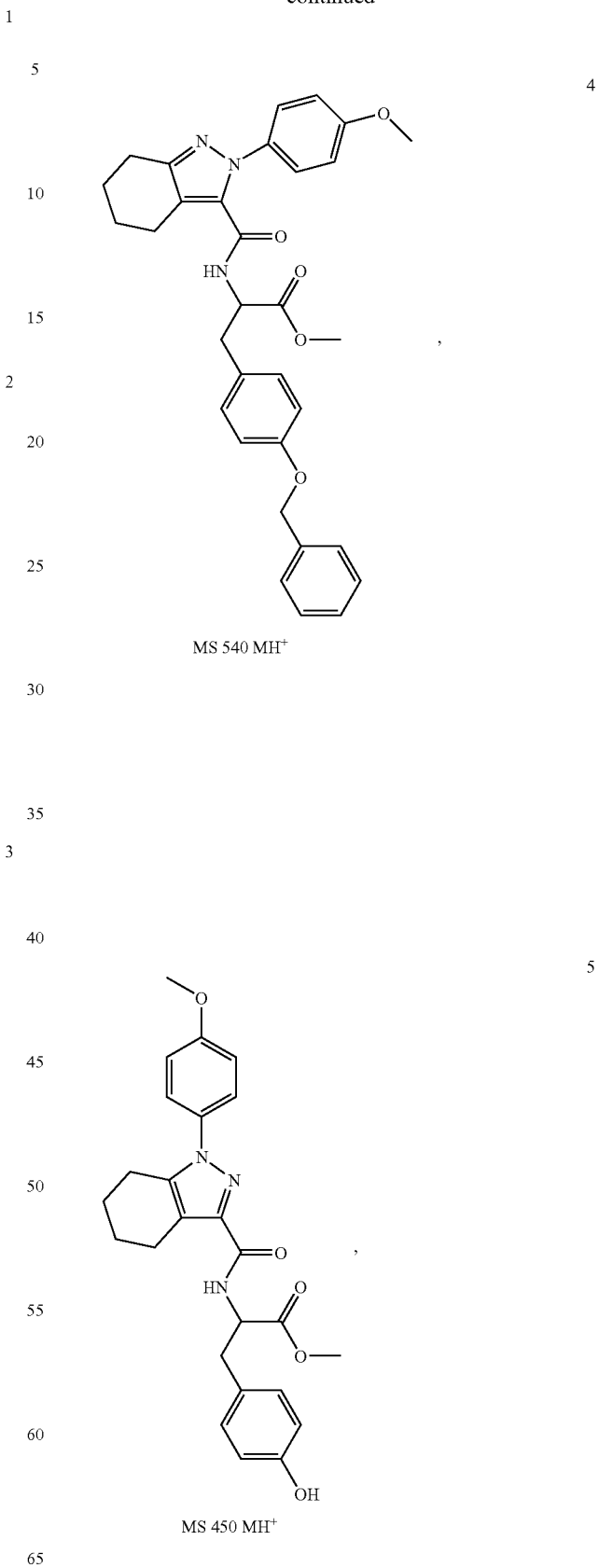

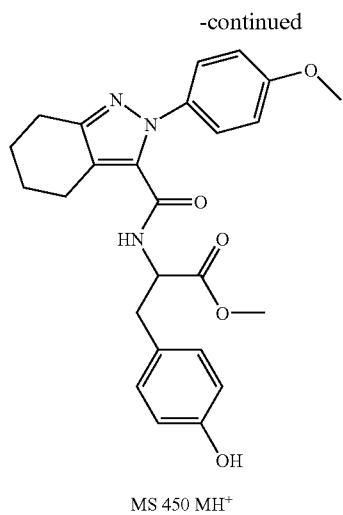
MS 450 MH+
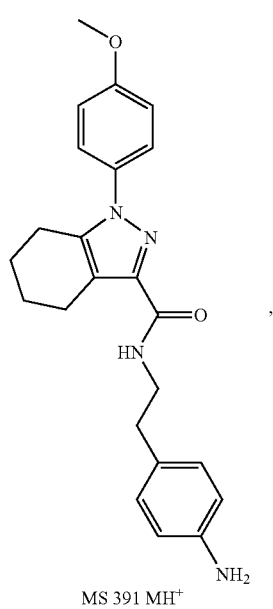
MS 391 MH+
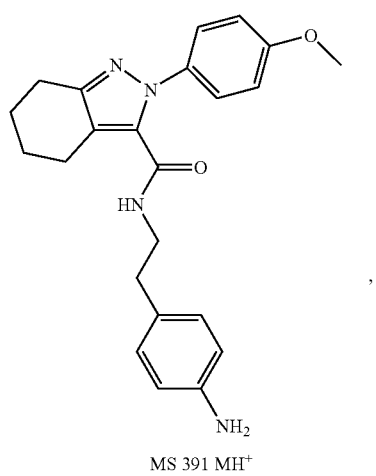
MS 391 MH+
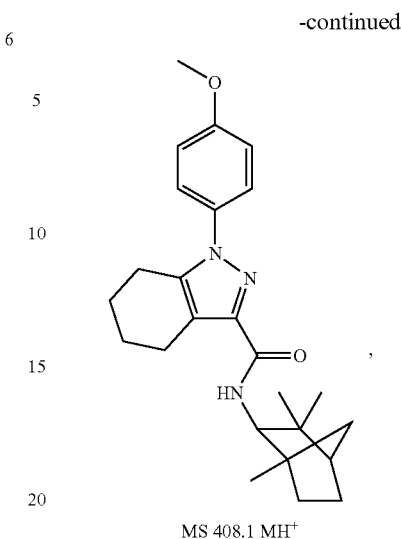
MS 408.1 MH+
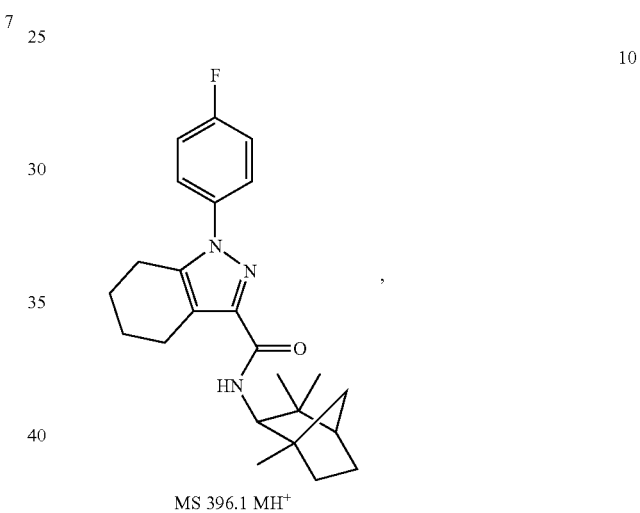
MS 396.1 MH+
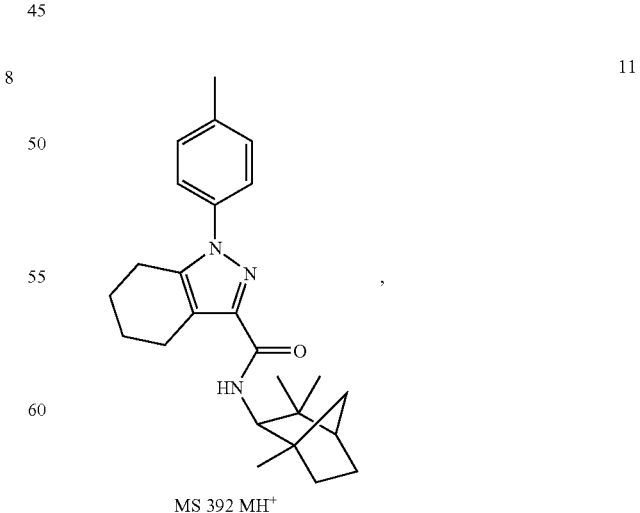
MS 392 MH+

31
-continued
12
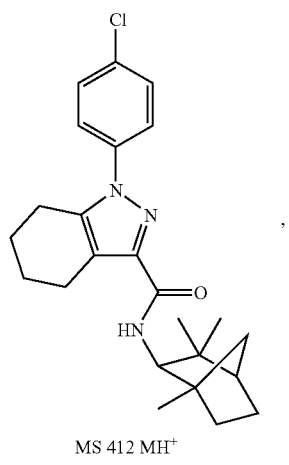
MS 412 MH+
13
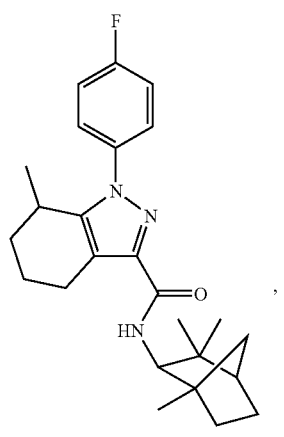
MS 410 MH+
14
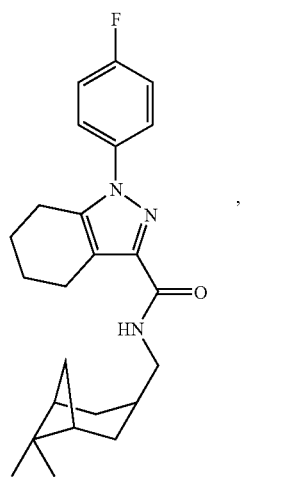
MS 396 MH+
32
-continued
15
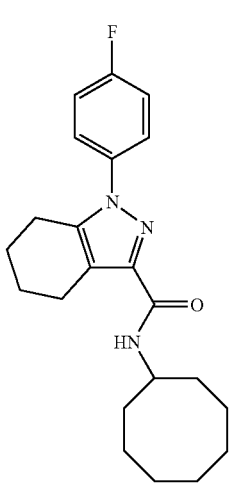
MS 370 MH+
16
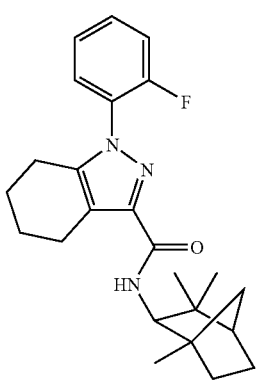
MS 396 MH+
17
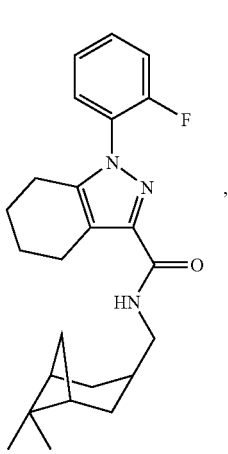
MS 396 MH+

18
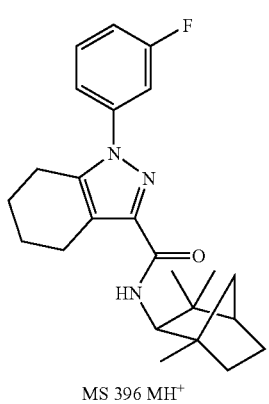
MS 396 MH+
19
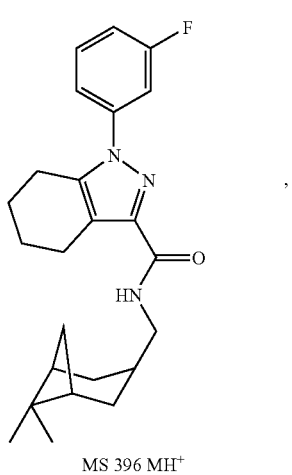
MS 396 MH+
20
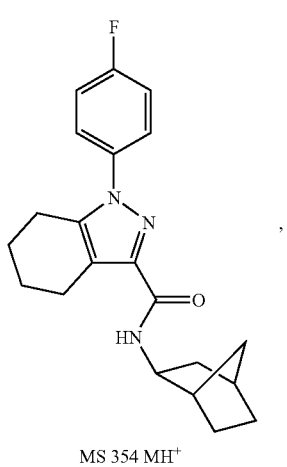
MS 354 MH+
21
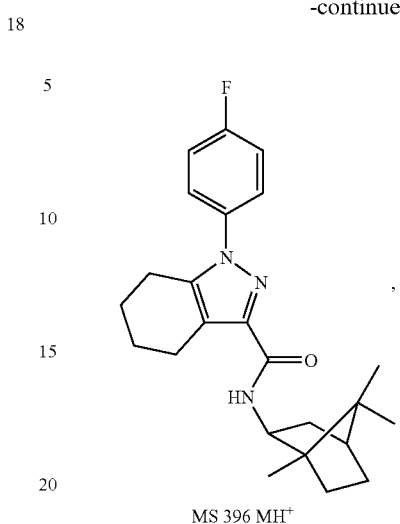
MS 396 MH+
22
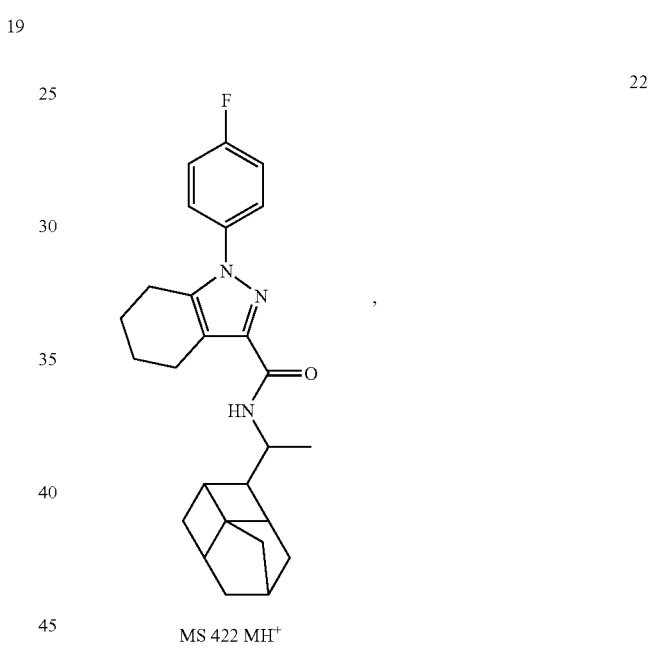
MS 422 MH+
23
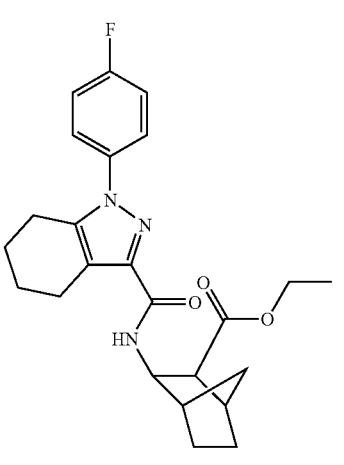
MS 426.2 MH+

-continued
24
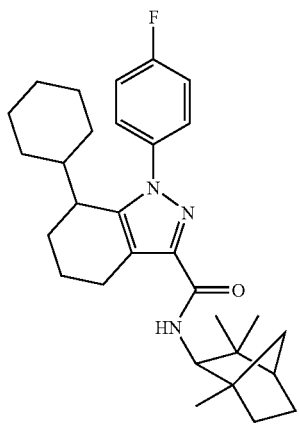
MS 478 MH+
25
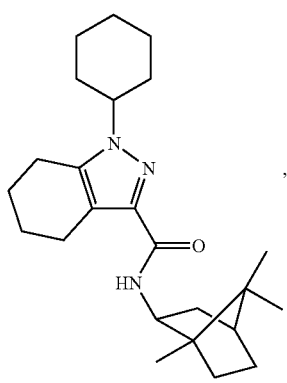
MS 384.1 MH+
26
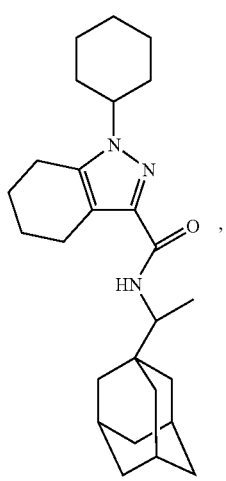
MS 410.1 MH+
-continued
27
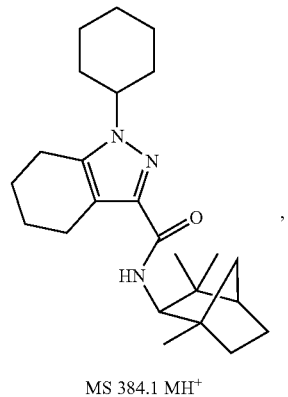
MS 384.1 MH+
28
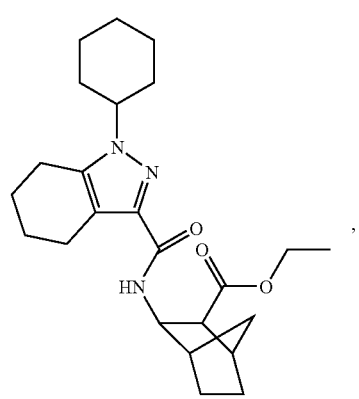
MS 414.1 MH+
29
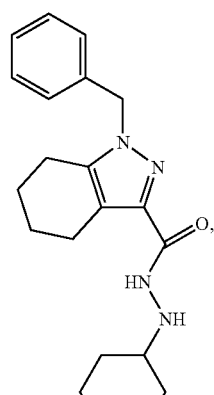
MS 352.9 MH+

30
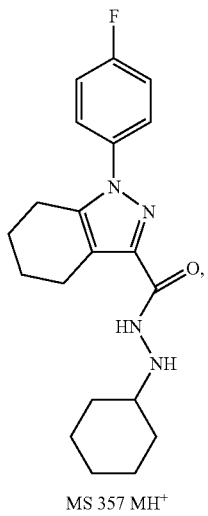
MS 357 MH+
31
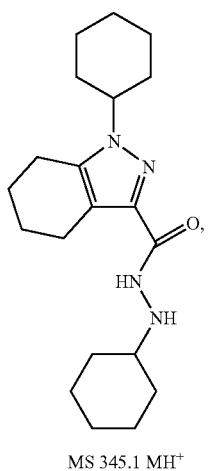
MS 345.1 MH+
32
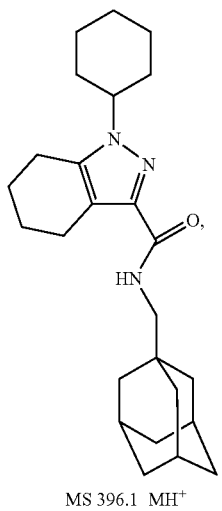
MS 396.1 MH+
33
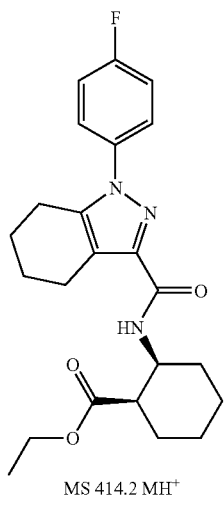
MS 414.2 MH+
34
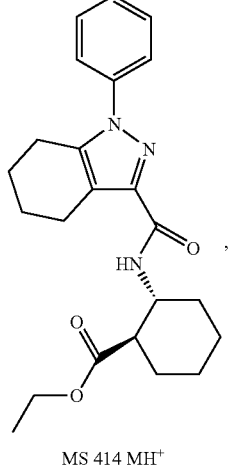
MS 414 MH+
35
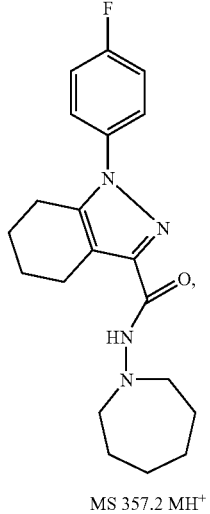
MS 357.2 MH+

-continued
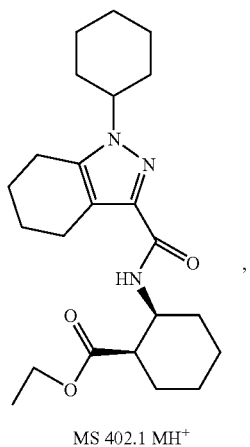
MS 402.1 MH+
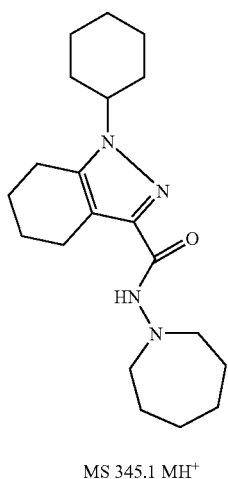
MS 345.1 MH+
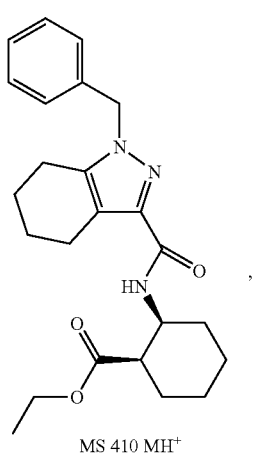
MS 410 MH+
-continued
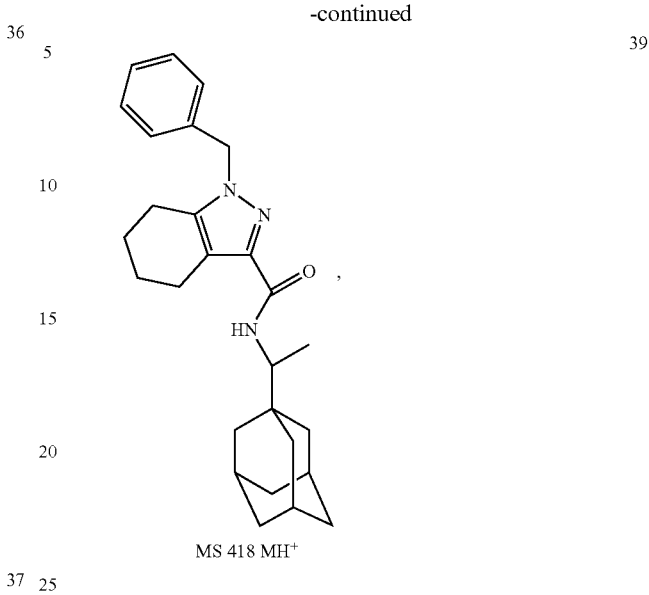
MS 418 MH+
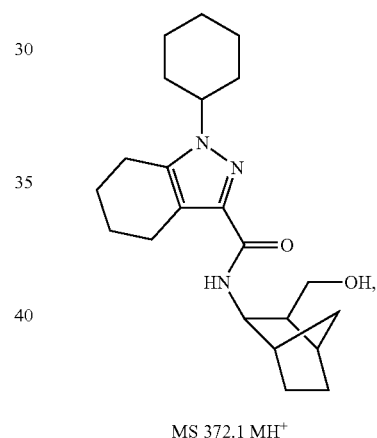
MS 372.1 MH+
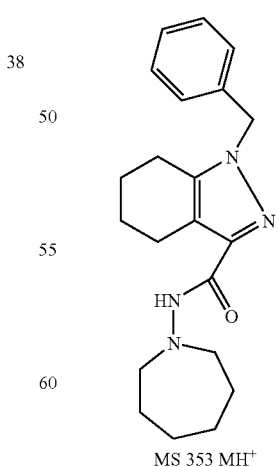
MS 353 MH+

-continued
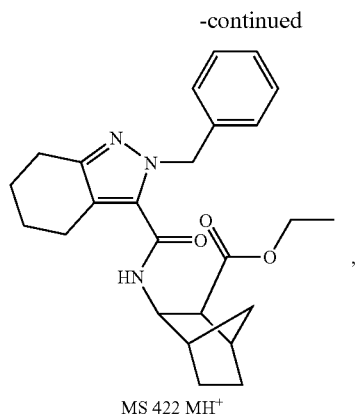
MS 422 MH+
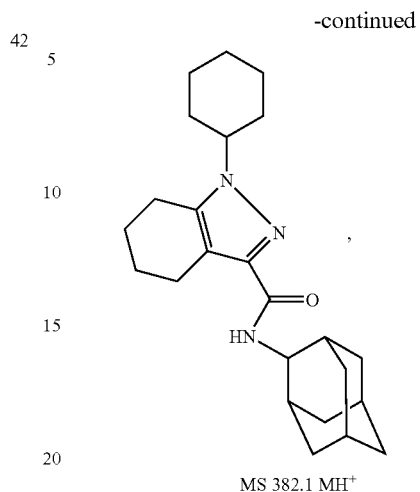
MS 382.1 MH+
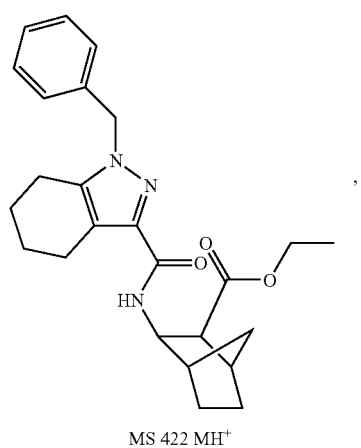
MS 422 MH+
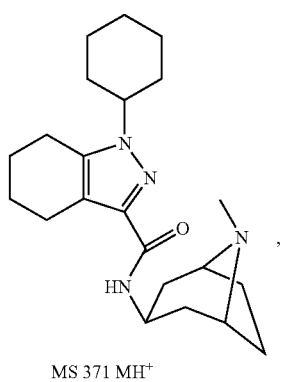
MS 371 MH+
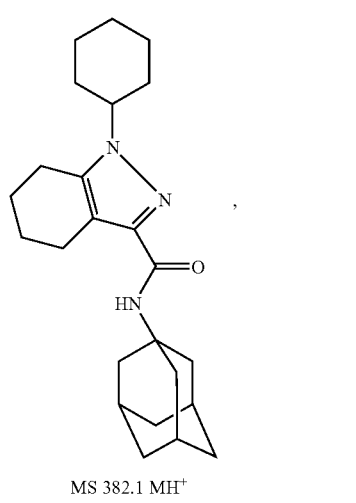
MS 382.1 MH+
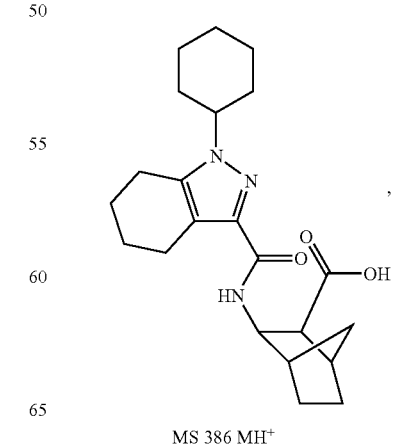
MS 386 MH+

48
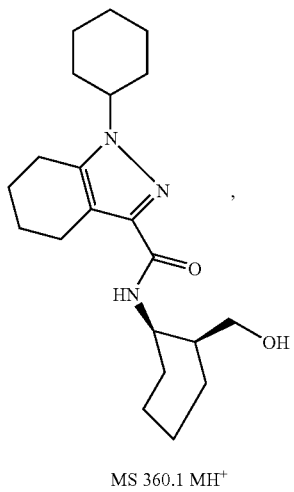
MS 360.1 MH⁺
49
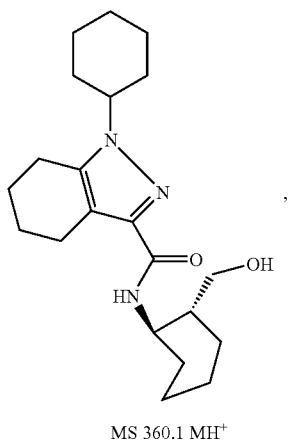
MS 360.1 MH⁺
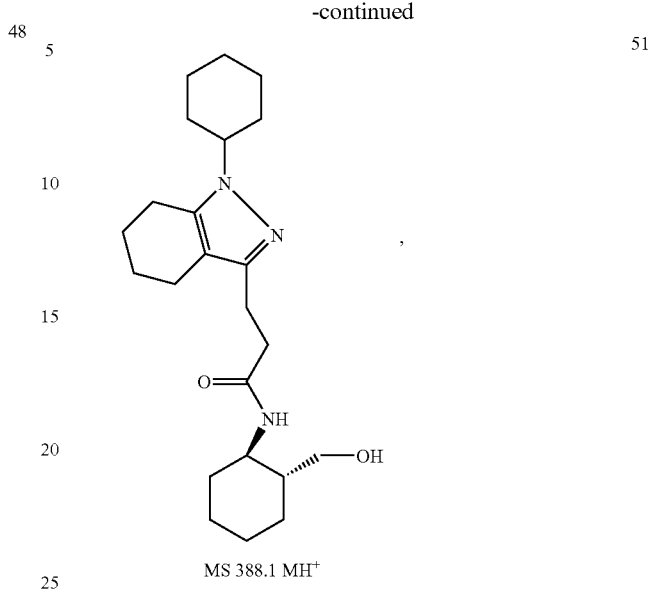
MS 388.1 MH⁺
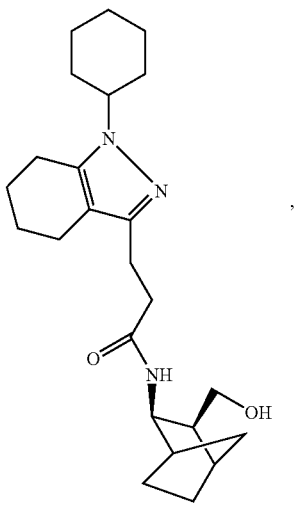
MS 400 MH⁺
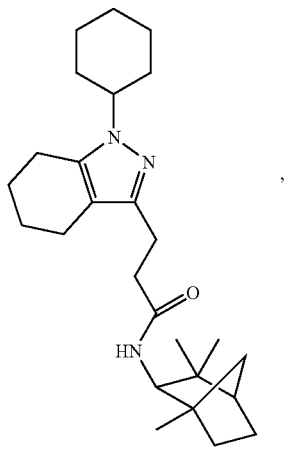
Example 15

53
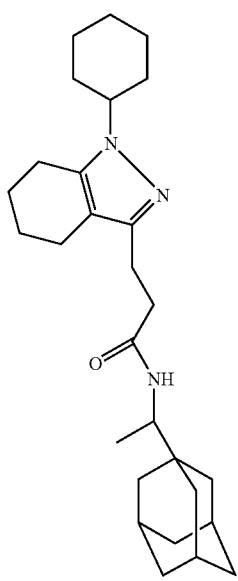
MS 442.1 MH⁺
54
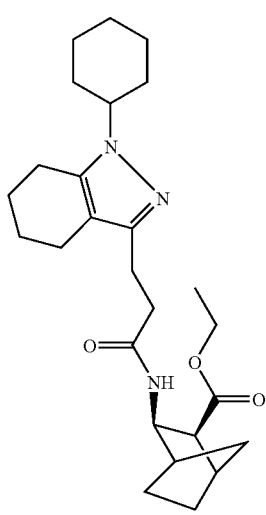
MS 442 MH⁺
55
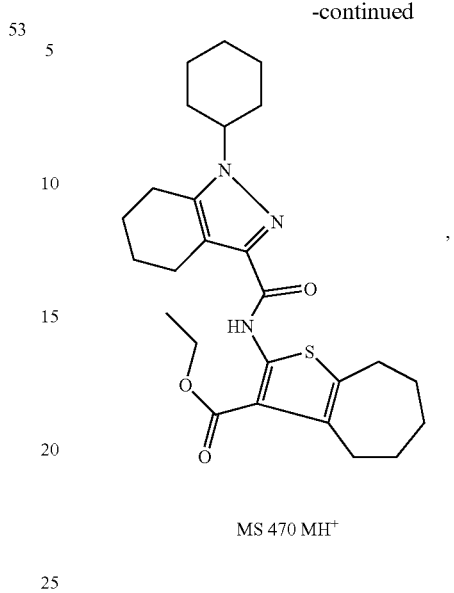
MS 470 MH⁺
56
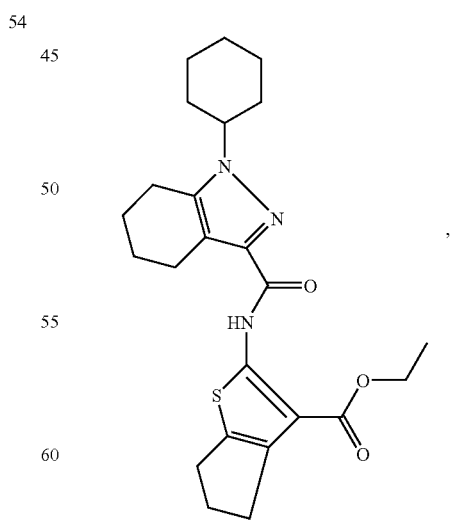
MS 442 MH⁺

-continued
57
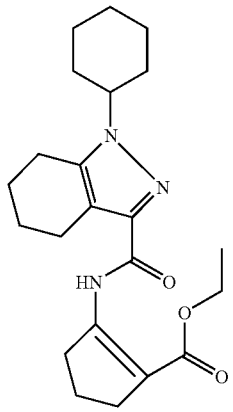
MS 386 MH+
58
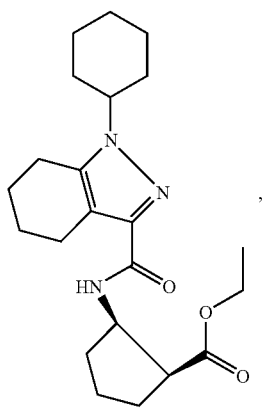
MS 388 MH+
59
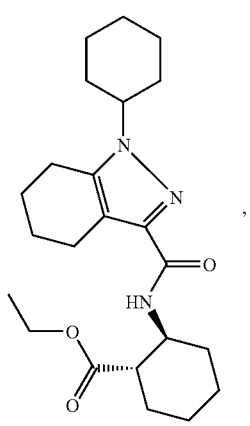
MS 402.1 MH+
-continued
60
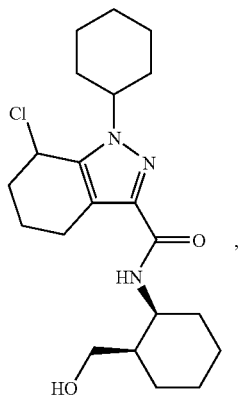
Example 23
61
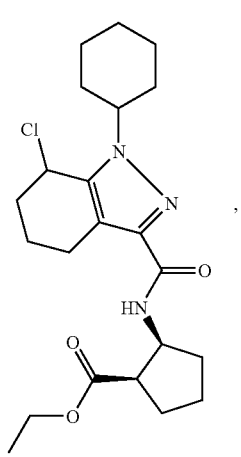
Example 422 MH+
62
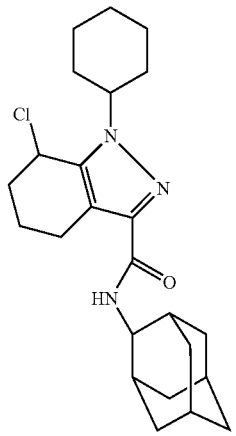
Example 416 MH+

63

MS 448 MH+

64

MS 444.1 MH+

65

MS 466.1 MH+

66

Example 16

67

MS 456 MH+

68

MS 454 MH+

69
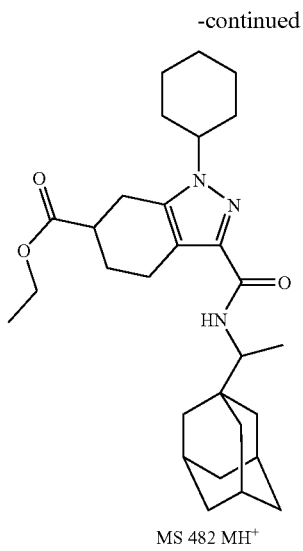
MS 482 MH+
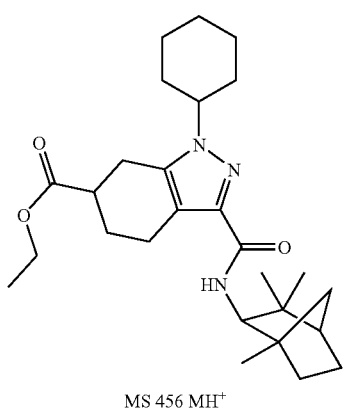
MS 456 MH+
71
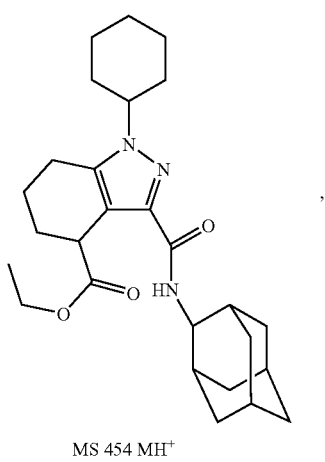
MS 454 MH+
72
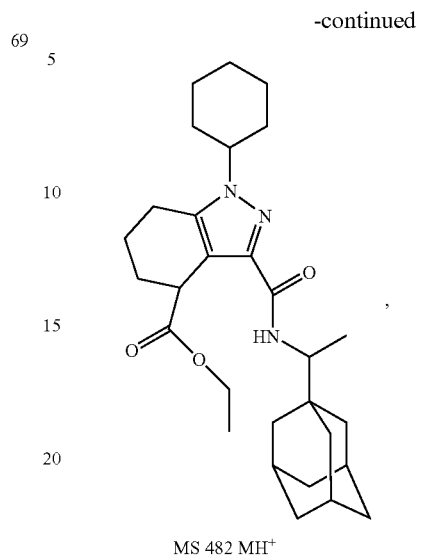
MS 482 MH+
73
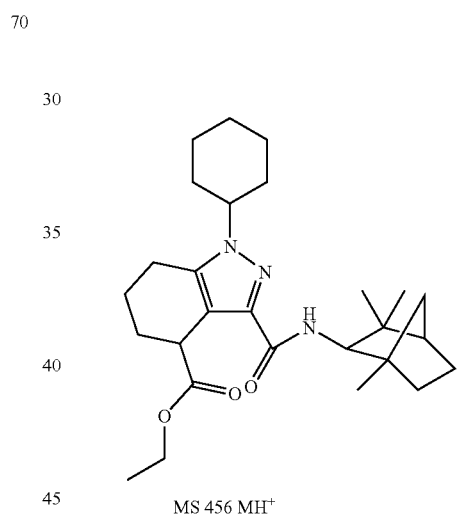
MS 456 MH+
74
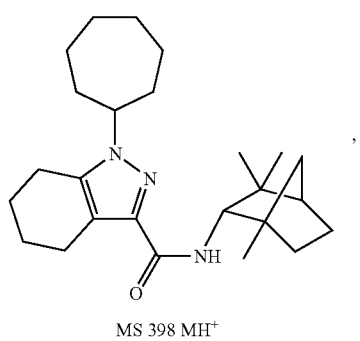
MS 398 MH+

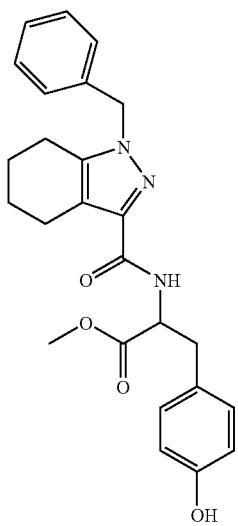
MS 434.2 MH+
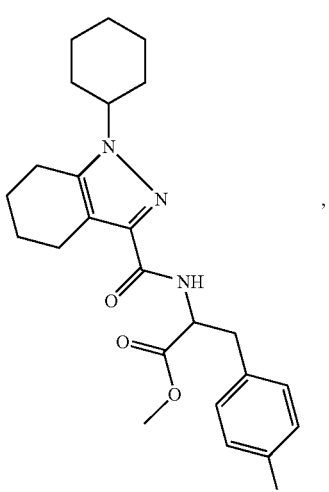
MS 426.2 MH+
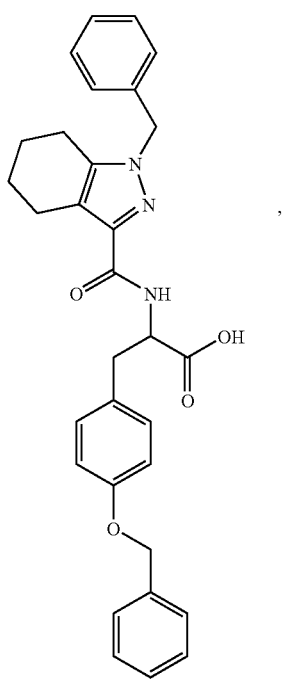
MS 510.2 MH+
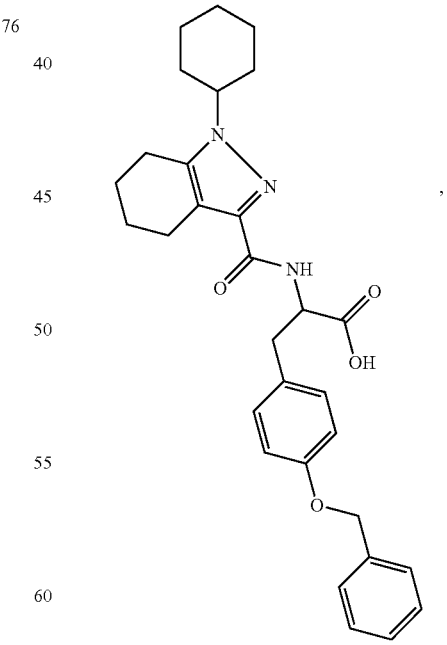
MS 502.3 MH+

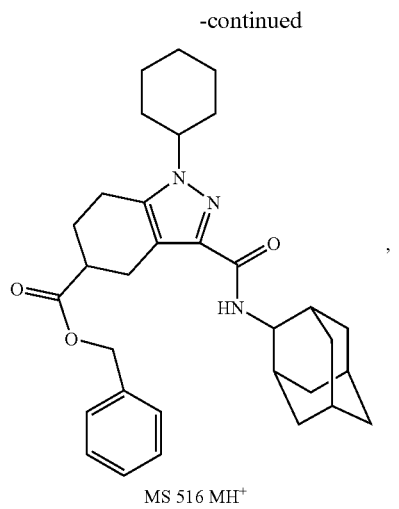

-continued
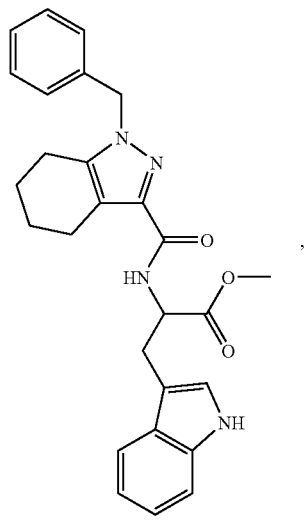
MS 457 MH+
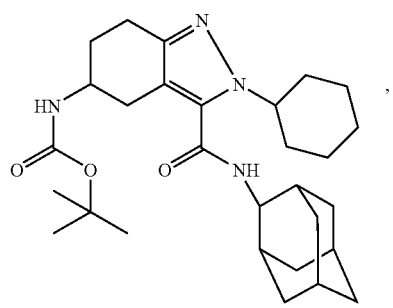
MS 497 MH+
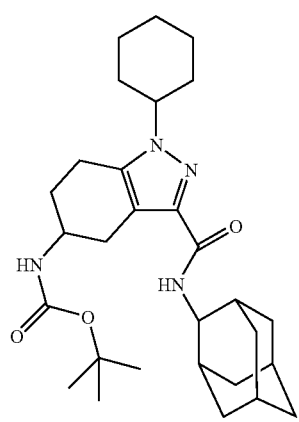
MS 497 MH+
-continued
83
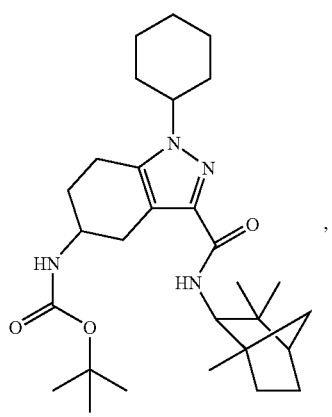
Example 8
84
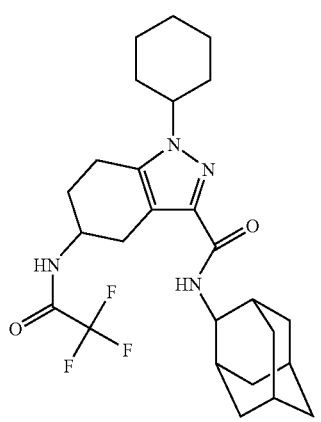
MS 493 MH+
85
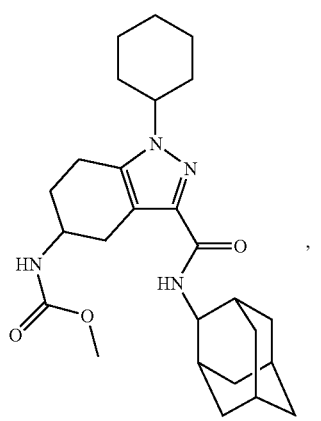
MS 455 MH+
86
87
88

-continued
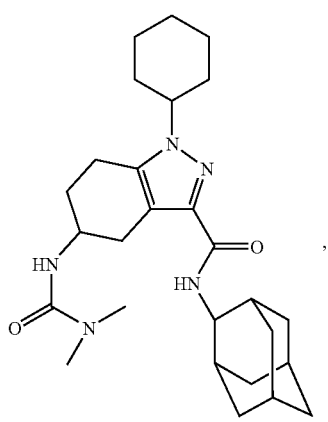
Example 9
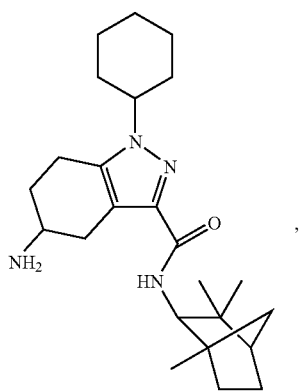
Example 8
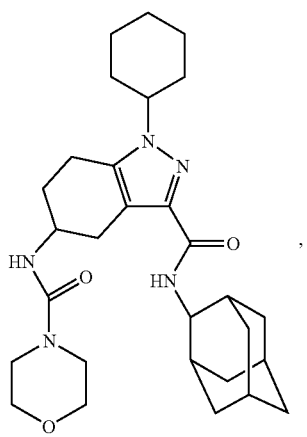
MS 510 MH+
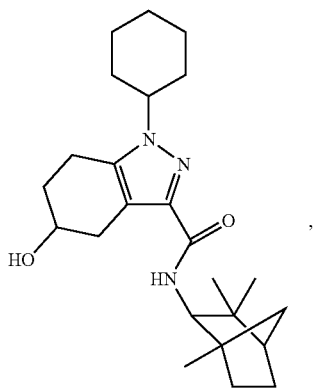
Example 8
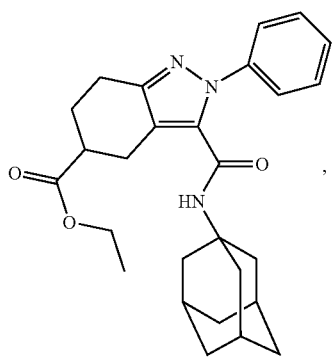
MS 448 MH+
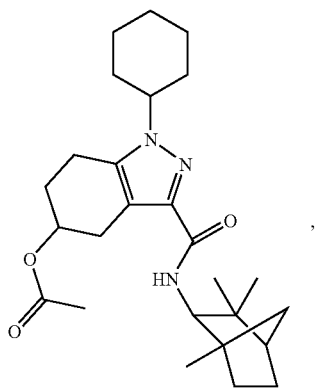
MS 442 MH+

-continued
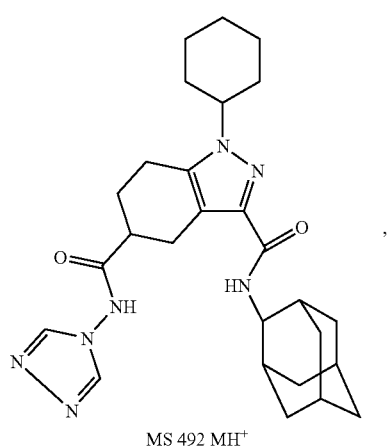
MS 492 MH+
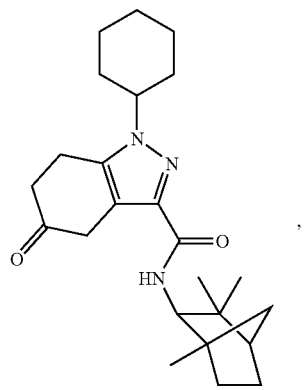
Example 22
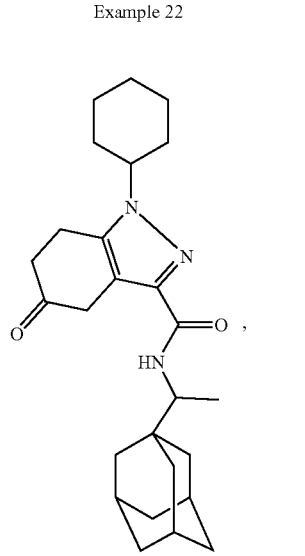
MS 422.2 MH+
-continued
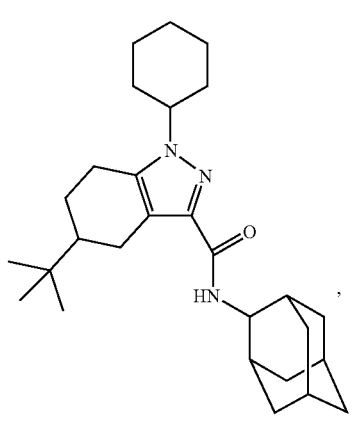
MS 438 MH+
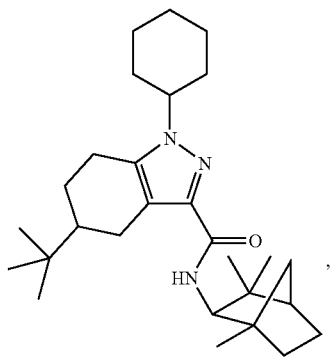
MS 440 MH+
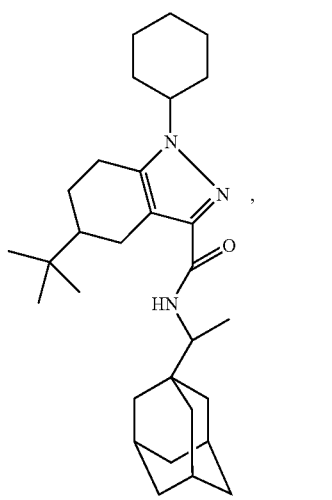
MS 446 MH+

-continued
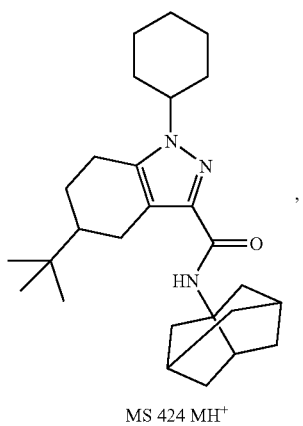
MS 424 MH+
101
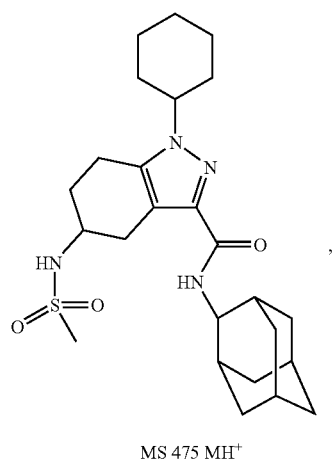
MS 475 MH+
104
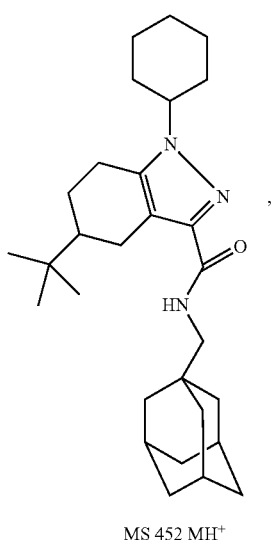
MS 452 MH+
102
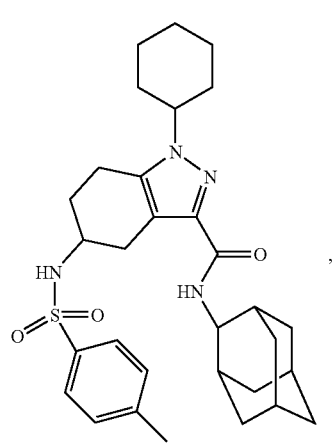
MS 551 MH+
105
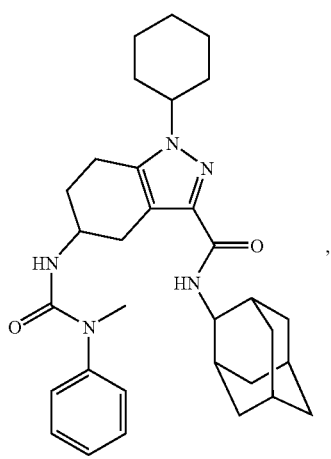
MS 530 MH+
103
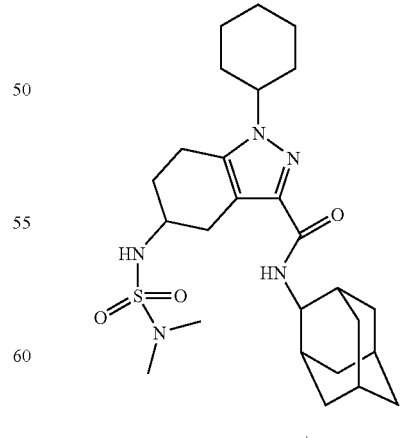
MS 504 MH+
106

-continued
107
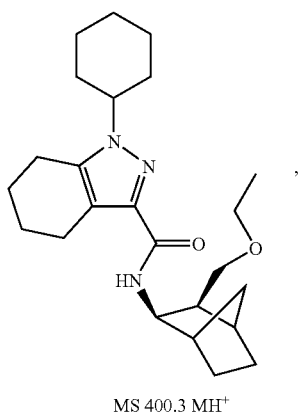
MS 400.3 MH⁺
108
MS 542.2 MH⁺
109
MS 432 MH⁺
-continued
110
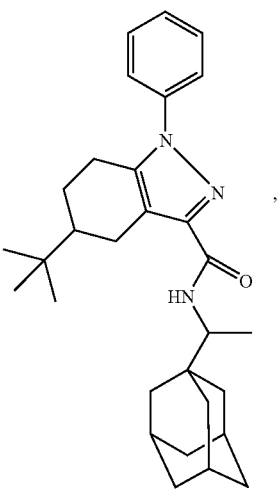
MS 460 MH⁺
111
MS 446 MH⁺
112
MS 446 MH⁺

-continued
113
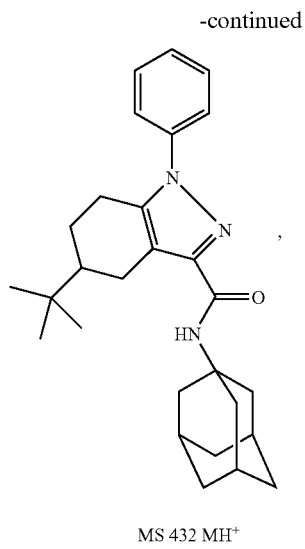
MS 432 MH+
114
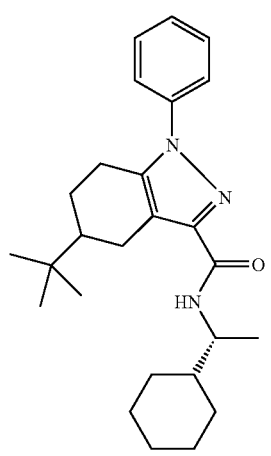
MS 408 MH+
115
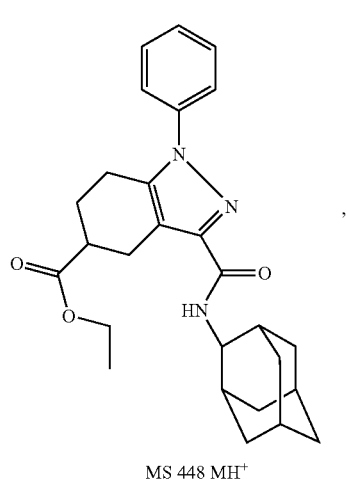
MS 448 MH+
-continued
116
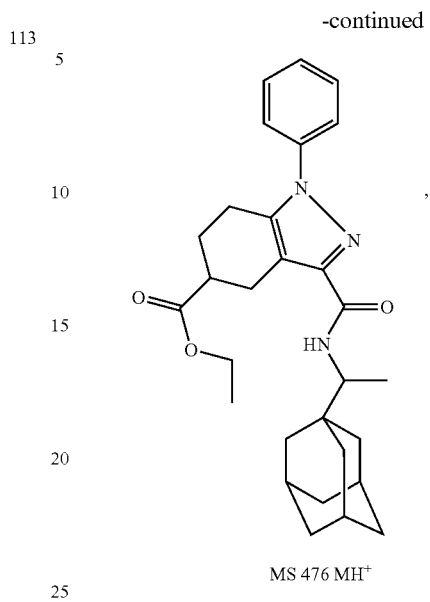
MS 476 MH+
117
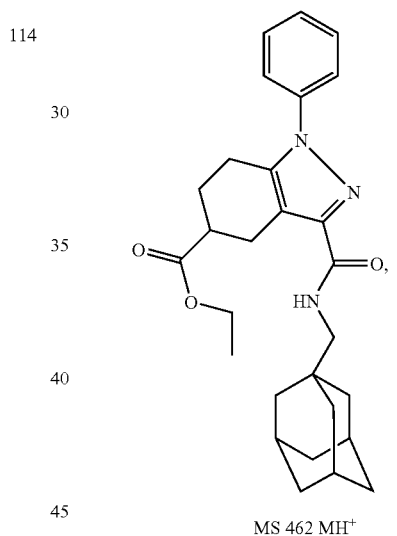
MS 462 MH+
118
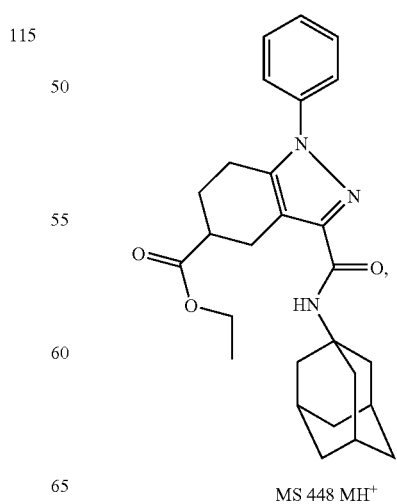
MS 448 MH+

-continued
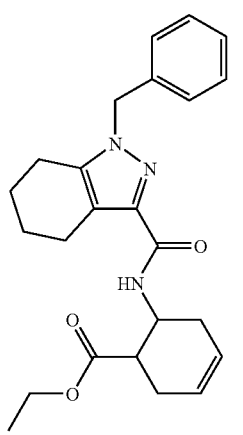
MS 408.1 MH+
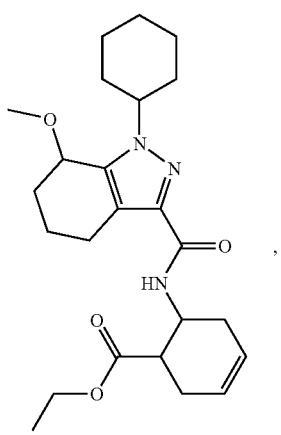
MS 430.1 MH+
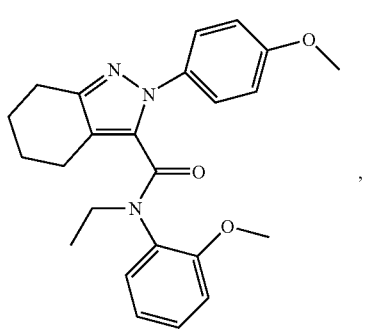
MS 406 MH+
-continued
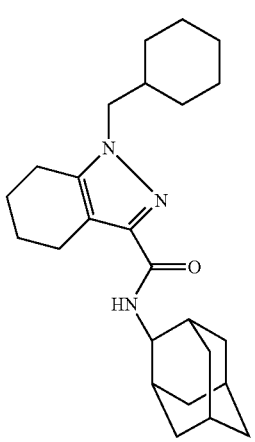
MS 396 MH+
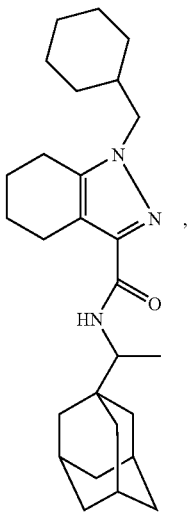
MS 424 MH+
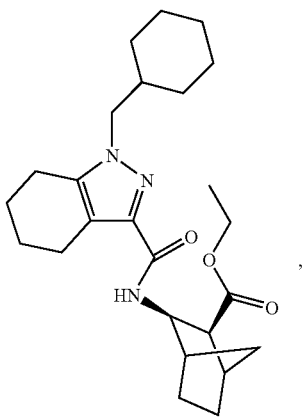
MS 428 MH+

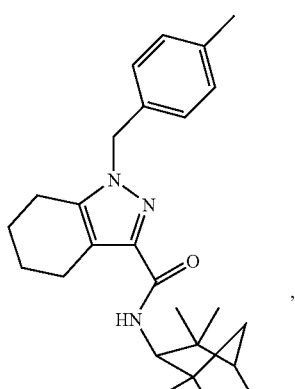
MS 406 MH+
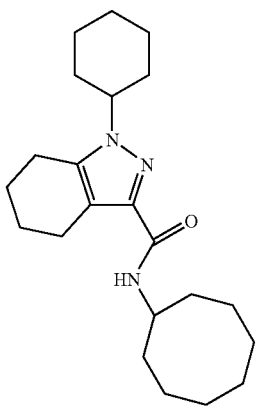
MS 358 MH+
125
128
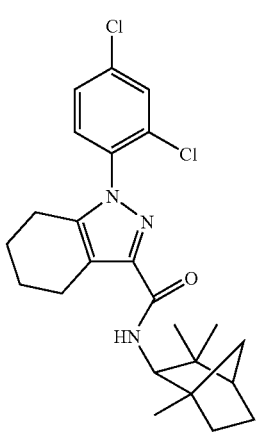
MS 436 MH+
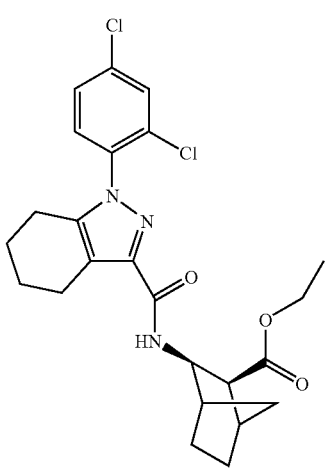
MS 446 MH+
126
129
MS 366 MH+
MS 476 MH+
127
130

-continued
131
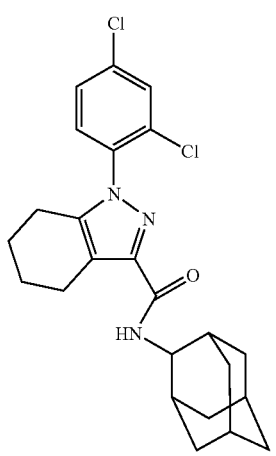
MS 444.1 MH+
132
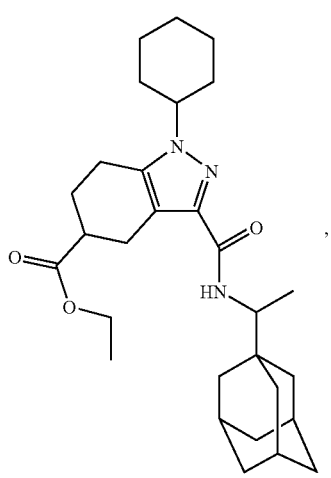
MS 482 MH+
133
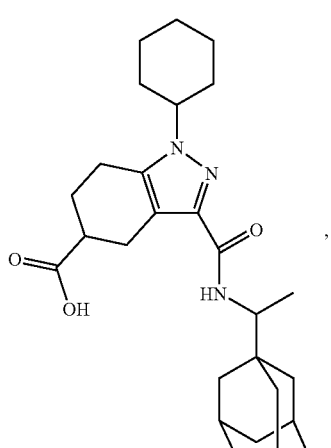
MS 454 MH+
-continued
134
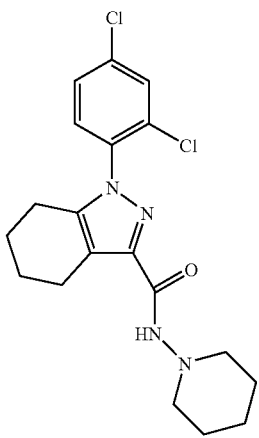
MS 407 MH+
135
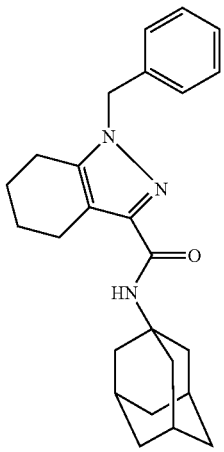
MS 404.2 MH+
136
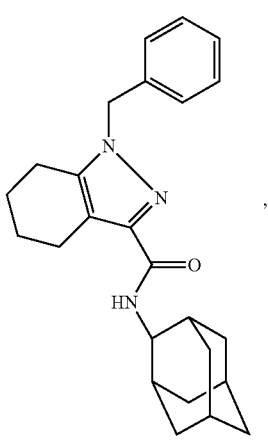
MS 390 MH+

137
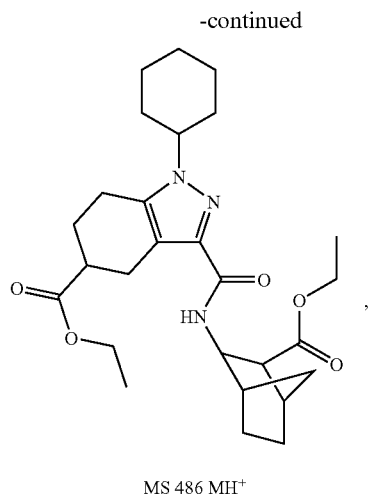
MS 486 MH+
138
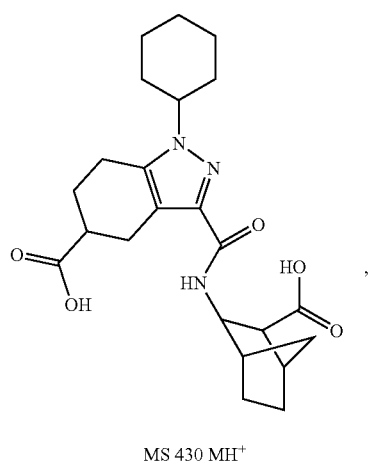
MS 430 MH+
139
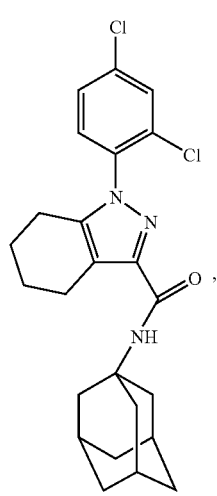
MS 444.1 MH+
140
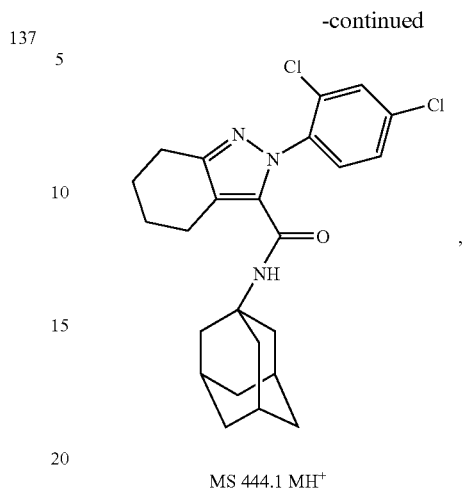
MS 444.1 MH+
141
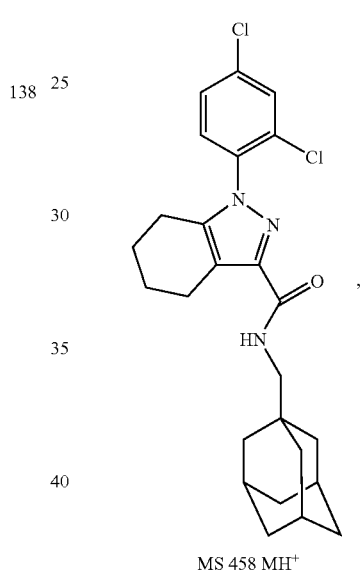
MS 458 MH+
142
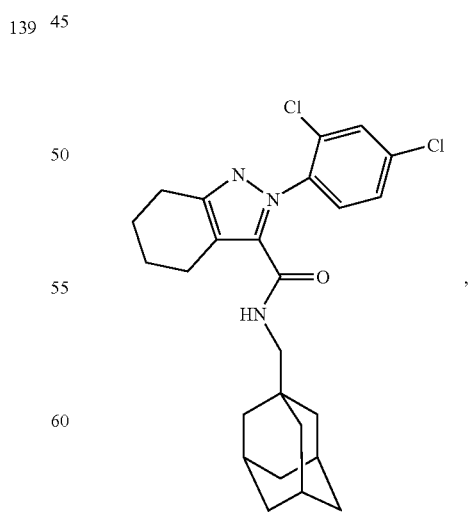
MS 458.1 MH+

-continued
143
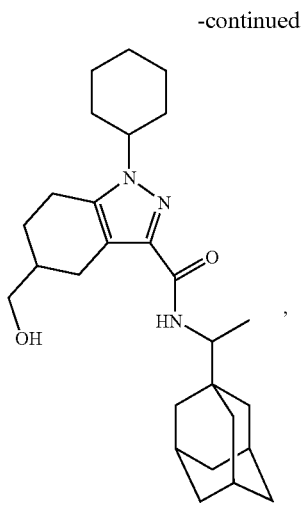
Example 19
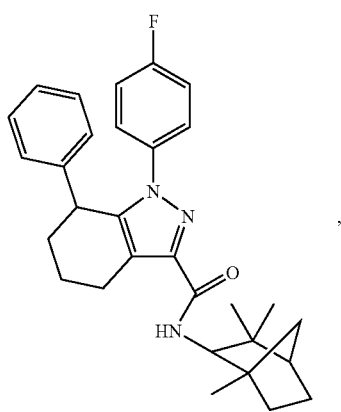
MS 472.1 MH+
145
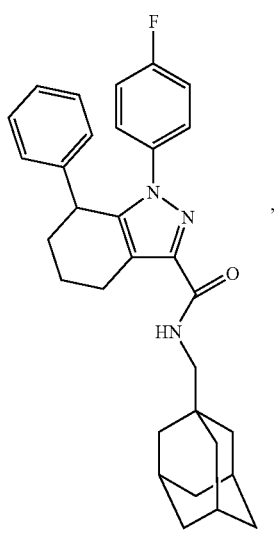
MS 484.1 MH+
-continued
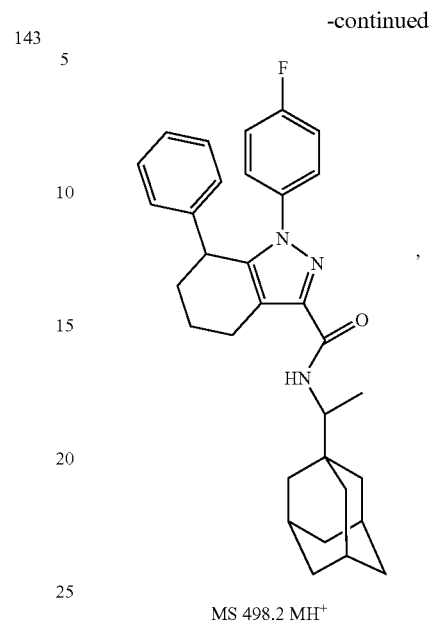
MS 498.2 MH+
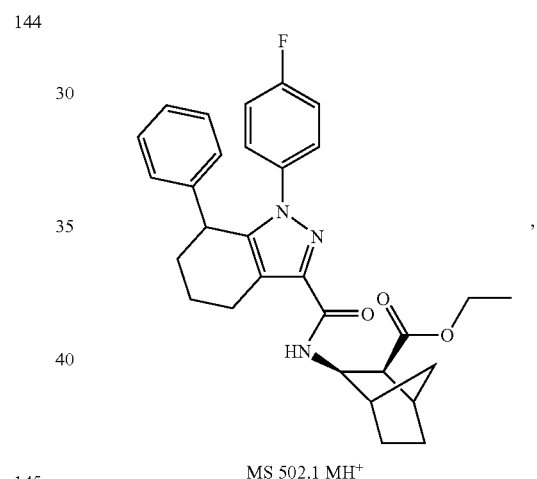
MS 502.1 MH+
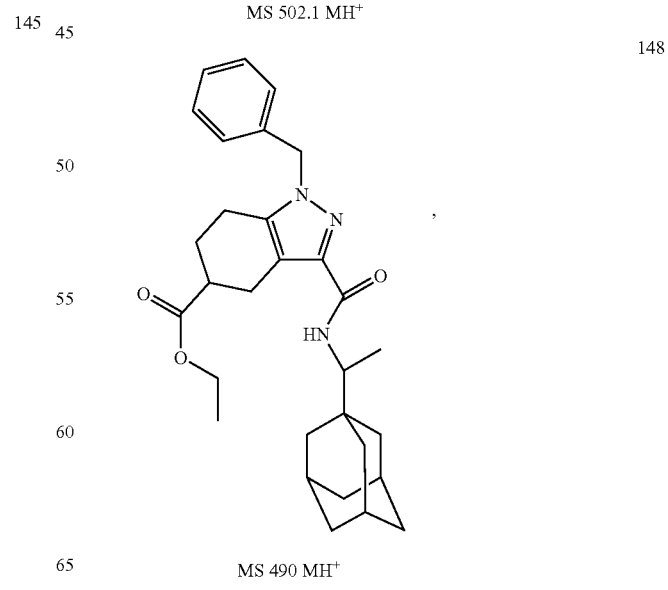
MS 490 MH+

149
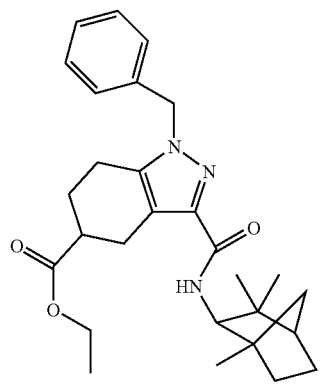
MS 464 MH+
150
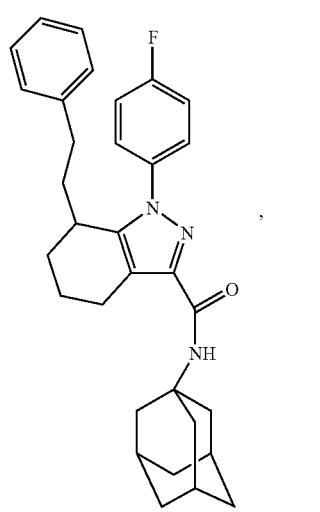
MS 498.2 MH+
151
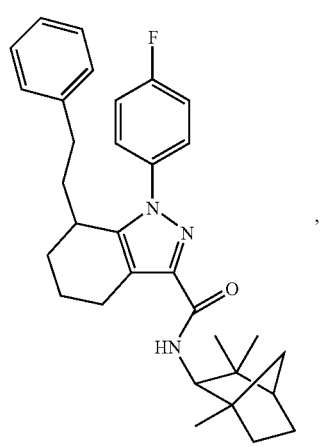
MS 500.2 MH+
152
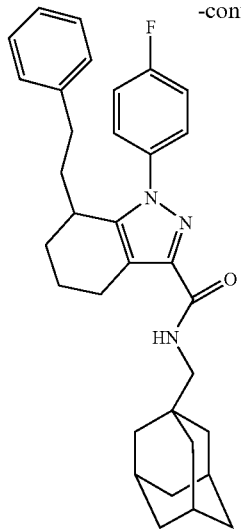
MS 512.2 MH+
153
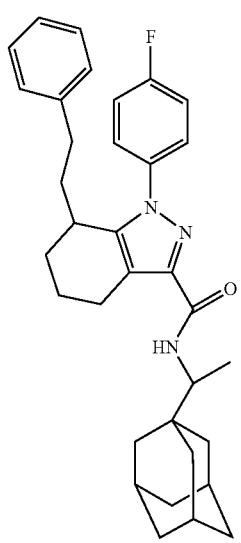
MS 526.3 MH+
154
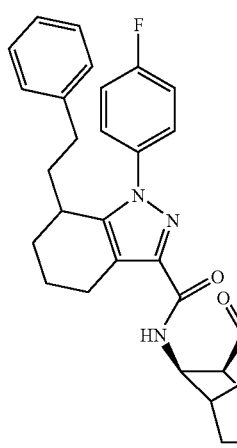
MS 530.2 MH+

155
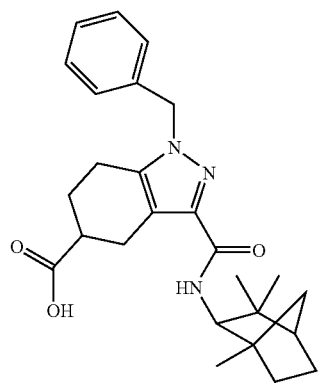
MS 436 MH+
156
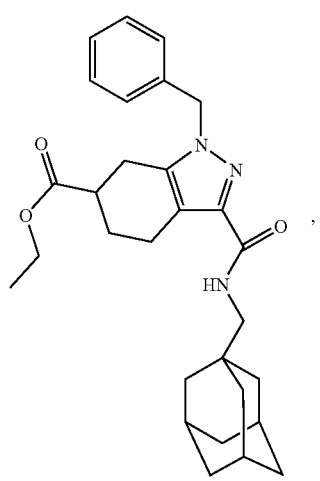
MS 476 MH+
157
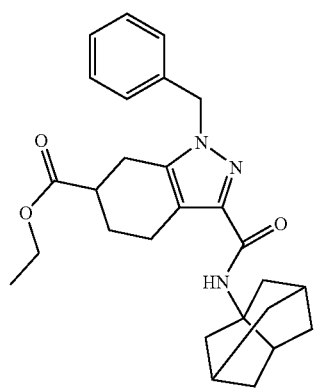
MS 448 MH+
158
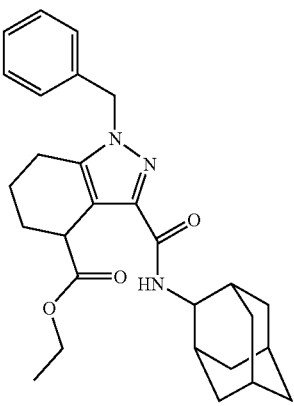
MS 462.3 MH+
162
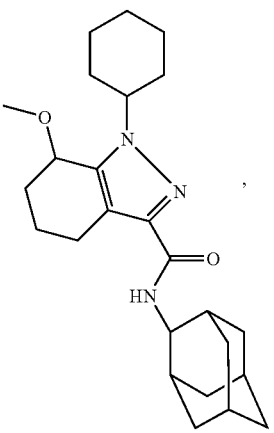
MS 412 MH+
163
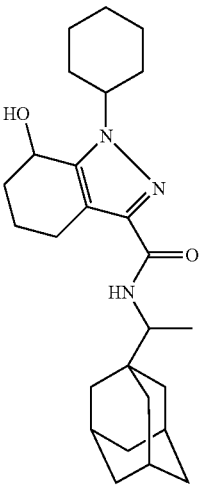
MS 425.8 MH+

-continued
164
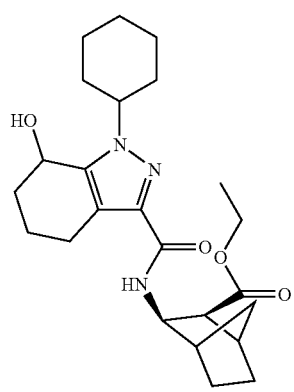
Example 24
165
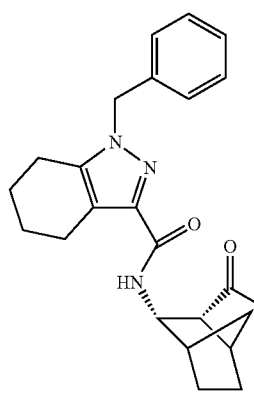
MS 470.2 MH+
166
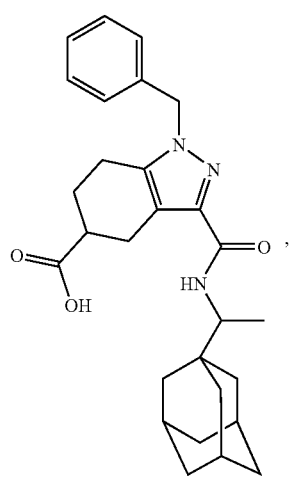
MS 462 MH+
-continued
167
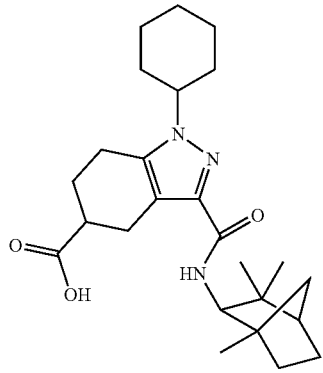
MS 421 MH+
168
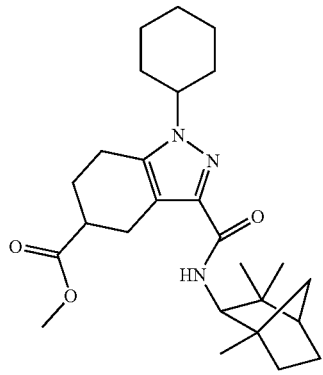
MS 428 MH+
169
MS 422 MH+

170 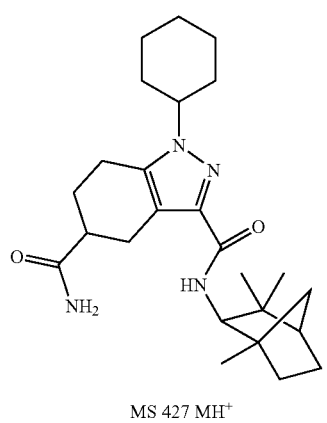
MS 427 MH+
171 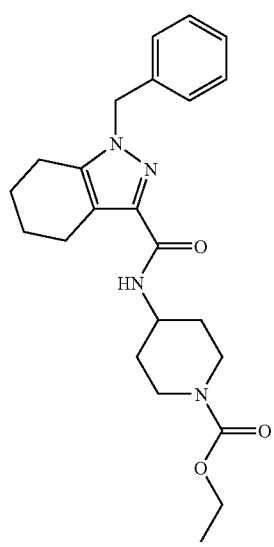
MS 411 MH+
172 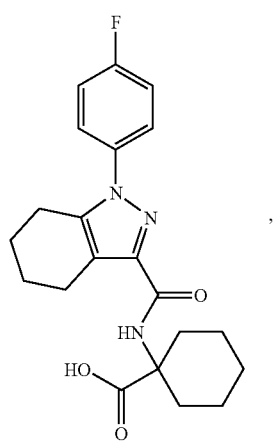
MS 386.2 MH+
173 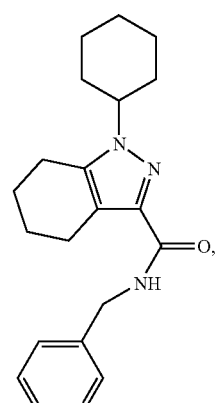
MS 339 MH+
174 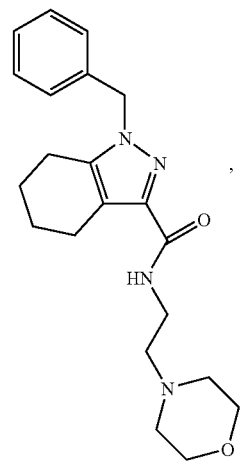
MS 369 MH+
175 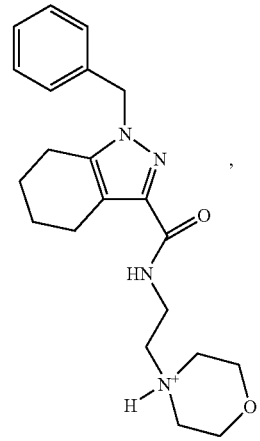
MS 370 MH+

-continued
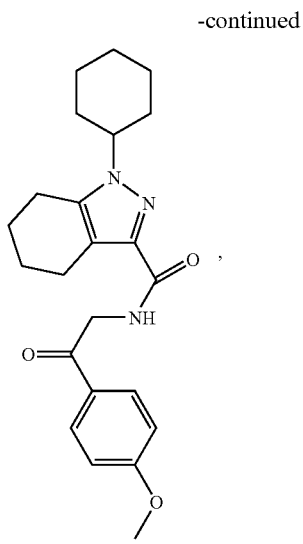
Example 4
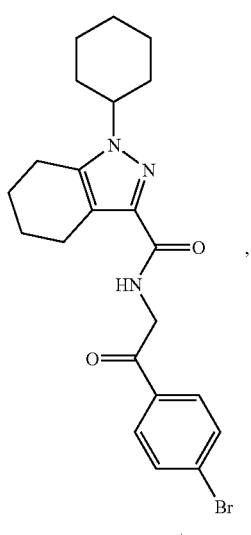
MS 445 MH+
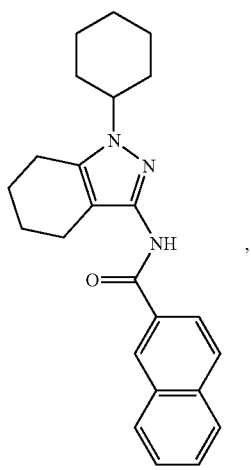
Example 6
-continued
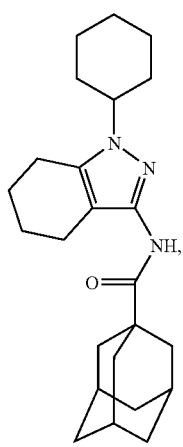
MS 382 MH+
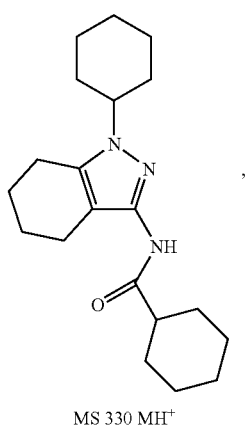
MS 330 MH+
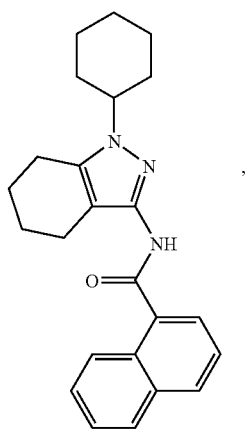
MS 374 MH+

-continued
182
Example 27
183
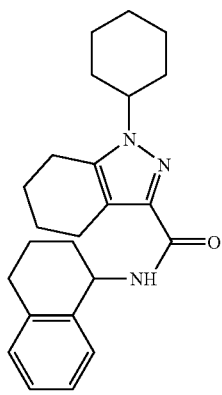
MS 378 MH+
184
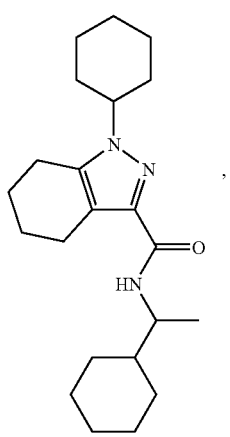
MS 358 MH+
-continued
185
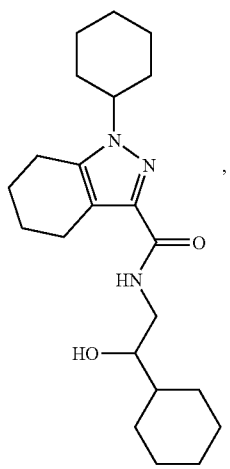
MS 374 MH+
186
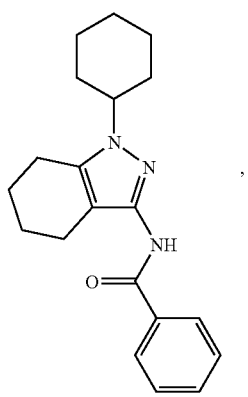
MS 324 MH+
187
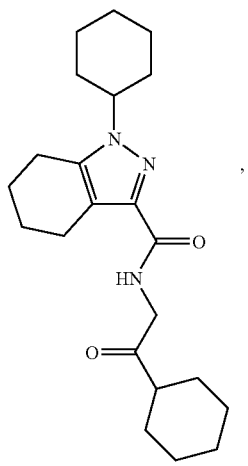
MS 372 MH+

-continued
188
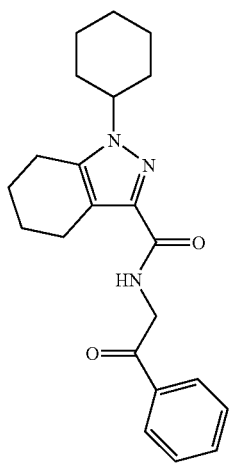
MS 366 MH+
189
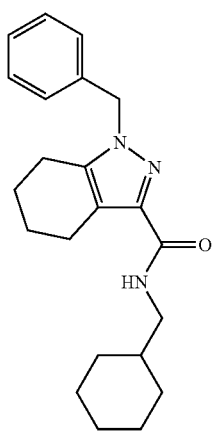
MS 352 MH+
190
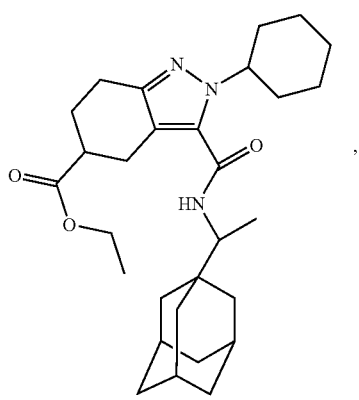
MS 482 MH+
-continued
191
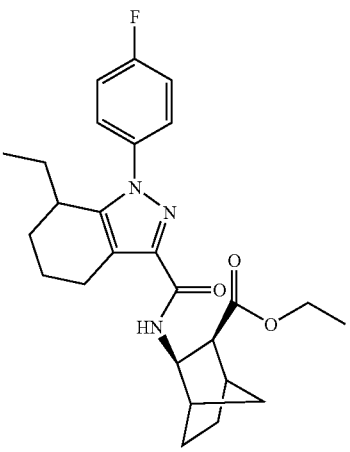
MS 454 MH+
192
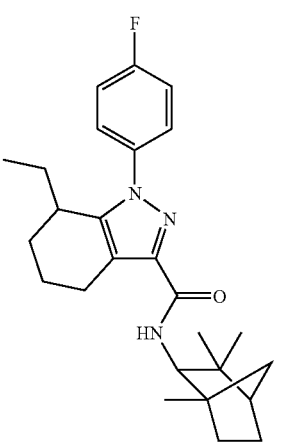
MS 424 MH+
193
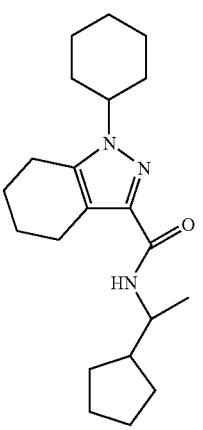
MS 344 MH+

| | |
|---|---|
| 194 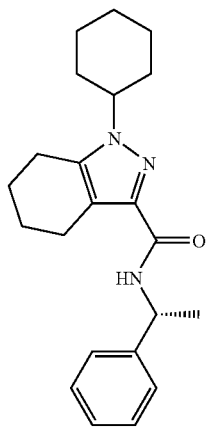<br>MS 352 MH+ | 197 |
| 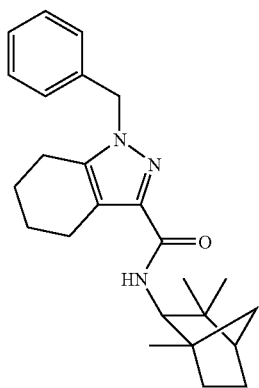<br>Example 2 | |
| 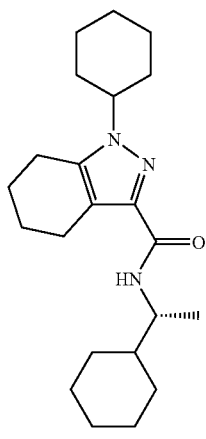<br>MS 358 MH+ | 195 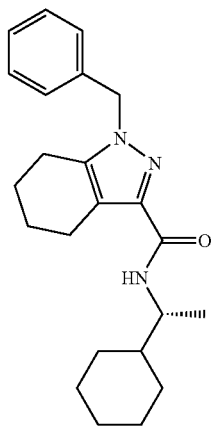<br>MS 366 MH+ | 198 |
| 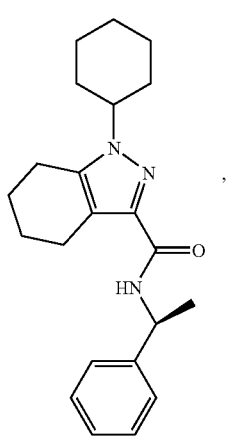<br>MS 352 MH+ | 196 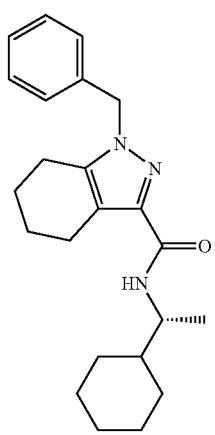<br>MS 360 MH+ | 199 |

-continued
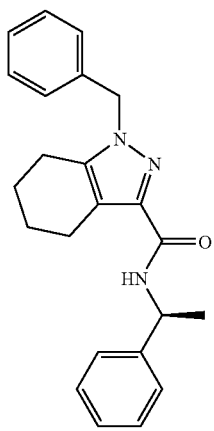
MS 360 MH+
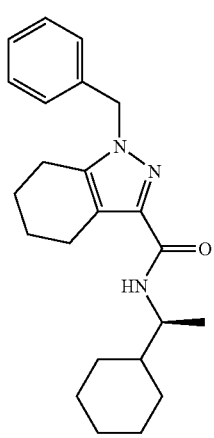
MS 366 MH+
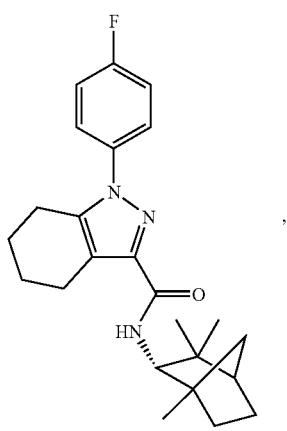
MS 396 MH+
-continued
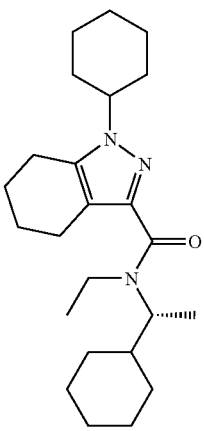
200
MS 386 MH+
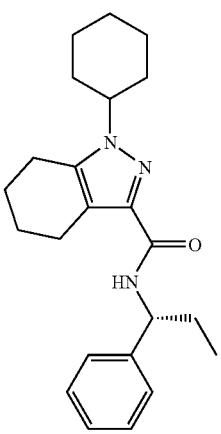
201
MS 366 MH+
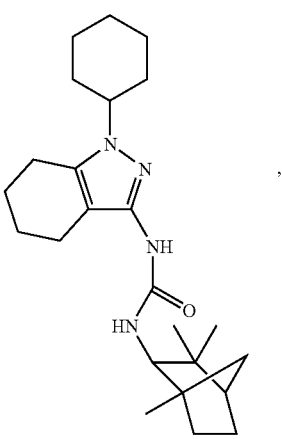
202
MS 399 MH+
203
204
205

-continued
| | |
|---|---|
| 206 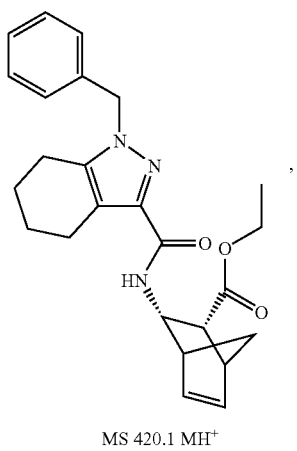<br>MS 420.1 MH+ | 209 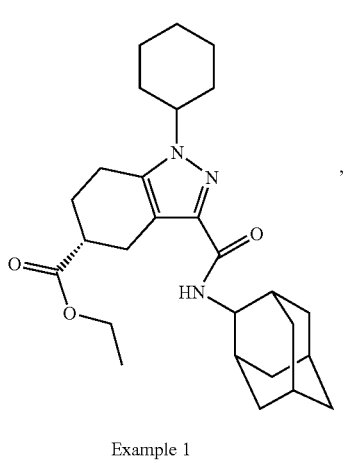<br>Example 1 |
| 207 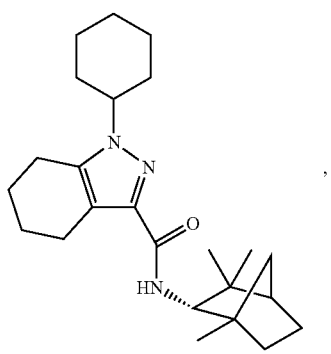<br>MS 384.1 MH+ | 210 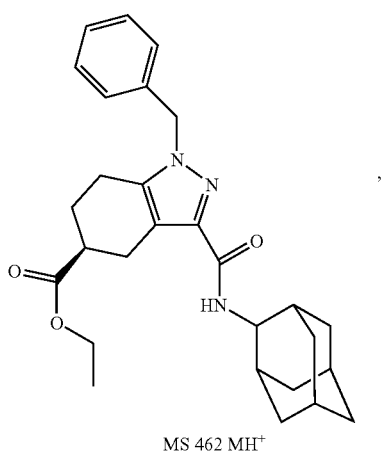<br>MS 462 MH+ |
| 208 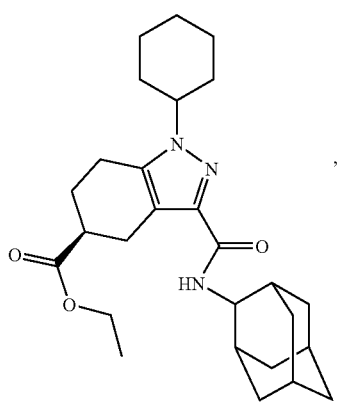<br>Example 1 | 211 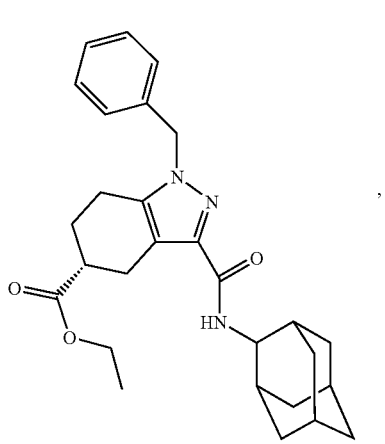<br>MS 462 MH+ |

-continued
212
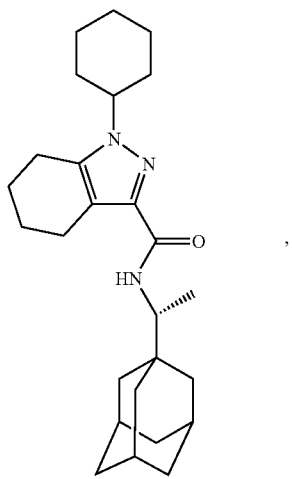
MS 410 MH+
213
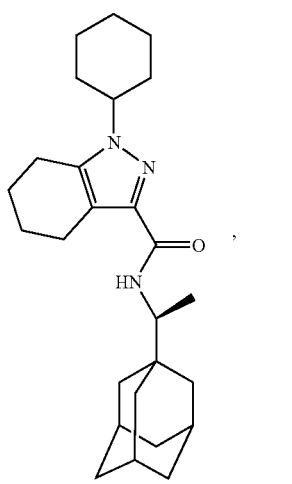
MS 410 MH+
214
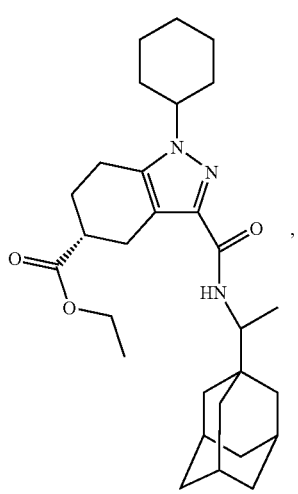
MS 482 MH+
-continued
215
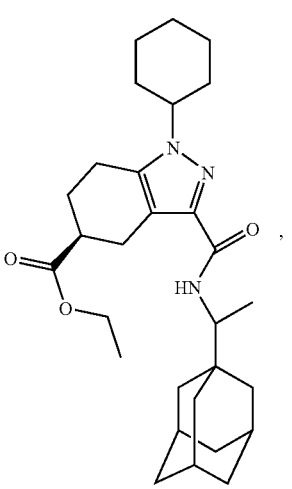
MS 482 MH+
216
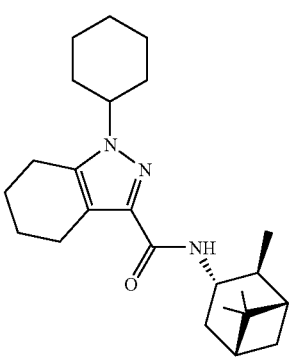
217
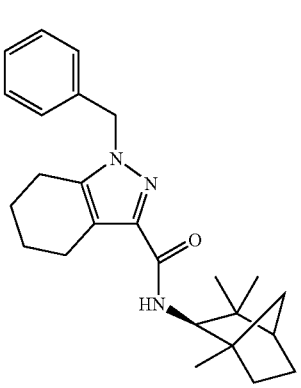
MS 392 MH+

-continued
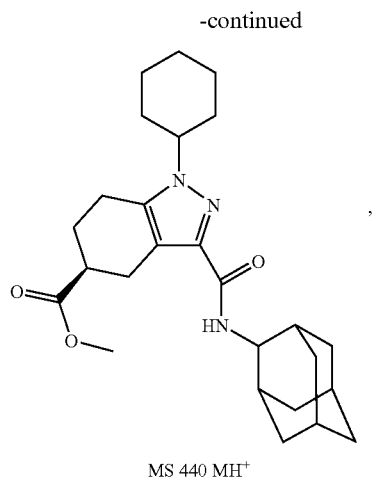
MS 440 MH+
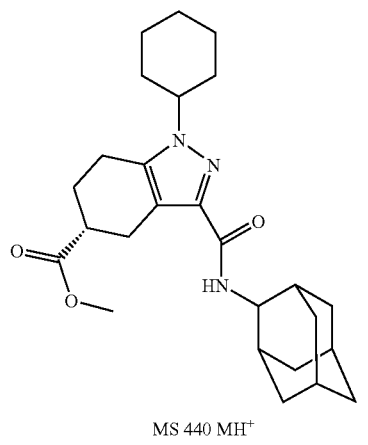
MS 440 MH+
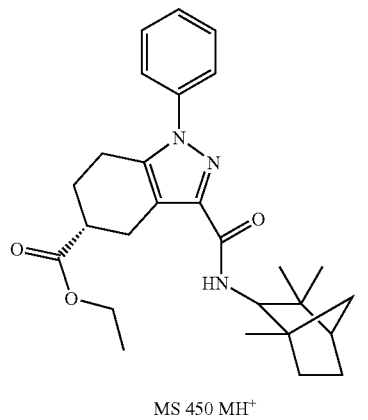
MS 450 MH+
-continued
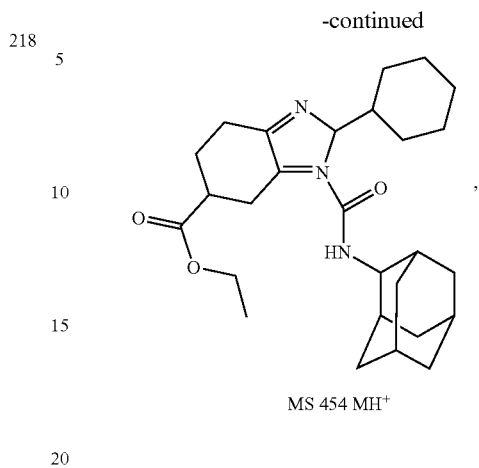
MS 454 MH+
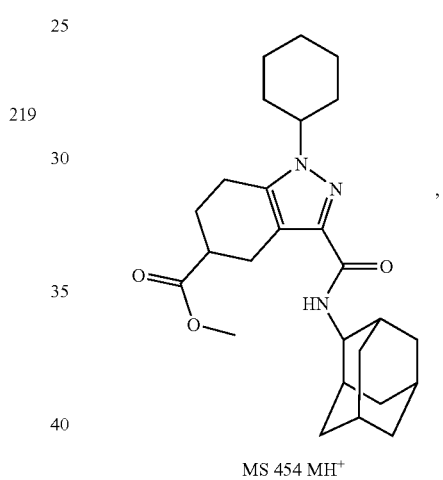
MS 454 MH+
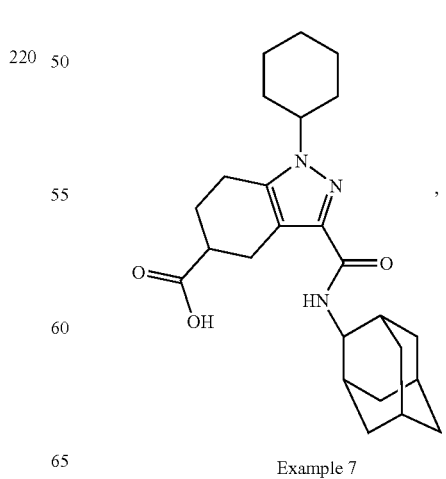
Example 7

-continued
224
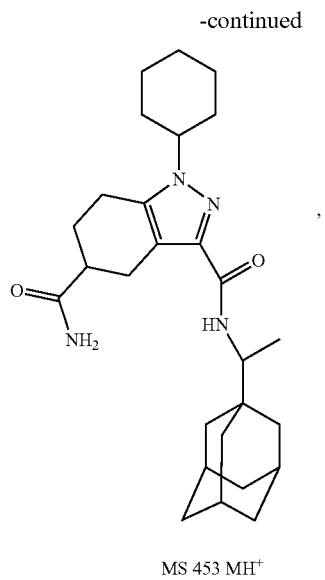
MS 453 MH+
225
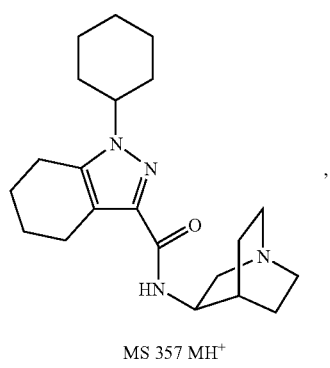
MS 357 MH+
226
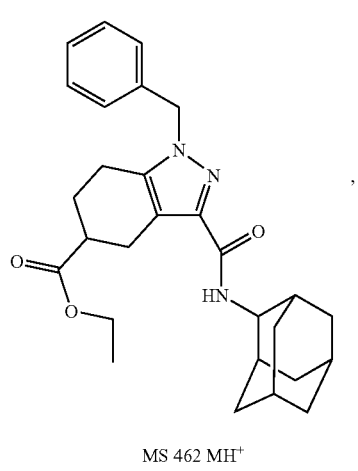
MS 462 MH+
-continued
227
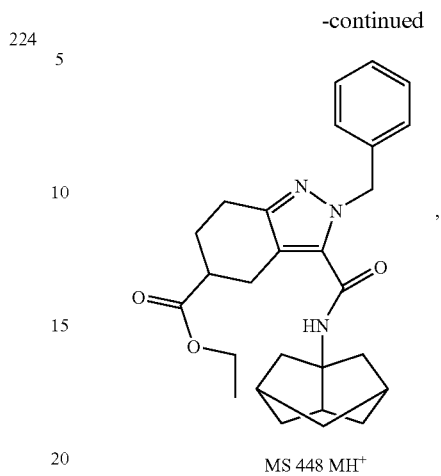
MS 448 MH+
228
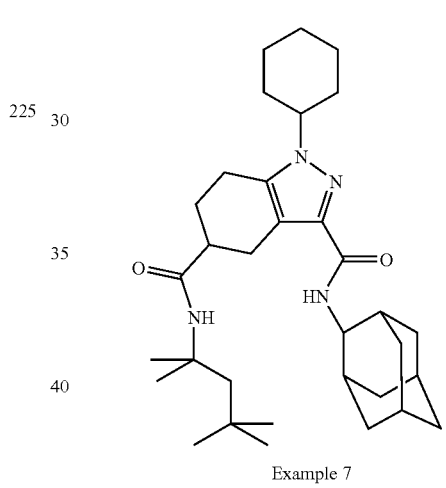
Example 7
229
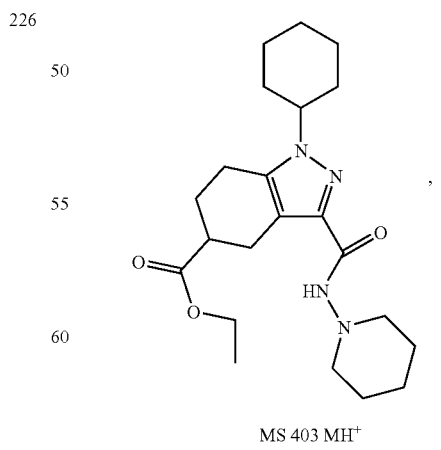
MS 403 MH+

-continued
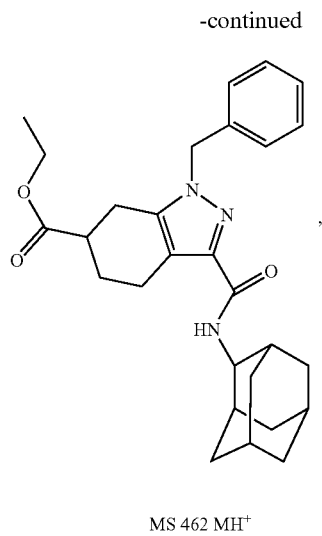
MS 462 MH+
230
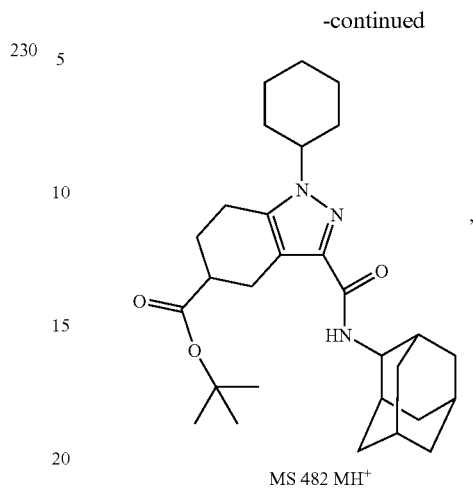
MS 482 MH+
233
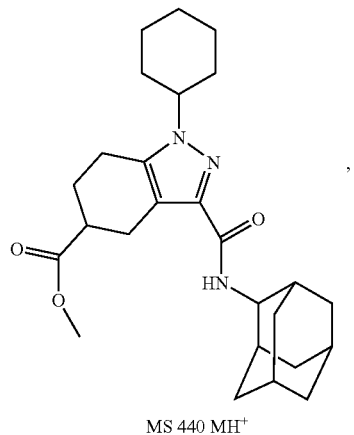
MS 440 MH+
231
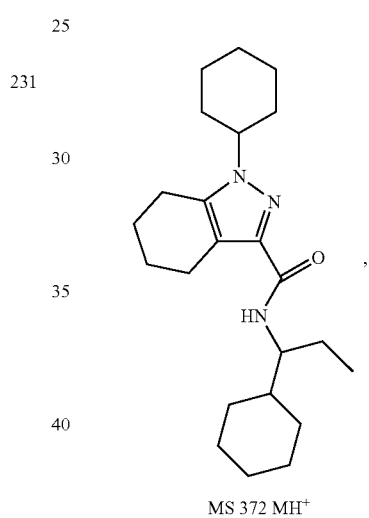
MS 372 MH+
234
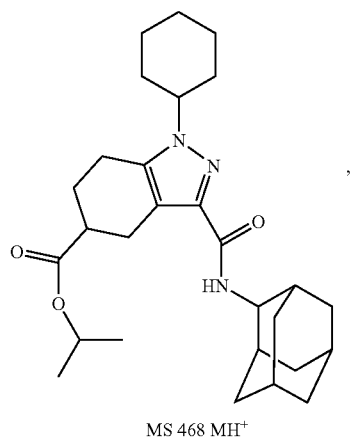
MS 468 MH+
232
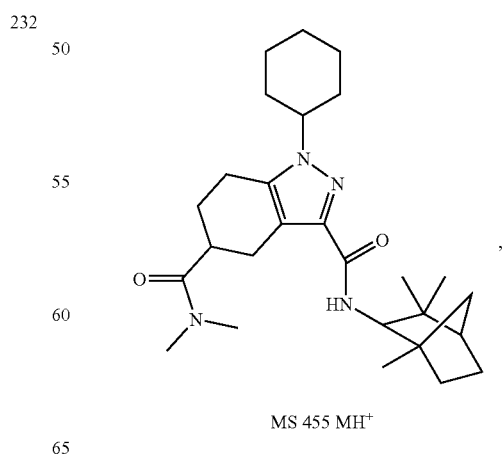
MS 455 MH+
235

-continued
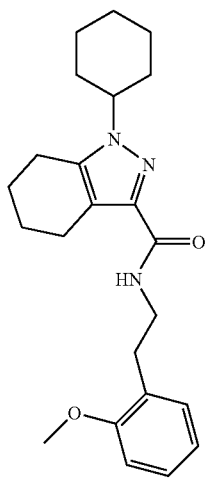
MS 382 MH⁺
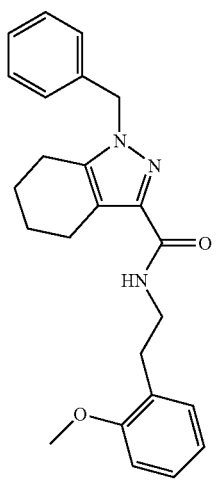
MS 390 MH⁺
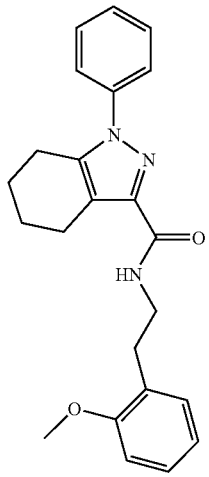
MS 376 MH⁺
-continued
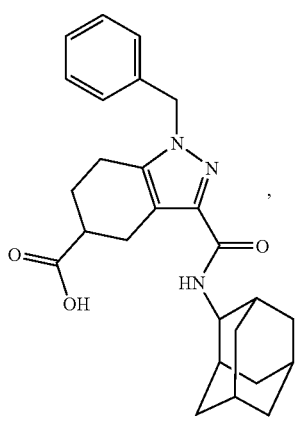
MS 434 MH⁺
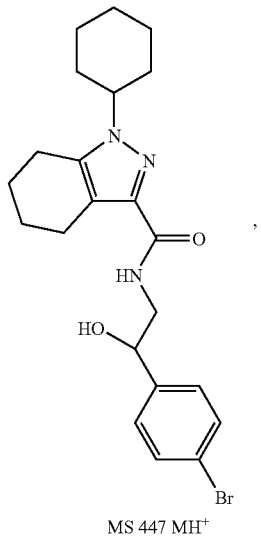
MS 447 MH⁺
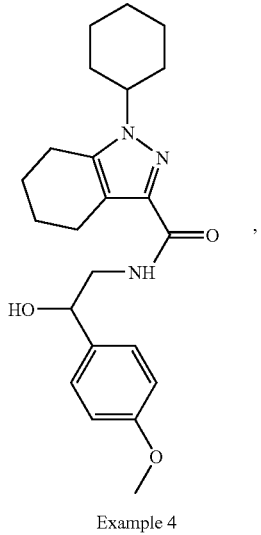
Example 4

-continued
242
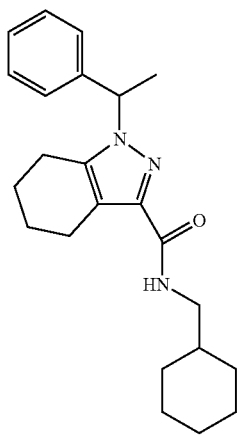
MS 366 MH+
243
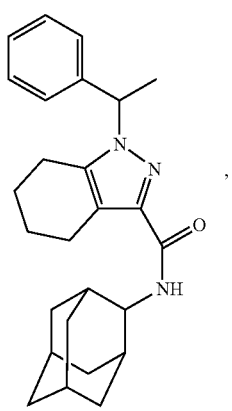
MS 404 MH+
244
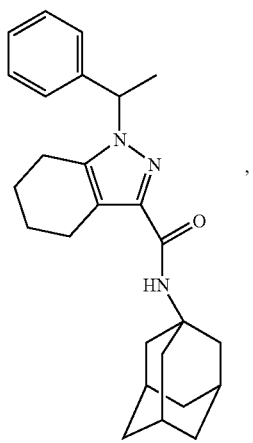
MS 404 MH+
-continued
245
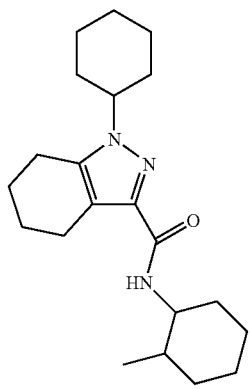
MS 344 MH+
246
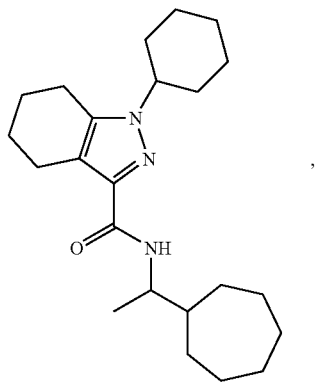
MS 372 MH+
247
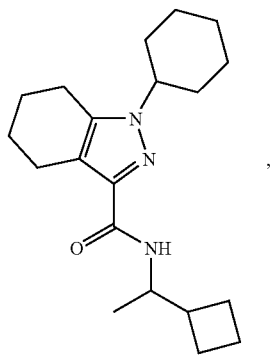
MS 330 MH+

248 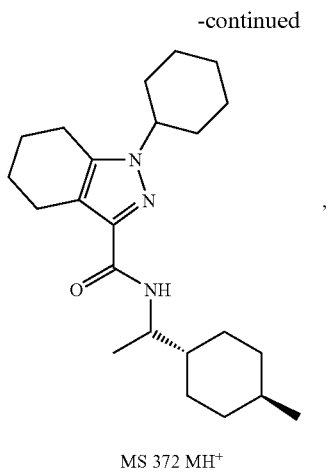
MS 372 MH+
251 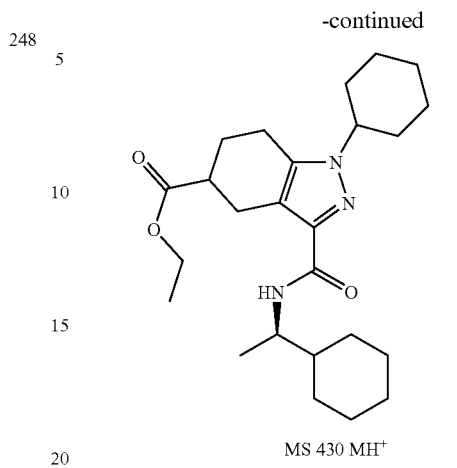
MS 430 MH+
249 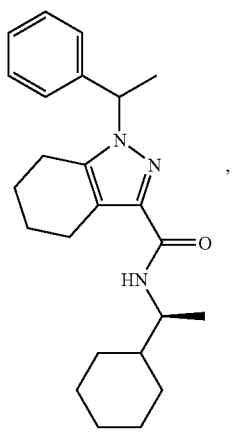
Example 3
252 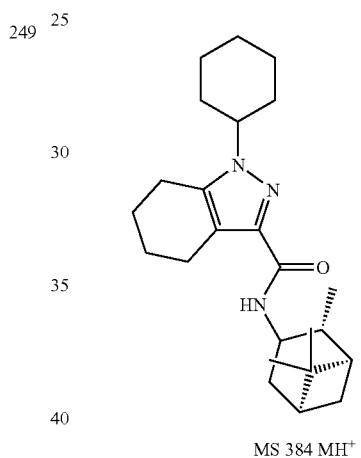
MS 384 MH+
250 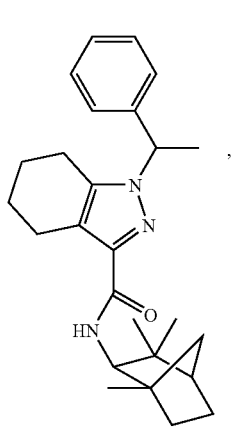
MS 406 MH+
253 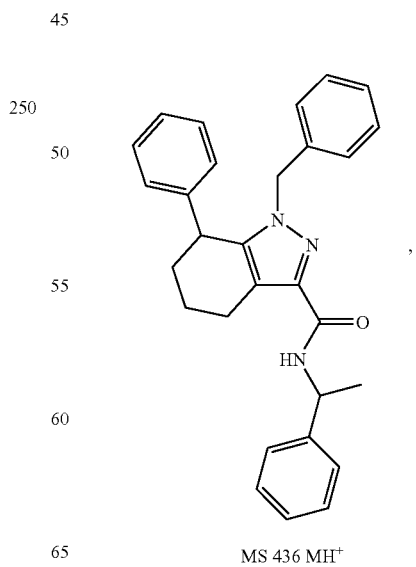
MS 436 MH+

-continued
254
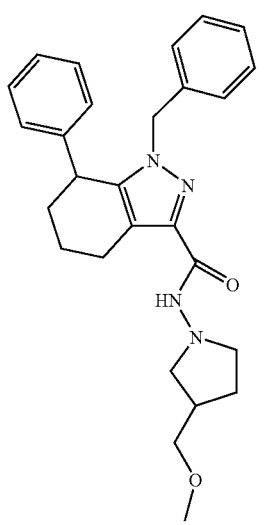
MS 445 MH+
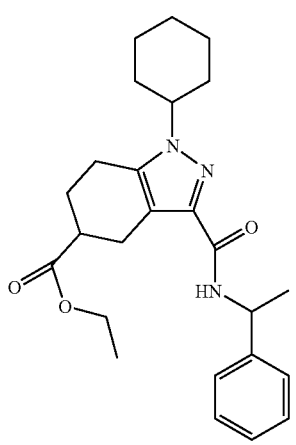
MS 424 MH+
255
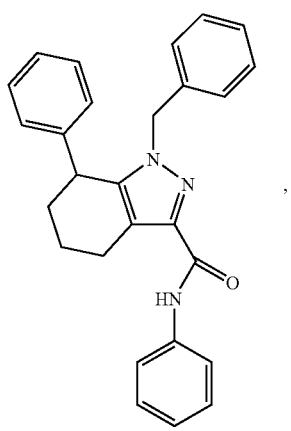
MS 408 MH+
256
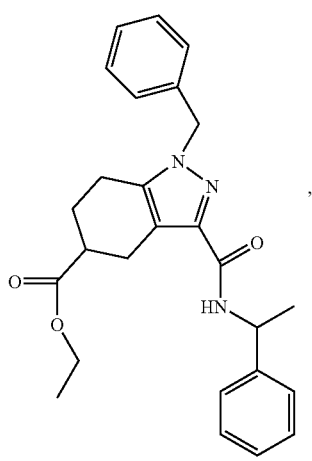
MS 432 MH+
257
258
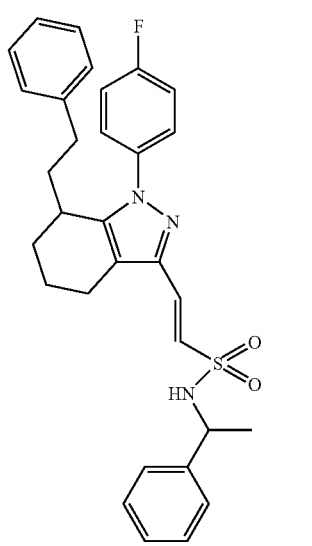
Example 20

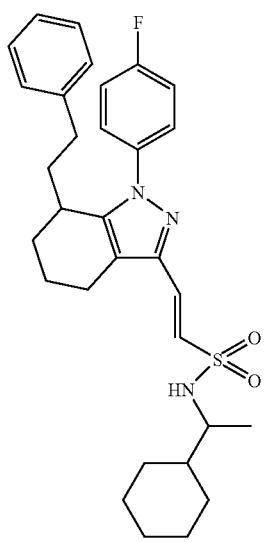
Example 20
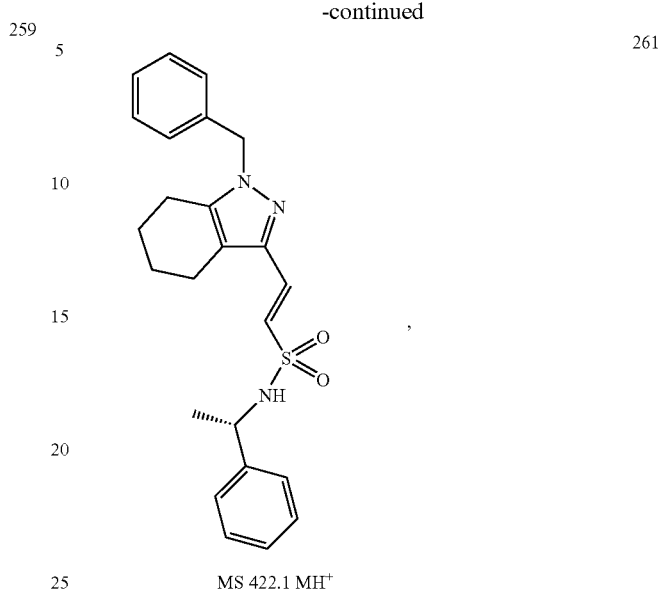
MS 422.1 MH+
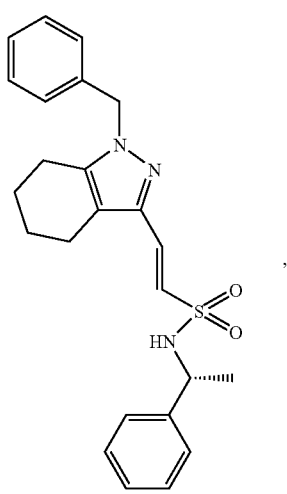
Example 11
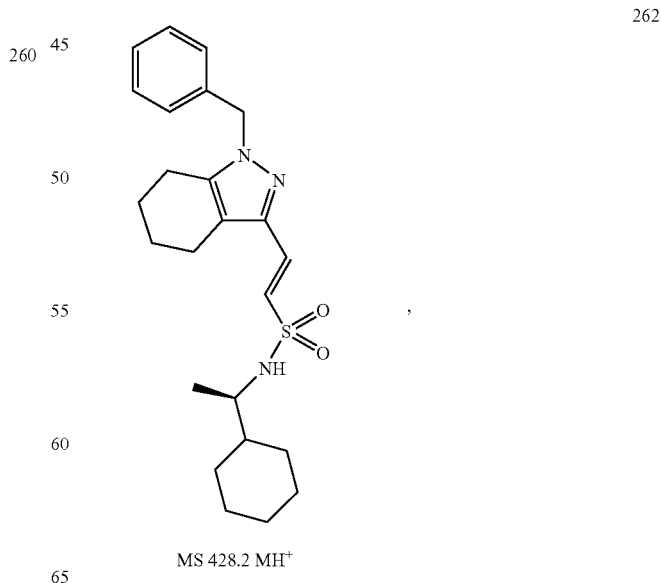
MS 428.2 MH+

-continued
263
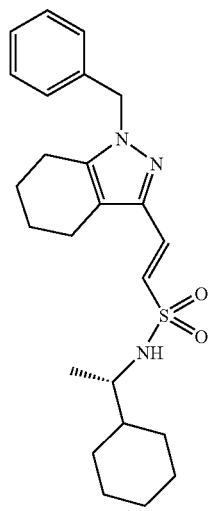
MS 428.1 MH+
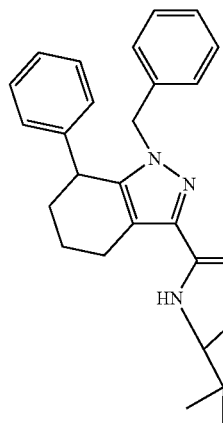
MS 468 MH+
264
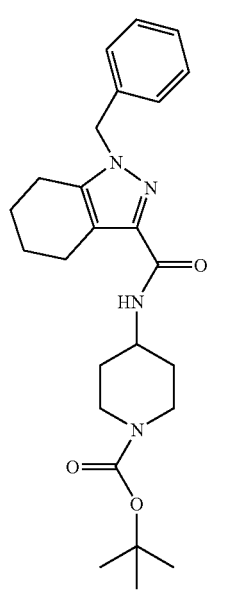
MS 439 MH+
265
266
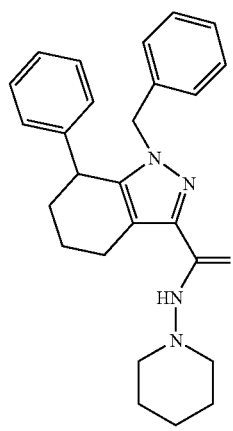
MS 415 MH+

-continued
267 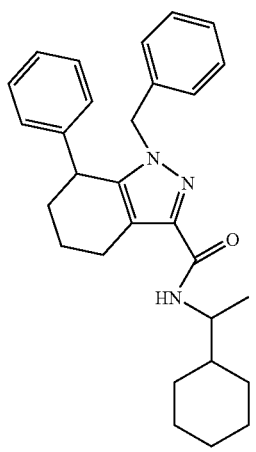
MS 442 MH+
268 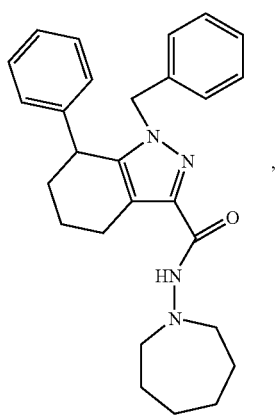
MS 429 MH+
269 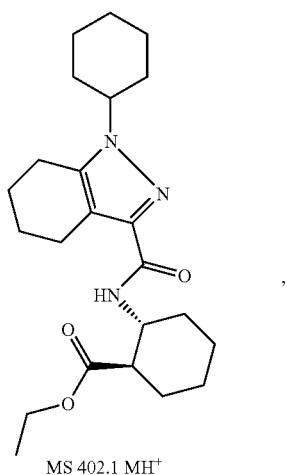
MS 402.1 MH+
-continued
270 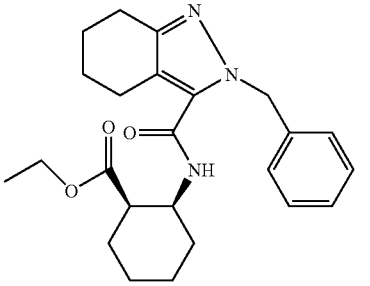
MS 410 MH+
271 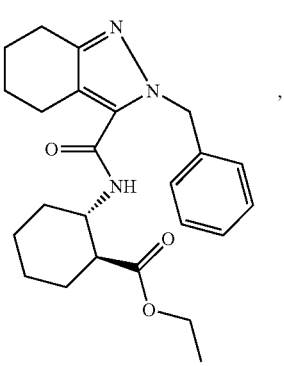
MS 410 MH+
272 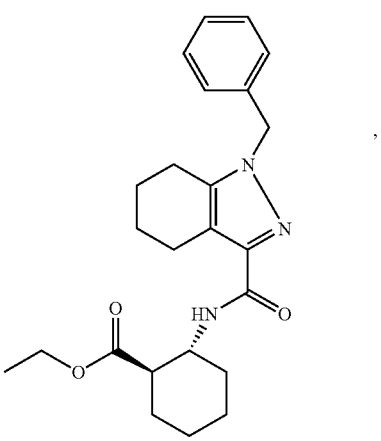
MS 410 MH+

-continued
273
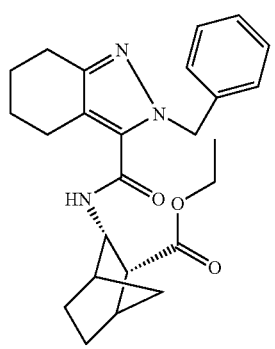
MS 422 MH+
274
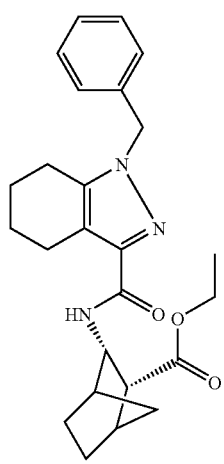
MS 422 MH+
-continued
276
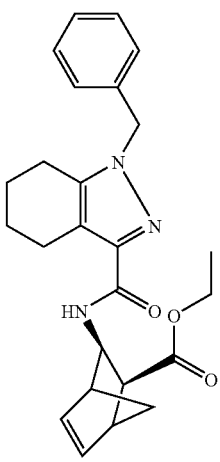
MS 420 MH+
277
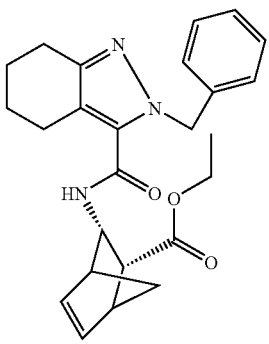
MS 420.1 MH+
275
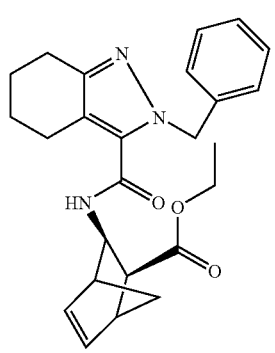
MS 420 MH+
278
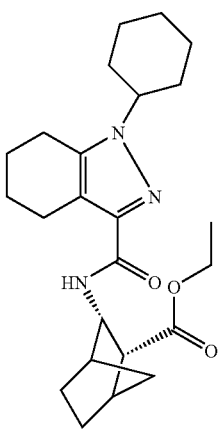
MS 414.2 MH+

-continued
279
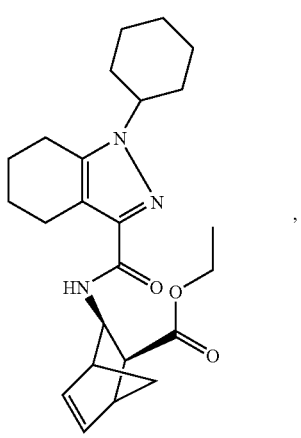
MS 412 MH+
280
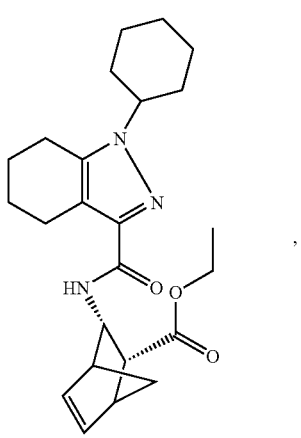
MS 412.1 MH+
281
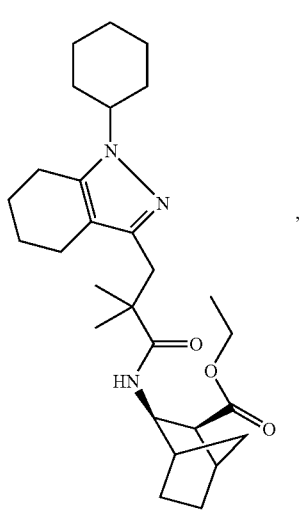
MS 470.1 MH+
-continued
282
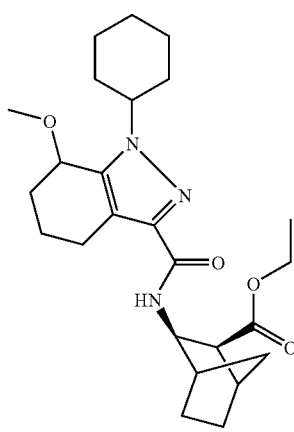
MS 444 MH+
283
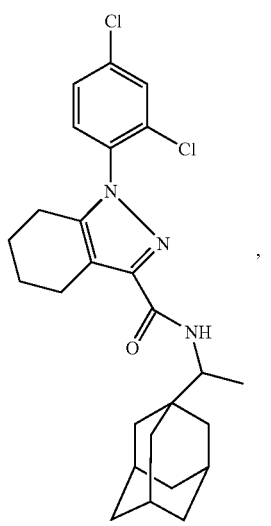
MS 472.1 MH+

-continued
284
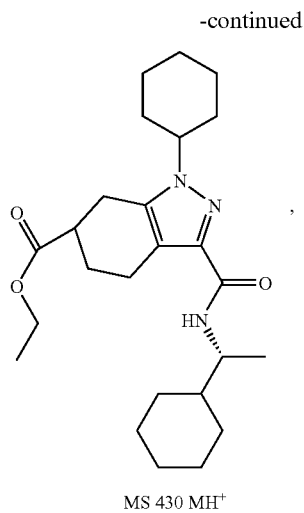
MS 430 MH+
285
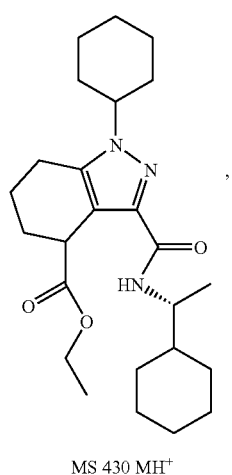
MS 430 MH+
286
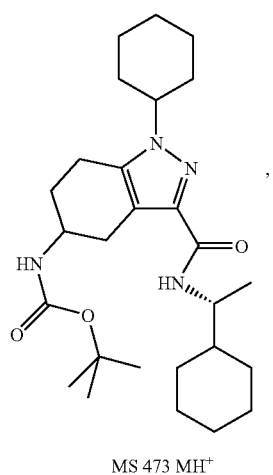
MS 473 MH+
-continued
287
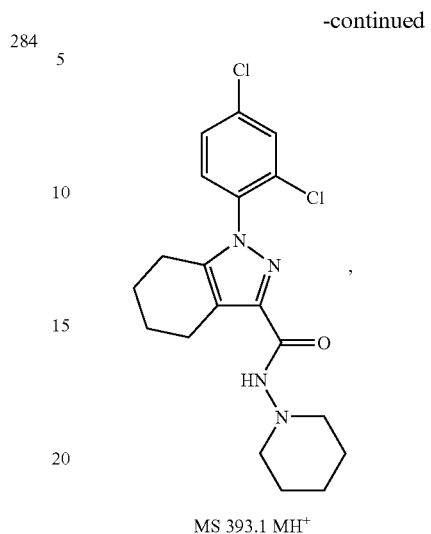
MS 393.1 MH+
288
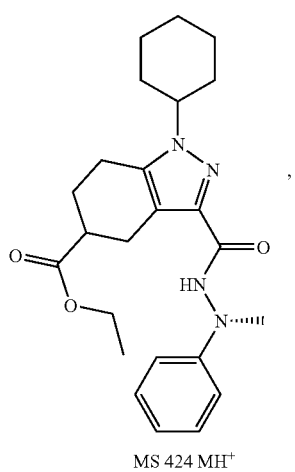
MS 424 MH+
289
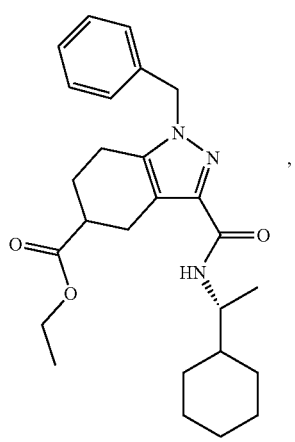
MS 438 MH+

-continued
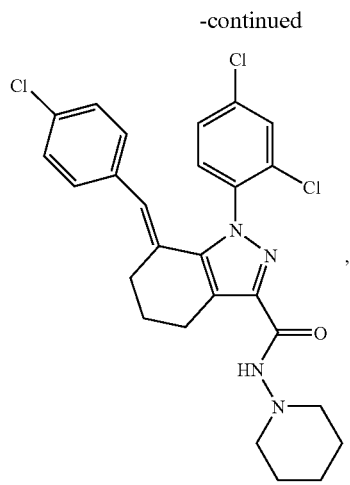
290
MS 515 MH+
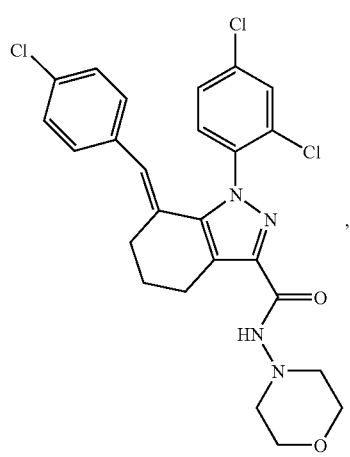
291
MS 517 MH+
-continued
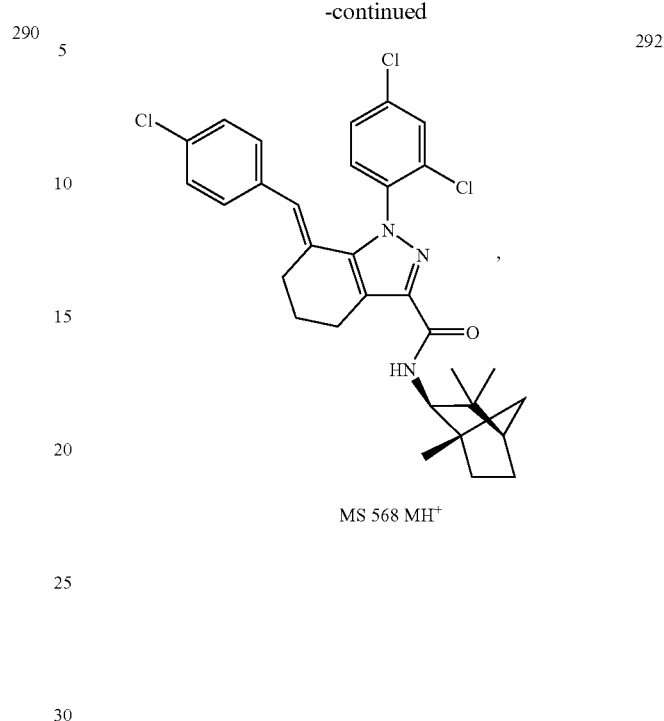
292
MS 568 MH+
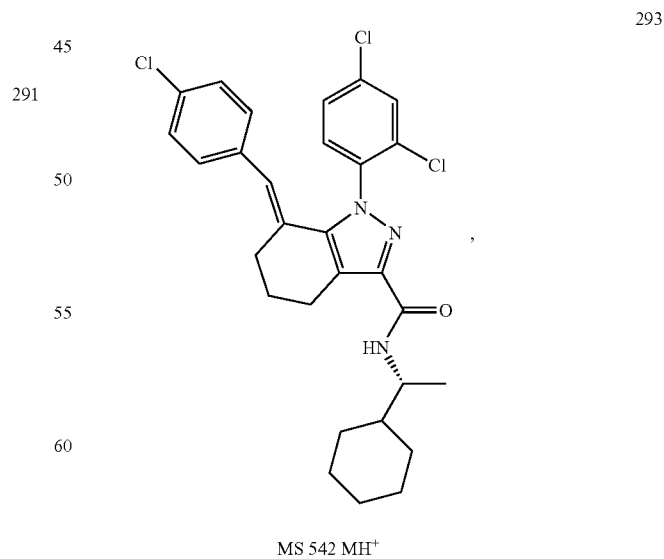
293
MS 542 MH+

-continued
294 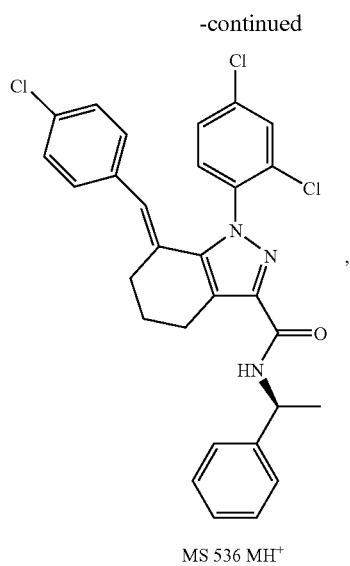
MS 536 MH+
295 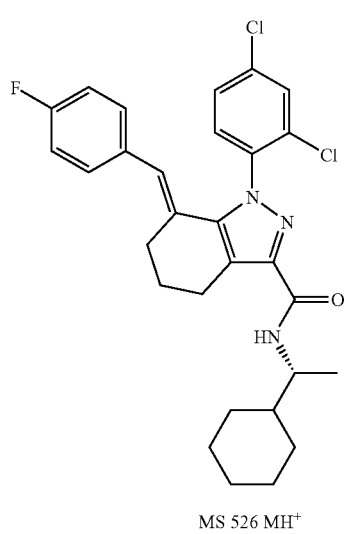
MS 526 MH+
296 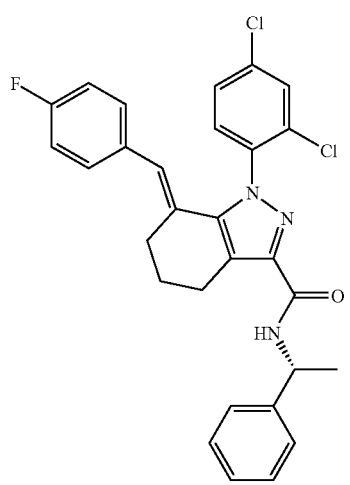
MS 520 MH+
-continued
297 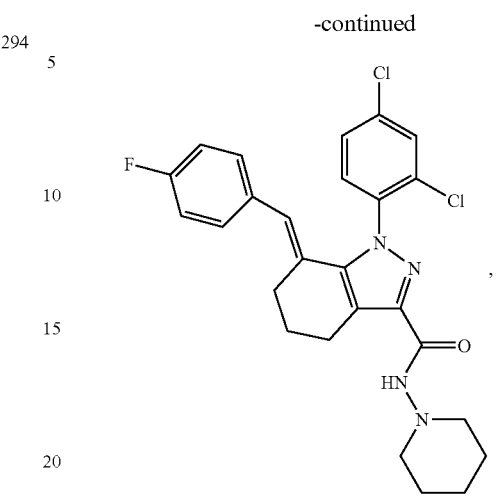
Example 10
298 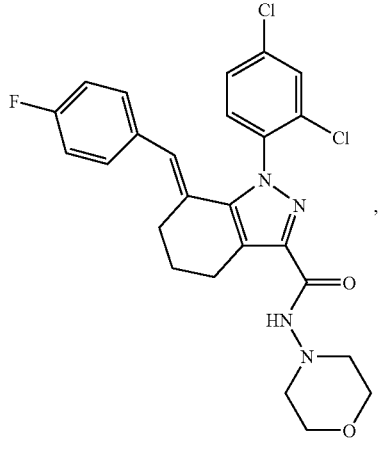
MS 501 MH+
299 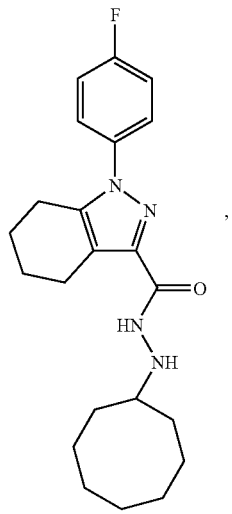
MS 385 MH+

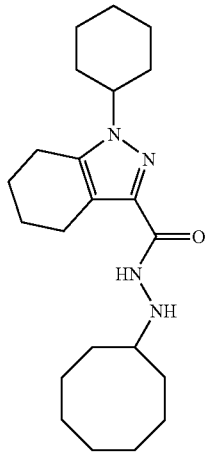
Example 21
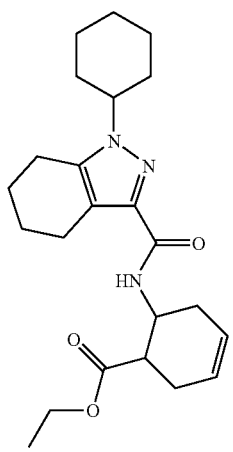
MS 400.1 MH+
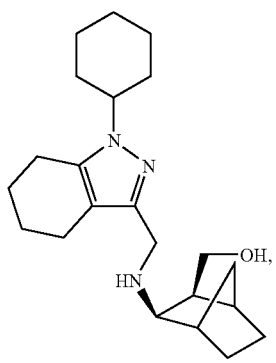
MS358.1 MH-
300
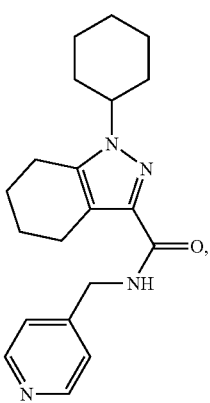
MS 399 MH+
301
303
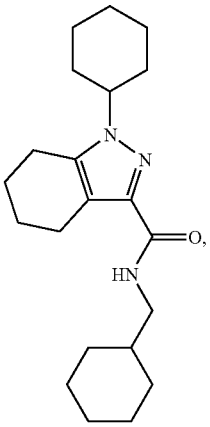
304 Eample 5
302
304
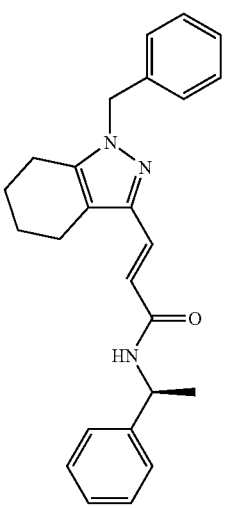
MS 386 MH+
305

-continued
306
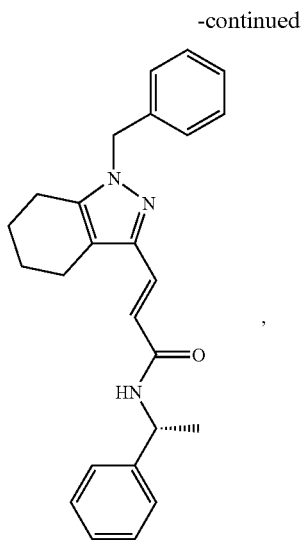
Example 12
307
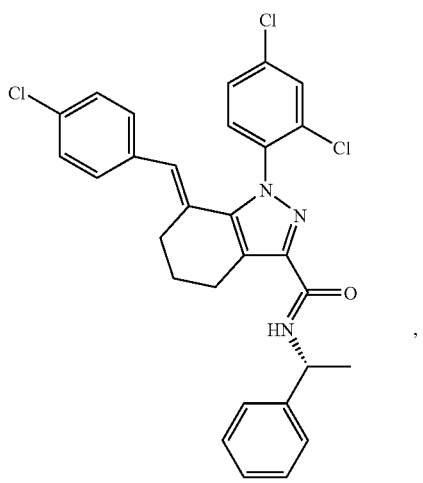
MS 536 MH⁺
-continued
308
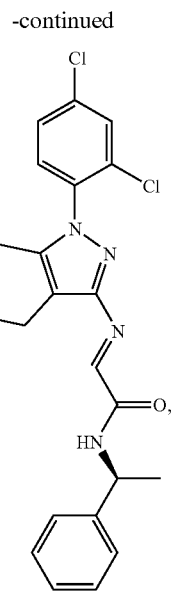
MS 520 MH⁺
309
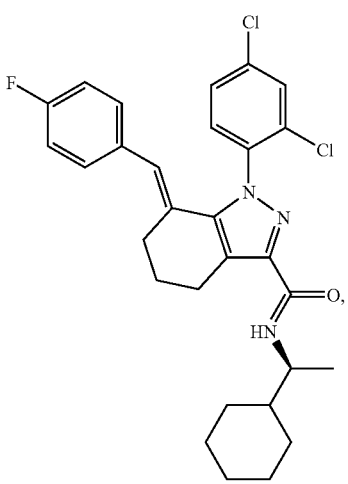
MS 526 MH⁺

-continued
| 310 | 312 |
|---|---|
| 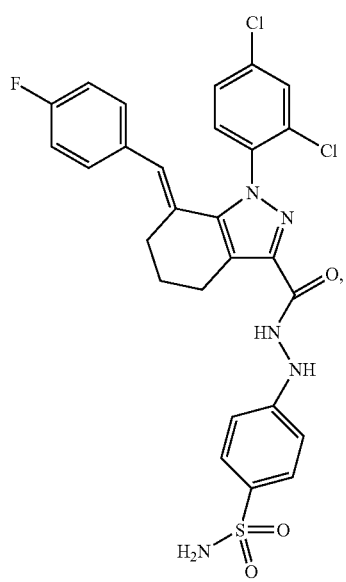 MS 586 MH+ | 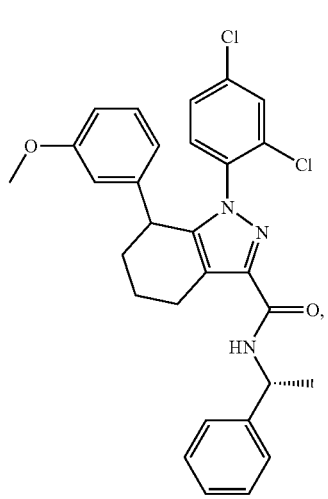 MS 520 MH+ |
| 311 | 313 |
| 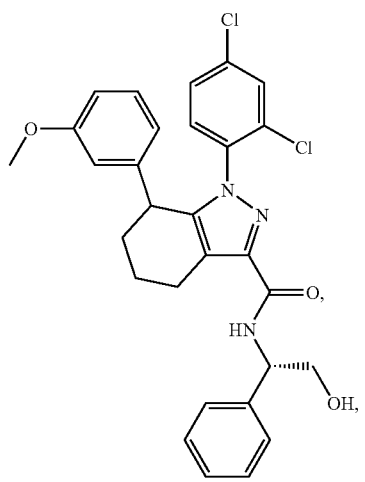 MS 508 MH+ | Example 25 |

-continued
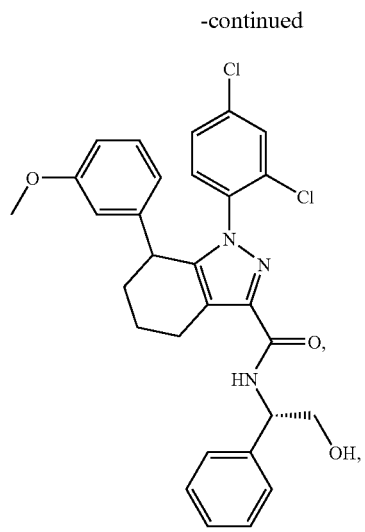
Example 25
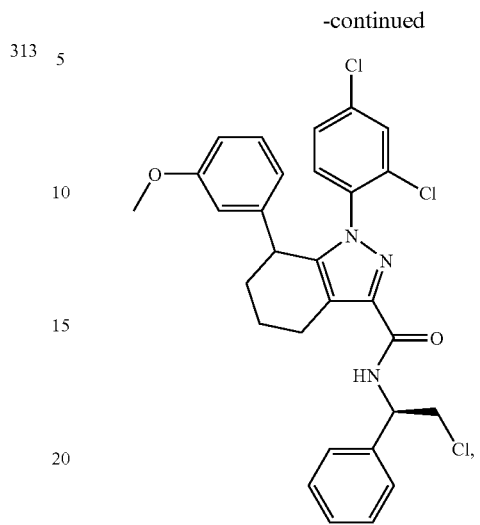
MS 556 MH+
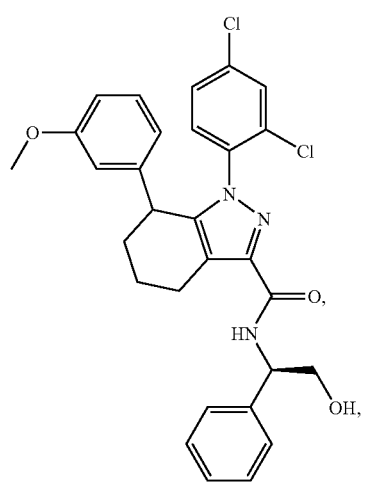
MS 536 MH+
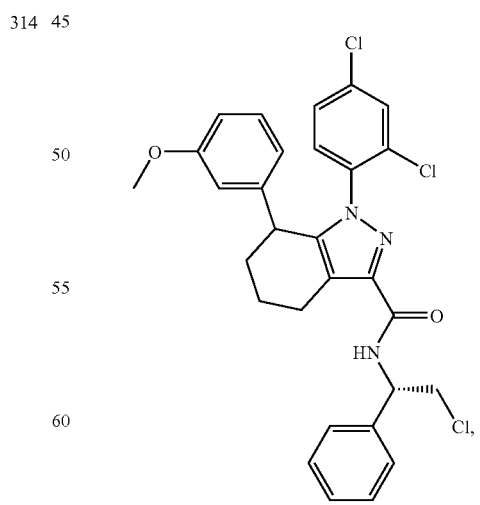
Example 26

317
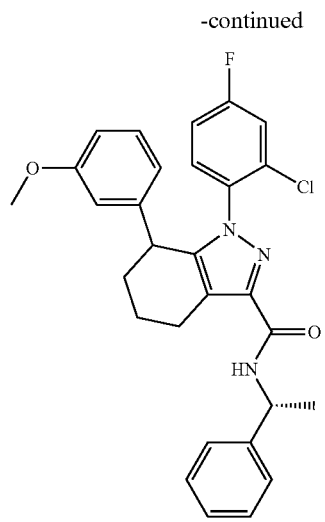
MS 488.2 MH⁺
318
MS 504.1 MH⁺
319
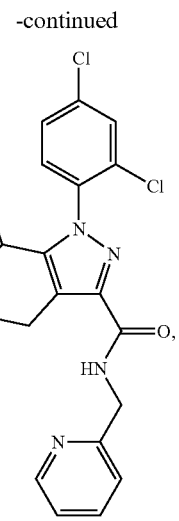
MS 523 MH⁺
320
MS 537 MH⁺

-continued
321
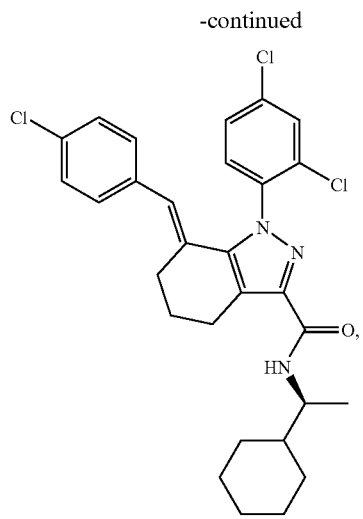
MS 542 MH+
322
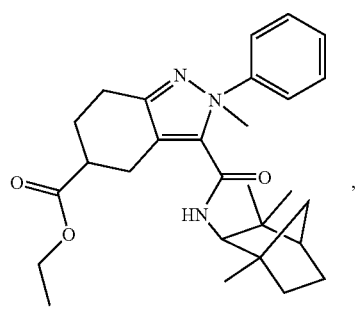
MS 450 MH+
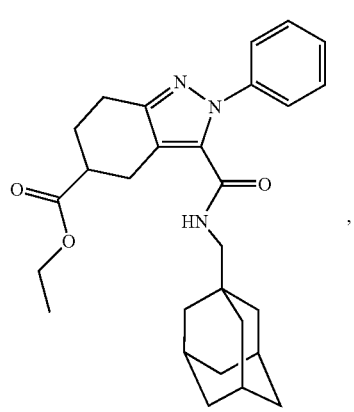
MS 462 MH+
-continued
324
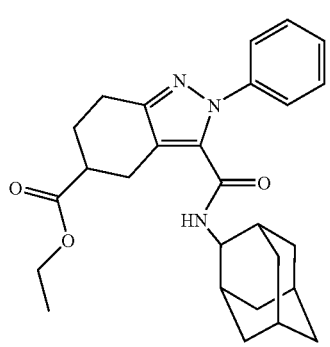
MS 448 MH+
325
MS 476 MH+
323
326
MS 505 MH+

| | |
|---|---|
| 327 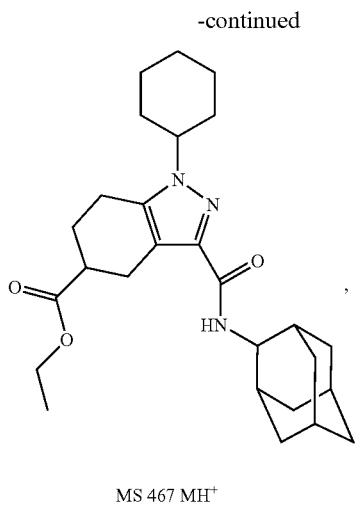<br>MS 467 MH+ | 330 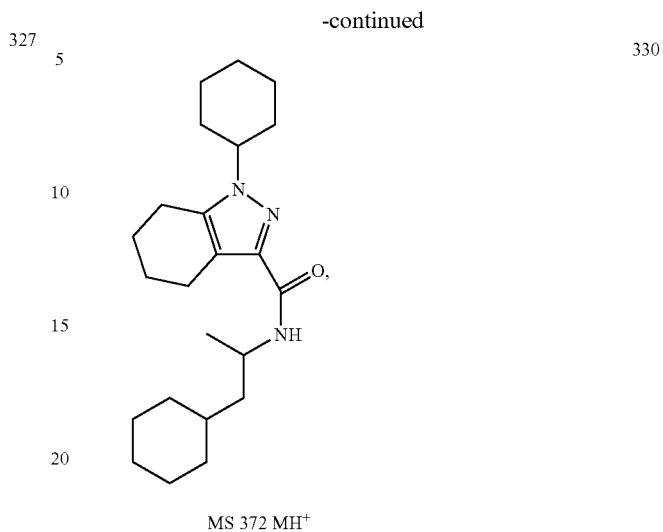<br>MS 372 MH+ |
| 328 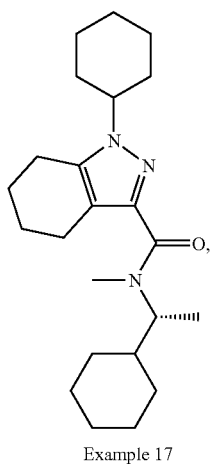<br>Example 17 | 331 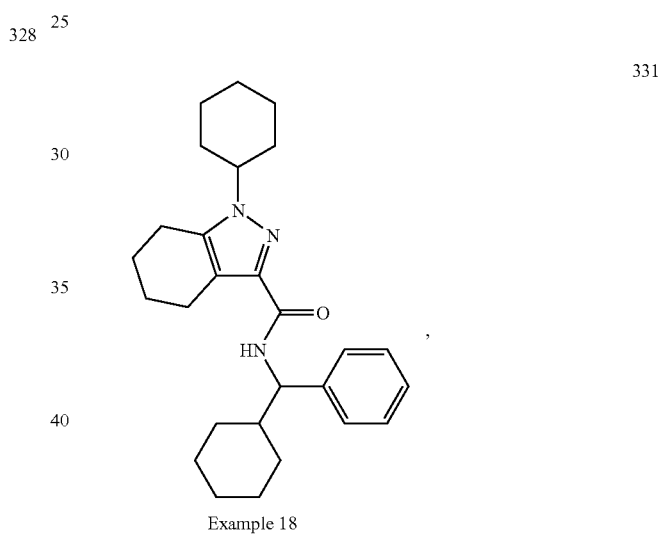<br>Example 18 |
| 329 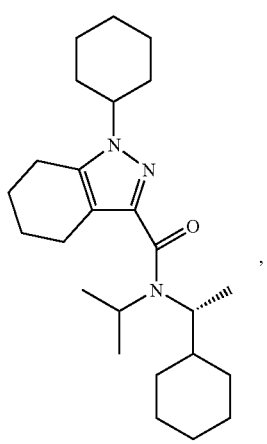<br>MS 400 MH+ | 332 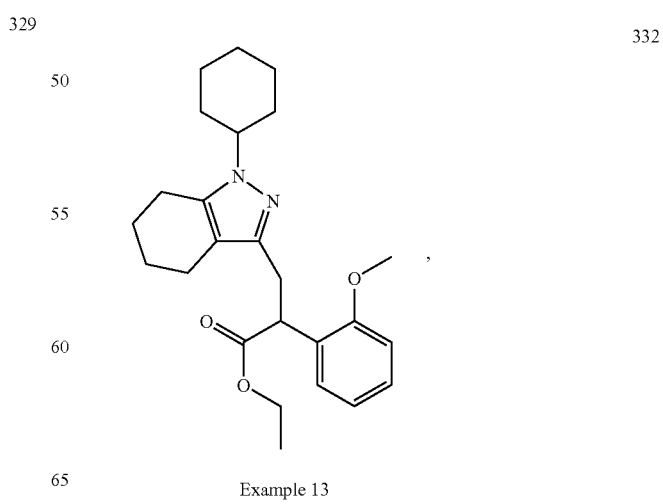<br>Example 13 |

-continued
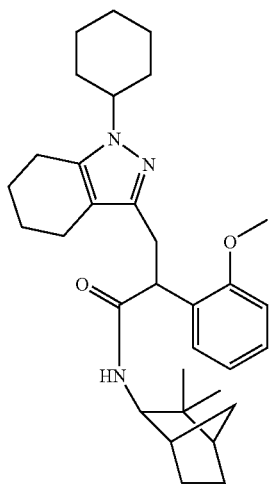
Example 14
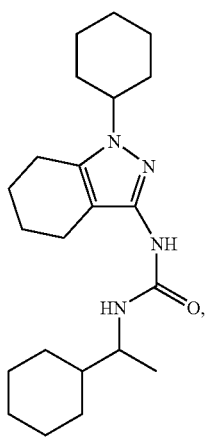
MS 373 MH+
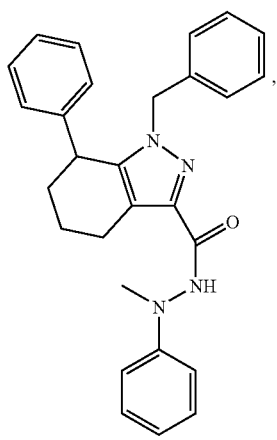
MS 459 MNa+
-continued
333
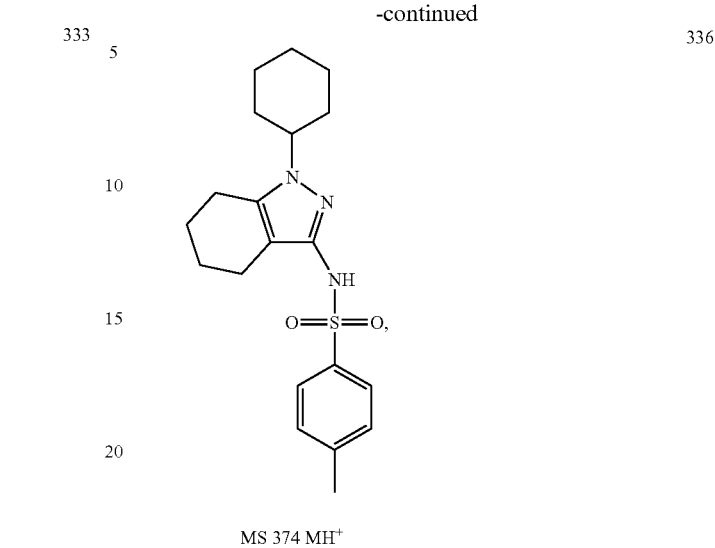
MS 374 MH+
334
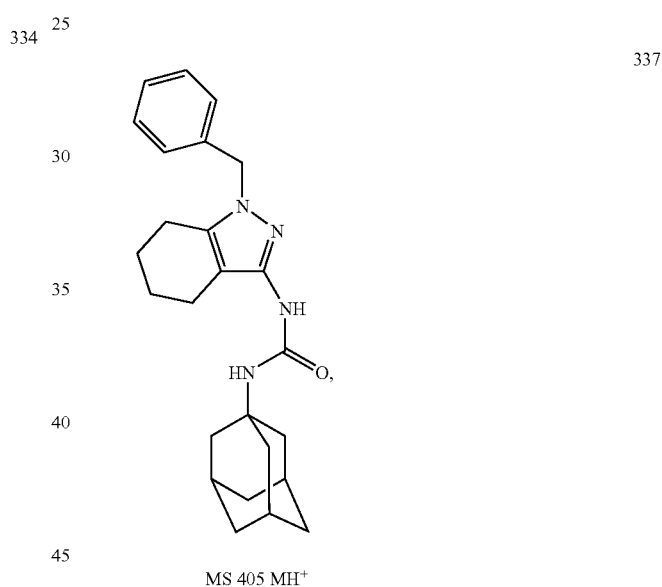
MS 405 MH+
335
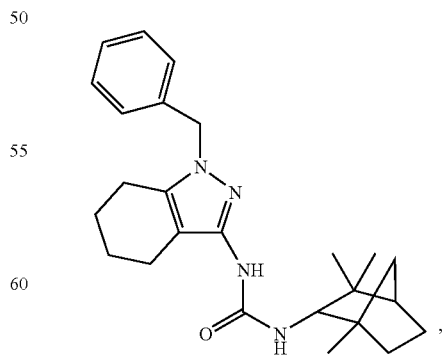
MS 407 MH+

-continued
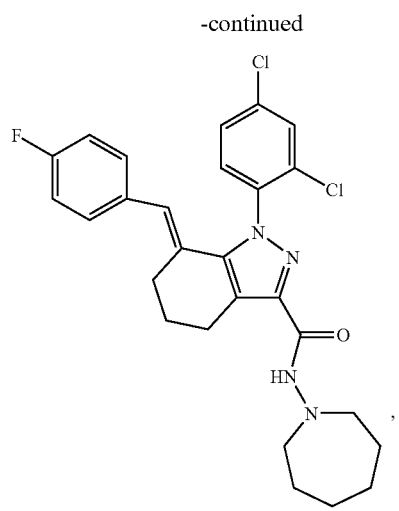
MS 373 MH+
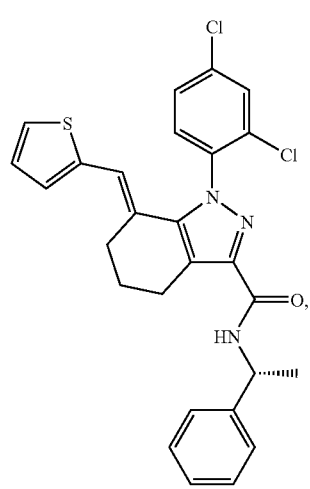
MS 508 MH+
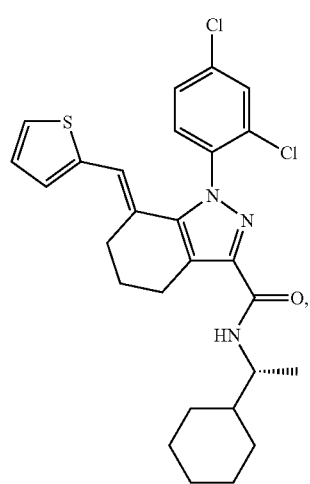
MS 514.1 MH+
-continued
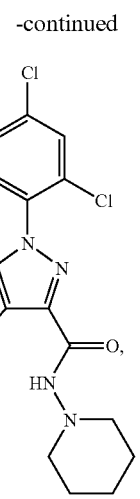
MS 487 MH+
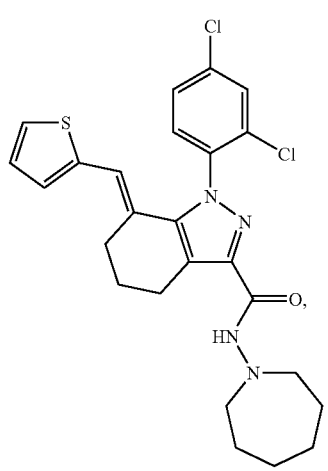
MS 501.1 MH+

-continued
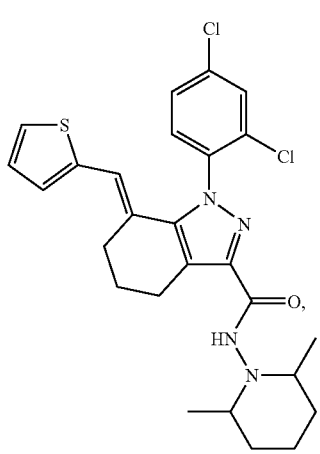
344
MS 515.1 MH[+]
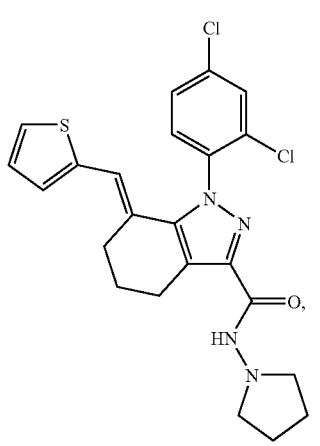
345
MS 473.1 MH[+]
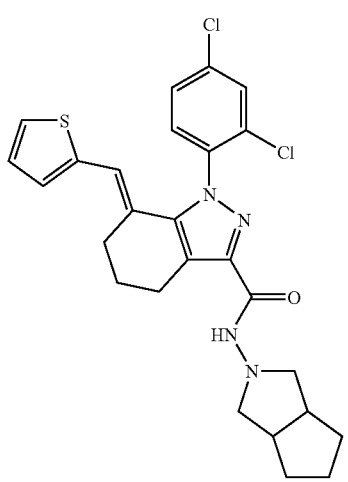
346
MS 513 MH[+]
-continued
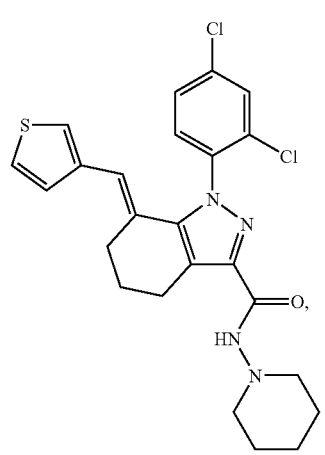
347
MS 487.1 MH[+]
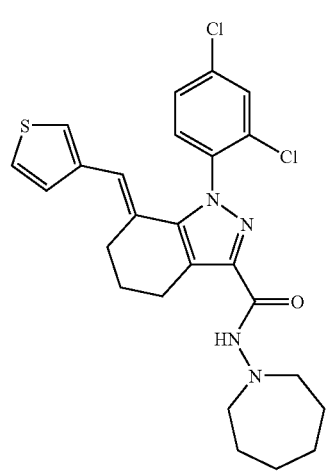
348
MS 501.1 MH[+]
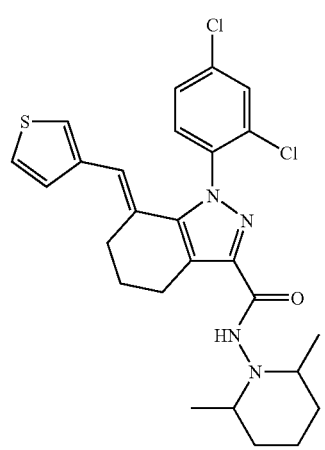
349
MS 515.1 MH[+]

-continued
350
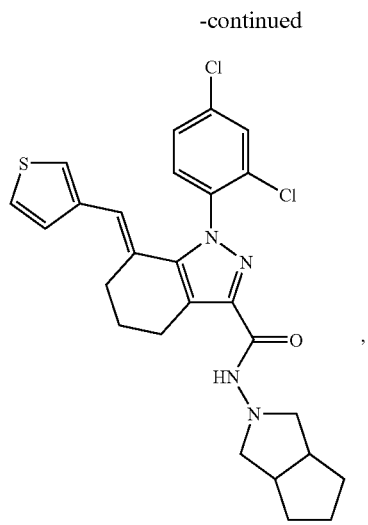
MS 513.2 MH+
351
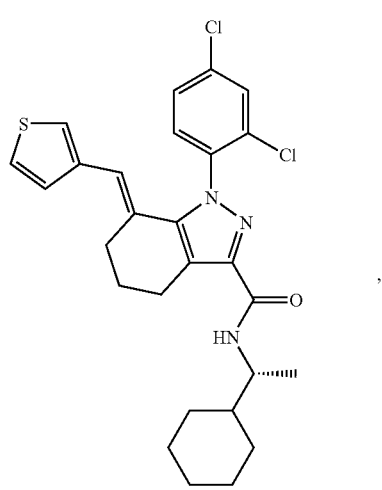
MS 514.2 MH+
352
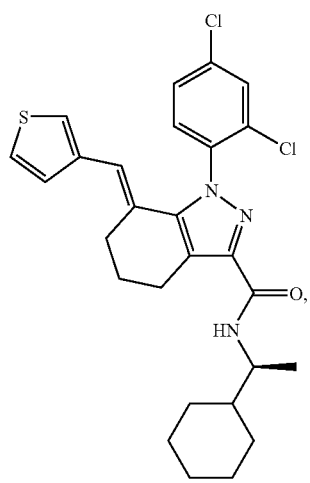
MS 514 MH+
-continued
353
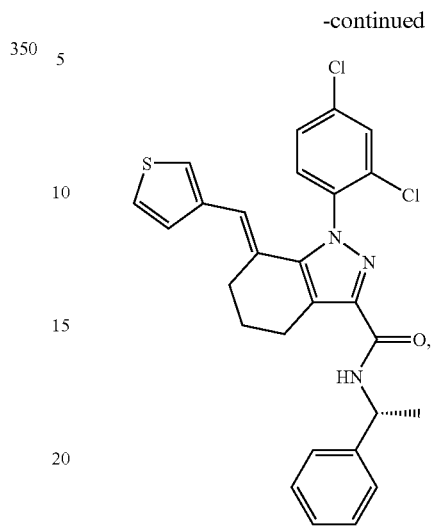
MS 507.9 MH+
354
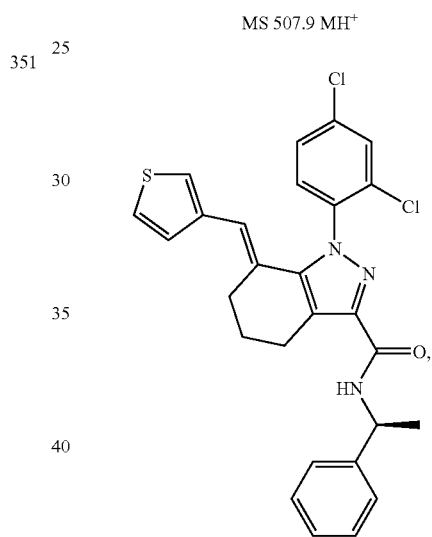
MS 507.9 MH+
355
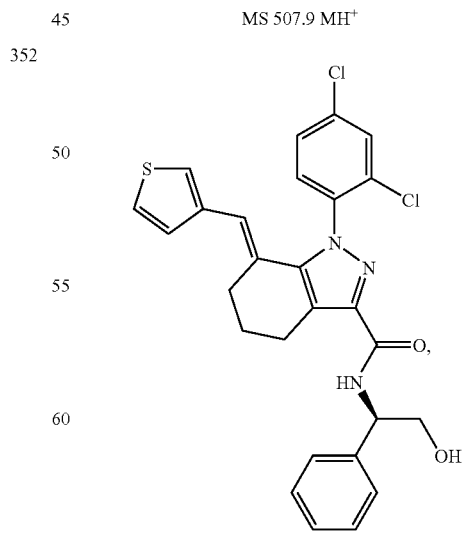
MS 524.1 MH+

-continued
356
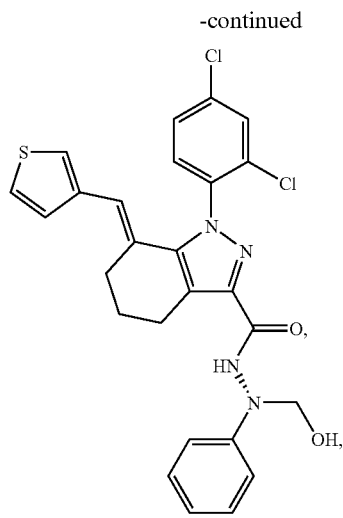
MS 524.1 MH+
357
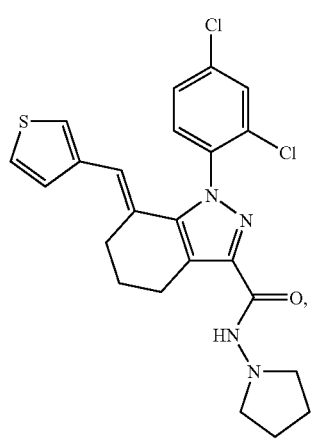
MS 473.1 MH+
358
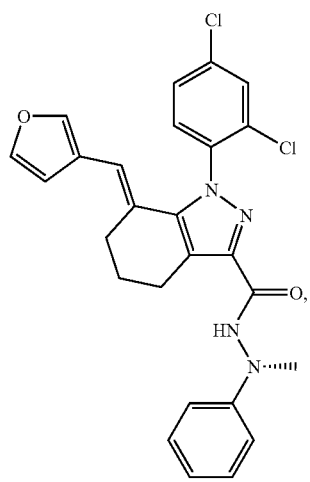
MS 492.1 MH+
-continued
359
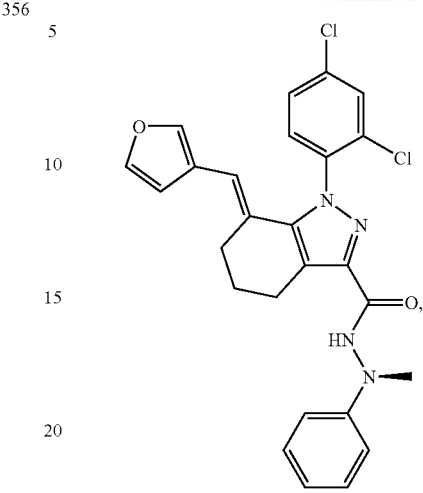
MS 492.1 MH+
360
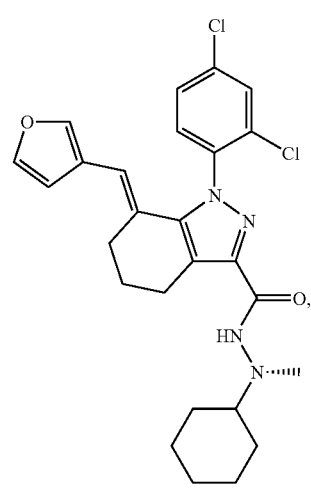
MS 498 MH+
361
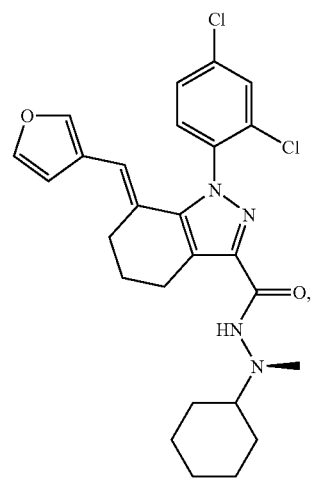
MS 498.1 MH+

-continued
362
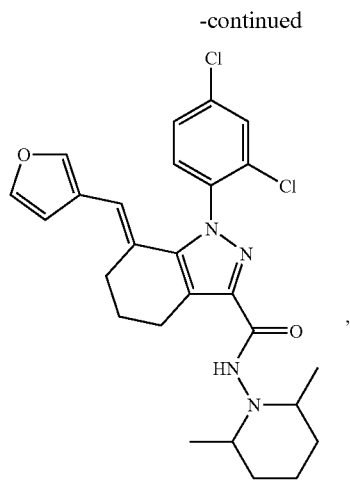
MS 499 MH+
363
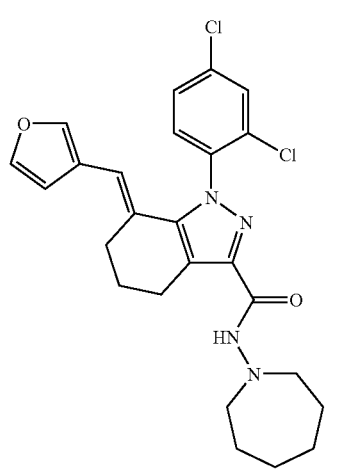
MS 485.1 MH+
364
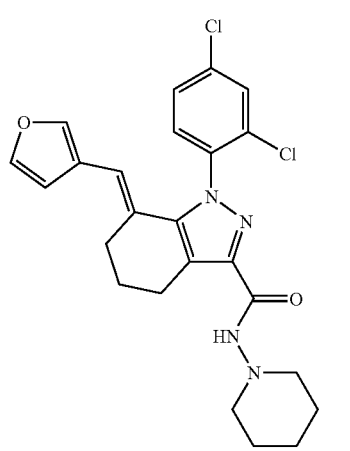
MS 472.1 MH+
-continued
365
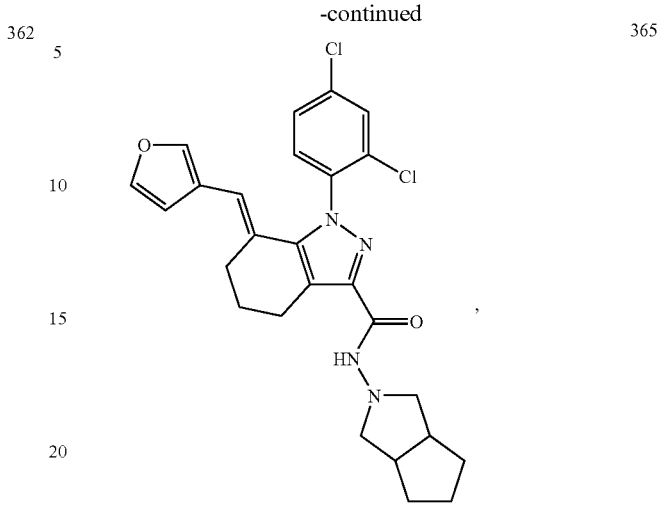
MS 497.1 MH+
366
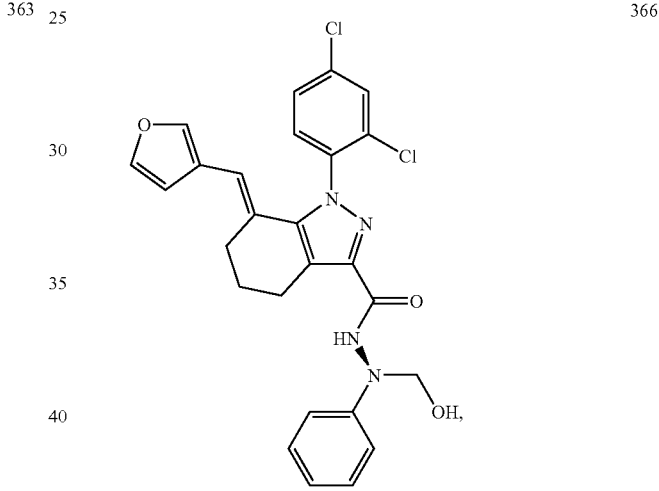
MS 510 MH+
367
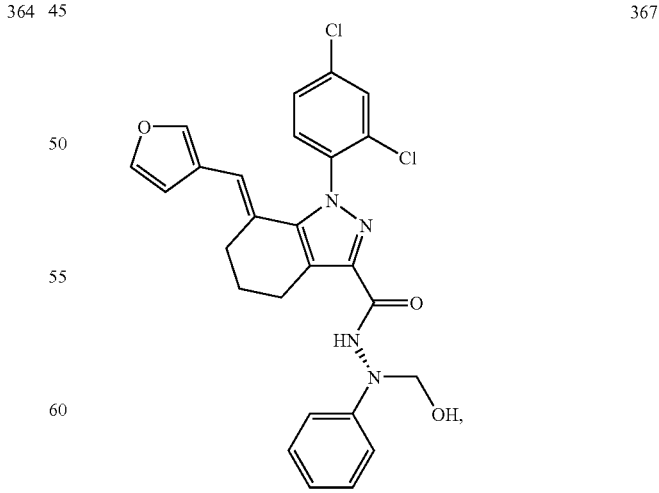
MS 509 MH+

-continued
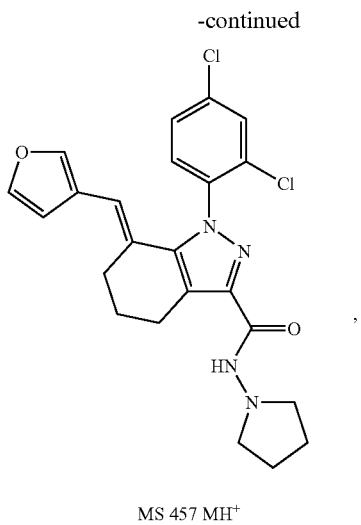
368
MS 457 MH+
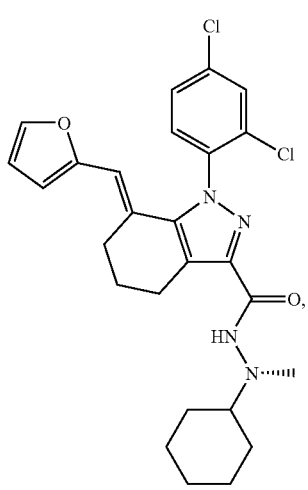
369
MS 498 MH+
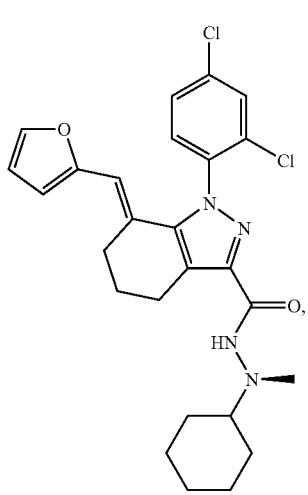
370
MS 498.1 MH+
-continued
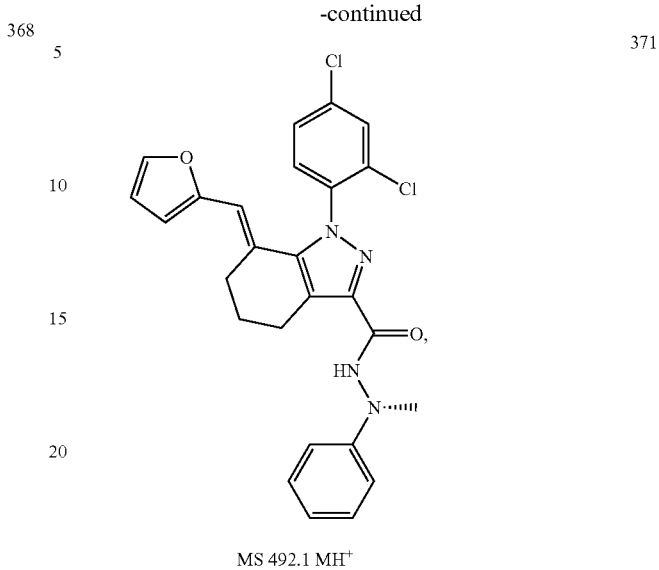
371
MS 492.1 MH+
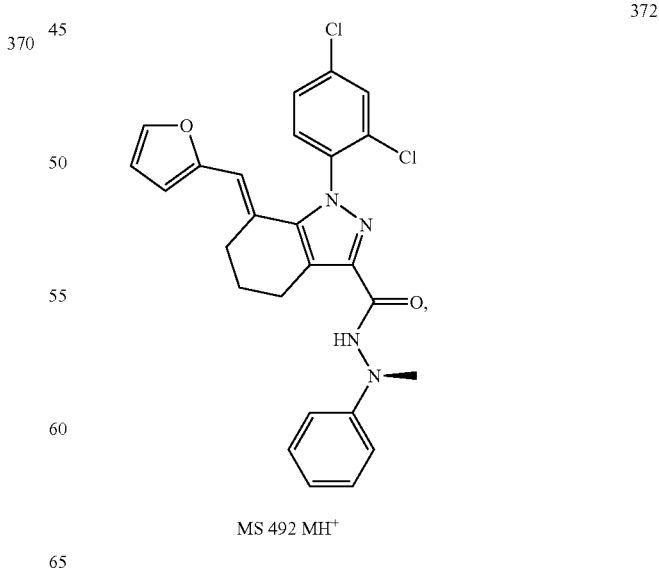
372
MS 492 MH+

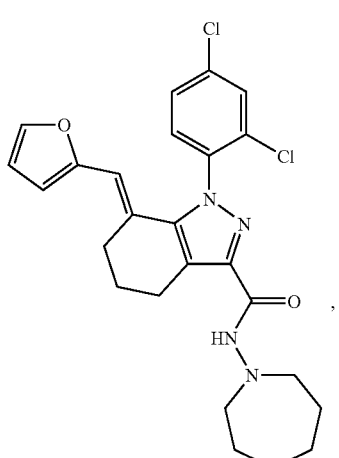
MS 485 MH+
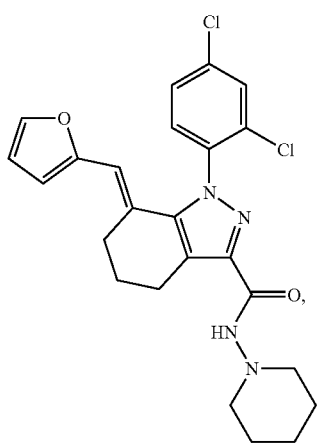
MS 471 MH+
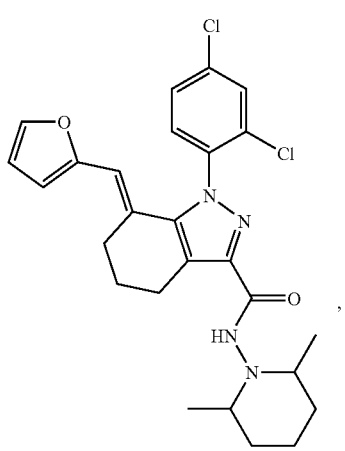
MS 499 MH+
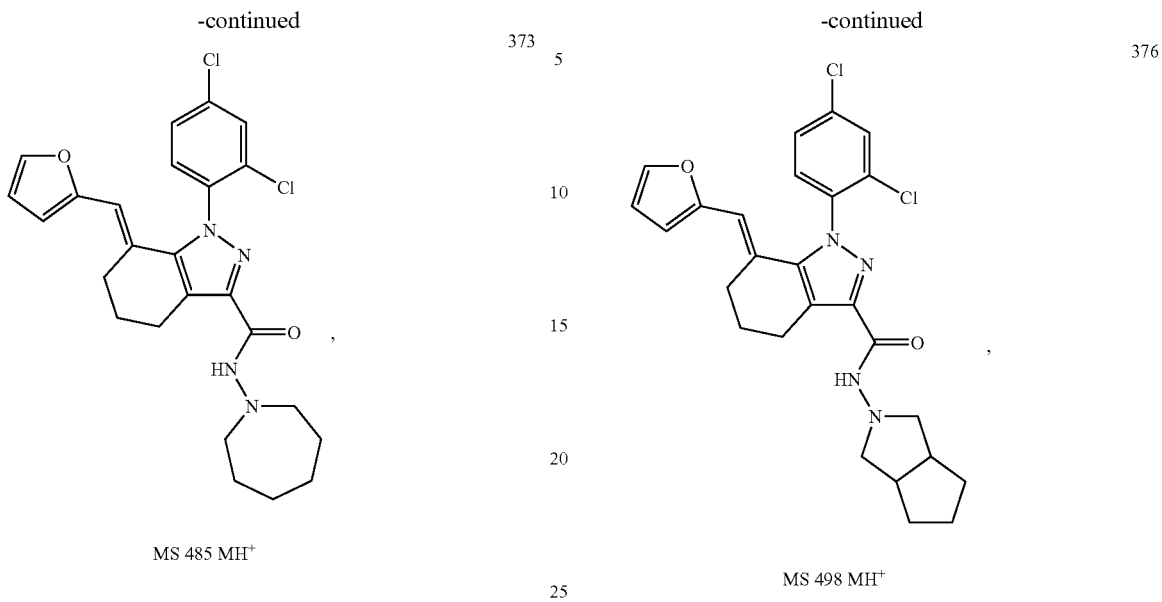
MS 498 MH+
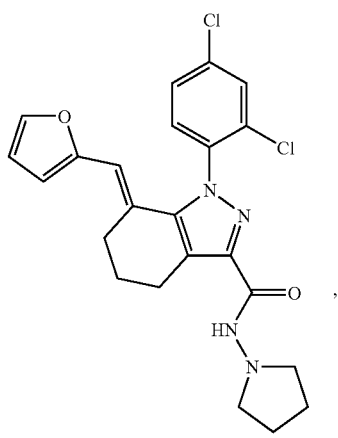
MS 457.1 MH+

-continued
378
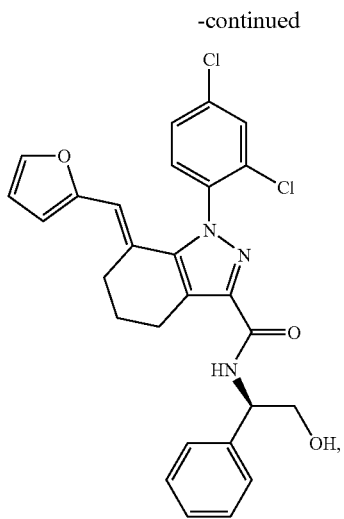
MS 498 MH+
379
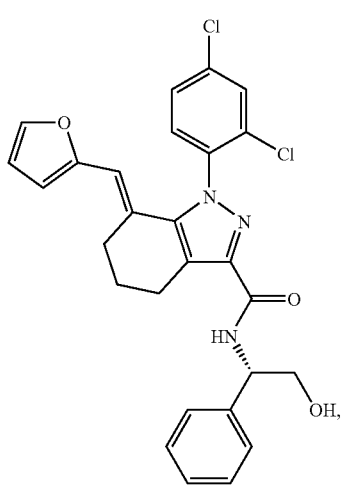
MS 508 MH+
380
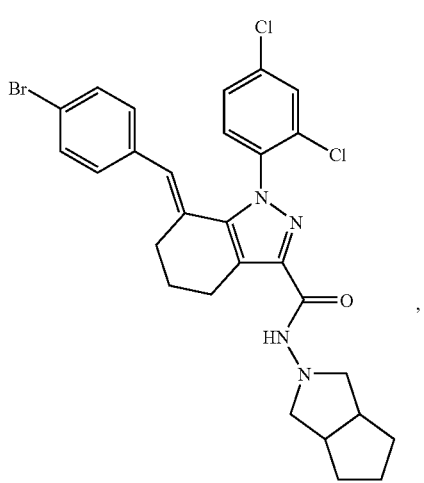
MS 585 MH+
-continued
381
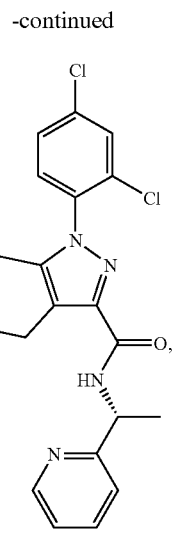
MS 581 MH+
382
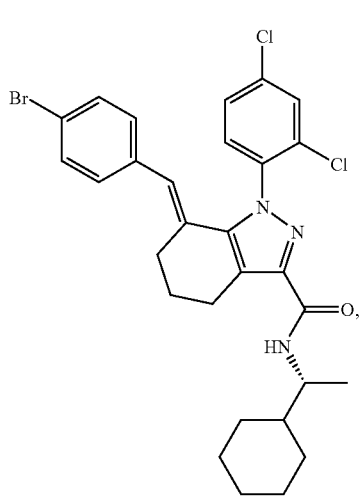
MS 586 MH+
383
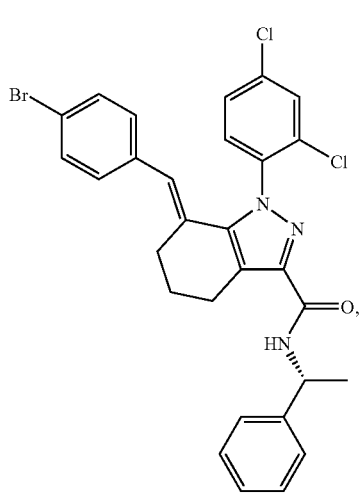
MS 581 MH+

-continued
384
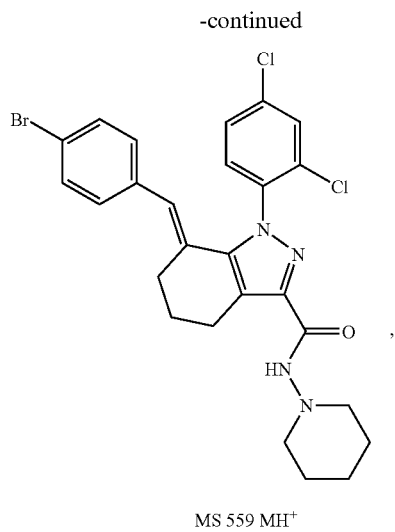
MS 559 MH+
385
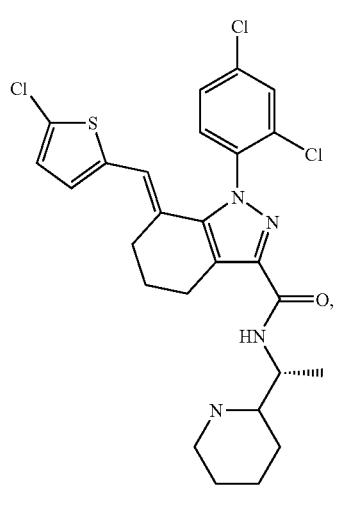
MS 549 MH+
386
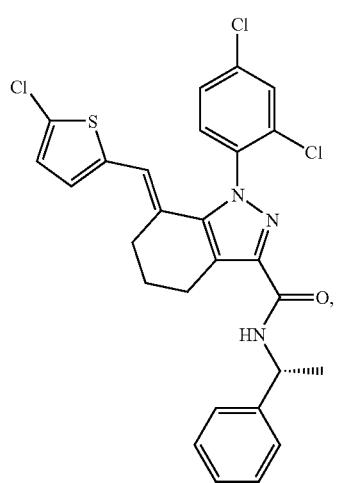
MS 544 MH+
-continued
387
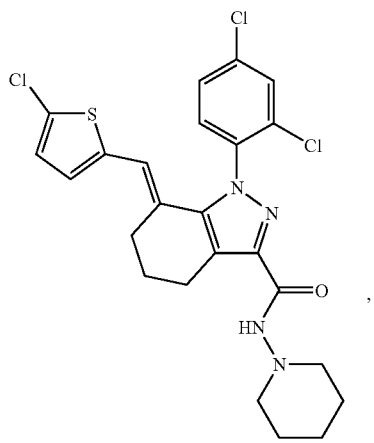
MS 522 MH+
388
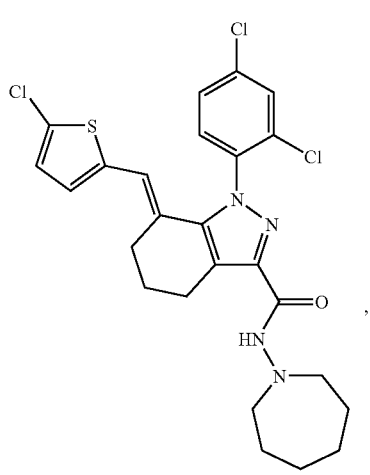
MS 537.1 MH+
389
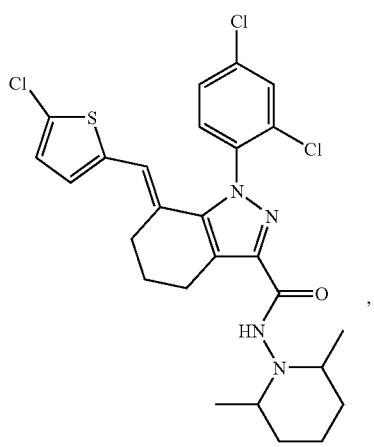
MS 548.1 MH+

-continued
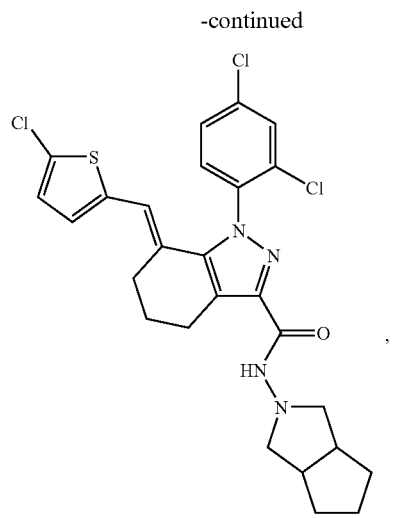
MS 547 MH+
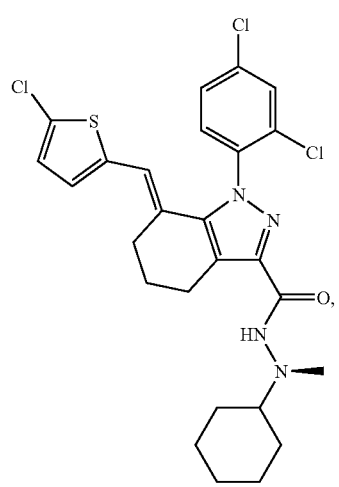
MS 548 MH+
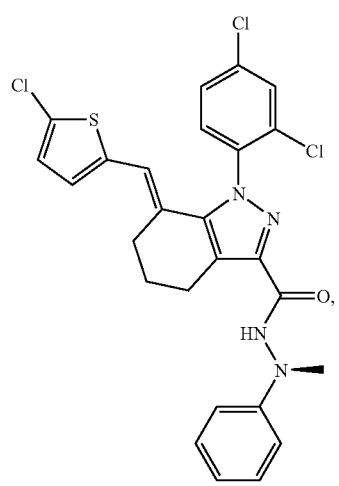
MS 542 MH+
-continued
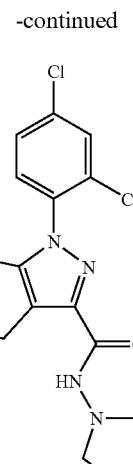
MS 506.9 MH+
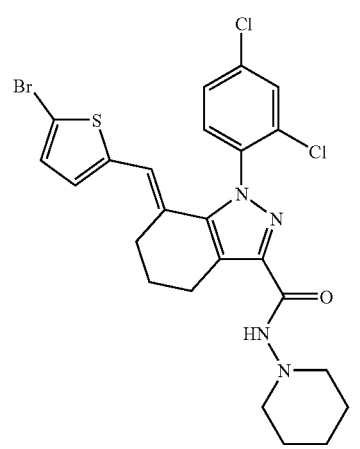
MS 550.9 MH+
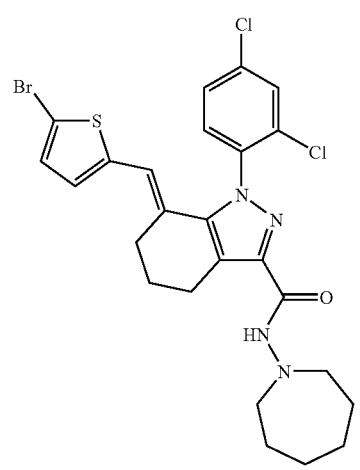
MS 564.9 MH+

-continued
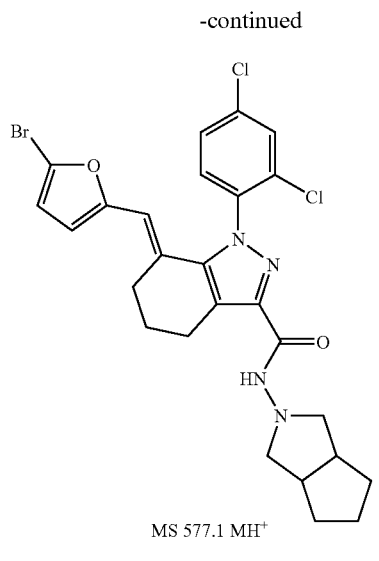
396
MS 577.1 MH+
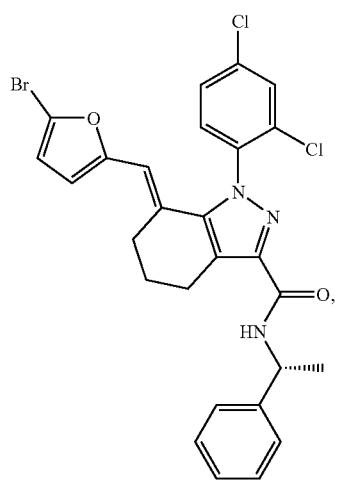
397
MS 571.8 MH+
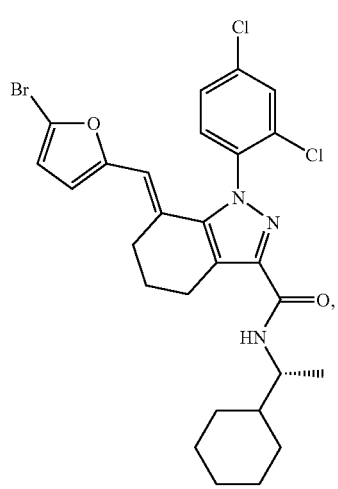
398
MS 578 MH+
-continued
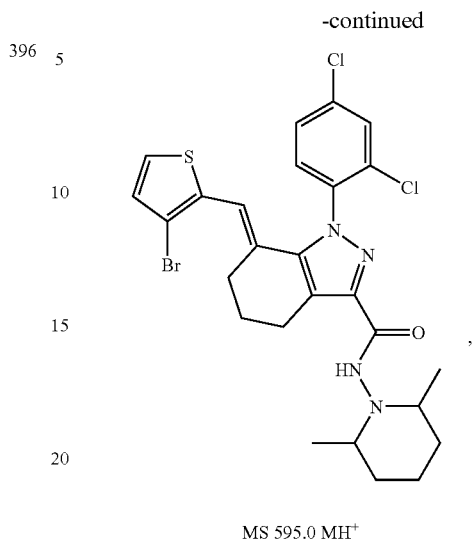
399
MS 595.0 MH+
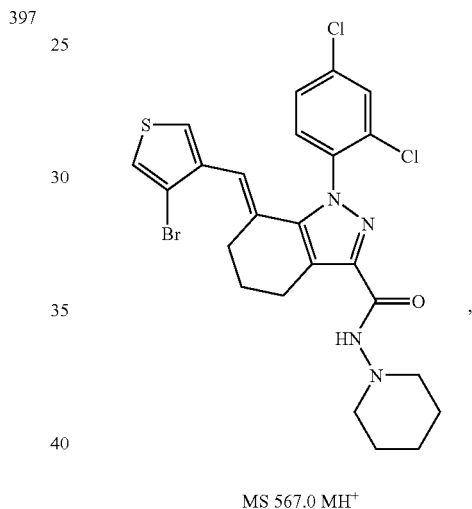
400
MS 567.0 MH+
and pharmaceutically acceptable forms thereof.
Another example of the present invention is a compound selected from:
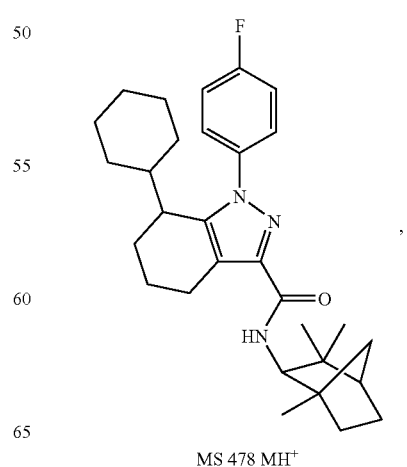
24
MS 478 MH+

-continued
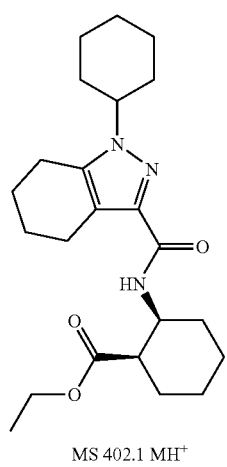
MS 402.1 MH+
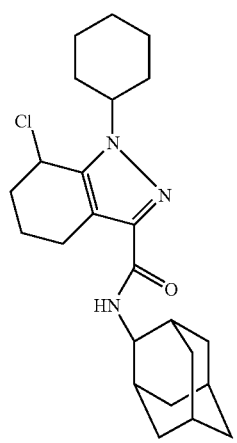
MS 416 MH+
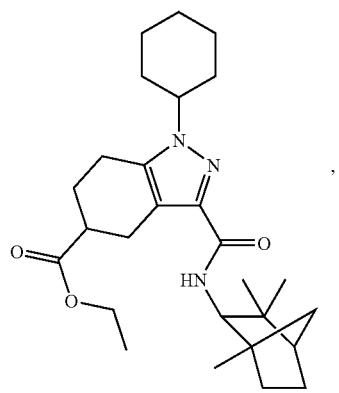
MS 456 MH+
-continued
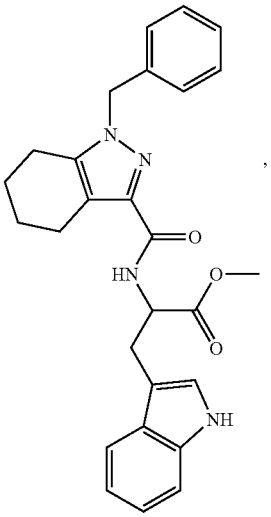
MS 457 MH+
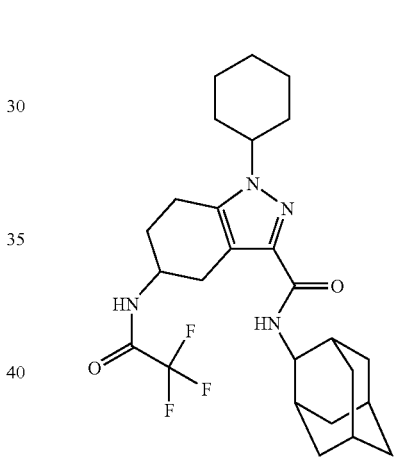
MS 493 MH+
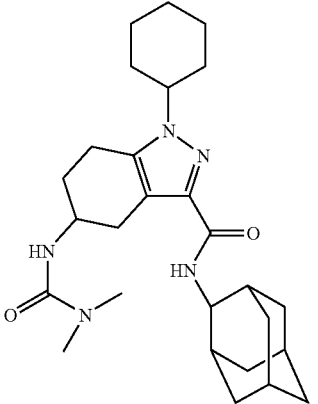
Example 9

92
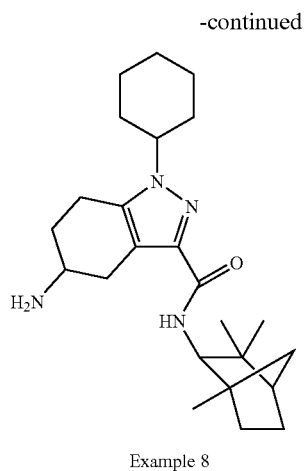
Example 8
93
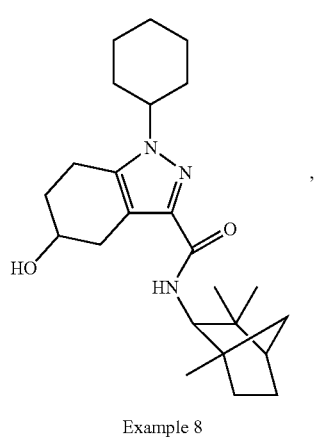
Example 8
94
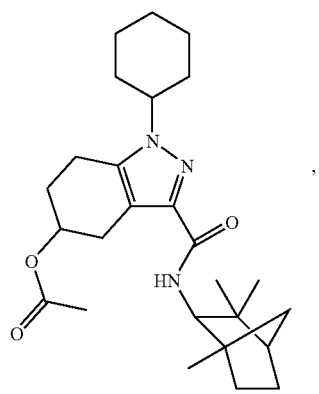
MS 442 MH+
103
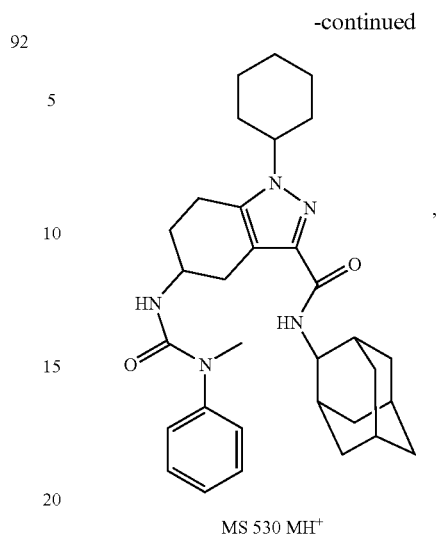
MS 530 MH+
106
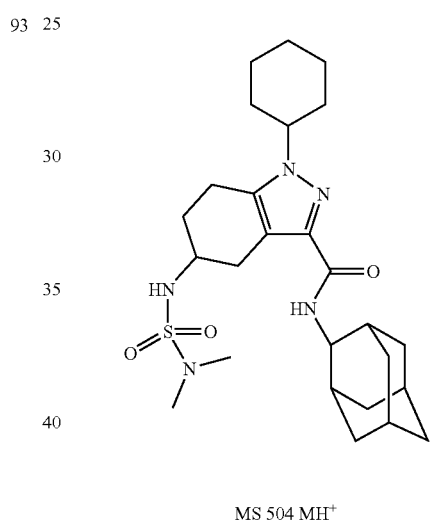
MS 504 MH+
154
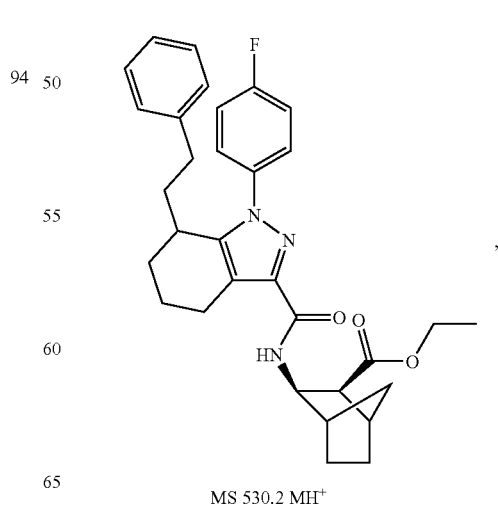
MS 530.2 MH+

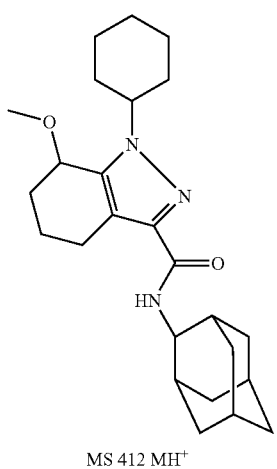
MS 412 MH+
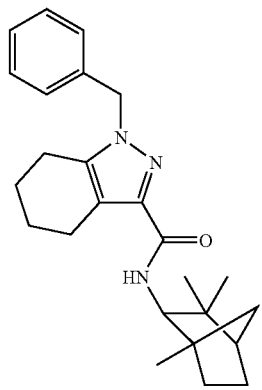
Example 2
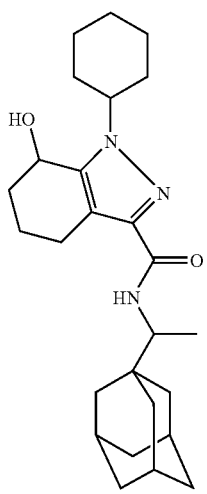
MS 425.8 MH+
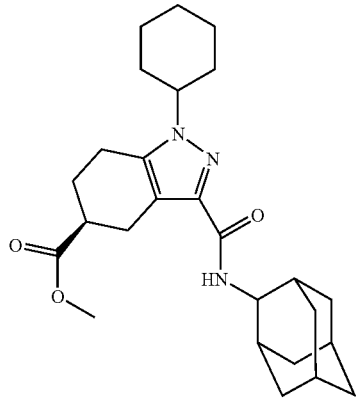
MS 440 MH+
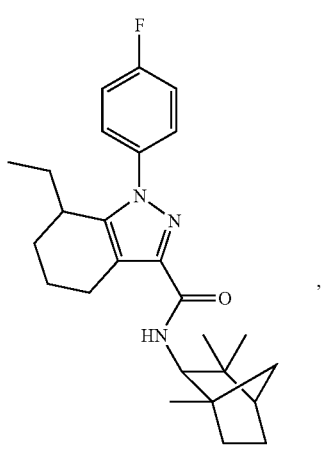
MS 424 MH+
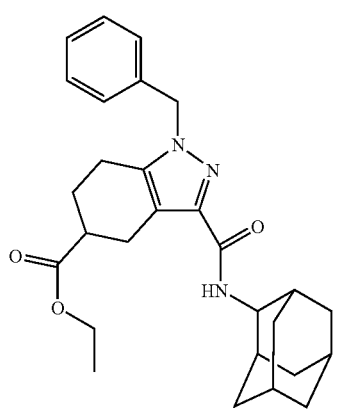
MS 462 MH+

-continued
253
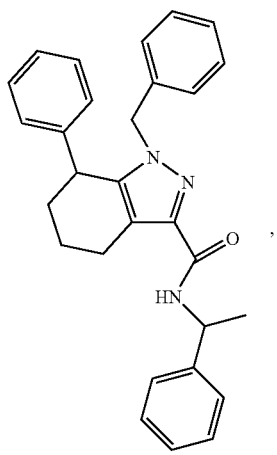
MS 436 MH+
256
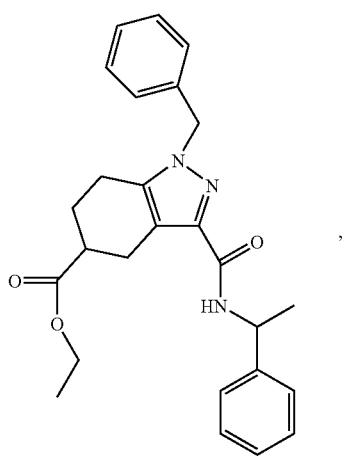
MS 432 MH+
261
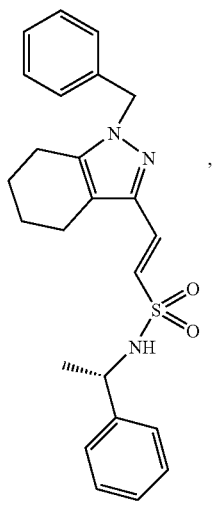
MS 422.1 MH+
-continued
290
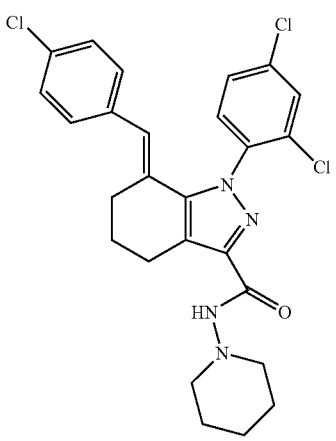
MS 515 MH+
292
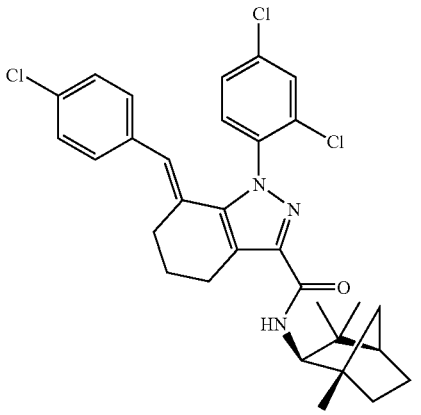
MS 568 MH+
293
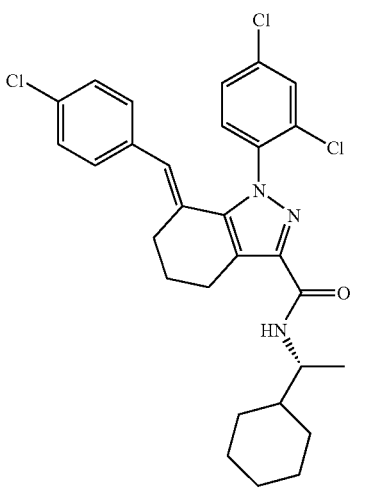
MS 542 MH+

295
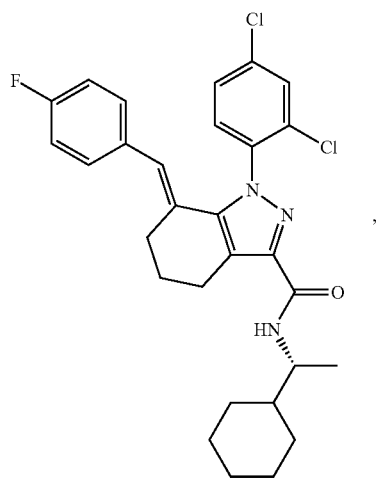
MS 526 MH+
296
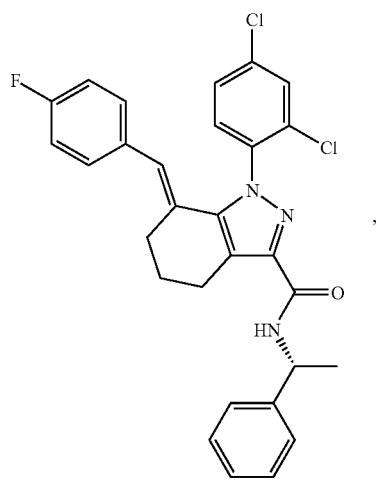
MS 520 MH+
297
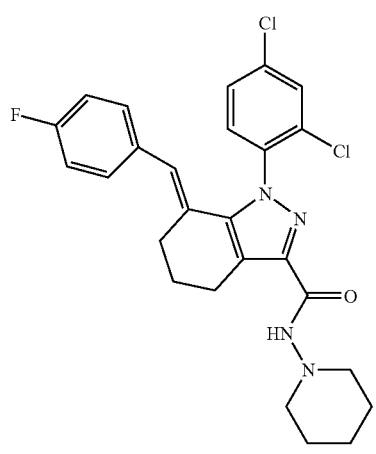
Example 10
298
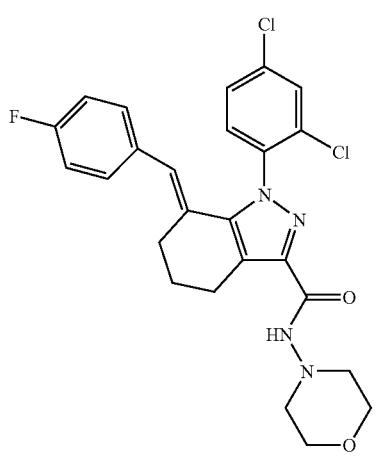
MS 501 MH+
305
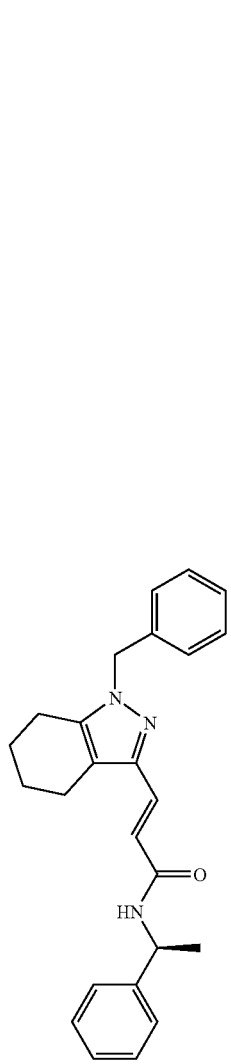
MS 386 MH+

-continued
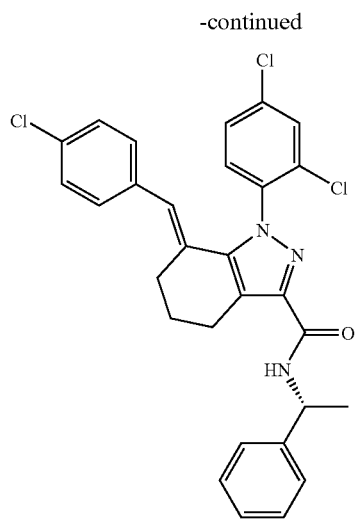
MS 536 MH+
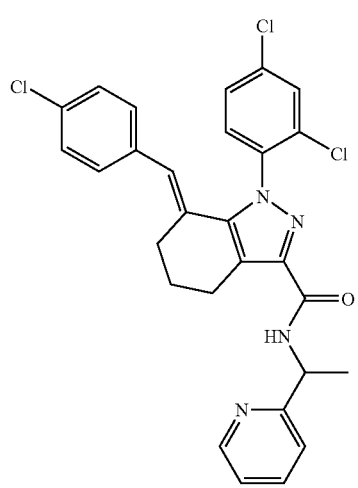
MS 537 MH+
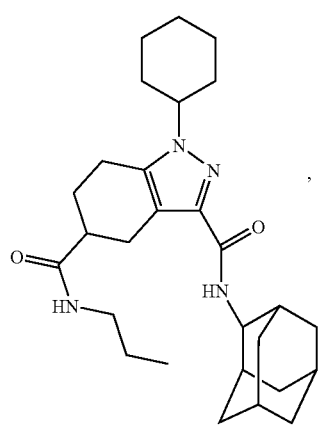
MS 467 MH+
-continued
307
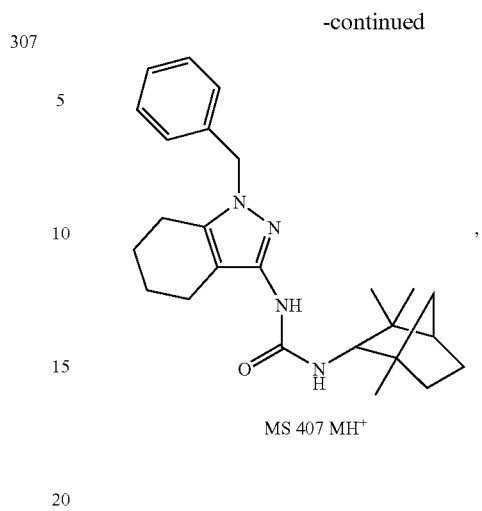
MS 407 MH+
353
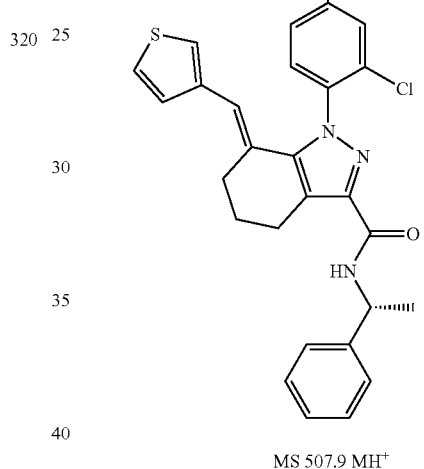
MS 507.9 MH+
358
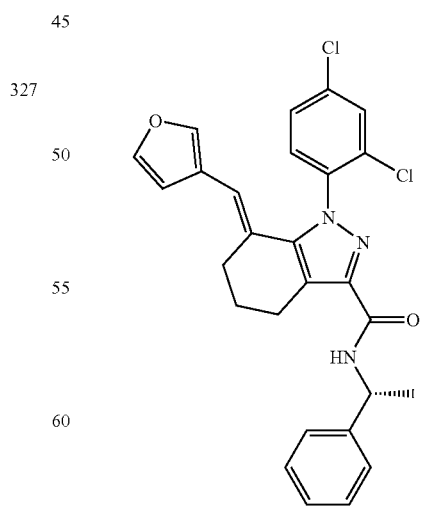
MS 492.1 MH+

| 364 | 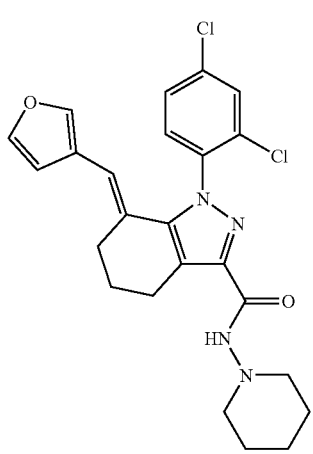 MS 472.1 MH+ | 381 | 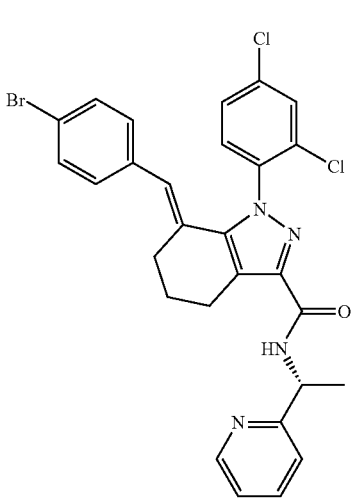 MS 581 MH+ |
| 367 | 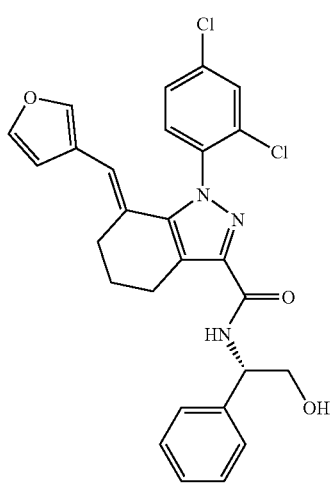 MS 509 MH+ | | |
| 374 | 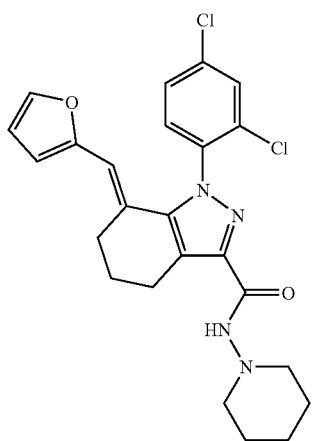 MS 471 MH+ | 384 | MS 559 MH+ |

385
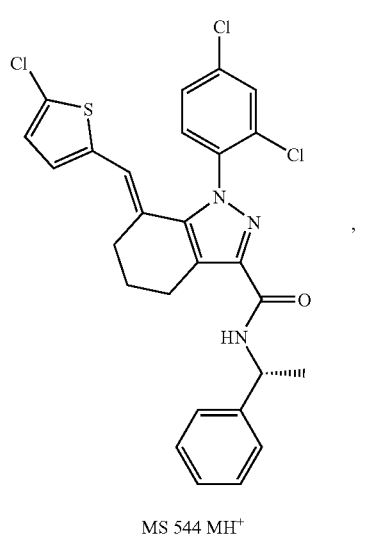
MS 544 MH+
386
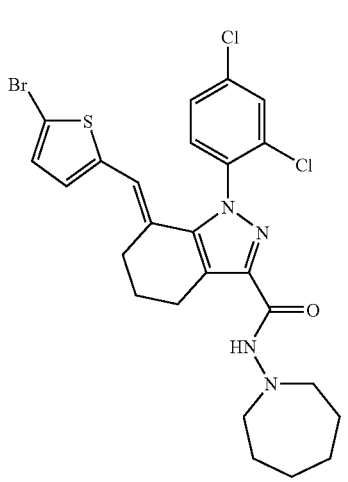
MS 564.9 MH+
390
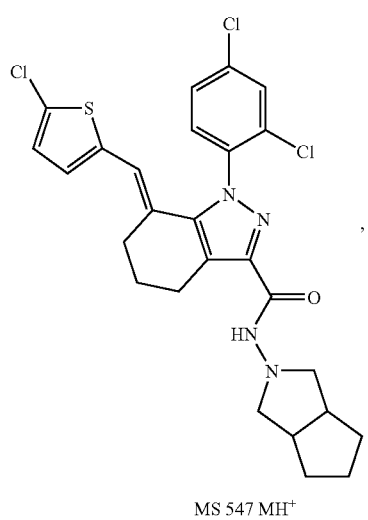
MS 547 MH+
398
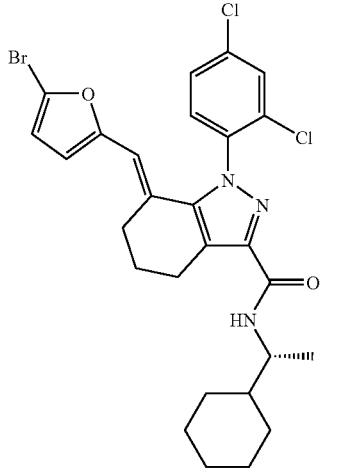
MS 578 MH+
394
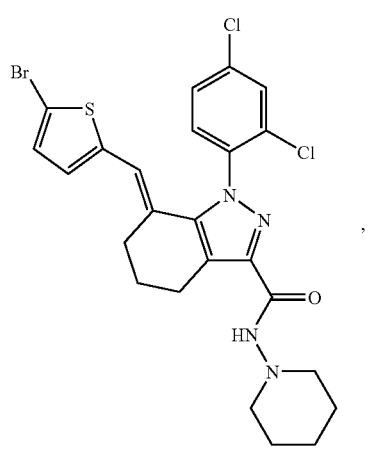
MS 550.9 MH+
399
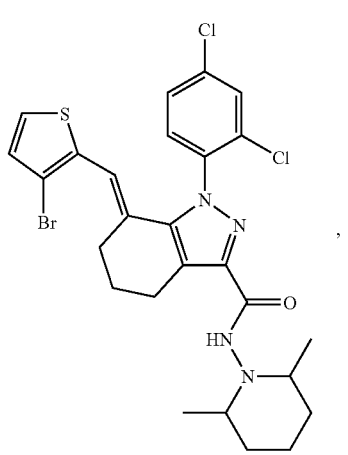
MS 595.0 MH+

-continued
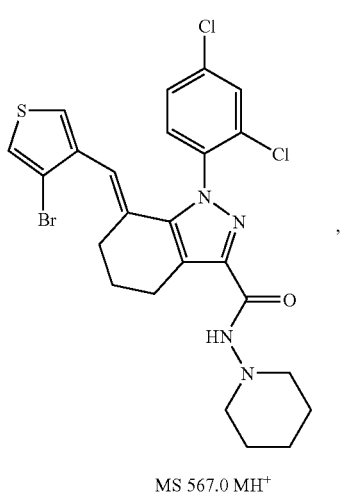
MS 567.0 MH⁺
and pharmaceutically acceptable forms thereof.
  Another example of the present invention is a compound selected from:
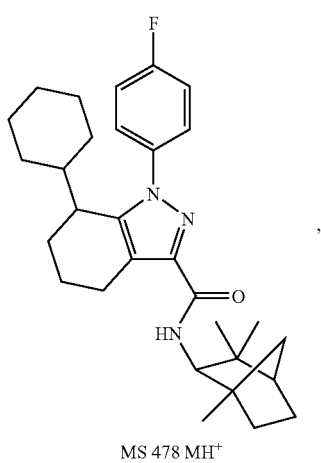
MS 478 MH⁺
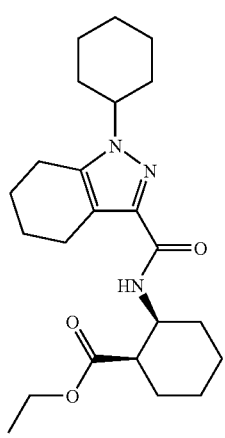
MS 402.1 MH⁺
-continued
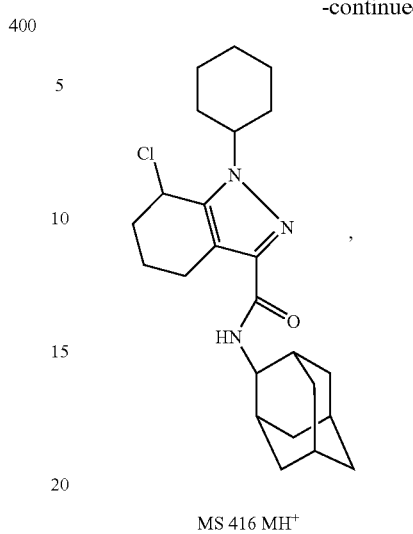
MS 416 MH⁺
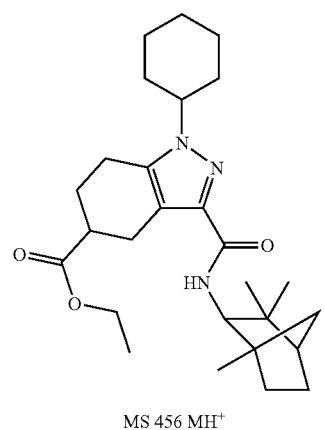
MS 456 MH⁺
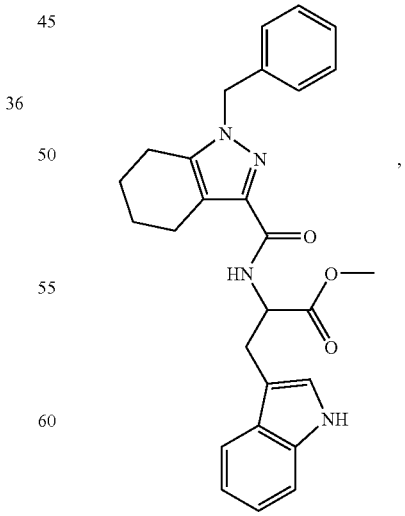
MS 457 MH⁺

| 154 | 192 |
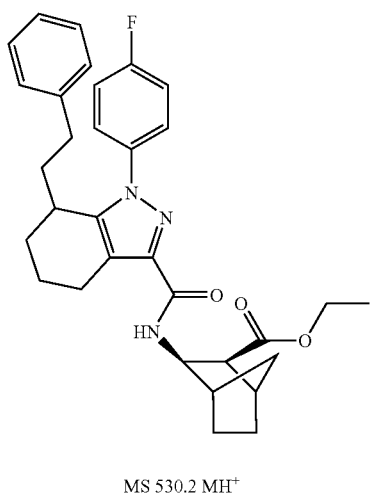
MS 530.2 MH⁺
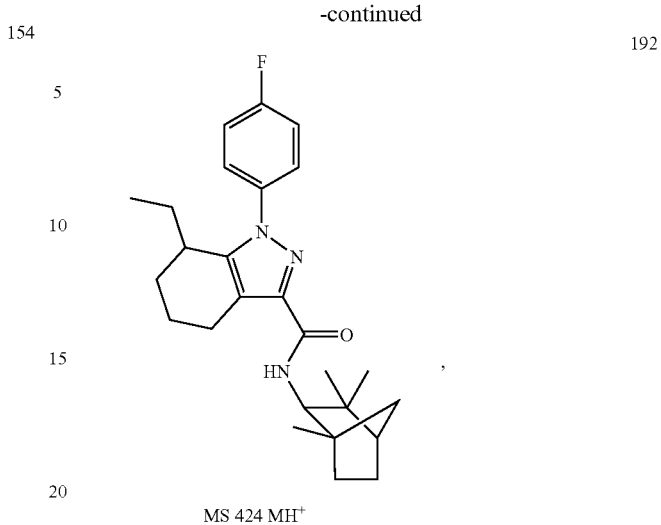
MS 424 MH⁺
| 162 | 194 |
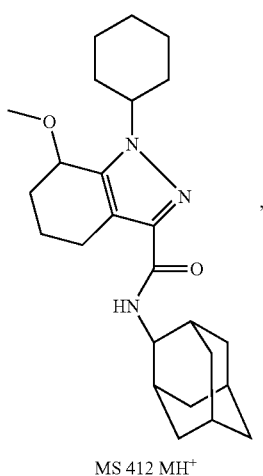
MS 412 MH⁺
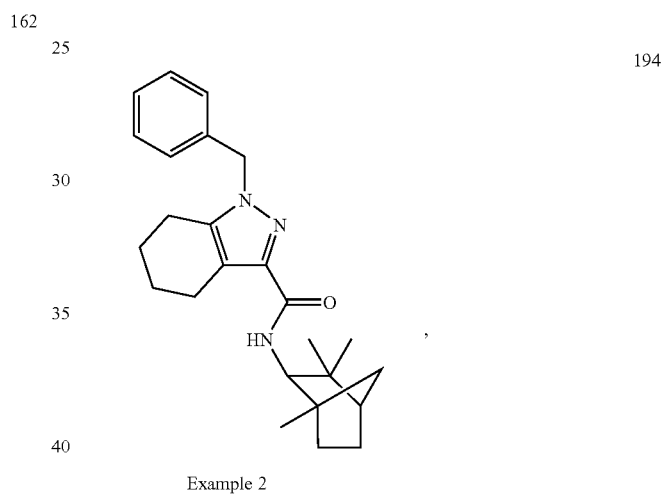
Example 2
| 163 | 226 |
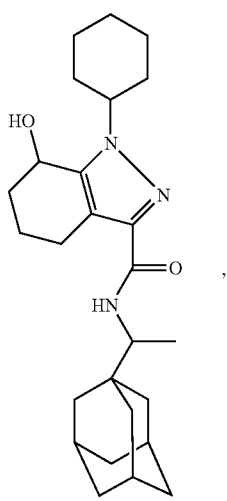
MS 425.8 MH⁺
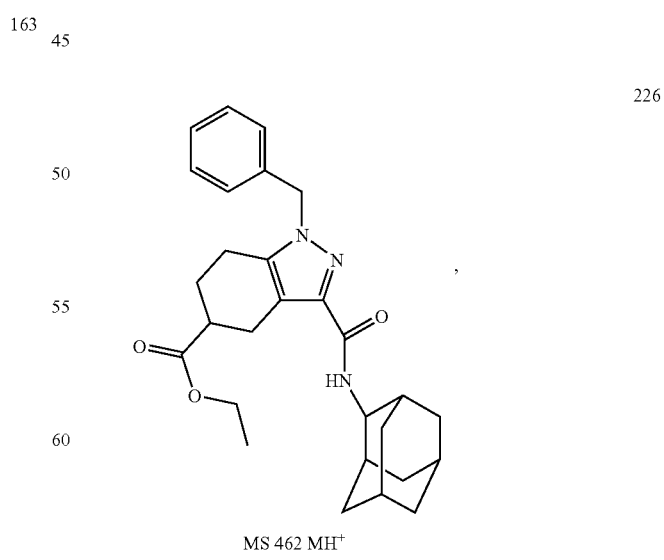
MS 462 MH⁺

253
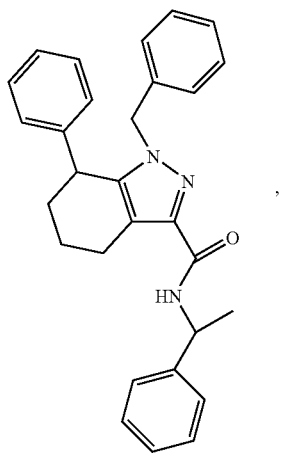
MS 436 MH+
256
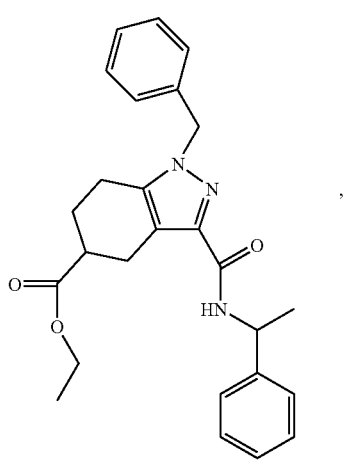
MS 432 MH+
261
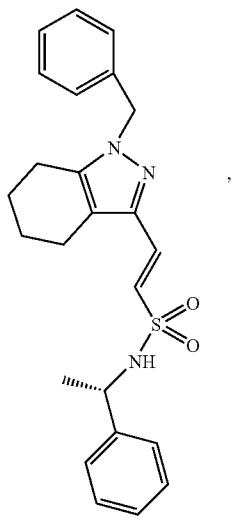
MS 422.1 MH+
290
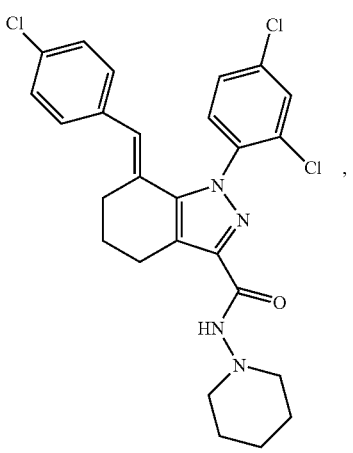
MS 515 MH+
292
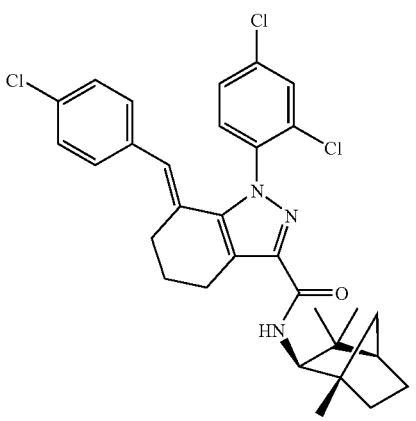
MS 568 MH+
293
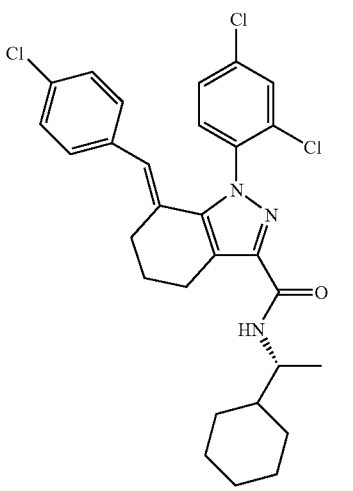
MS 526 MH+

-continued
295
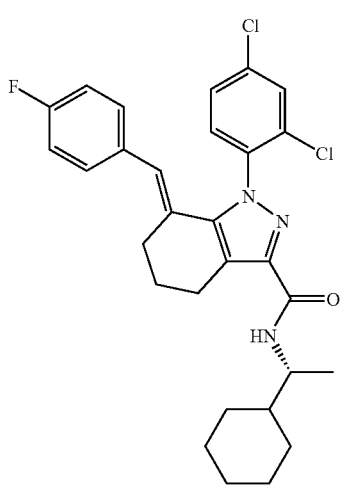
MS 526 MH+
296
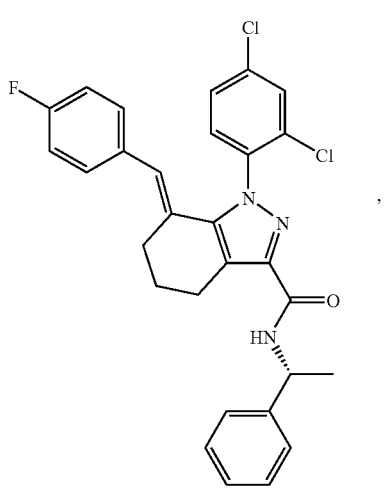
MS 520 MH+
Example 10
-continued
298
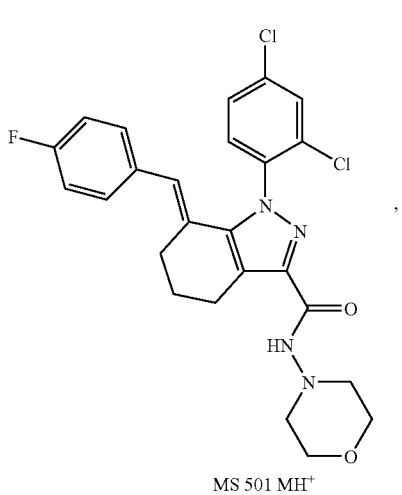
MS 501 MH+
305
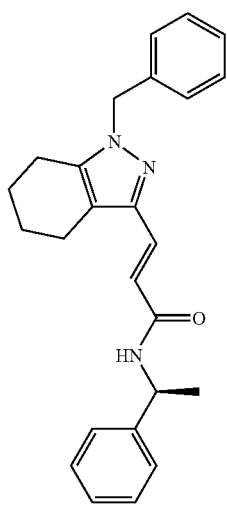
MS 386 MH+

307
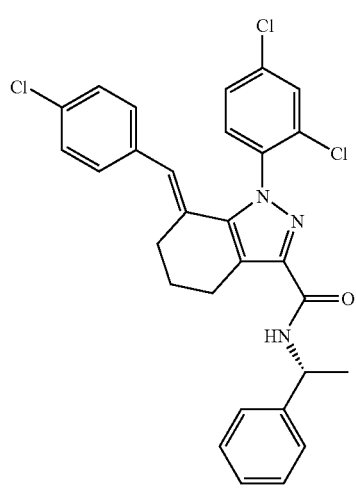
MS 536 MH+
320
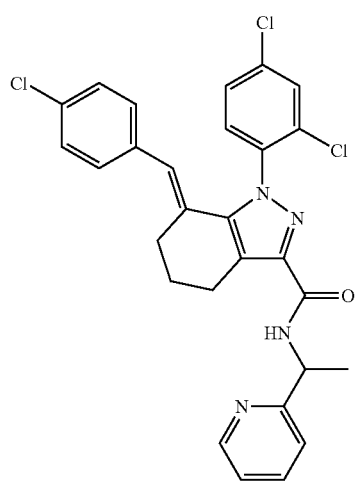
MS 537 MH+
338
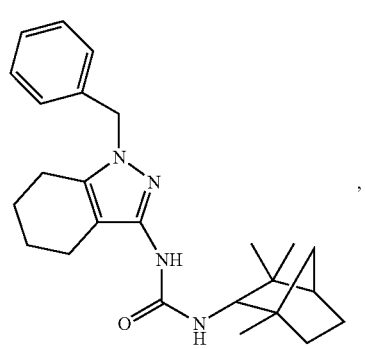
MS 407 MH+
353
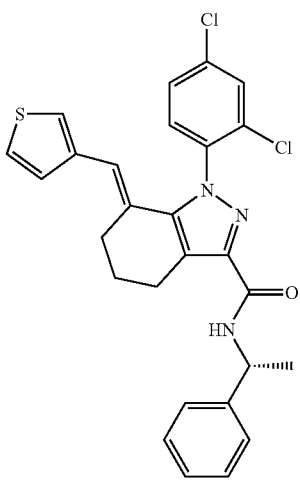
MS 507.9 MH+
364
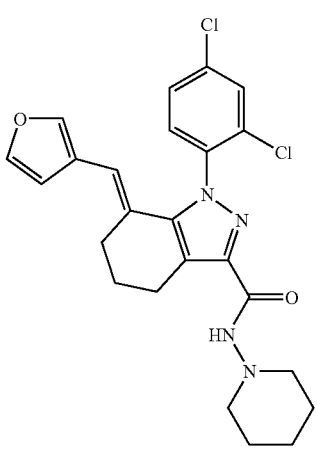
MS 472.1 MH+

374
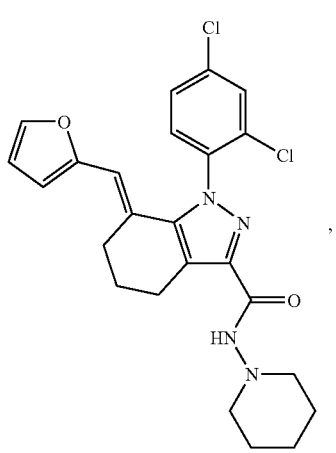
MS 471 MH+
384
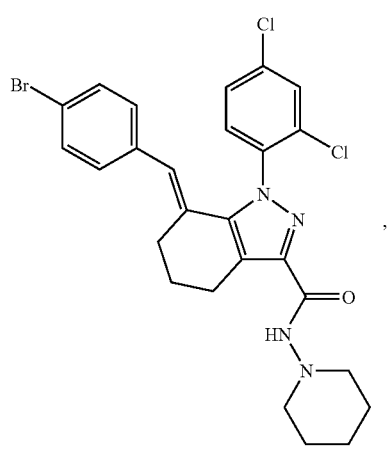
MS 559 MH+
386
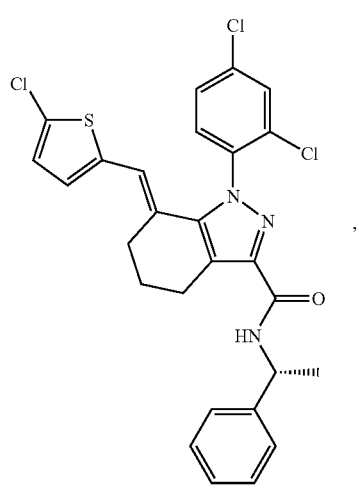
MS 544 MH+
394
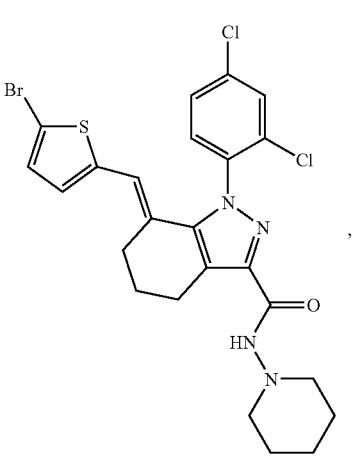
MS 550.9 MH+
398
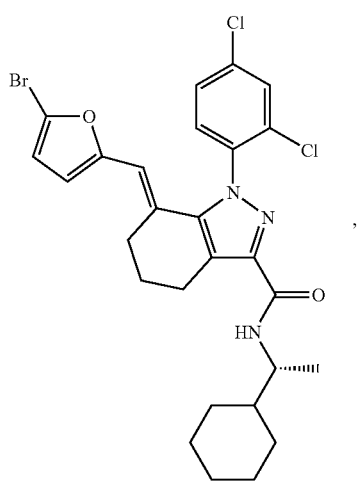
MS 578 MH+

399
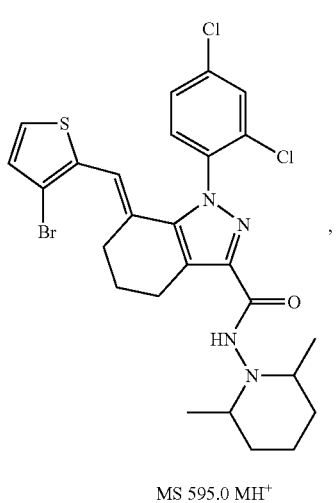
MS 595.0 MH+
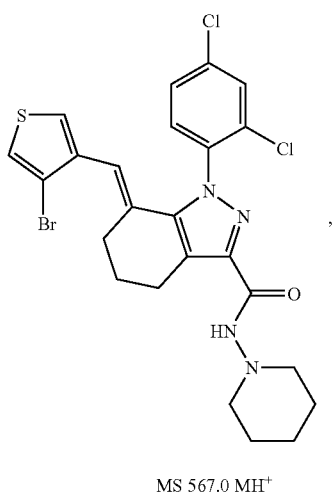
MS 567.0 MH+
and pharmaceutically acceptable forms thereof.
Another example of the present invention is a compound selected from:
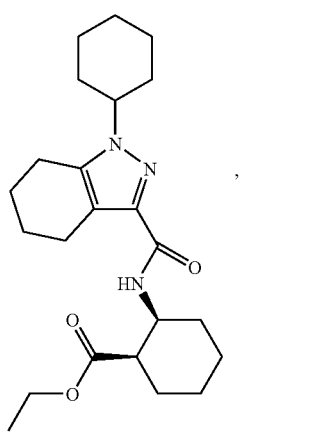
MS 402.1 MH+
83
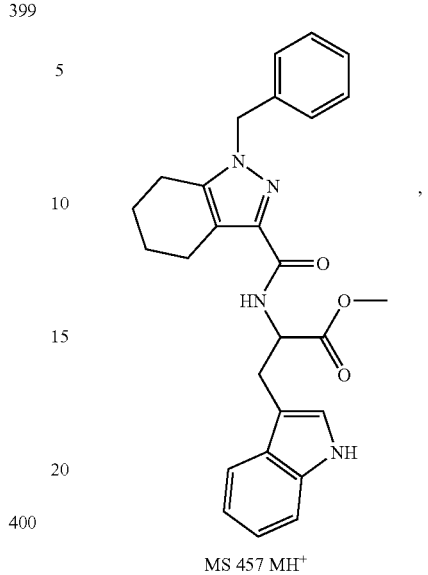
MS 457 MH+
154
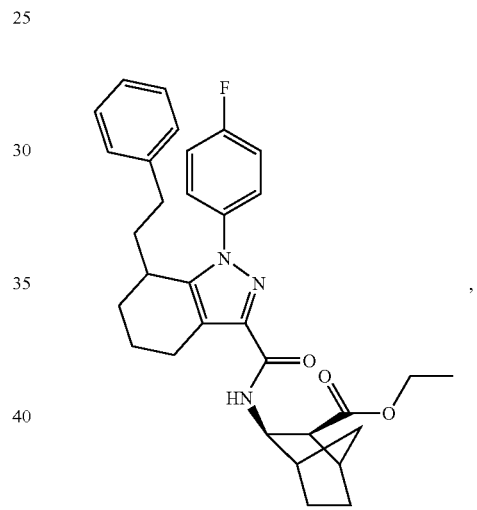
MS 530.2 MH+
194
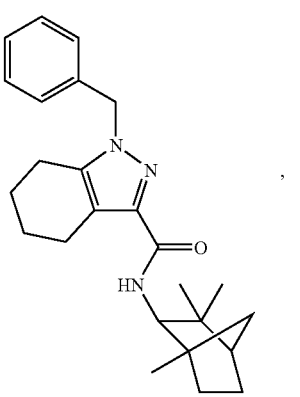
Example 2

-continued
253
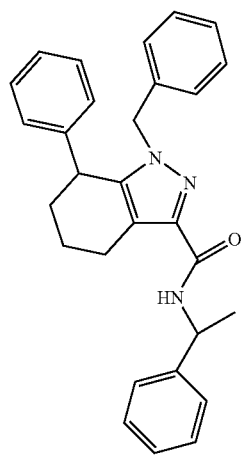
MS 436 MH+
295
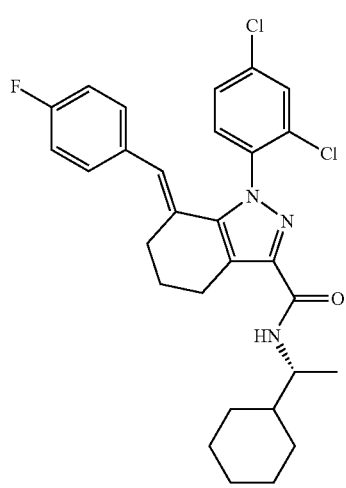
MS 526 MH+
296
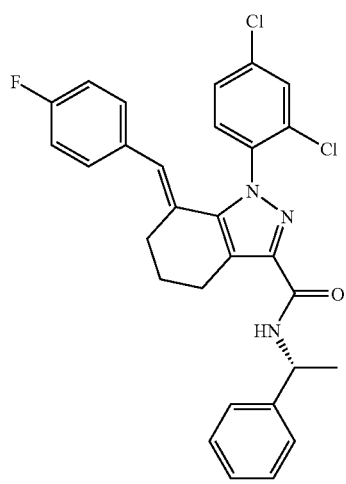
MS 520 MH+
-continued
297
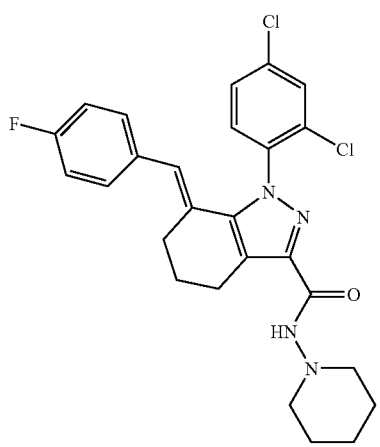
Example 10
298
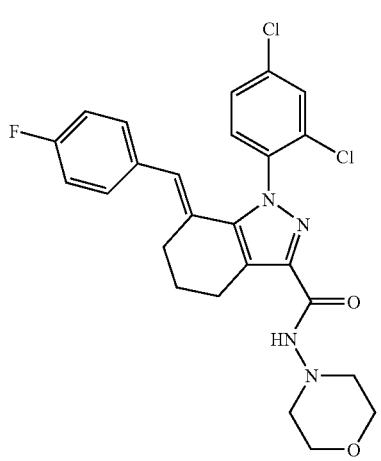
MS 501 MH+
320
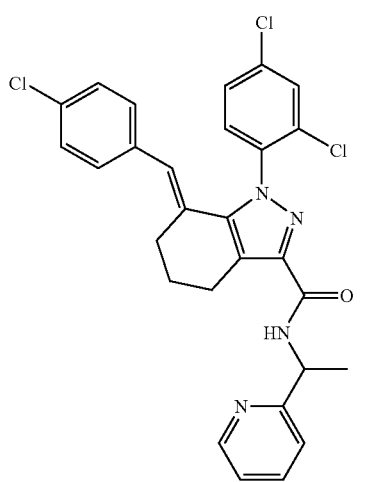
MS 537 MH+

-continued
338
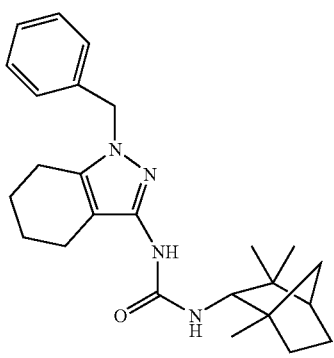
MS 407 MH+
353
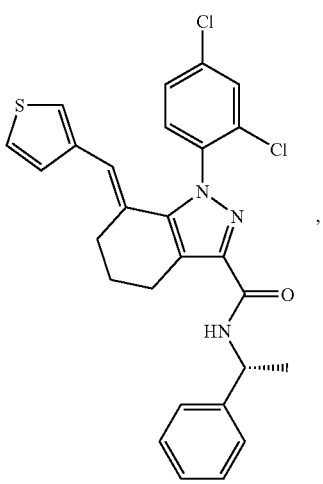
MS 507.9 MH+
364
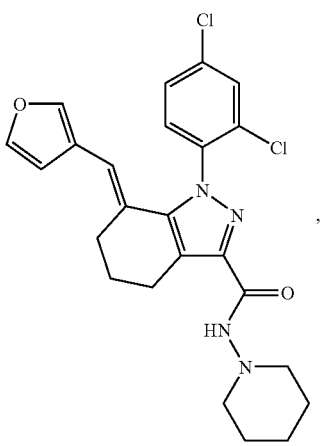
MS 472.1 MH+
-continued
384
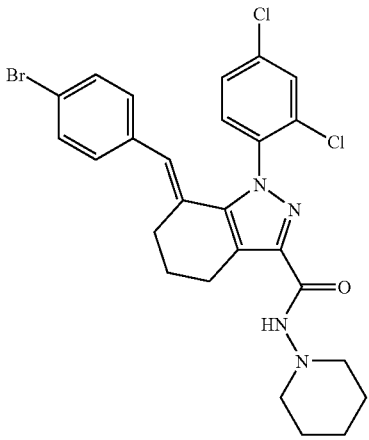
MS 559 MH+
386
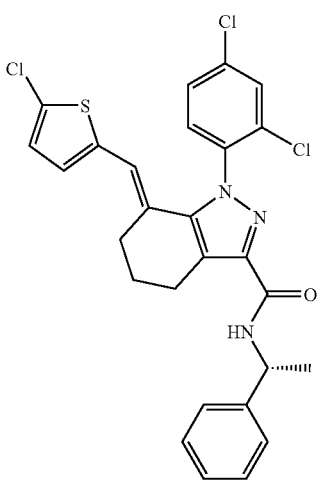
MS 544 MH+

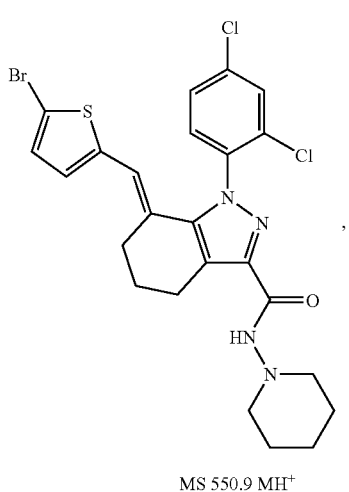

394

MS 550.9 MH⁺

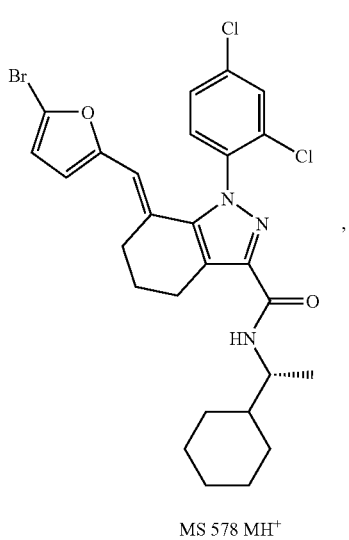

398

MS 578 MH⁺

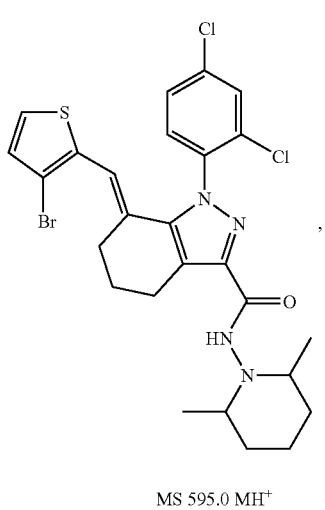

399

MS 595.0 MH⁺

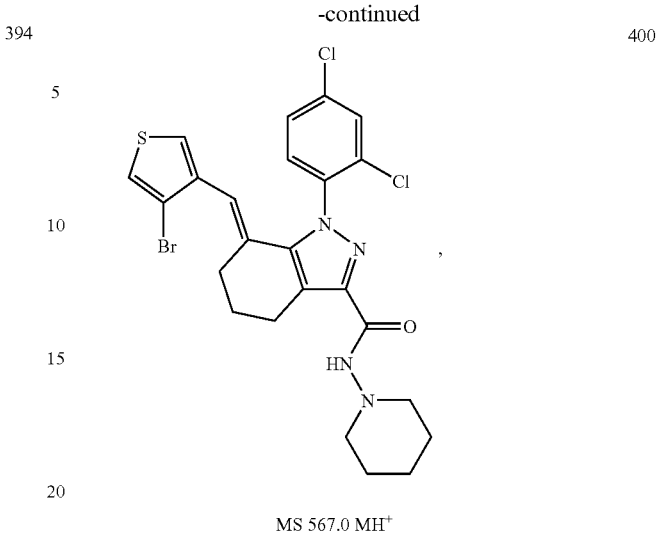

MS 567.0 MH⁺ and pharmaceutically acceptable forms thereof.

Definitions

As used herein, the following terms have the following meanings:

The term "alkyl" means a saturated branched or straight chain monovalent hydrocarbon radical of up to 10 carbon atoms. Alkyl typically includes, but is not limited to, methyl, ethyl, propyl, isopropyl, n-butyl, t-butyl, pentyl, hexyl, heptyl and the like.

The term "lower alkyl" means an alkyl radical of up to 4 carbon atoms. The point of attachment may be on any alkyl or lower alkyl carbon atom and, when further substituted, substituent variables may be placed on any carbon atom.

The term "alkylene" means a saturated branched or straight chain monovalent hydrocarbon linking group of up to 10 carbon atoms, whereby the linking group is derived by the removal of one hydrogen atom each from two carbon atoms. Alkylene typically includes, but is not limited to, methylene, ethylene, propylene, isopropylene, n-butylene, t-butylene, pentylene, hexylene, heptylene and the like. The term "lower alkylene" means an alkylene linking group of up to 4 carbon atoms. The point of attachment may be on any alkylene or lower alkylene carbon atom and, when further substituted, substituent variables may be placed on any carbon atom.

The term "alkylidene" means an alkylene linking group of from 1 to 10 carbon atoms having at least one double bond formed between two adjacent carbon atoms, wherein the double bond is derived by the removal of one hydrogen atom each from the two carbon atoms. Atoms may be oriented about the double bond in either the cis (E) or trans (Z) conformation. Alkylidene typically includes, but is not limited to, methylidene, vinylidene, propylidene, iso-propylidene, methallylene, allylidene (2-propenylidene), crotylene (2-butenylene), prenylene (3-methyl-2-butenylene) and the like. The term "lower alkylidene" means a radical or linking group of from 1 to 4 carbon atoms. The point of attachment may be on any alkylidene or lower alkylidene carbon atom and, when further substituted, substituent variables may be placed on any carbon atom.

The term "alkoxy" means an alkyl, alkylene or alkylidene radical of up to 10 carbon atoms attached via an oxygen atom, whereby the point of attachment is formed by the removal of the hydrogen atom from a hydroxide substituent on a parent radical. The term "lower alkoxy" means an alkyl, alkylene or alkylidene radical of up to 4 carbon atoms. Lower alkoxy typically includes, but is not limited to, methoxy, ethoxy, propoxy, butoxy and the like. When further substituted, substituent variables may be placed on any alkoxy carbon atom.

The term "cycloalkyl" means a saturated or partially unsaturated monocyclic, polycyclic or bridged hydrocarbon ring system radical or linking group. A ring of 3 to 20 carbon atoms may be designated by $C_{3-20}$ cycloalkyl; a ring of 3 to 12 carbon atoms may be designated by $C_{3-12}$ cycloalkyl, a ring of 3 to 8 carbon atoms may be designated by $C_{3-8}$ cycloalkyl and the like.

Cycloalkyl typically includes, but is not limited to, cyclopropyl, cyclobutyl, cyclopentyl, cyclohexyl, cyclohexenyl, cycloheptyl, cyclooctyl, indanyl, indenyl, 1,2,3,4-tetrahydronaphthalenyl, 5,6,7,8-tetrahydro-naphthalenyl, 6,7,8,9-tetrahydro-5H-benzocycloheptenyl, 5,6,7,8,9,10-hexahydro-benzocyclooctenyl, fluorenyl, bicyclo[2.2.1]heptyl, bicyclo[2.2.1]heptenyl, bicyclo[2.2.2]octyl, bicyclo[3.1.1]heptyl, bicyclo[3.2.1]octyl, bicyclo[2.2.2]octenyl, bicyclo[3.2.1]octenyl, adamantanyl, octahydro-4,7-methano-1H-indenyl, octahydro-2,5-methano-pentalenyl and the like. When further substituted, substituent variables may be placed on any ring carbon atom.

The term "heterocyclyl" means a saturated, partially unsaturated or unsaturated monocyclic, polycyclic or bridged hydrocarbon ring system radical or linking group, wherein at least one ring carbon atom has been replaced with one or more heteroatoms independently selected from N, O or S. A heterocyclyl ring system further includes a ring system having up to 4 nitrogen atom ring members or a ring system having from 0 to 3 nitrogen atom ring members and 1 oxygen or sulfur atom ring member. When allowed by available valences, up to two adjacent ring members may be a heteroatom, wherein one heteroatom is nitrogen and the other is selected from N, O or S. A heterocyclyl radical is derived by the removal of one hydrogen atom from a single carbon or nitrogen ring atom. A heterocyclyl linking group is derived by the removal of two hydrogen atoms each from either carbon or nitrogen ring atoms.

Heterocyclyl typically includes, but is not limited to, furyl, thienyl, 2H-pyrrole, 2-pyrrolinyl, 3-pyrrolinyl, pyrrolidinyl, pyrrolyl, 1,3-dioxolanyl, oxazolyl, thiazolyl, imidazolyl, 2-imidazolinyl (also referred to as 4,5-dihydro-1H-imidazolyl), imidazolidinyl, 2-pyrazolinyl, pyrazolidinyl, pyrazolyl, isoxazolyl, isothiazolyl, oxadiazolyl, triazolyl, thiadiazolyl, tetrazolyl, 2H-pyran, 4H-pyran, pyridinyl, piperidinyl, 1,4-dioxanyl, morpholinyl, 1,4-dithianyl, thiomorpholinyl, pyridazinyl, pyrimidinyl, pyrazinyl, piperazinyl, azepanyl, indolizinyl, indolyl, isoindolyl, 3H-indolyl, indolinyl, benzo[b]furyl, benzo[b]thienyl, 1H-indazolyl, benzimidazolyl, benzthiazolyl, purinyl, 4H-quinolizinyl, quinolinyl, isoquinolinyl, cinnolinyl, phthalzinyl, quinazolinyl, quinoxalinyl, 1,8-naphthyridinyl, pteridinyl, quinuclidinyl, hexahydro-1,4-diazepinyl, 1,3-benzodioxolyl (also known as 1,3-methylenedioxyphenyl), 2,3-dihydro-1,4-benzodioxinyl (also known as 1,4-ethylenedioxyphenyl), benzo-dihydro-furyl, benzo-tetrahydro-pyranyl, benzo-dihydro-thienyl, 5,6,7,8-tetrahydro-4H-cyclohepta(b)thienyl, 5,6,7-trihydro-4H-cyclohexa(b)thienyl, 5,6-dihydro-4H-cyclopenta(b)thienyl, 2-aza-bicyclo[2.2.1]heptyl, 1-aza-bicyclo[2.2.2]octyl, 8-aza-bicyclo[3.2.1]octyl, 7-oxa-bicyclo[2.2.1]heptyl and the like.

The term "aryl" means an unsaturated, conjugated π electron monocyclic or polycyclic hydrocarbon ring system radical or linking group of 6, 9, 10 or 14 carbon atoms. An aryl radical is derived by the removal of one hydrogen atom from a single carbon ring atom. An arylene linking group is derived by the removal of two hydrogen atoms each of two carbon ring atoms. Aryl typically includes, but is not limited to, phenyl, naphthalenyl, azulenyl, anthracenyl and the like.

The term "carbonyl" means a linking group of the formula —C(O)— or —C(=O)—.

The term "alkoxycarbonyl" means a radical of the formula —C(O)O-alkyl.

The term "carboxy" means a radical of the formula —COOH or —CO₂H.

The term "aryloxy" means a radical of the formula —O-aryl.

The term "aryloxycarbonyl" means a radical of the formula —C(O)O-aryl.

The term "arylalkoxycarbonyl" means a radical of the formula —C(O)O-alkyl-aryl.

The term "halo" or "halogen" means fluoro, chloro, bromo or iodo.

The term "substituted" means one or more hydrogen atoms on a core molecule have been replaced with one or more radicals or linking groups, wherein the linking group, by definition is also further substituted.

The term "dependently selected" means one or more substituent variables are present in a specified combination (e.g. groups of substituents commonly appearing in a tabular list).

The substituent nomenclature used in the disclosure of the present invention was derived using nomenclature rules well known to those skilled in the art (e.g., IUPAC).

Pharmaceutical Preparations and Methods of Use

The compounds of the present invention may also be present in the form of pharmaceutically acceptable salts. For use in medicines, the salts of the compounds of this invention refer to non-toxic "pharmaceutically acceptable salts." FDA approved pharmaceutically acceptable salt forms (Ref. International J. Pharm. 1986, 33, 201-217; J. Pharm. Sci., 1977, January, 66(1), p1) include pharmaceutically acceptable acidic/anionic or basic/cationic salts.

Pharmaceutically acceptable acidic/anionic salts include, and are not limited to acetate, benzenesulfonate, benzoate, bicarbonate, bitartrate, bromide, calcium edetate, camsylate, carbonate, chloride, citrate, dihydrochloride, edetate, edisylate, estolate, esylate, fumarate, glyceptate, gluconate, glutamate, glycollylarsanilate, hexylresorcinate, hydrabamine, hydrobromide, hydrochloride, hydroxynaphthoate, iodide, isethionate, lactate, lactobionate, malate, maleate, mandelate, mesylate, methylbromide, methylnitrate, methylsulfate, mucate, napsylate, nitrate, pamoate, pantothenate, phosphate/diphosphate, polygalacturonate, salicylate, stearate, subacetate, succinate, sulfate, tannate, tartrate, teoclate, tosylate and triethiodide. Organic or inorganic acids also include, and are not limited to, hydroiodic, perchloric, sulfuric, phosphoric, propionic, glycolic, methanesulfonic, hydroxyethanesulfonic, oxalic, 2-naphthalenesulfonic, p-toluenesulfonic, cyclohexanesulfamic, saccharinic or trifluoroacetic acid.

Pharmaceutically acceptable basic/cationic salts include, and are not limited to aluminum, 2-amino-2-hydroxymethyl-propane-1,3-diol (also known as tris(hydroxymethyl)aminomethane, tromethane or "TRIS"), ammonia, benzathine, t-butylamine, calcium, calcium gluconate, calcium hydroxide, chloroprocaine, choline, choline bicarbonate, choline chloride, cyclohexylamine, diethanolamine, ethylenediamine, lithium, LiOMe, L-lysine, magnesium, meglumine, $NH_3$, $NH_4OH$, N-methyl-D-glucamine, piperidine, potassium, potassium-t-butoxide, potassium hydroxide (aqueous), procaine, quinine, sodium, sodium carbonate, sodium-2-ethylhexanoate (SEH), sodium hydroxide, triethanolamine (TEA) or zinc.

The present invention includes within its scope prodrugs and metabolites of the compounds of this invention. In general, such prodrugs and metabolites will be functional derivatives of the compounds that are readily convertible in vivo into an active compound.

Thus, in the methods of treatment of the present invention, the term "administering" shall encompass the means for treating, ameliorating or preventing a syndrome, disorder or disease described herein with a compound specifically disclosed or a compound, or prodrug or metabolite thereof, which would obviously be included within the scope of the invention albeit not specifically disclosed for certain of the instant compounds.

The term "prodrug" means a pharmaceutically acceptable form of a functional derivative of a compound of the invention (or a salt thereof), wherein the prodrug may be: 1) a relatively active precursor which converts in vivo to an active prodrug component; 2) a relatively inactive precursor which converts in vivo to an active prodrug component; or 3) a relatively less active component of the compound that contributes to therapeutic biological activity after becoming available in vivo (i.e., as a metabolite). Conventional procedures for the selection and preparation of suitable prodrug derivatives are described in, for example, "*Design of Prodrugs*", ed. H. Bundgaard, Elsevier, 1985.

The term "metabolite" means a pharmaceutically acceptable form of a metabolic derivative of a compound of the invention (or a salt thereof), wherein the derivative is a relatively less active component of the compound that contributes to therapeutic biological activity after becoming available in vivo.

The present invention contemplates compounds of various isomers and mixtures thereof. The term "isomer" refers to compounds that have the same composition and molecular weight but differ in physical and/or chemical properties. Such substances have the same number and kind of atoms but differ in structure. The structural difference may be in constitution (geometric isomers) or in an ability to rotate the plane of polarized light (stereoisomers).

The term "stereolsomer" refers to isomers of identical constitution that differ in the arrangement of their atoms in space. Enantiomers and diastereomers are stereoisomers wherein an asymmetrically substituted carbon atom acts as a chiral center. The term "chiral" refers to a molecule that is not superposable on its mirror image, implying the absence of an axis and a plane or center of symmetry. The term "enantiomer" refers to one of a pair of molecular species that are mirror images of each other and are not superposable. The term "diastereomer" refers to stereoisomers that are not related as mirror images. The symbols "R" and "S" represent the configuration of substituents around a chiral carbon atom(s). The symbols "R*" and "S*" denote the relative configurations of substituents around a chiral carbon atom(s).

The term "racemate" or "racemic mixture" refers to a compound of equimolar quantities of two enantiomeric species, wherein the compound is devoid of optical activity. The term "optical activity" refers to the degree to which a chiral molecule or nonracemic mixture of chiral molecules rotates the plane of polarized light.

The term "geometric isomer" refers to isomers that differ in the orientation of substituent atoms in relationship to a carbon-carbon double bond, to a cycloalkyl ring or to a bridged bicyclic system. Substituent atoms (other than H) on each side of a carbon-carbon double bond may be in an E or Z configuration. In the "E" (opposite sided) or "chair" configuration, the substituents are on opposite sides in relationship to the carbon-carbon double bond; in the "Z" (same sided) or "boat" configuration, the substituents are oriented on the same side in relationship to the carbon-carbon double bond. Substituent atoms (other than H) attached to a carbocyclic ring may be in a cis or trans configuration. In the "cis" configuration, the substituents are on the same side in relationship to the plane of the ring; in the "trans" configuration, the substituents are on opposite sides in relationship to the plane of the ring. Compounds having a mixture of "cis" and "trans" species are designated "cis/trans". Substituent atoms (other than H) attached to a bridged bicyclic system may be in an "endo" or "exo" configuration. In the "endo" configuration, the substituents attached to a bridge (not a bridgehead) point toward the larger of the two remaining bridges; in the "exo" configuration, the substituents attached to a bridge point toward the smaller of the two remaining bridges.

It is to be understood that the various substituent stereoisomers, geometric isomers and mixtures thereof used to prepare compounds of the present invention are either commercially available, can be prepared synthetically from commercially available starting materials or can be prepared as isomeric mixtures and then obtained as resolved isomers using techniques well-known to those of ordinary skill in the art.

The isomeric descriptors "R," "S," "S*," "R*," "E," "Z," "cis," "trans," "exo" and "endo" are used as described herein for indicating atom configuration(s) relative to a core molecule and are intended to be used as defined in the literature (IUPAC Recommendations for Fundamental Stereochemistry (Section E), *Pure Appl. Chem.*, 1976, 45:13-30).

The compounds of the present invention may be prepared as individual isomers by either isomer-specific synthesis or resolved from an isomeric mixture. Conventional resolution techniques include forming the free base of each isomer of an isomeric pair using an optically active salt (followed by fractional crystallization and regeneration of the free base), forming an ester or amide of each of the isomers of an isomeric pair (followed by chromatographic separation and removal of the chiral auxiliary) or resolving an isomeric mixture of either a starting material or a final product using preparative TLC (thin layer chromatography) or a chiral HPLC column.

Furthermore, compounds of the present invention may have one or more polymorph or amorphous crystalline forms and as such are intended to be included in the scope of the invention. In addition, some of the compounds may form solvates with water (i.e., hydrates) or common organic solvents, and such are also intended to be encompassed within the scope of this invention.

During any of the processes for preparation of the compounds of the present invention, it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991. The protecting groups may be removed at a convenient subsequent stage using methods known in the art.

Therapeutic Use

CB1 and CB2 cannabinoid receptors belong to the G-protein-coupled receptor (GCPR) family, a receptor super-family with a distinctive pattern of seven transmembrane domains, which inhibits N-type calcium channels and/or adenylate cyclase to inhibit Q-type calcium channels. CB1 receptors are present in the CNS, predominately expressed in brain regions associated with memory and movement such as the hippocampus (memory storage), cerebellum (coordination of motor function, posture and balance), basal ganglia (movement control), hypothalamus (thermal regulation, neuroendocrine release, appetite), spinal cord (nociception), cerebral cortex (emesis) and periphery regions such as lymphoid organs (cell mediated and innate immunity), vascular smooth muscle cells (blood pressure), gastrointestinal tract (duodenum, ileum and myenteric plexus for emesis control), lung smooth muscle cells (bronchodilation), eye ciliary body (intraocular pressure). CB2 receptors appear to be primarily expressed peripherally in lymphoid tissue (cell mediated and innate immunity), peripheral nerve terminals (peripheral nervous system), spleen immune cells (immune system modulation) and retina (intraocular pressure) and in the CNS in cerebellar granule cell mRNA (coordination of motor function). Pharmacological and physiological evidence also suggests that there may be other cannabinoid receptor subtypes that have yet to be cloned and characterized.

Where activation or inhibition of a CB receptor appears to mediate various syndromes, disorders or diseases, potential areas of clinical application include, but are not limited to, controlling appetite, regulating metabolism, diabetes, reducing glaucoma-associated intraocular pressure, treating social and mood disorders, treating seizure-related disorders, treating substance abuse disorders, enhancing learning, cognition and memory, controlling organ contraction and muscle spasm, treating respiratory disorders, treating locomotor activity or movement disorders, treating immune and inflammation disorders, regulating cell growth, use in pain management, use as a neuroprotective agent and the like.

Thus, cannabinoid receptor modulators, including the compounds of the formula (I), (Ia), (Ib) or (Ic) of the present invention, are useful for treating, ameliorating or preventing a cannabinoid receptor mediated syndrome, disorder or disease including, but not limited to, controlling appetite, regulating metabolism, diabetes, glaucoma-associated intraocular pressure, pain, social and mood disorders, seizure-related disorders, substance abuse disorders, learning, cognition and/or memory disorders, respiratory disorders, locomotor activity disorders, movement disorders, immune disorders or inflammation disorders, controlling organ contraction and muscle spasm, enhancing learning, cognition and/or memory, regulating cell growth, providing neuroprotection and the like.

The present invention is directed to a method for treating, ameliorating or preventing a cannabinoid receptor mediated syndrome, disorder or disease in a subject in need thereof comprising the step of administering to the subject an effective amount of a compound of formula (I).

The present invention is directed to a method for treating, ameliorating or preventing a cannabinoid receptor mediated syndrome, disorder or disease in a subject in need thereof comprising the step of administering to the subject an effective amount of a compound of formulae (Ia), (Ib) or (Ic) or prodrug, metabolite, or composition thereof.

The present invention is directed to a method for treating, ameliorating or preventing a cannabinoid receptor mediated syndrome, disorder or disease in a subject in need thereof comprising the step of administering to the subject a combination product and/or therapy comprising an effective amount of a compound of formula (I) and a therapeutic agent.

The present invention is directed to a method for treating, ameliorating or preventing a cannabinoid receptor mediated syndrome, disorder or disease in a subject in need thereof comprising the step of administering to the subject a combination product and/or therapy comprising an effective amount of a compound of formulae (Ia), (Ib), or (Ic) and a therapeutic agent.

Therapeutic agents contemplated for use in a combination product and/or therapies of the present invention include an anticonvulsant or a contraceptive agent. The anticonvulsant agents include, and are not limited to, topiramate, analogs of topiramate, carbamazepine, valproic acid, lamotrigine, gabapentin, phenyloin and the like and mixtures or pharmaceutically acceptable salts thereof. The contraceptive agents include, and are not limited to, such as progestin-only contraceptives and contraceptives that include both a progestin component and an estrogen component. The invention further includes a pharmaceutical composition wherein the contraceptive is an oral contraceptive, and wherein the contraceptive optionally includes a folic acid component.

The invention also includes a method of contraception in a subject comprising the step of administering to the subject a composition, wherein the composition comprises a contraceptive and a CB1 receptor inverse-agonist or antagonist compound of formulae (I), (Ia), (Ib) or (Ic), wherein the composition reduces the urge to smoke in the subject and/or assists the subject in losing weight.

The present invention includes cannabinoid receptor modulators useful for treating, ameliorating or preventing a CB receptor mediated syndrome, disorder or disease. The usefulness of a compound of the present invention or composition thereof as a CB modulator can be determined according to the methods disclosed herein. The scope of such use includes treating, ameliorating or preventing a plurality of CB receptor mediated syndromes, disorders or diseases.

The present invention is also directed to a method for treating, ameliorating or preventing a CB receptor mediated syndrome, disorder or disease in a subject in need thereof wherein the syndrome, disorder or disease is related to appetite, metabolism, diabetes, glaucoma-associated intraocular pressure, social and mood disorders, seizures, substance abuse, learning, cognition or memory, organ contraction or muscle spasm, respiratory disorders, locomotor activity or movement disorders, immune and inflammation disorders, unregulated cell growth, pain management, neuroprotection and the like.

A compound of formulae (I), (Ia), (Ib) or (Ic) for use as a CB receptor modulator includes a compound having a mean inhibition constant ($IC_{50}$) for CB receptor binding activity of between about 5 µM to about 0.01 nM; between about 1 µM to about 0.01 nM; between about 800 nM to about 0.01 nM; between about 200 nM to about 0.01 nM; between about 100 nM to about 0.01 nM; between about 80 nM to about 0.01 nM; between about 20 nM to about 0.01 nM; between about 10 nM to about 0.1 nM; or about 1 nM.

A compound of formulae (I), (Ia), (Ib) or (Ic) for use as a CB receptor modulator of the invention includes a compound having a CB1 agonist $IC_{50}$ for CB1 agonist binding activity of between about 5 µM to about 0.01 nM; between about 1 µM to about 0.01 nM; between about 800 nM to about 0.01 nM; between about 200 nM to about 0.01 nM; between about 100 nM to about 0.01 nM; between about 80 nM to about 0.01 nM; between about 20 nM to about 0.01 nM; between about 10 nM to about 0.1 nM; or about 1 nM.

A compound of formulae (I), (Ia), (Ib) or (Ic) for use as a CB receptor modulator of the invention includes a compound having a CB1 antagonist $IC_{50}$ for CB1 antagonist binding activity of between about 5 µM to about 0.01 nM; between about 1 µM to about 0.01 nM; between about 800 nM to about 0.01 nM; between about 200 nM to about 0.01 nM; between about 100 nM to about 0.01 nM; between about 80 nM to about 0.01 nM; between about 20 nM to about 0.01 nM; between about 10 nM to about 0.1 nM; or about 1 nM.

A compound of formulae (I), (Ia), (Ib) or (Ic) for use as a CB receptor modulator of the invention includes a compound having a CB1 inverse-agonist $IC_{50}$ for CB1 inverse-agonist binding activity of between about 5 µM to about 0.01 nM; between about 1 µM to about 0.01 nM; between about 800 nM to about 0.01 nM; between about 200 nM to about 0.01 nM; between about 100 nM to about 0.01 nM; between about 80 nM to about 0.01 nM; between about 20 nM to about 0.01 nM; between about 10 nM to about 0.1 nM; or about 1 nM.

A compound of formulae (I), (Ia), (Ib) or (Ic) for use as a CB receptor modulator of the invention includes a compound having a CB2 agonist $IC_{50}$ for CB2 agonist binding activity of between about 5 µM to about 0.01 nM; between about 1 µM to about 0.01 nM; between about 800 nM to about 0.01 nM; between about 200 nM to about 0.01 nM; between about 100 nM to about 0.01 nM; between about 80 nM to about 0.01 nM; between about 20 nM to about 0.01 nM; between about 10 nM to about 0.1 nM; or about 1 nM.

A compound of formulae (I), (Ia), (Ib) or (Ic) for use as a CB receptor modulator of the invention includes a compound having a CB2 antagonist $IC_{50}$ for CB2 antagonist binding activity of between about 5 µM to about 0.01 nM; between about 1 µM to about 0.01 nM; between about 800 nM to about 0.01 nM; between about 200 nM to about 0.01 nM; between about 100 nM to about 0.01 nM; between about 80 nM to about 0.01 nM; between about 20 nM to about 0.01 nM; between about 10 nM to about 0.1 nM; or about 1 nM.

A compound of formulae (I), (Ia), (Ib) or (Ic) for use as a CB receptor modulator of the invention includes a compound having a CB2 inverse-agonist $IC_{50}$ for CB2 inverse-agonist binding activity of between about 5 µM to about 0.01 nM; between about 1 µM to about 0.01 nM; between about 800 nM to about 0.01 nM; between about 200 nM to about 0.01 nM; between about 100 nM to about 0.01 nM; between about 80 nM to about 0.01 nM; between about 20 nM to about 0.01 nM; between about 10 nM to about 0.1 nM; or about 1 nM.

The term "cannabinoid receptor" refers to any one of the known or heretofore unknown subtypes of the class of cannabinoid receptors that may be bound by a cannabinoid modulator compound of the present invention; in particular, a cannabinoid receptor selected from the group consisting of a CB1 receptor and a CB2 receptor. The term "modulator" further refers to the use of a compound of the invention as a CB receptor agonist, antagonist or inverse-agonist.

The present invention includes a method for treating, ameliorating or preventing a CB receptor mediated syndrome, disorder or disease in a subject in need thereof comprising the step of administering to the subject an effective amount of a compound of the present invention or composition thereof, wherein the cannabinoid receptor is a CB1 or CB2 receptor; and, the compound is an agonist, antagonist or inverse-agonist of the receptor.

The present invention includes a method for treating, ameliorating or preventing a CB receptor mediated syndrome, disorder or disease in a subject in need thereof comprising the step of administering to the subject an effective amount of a compound of the present invention in a combination product and/or therapy with a therapeutic agent such as an anticonvulsant or contraceptive agent or composition thereof, wherein the cannabinoid receptor is a CB1 or CB2 receptor; and, the compound is an agonist, antagonist or inverse-agonist of the receptor.

It should be understood that contraceptive agents suitable for use in a combination product and/or therapy are not limited to oral contraceptives, but also include other commonly available contraceptives such as those that are administered transdermally, by injection or via implant.

Except as further specified, "combination product and/or therapy" means a pharmaceutical composition comprising a compound of formulae (I), (Ia), (Ib) or (Ic) in combination with one or more therapeutic agents. The dosages of the compound of formula (I) and the one or more therapeutic agents are adjusted when combined to achieve an effective amount.

The term "subject" as used herein, refers to a patient, which may be an animal, preferably a mammal, most preferably a human, which has been the object of treatment, observation or experiment and is at risk of (or susceptible to) developing a CB receptor mediated syndrome, disorder or disease.

The term "administering" is to be interpreted in accordance with the methods of the present invention. Such methods include therapeutically or prophylactically administering an effective amount of a composition or medicament of the present invention at different times during the course of a therapy or concurrently as a product in a combination form.

Prophylactic administration can occur prior to the manifestation of symptoms characteristic of a CB receptor mediated syndrome, disorder or disease such that the syndrome, disorder or disease is treated, ameliorated, prevented or otherwise delayed in its progression. The methods of the present invention are further to be understood as embracing all therapeutic or prophylactic treatment regimens used by those skilled in the art.

The term "effective amount" refers to that amount of active compound or pharmaceutical agent that elicits the biological or medicinal response in a tissue system, animal or human, that is being sought by a researcher, veterinarian, medical doctor, or other clinician, which includes alleviation of the symptoms of the syndrome, disorder or disease being treated. The effective amount of a compound of the invention is from about 0.001 mg/kg/day to about 300 mg/kg/day.

Wherein the present invention is directed to the administration of a combination of a compound of formula (I) and an anticonvulsant or contraceptive agent, the term "effective amount" means that amount of the combination of agents taken together so that the combined effect elicits the desired biological or medicinal response.

As those skilled in the art will appreciate, the effective amounts of the components comprising the combination product may be independently optimized and combined to achieve a synergistic result whereby the pathology is reduced more than it would be if the components of the combination product were used alone.

For example, the effective amount of a combination product and/or therapy comprising administration of a compound of formula (I) and topiramate would be the amount of the compound of formula (I) and the amount of topiramate that when taken together or sequentially have a combined effect that is effective. Further, it will be recognized by one skilled in the art that in the case of combination product and/or therapy with an effective amount, as in the example above, the amount of the compound of formula (I) and/or the amount of the anticonvulsant (e.g., topiramate) individually may or may not be effective.

Wherein the present invention is directed to the administration of a combination product and/or therapy, the instant compound and the anticonvulsant or contraceptive agent may be co-administered by any suitable means, simultaneously, sequentially or in a single pharmaceutical composition. Where the instant compound(s) and the anticonvulsant or contraceptive agent components are administered separately, the number of dosages of each compound(s) given per day, may not necessarily be the same, e.g. where one compound may have a greater duration of activity, and will therefore, be administered less frequently.

The compound(s) of formula (I) and the anticonvulsant(s) or contraceptive agent(s) may be administered via the same or different routes of administration. The compound(s) of formula (I) and the anticonvulsant(s) or contraceptive agent(s) may be administered via the same or different routes of administration.

Suitable examples of methods of administration are orally, intravenous (iv), intramuscular (im), and subcutaneous (sc). Compounds may also be administrated directly to the nervous system including, but not limited to the intracerebral, intraventricular, intracerebroventricular, intrathecal, intracisternal, intraspinal and/or peri-spinal routes of administration by delivery via intracranial or intravertebral needles and/or catheters with or without pump devices.

The compound(s) of formula (I) and the anticonvulsant(s) or contraceptive agent(s) may be administered according to simultaneous or alternating regimens, at the same or different times during the course of the therapy, concurrently in divided or single forms.

Optimal dosages to be administered may be readily determined by those skilled in the art, and will vary with the particular compound used, the mode of administration, the strength of the preparation and the advancement of the disease condition. In addition, factors associated with the particular patient being treated, including patient's sex, age, weight, diet, time of administration and concomitant diseases, will result in the need to adjust dosages.

The term "CB receptor mediated syndrome, disorder, or disease" refers to syndromes, disorders or diseases associated with a biological response mediated by a CB receptor such that there is discomfort or decreased life expectancy to the organism.

CB receptor mediated syndromes, disorders or diseases can occur in both animals and humans and include appetite, metabolism, diabetes, obesity, glaucoma-associated intraocular pressure, social, mood, seizure, substance abuse, learning, cognition, memory, organ contraction, muscle spasm, respiratory, locomotor activity, movement, immune, inflammation, cell growth, pain or neurodegenerative related syndromes, disorders or diseases.

Appetite related syndromes, disorders or diseases include obesity, overweight condition, anorexia, bulimia, cachexia, dysregulated appetite and the like.

Obesity related syndromes, disorders or diseases include obesity as a result of genetics, diet, food intake volume, metabolic syndrome, disorder or disease, hypothalmic disorder or disease, age, reduced activity, abnormal adipose mass distribution, abnormal adipose compartment distribution and the like.

Metabolism related syndromes, disorders or diseases include metabolic syndrome, dyslipidemia, elevated blood pressure, diabetes, insulin sensitivity or resistance, hyperinsulinemia, hypercholesterolemia, hyperi pidemias, hypertriglyceridemias, atherosclerosis, hepatomegaly, steatosis, abnormal alanine aminotransferase levels, inflammation, atherosclerosis and the like.

Diabetes related syndromes, disorders or diseases include glucose dysregulation, insulin resistance, glucose intolerance, hyperinsulinemia, dyslipidemia, hypertension, obesity and the like.

Type II diabetes mellitus (non-insulin-dependent diabetes mellitus) is a metabolic disorder (i.e., a metabolism related syndrome, disorder or disease) in which glucose dysregulation and insulin resistance results in chronic, long-term medical complications for both adolescents and adults affecting the eyes, kidneys, nerves and blood vessels and can lead to blindness, end-stage renal disease, myocardial infarction or limb amputation and the like. Glucose dysregulation includes the inability to make sufficient insulin (abnormal insulin secretion) and the inability to effectively use insulin (resistance to insulin action in target organs and tissues). Individuals suffering from Type II diabetes mellitus have a relative insulin deficiency. That is, in such individuals, plasma insulin levels are normal to high in absolute terms, although they are lower than predicted for the level of plasma glucose that is present.

Type II diabetes mellitus is characterized by the following clinical signs or symptoms: persistently elevated plasma glucose concentration or hyperglycemia; polyuria; polydipsia and/or polyphagia; chronic microvascular complications such as retinopathy, nephropathy and neuropathy; and macrovascular complications such as hyperlipidemia and hypertension. These micro-and macro-vascular complications can lead to blindness, end-stage renal disease, limb amputation and myocardial infarction.

Insulin Resistance Syndrome (IRS) (also referred to as Syndrome X, Metabolic Syndrome or Metabolic Syndrome X) is a disorder that presents risk factors for the development of Type II diabetes and cardiovascular disease including glucose intolerance, hyperinsulinemia, insulin resistance, dyslipidemia (e.g. high triglycerides, low HDL-cholesterol and the like), hypertension and obesity.

Social or mood related syndromes, disorders or diseases include depression, anxiety, psychosis, social affective disorders or cognitive disorders and the like.

Substance abuse related syndromes, disorders or diseases include drug abuse, drug withdrawal, alcohol abuse, alcohol withdrawal, nicotine withdrawal, cocaine abuse, cocaine withdrawal, heroin abuse, heroin withdrawal and the like.

Learning, cognition or memory related syndromes, disorders or diseases include memory loss or impairment as a result of age, disease, side effects of medications (adverse events) and the like.

Muscle spasm syndromes, disorders or diseases include multiple sclerosis, cerebral palsy and the like.

Locomotor activity and movement syndromes, disorders or diseases include stroke, Parkinson's disease, multiple sclerosis, epilepsy and the like.

Respiratory related syndromes, disorders or diseases include chronic pulmonary obstructive disorder, emphysema, asthma, bronchitis and the like.

Immune or inflammation related syndromes, disorders or diseases include allergy, rheumatoid arthritis, dermatitis, autoimmune disease, immunodeficiency, chronic neuropathic pain and the like.

Cell growth related syndromes, disorders or diseases include dysregulated mammalian cell proliferation, breast cancer cell proliferation, prostrate cancer cell proliferation and the like.

Pain related syndromes, disorders or diseases include central and peripheral pathway mediated pain, bone and joint pain, migraine headache associated pain, cancer pain, menstrual cramps, labor pain and the like.

Neurodegenerative related syndromes, disorders or diseases include Parkinson's Disease, multiple sclerosis, epilepsy, ischemia or secondary biochemical injury collateral to traumatic head or brain injury, brain inflammation, eye injury or stroke and the like.

The present invention includes a method for treating, ameliorating or preventing a cannabinoid receptor agonist mediated syndrome, disorder or disease in a subject in need thereof comprising the step of administering to the subject an effective amount of a cannabinoid agonist compound of the present invention or composition thereof.

The present invention includes a method for treating, ameliorating or preventing a cannabinoid receptor agonist mediated syndrome, disorder or disease in a subject in need thereof comprising the step of administering to the subject an effective amount of a cannabinoid agonist compound of the present invention in a combination product and/or therapy with an anticonvulsant or composition thereof.

The present invention includes a method for treating, ameliorating or preventing a cannabinoid receptor inverse-agonist mediated syndrome, disorder or disease in a subject in need thereof comprising the step of administering to the subject an effective amount of a cannabinoid inverse-agonist compound of the present invention or composition thereof.

The present invention includes a method for treating, ameliorating or preventing a cannabinoid receptor inverse-agonist mediated syndrome, disorder or disease in a subject in need thereof comprising the step of administering to the subject an effective amount of a cannabinoid inverse-agonist compound of the present invention in a combination product and/or therapy with an anticonvulsant or composition thereof.

The present invention includes a method for treating, ameliorating or preventing a cannabinoid receptor inverse-agonist mediated syndrome, disorder or disease in a subject in need thereof comprising the step of administering to the subject an effective amount of a cannabinoid inverse-agonist compound of the present invention in a combination product and/or therapy with one or more contraceptives or composition thereof.

The present invention includes a method for treating, ameliorating or preventing a cannabinoid receptor antagonist mediated syndrome, disorder or disease in a subject in need thereof comprising the step of administering to the subject an effective amount of a cannabinoid antagonist compound of the present invention or composition thereof.

The present invention includes a method for treating, ameliorating or preventing a cannabinoid receptor antagonist mediated syndrome, disorder or disease in a subject in need thereof comprising the step of administering to the subject an effective amount of a cannabinoid antagonist compound of the present invention in a combination product and/or therapy with an anticonvulsant or composition thereof.

The present invention includes a method for treating, ameliorating or preventing a cannabinoid receptor antagonist mediated syndrome, disorder or disease in a subject in need thereof comprising the step of administering to the subject a therapeutically or prophylactically effective amount of a cannabinoid antagonist compound of the present invention in a combination product and/or therapy with one or more contraceptives or composition thereof.

The present invention includes a method for treating, ameliorating or preventing a CB1 receptor agonist mediated syndrome, disorder or disease in a subject in need thereof comprising the step of administering to the subject an effective amount of a CB1 agonist compound of the present invention or composition thereof.

The present invention includes a method for treating, ameliorating or preventing a CB1 receptor agonist mediated syndrome, disorder or disease in a subject in need thereof comprising the step of administering to the subject an effective amount of a CB1 agonist compound of the present invention in a combination product and/or therapy with an anticonvulsant or composition thereof.

The present invention includes a method for treating, ameliorating or preventing a CB1 receptor inverse-agonist mediated syndrome, disorder or disease in a subject in need thereof comprising the step of administering to the subject an effective amount of a CB1 inverse-agonist compound of the present invention or composition thereof.

The present invention includes a method for treating, ameliorating or preventing a CB1 receptor inverse-agonist mediated syndrome, disorder or disease in a subject in need thereof comprising the step of administering to the subject an effective amount of a CB1 inverse-agonist compound of the present invention in a combination product and/or therapy with an anticonvulsant or composition thereof.

The present invention includes a method for treating, ameliorating or preventing a CB1 receptor inverse-agonist mediated syndrome, disorder or disease in a subject in need thereof comprising the step of administering to the subject an effective amount of a CB1 inverse-agonist compound of the present invention in a combination product and/or therapy with one or more contraceptives or composition thereof.

The present invention includes a method for treating, ameliorating or preventing a CB1 receptor inverse-agonist mediated appetite related obesity related or metabolism related syndrome, disorder or disease in a subject in need thereof comprising the step of administering to the subject an effective amount of a CB1 inverse-agonist compound of the present invention or composition thereof.

The present invention includes a method for treating, ameliorating or preventing a CB1 receptor inverse-agonist mediated appetite related obesity related or metabolism related syndrome, disorder or disease in a subject in need thereof comprising the step of administering to the subject an effective amount of a CB1 inverse-agonist compound of the present invention in a combination product and/or therapy with an anticonvulsant or composition thereof.

The present invention includes a method for treating, ameliorating or preventing a CB1 receptor inverse-agonist mediated appetite related obesity related or metabolism related syndrome, disorder or disease in a subject in need thereof comprising the step of administering to the subject an effective amount of a CB1 inverse-agonist compound of the present invention in a combination product and/or therapy with one or more contraceptives or composition thereof.

Appetite related syndromes, disorders or diseases include obesity, overweight condition, anorexia, bulimia, cachexia, dysregulated appetite and the like.

Obesity related syndromes, disorders or diseases include obesity as a result of genetics, diet, food intake volume, metabolic syndrome, disorder or disease, hypothalmic disorder or disease, age, reduced activity, abnormal adipose mass distribution, abnormal adipose compartment distribution and the like.

Metabolism related syndromes, disorders or diseases include metabolic syndrome, dyslipidemia, elevated blood pressure, diabetes, insulin sensitivity or resistance, hyperinsulinemia, hypercholesterolemia, hyperlipidemias, hypertriglyceridemias, atherosclerosis, hepatomegaly, steatosis, abnormal alanine aminotransferase levels, inflammation, atherosclerosis and the like.

The present invention includes a method for treating, ameliorating or preventing a CB1 receptor antagonist mediated syndrome, disorder or disease in a subject in need thereof comprising the step of administering to the subject an effective amount of a CB1 antagonist compound of the present invention or composition thereof.

The present invention includes a method for treating, ameliorating or preventing a CB1 receptor antagonist mediated syndrome, disorder or disease in a subject in need thereof comprising the step of administering to the subject an effective amount of a CB1 antagonist compound of the present invention in a combination product and/or therapy with an anticonvulsant or composition thereof.

The present invention includes a method for treating, ameliorating or preventing a CB1 receptor antagonist mediated syndrome, disorder or disease in a subject in need thereof comprising the step of administering to the subject an effective amount of a CB1 antagonist compound of the present invention in a combination product and/or therapy with one or more contraceptives or composition thereof.

The present invention includes a method for treating, ameliorating or preventing a CB2 receptor agonist mediated syndrome, disorder or disease in a subject in need thereof comprising the step of administering to the subject an effective amount of a CB2 agonist compound of the present invention or composition thereof.

The present invention includes a method for treating, ameliorating or preventing a CB2 receptor agonist mediated syndrome, disorder or disease in a subject in need thereof comprising the step of administering to the subject an effective amount of a CB2 agonist compound of the present invention in a combination product and/or therapy with an anticonvulsant or composition thereof.

The present invention includes include a method for treating, ameliorating or preventing a CB2 receptor inverse-agonist mediated syndrome, disorder or disease in a subject in need thereof comprising the step of administering to the subject an effective amount of a CB2 inverse-agonist compound of the present invention or composition thereof.

The present invention includes a method for treating, ameliorating or preventing a CB2 receptor inverse-agonist mediated syndrome, disorder or disease in a subject in need thereof comprising the step of administering to the subject an effective amount of a CB2 inverse-agonist compound of the present invention in a combination product and/or therapy with an anticonvulsant or composition thereof.

The present invention includes a method for treating, ameliorating or preventing a CB2 receptor antagonist mediated syndrome, disorder or disease in a subject in need thereof comprising the step of administering to the subject an effective amount of a CB2 antagonist compound of the present invention or composition thereof.

The present invention includes a method for treating, ameliorating or preventing a CB2 receptor antagonist mediated syndrome, disorder or disease in a subject in need thereof comprising the step of administering to the subject an effective amount of a CB2 antagonist compound of the present invention in a combination product and/or therapy with an anticonvulsant or composition thereof.

The present invention includes a method for treating, ameliorating or preventing a metabolism related syndrome, disorder or disease, an appetite related syndrome, disorder or disease, a diabetes related syndrome, disorder or disease, an obesity related syndrome, disorder or disease or a learning, cognition or memory related syndrome, disorder or disease in a subject in need thereof comprising the step of administering to the subject an effective amount of a compound of the present invention or composition thereof.

The present invention includes a method for treating, ameliorating or preventing a metabolism related syndrome, disorder or disease, an appetite related syndrome, disorder or disease, a diabetes related syndrome, disorder or disease, an obesity related syndrome, disorder or disease or a learning, cognition or memory related syndrome, disorder or disease in a subject in need thereof comprising the step of administering to the subject an effective amount of a compound of the present invention in a combination product and/or therapy with an anticonvulsant or composition thereof.

The present invention includes a pharmaceutical composition or medicament comprising an admixture of a compound of the present invention and an optional pharmaceutically acceptable carrier.

The present invention includes a pharmaceutical composition or medicament comprising an admixture of two or more compounds of the present invention and an optional pharmaceutically acceptable carrier.

The present invention also includes a pharmaceutical composition or medicament comprising an admixture of a compound of formula (I), an anticonvulsant and an optional pharmaceutically acceptable carrier.

Such pharmaceutical compositions are particularly useful for treating a subject suffering from a metabolism related syndrome, disorder or disease, an appetite related syndrome, disorder or disease, a diabetes related syndrome, disorder or disease, an obesity related syndrome, disorder or disease, or a learning, cognition or memory related syndrome, disorder or disease.

Anticonvulsants useful in the methods and compositions of the present invention in combination with a compound of formula (I), (Ia), (Ib) or (Ic) include, but are not limited to, topiramate, analogs of topiramate, carbamazepine, valproic acid, lamotrigine, gabapentin, phenyloin and the like and mixtures or pharmaceutically acceptable salts thereof.

Topiramate, 2,3:4,5-bis-O-(1-methylethylidene)-β-D-fructopyranose sulfamate, is currently marketed for the treatment of seizures in patients with simple and complex partial epilepsy and seizures in patients with primary or secondary generalized seizures in the United States, Europe and most other markets throughout the world. Topiramate is currently available for oral administration in round tablets containing 25 mg, 100 mg or 200 mg of active agent, and as 15 mg and 25 mg sprinkle capsules for oral administration as whole capsules or opened and sprinkled onto soft food. U.S. Pat. No. 4,513,006, incorporated herein by reference, discloses topiramate and analogs of topiramate, their manufacture and use for treating epilepsy. Additionally, topiramate may also be made by the process disclosed in U.S. Pat. Nos. 5,242,942 and 5,384,327, which are incorporated by reference herein. The term "analogs of topiramate", as used herein, refers to the sulfamate compounds of formula (I), which are disclosed in U.S. Pat. No. 4,513,006 (see, e.g., column 1, lines 36-65 of U.S. Pat. No. 4,513,006).

For use in the methods of the present invention in combination with a compound of the formula (I), (Ia), (Ib) or (Ic), topiramate (or an analog of topiramate) can be administered in the range of about 10 to about 1000 mg daily, preferably in the range of about 10 to about 650 mg daily, more preferably in the range of about 15 to about 325 mg once or twice daily.

Carbamazepine, 5H-dibenz[b,f]azepine-5-carboxamide, is an anticonvulsant and specific analgesic for trigeminal neuralgia, available for oral administration as chewable tablets of 100 mg, tablets of 200 mg, XR (extended release) tablets of 100, 200, and 400 mg, and as a suspension of 100 mg/5 mL (teaspoon); U.S. Pat. No. 2,948,718, herein incorporated by reference in its entirety, discloses carbamazepine and its methods of use.

For use in the methods of the present invention in combination with a compound of the formula (I), (Ia), (Ib) or (Ic), carbamazepine can be administered in the range of about 200 to about 1200 mg/day; preferably, about 400 mg/day.

Valproic acid, 2-propylpentanoic acid or dipropylacetic acid, is an antiepileptic agent commercially available as soft elastic capsules containing 250 mg valproic acid, and as syrup containing the equivalent of 250 mg valproic acid per 5 mL as the sodium salt. Valproic acid and various pharmaceutically acceptable salts are disclosed in U.S. Pat. No. 4,699,927, which is incorporated by reference herein in its entirety.

For use in the methods of the present invention in combination with a compound of the formula (I), (Ia), (Ib) or (Ic), valproic acid can be administered in the range of about 250 to about 2500 mg/day; preferably, about 1000 mg/day.

Lamotrigine, 3,5-diamino-6-(2,3-dichlorophenyl)-1,2,4-triazine, is an antiepileptic drug commercially available for oral administration as tablets containing 25 mg, 100 mg, 150 mg, and 200 mg of lamotrigine, and as chewable dispersible tablets containing 2 mg, 5 mg, or 25 mg of lamotrigine. Lamotrigine and its uses are disclosed in U.S. Pat. No. 4,486,354, incorporated by reference herein in its entirety.

For use in the methods of the present invention in combination with a compound of the formula (I), (Ia), (Ib) or (Ic), lamotrigine can be administered in the range of about 50 to about 600 mg/day in one to two doses; preferably, about 200 to about 400 mg/day; most preferably, about 200 mg/day.

Gabapentin, 1-(aminomethyl)cyclohexaneacetic acid, is commercially available for the adjunctive treatment of epilepsy and for postherpetic neuralgia in adults as capsules containing 100 mg, 300 mg, and 400 mg of gabapentin, film-coated tablets containing 600 mg and 800 mg of gabapentin, and an oral solution containing 250 mg/5 mL of gabapentin. Gabapentin and its methods of use are described in U.S. Pat. Nos. 4,024,175 and 4,087,544, herein incorporated by reference in their entirety.

For use in the methods of the present invention in combination with a compound of the formula (I), (Ia), (Ib) or (Ic), gabapentin can be administered in the range of about 300 to about 3600 mg/day in two to three divided doses; preferably, about 300 to about 1800 mg/day; most preferably, about 900 mg/day.

Phenytoin sodium, 5,5-diphenylhydantoin sodium salt, is an anticonvulsant, which is commercially available for oral administration as capsules containing 100 mg, 200 mg or 300 mg of phenytoin sodium.

For use in the methods of the present invention in combination with a compound of the formula (I), (Ia), (Ib) or (Ic), phenytoin sodium can be administered in the range of about 100 to about 500 mg/day; preferably, about 300 to about 400 mg/day; most preferably, about 300-mg/day.

The present invention also includes a pharmaceutical composition or medicament comprising an admixture of a compound of formula (I), (Ia), (Ib) or (Ic), one or more contraceptives and an optional pharmaceutically acceptable carrier.

Contraceptives suitable for use in a combination product and/or therapy include, for example, ORTHO CYCLEN®, ORTHO TRI-CYCLEN®, ORTHO TRI-CYCLEN LO®, and ORTHO EVRA®, all available from Ortho-McNeil Pharmaceutical, Inc., Raritan, N.J. It should also be understood that contraceptives suitable for use in the invention encompass those contraceptives that include a folic acid component.

Smoking and/or obesity have been identified as risk factors in women taking oral contraceptives. CB1 receptor antagonists and inverse agonists have been found to be useful therapeutic agents for reducing the urge to smoke and for assisting patients with eating disorders to lose weight.

Accordingly, the invention further includes a method of reducing the risk factors associated with smoking and/or obesity for women taking contraceptives by co-administering with a contraceptive at least one of a CB1 receptor antagonist and/or CB1 receptor inverse-agonist compound of formula (I), (Ia), (Ib) or (Ic).

The use of such compounds or a pharmaceutical composition or medicament thereof is to reduce the desire to smoke and/or to assist in weight loss for patients taking contraceptives.

The term "composition" refers to a product comprising the specified ingredients in the specified amounts, as well as any product that results, directly or indirectly, from combinations of the specified ingredients in the specified amounts. The invention further comprises mixing one or more of the compounds of the invention and a pharmaceutically acceptable carrier; and, includes those compositions resulting from such a process. Contemplated processes include both traditional and modern pharmaceutical techniques.

Pharmaceutical compositions of the invention may, alternatively or in addition to a compound of formula (I), (Ia), (Ib) or (Ic), comprise a pharmaceutically acceptable salt of a compound of formula (I), (Ia), (Ib) or (Ic) or a prodrug or pharmaceutically active metabolite of such a compound or salt in admixture with a pharmaceutically acceptable carrier.

The term "medicament" refers to a product for use in treating, ameliorating or preventing a cannabinoid receptor mediated syndrome, disorder or disease.

"Pharmaceutically acceptable carrier" means molecular entities and compositions that are of sufficient purity and quality for use in the formulation of a composition of the invention and that, when appropriately administered to an animal or a human, do not produce an adverse, allergic, or other untoward reaction.

Since both clinical and veterinary uses are equally included within the scope of the present invention, a pharmaceutically acceptable formulation would include a composition or medicament formulation for either clinical or veterinary use.

The present invention includes a process for making the composition or medicament comprising mixing any of the instant compounds and a pharmaceutically acceptable carrier and include those compositions or medicaments resulting from such a process. Contemplated processes include both conventional and unconventional pharmaceutical techniques. Other examples include a composition or medicament comprising a mixture of at least two of the instant compounds in association with a pharmaceutically acceptable carrier.

The composition or medicament may be administered in a wide variety of dosage unit forms depending on the method of administration; wherein such methods include (without limitation) oral, sublingual, nasal (inhaled or insufflated), transdermal, rectal, vaginal, topical (with or without occlusion), intravenous (bolus or infusion) or for injection (intraperitoneally, subcutaneously, intramuscularly, intratumorally or parenterally) using a suitable dosage form well known to those of ordinary skill in the area of pharmaceutical administration. Accordingly, the term "dosage unit" or "dosage form" is alternatively used to refer to (without limitation) a tablet, pill, capsule, solution, syrup, elixir, emulsion, suspension, suppository, powder, granule or sterile solution, emulsion or suspension (for injection from an ampoule or using a device such as an auto-injector or for use as an aerosol, spray or drop). Furthermore, the composition may be provided in a form suitable for weekly or monthly administration (e.g. as an insoluble salt of the active compound (such as the decanoate salt) adapted to provide a depot preparation for intramuscular injection).

In preparing a dosage form, the principal active ingredient (such as a compound of the present invention or a pharmaceutically acceptable salt, racemate, enantiomer, or diastereomer thereof) is optionally mixed with one or more pharmaceutical carriers (such as a starch, sugar, diluent, granulating agent, lubricant, glidant, binder, disintegrating agent and the like), one or more inert pharmaceutical excipients (such as water, glycols, oils, alcohols, flavoring agents, preservatives, coloring agents, syrup and the like), one or more conventional tableting ingredient (such as corn starch, lactose, sucrose, sorbitol, talc, stearic acid, magnesium stearate, dicalcium phosphate, any of a variety of gums and the like) and a diluent (such as water and the like) to form a homogeneous composition (whereby the active ingredient is dispersed or suspended evenly throughout the mixture) which may be readily subdivided into dosage units containing equal amounts of a compound of the present invention.

Binders include, without limitation, starch, gelatin, natural sugars (such as glucose, beta-lactose and the like), corn sweeteners and natural and synthetic gums (such as acacia, tragacanth, sodium oleate, sodium stearate, magnesium stearate, sodium benzoate, sodium acetate, sodium chloride and the like). Disintegrating agents include, without limitation, starch, methyl cellulose, agar, bentonite, xanthan gum and the like.

Because of the ease of administration, tablets and capsules represent an advantageous oral dosage unit form, wherein solid pharmaceutical carriers are employed. If desired, tablets may be sugar or film coated or enteric-coated by standard techniques. Tablets may also be coated or otherwise compounded to provide a prolonged therapeutic effect. For example, the dosage form may comprise an inner dosage and an outer dosage component, whereby the outer component is in the form of an envelope over the inner component. The two components may further be separated by a layer, which resists disintegration in the stomach (such as an enteric layer) and permits the inner component to pass intact into the duodenum or a layer which delays or sustains release. A variety of enteric and nonenteric layer or coating materials may be used (such as polymeric acids, shellacs, acetyl alcohol, cellulose acetate and the like) or combinations thereof.

The liquid forms in which a compound of the present invention may be incorporated for oral administration include (without limitation), aqueous solutions, suitably flavored syrups, aqueous or oil suspensions (using a suitable synthetic or natural gum dispersing or suspending agent such as tragacanth, acacia, alginate, dextran, sodium carboxymethylcellulose, methylcellulose, polyvinyl-pyrrolidone, gelatin and the like), flavored emulsions (using a suitable edible oil such as cottonseed oil, sesame oil, coconut oil, peanut oil and the like), elixirs and other similar liquid forms with a variety of pharmaceutically acceptable vehicles.

As is also known in the art, the compounds may alternatively be administered parenterally via injection. For parenteral administration, sterile solutions or injectable suspensions may be parenteral vehicles wherein appropriate liquid carriers, suspending agents and the like are employed. Sterile solutions are a preferred parenteral vehicle. Isotonic preparations that generally contain suitable preservatives are employed when intravenous administration is desired. A parenteral formulation may consist of the active ingredient dissolved in or mixed with an appropriate inert liquid carrier. Acceptable liquid carriers comprise aqueous solvents and the like and other optional ingredients for aiding solubility or preservation. Such aqueous solvents include sterile water, Ringer's solution or an isotonic aqueous saline solution. Alternatively, a sterile non-volatile oil may be employed as a solvent agent. Other optional ingredients include vegetable oils (such as peanut oil, cottonseed oil, sesame oil and the like), organic solvents (such as solketal, glycerol, formyl and the like), preservatives, isotonizers, solubilizers, stabilizers, pain-soothing agents and the like. A parenteral formulation is prepared by dissolving or suspending the active ingredient in the liquid carrier whereby the final dosage unit contains from 0.005 to 10% by weight of the active ingredient.

Compounds of the present invention may be administered intranasally using a suitable intranasal vehicle. Compounds of the present invention may be administered topically using a suitable topical transdermal vehicle or a transdermal patch. Administration via a transdermal delivery system requires a continuous rather than intermittent dosage regimen.

Compounds of the present invention may also be administered via a rapid dissolving or a slow release composition, wherein the composition includes a biodegradable rapid dissolving or slow release carrier (such as a polymer carrier and the like) and a compound of the invention. Rapid dissolving or slow release carriers are well known in the art and are used to form complexes that capture therein an active compound(s) and either rapidly or slowly degrade/dissolve in a suitable environment (e.g., aqueous, acidic, basic, etc). Such particles are useful because they degrade/dissolve in body fluids and release the active compound(s) therein. The particle size of a compound of the present invention, carrier or any excipient used in such a composition may be optimally adjusted using techniques known to those of ordinary skill in the art.

The present invention includes a composition of an instant compound or prodrug thereof present in a prophylactically or therapeutically effective amount necessary for symptomatic relief to a subject in need thereof. A prophylactically or therapeutically effective amount of an instant compound or prodrug thereof may range from about 0.01 ng to about 1 g and may be constituted into any form suitable for the administration method and regimen selected for the subject.

Depending on the subject and disease to be treated, the prophylactically or therapeutically effective amount for a person of average body weight of about 70 kg per day may range from about 0.01 µg/kg to about 300 mg/kg; from about 0.1 µg/kg to about 200 mg/kg; from about 0.5 µg/kg to about 100 mg/kg; or, from about 1 µg/kg to about 50 mg/kg.

An optimal prophylactically or therapeutically effective amount and administration method and regimen may be readily determined by those skilled in the art, and will vary depending on factors associated with the particular patient being treated (age, weight, diet and time of administration), the severity of the condition being treated, the compound and dosage unit being employed, the mode of administration and the strength of the preparation.

Dosage unit(s) may be administered to achieve the therapeutically or prophylactically effective amount in a regimen of from about once per day to about 5 times per day. The preferred dosage unit for oral administration is a tablet containing 0.01, 0.05, 0.1, 0.5, 1.0, 2.5, 5.0, 10.0, 15.0, 25.0, 50.0, 100, 150, 200, 250 or 500 mg of the active ingredient.

Synthetic Methods

Representative compounds of the present invention can be synthesized in accordance with the general synthetic schemes described below and are illustrated more particularly in the specific synthetic examples that follow. The general schemes and specific examples are offered by way of illustration; the invention should not be construed as being limited by the chemical reactions and conditions expressed. The methods for preparing the various starting materials used in the schemes and examples are well within the skill of persons versed in the art. No attempt has been made to optimize the yields obtained in any of the example reactions. One skilled in the art would know how to increase such yields through routine variations in reaction times, temperatures, solvents and/or reagents.

The terms used in describing the invention are commonly used and known to those skilled in the art. When used herein, the following abbreviations have the indicated meanings:

| | |
|---|---|
| Boc | tert-butoxy carbonyl |
| Cpd | compound |
| DMF | N,N-dimethyl formamide |
| EtOAc | ethyl acetate |
| $Et_2O$ | anhydrous ether |
| KOH | potassium hydroxide |
| LHMDS | lithium hexamethyl disilane |
| LiOH | lithium hydroxide |
| min/hr(s)/d(s)/mp | minute/hour(s)/day(s)/melting point |
| $N_2$ | nitrogen |
| RT/rt/r.t. | room temperature |
| TEA or $Et_3N$ | triethylamine |
| TFA | trifluoroacetic acid |
| THF | tetrahydrofuran |

Except where indicated, all reagents, solvents and starting materials are commercially available and were used without further purification. Where a particular component or piece of equipment was used, such are also commercially available.

Scheme A
Synthesis of Tetrahydro-Indazole Compounds

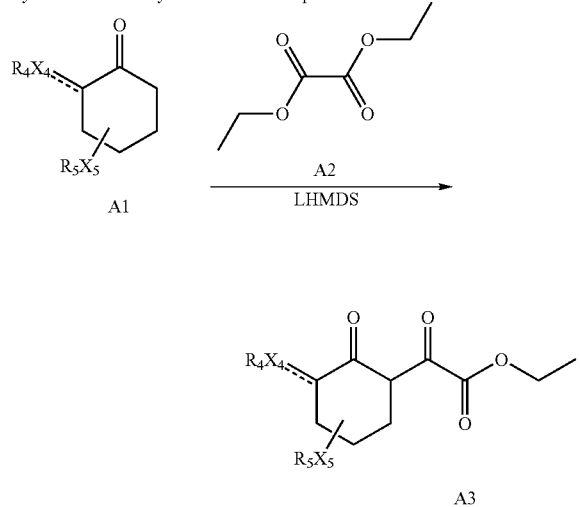

An optionally substituted cyclohexanone Compound A1 in solution (with one or more of $Et_2O$, THF and the like) is rapidly added to a reagent solution (containing a mixture of LHMDS and the like in one or more of $Et_2O$ or THF and the like) at a temperature of about −78° C. under an inert atmosphere (using nitrogen and the like) and stirred at about −78° C. for about 40 mins. An optionally substituted oxalic acid di-ethyl ester Compound A2 in solution (with $Et_2O$ and the like) is then added to the Compound A1 mixture.

The reaction mixture is stirred at about −78° C. for about 1 hr, then allowed to warm to r.t. over an additional 2 hr period of time. The reaction is quenched (using saturated $NH_4Cl$, 1N HCl and the like) and the organic layer is extracted (with one or more of EtOAc, $Et_2O$ and the like) and washed (with brine and the like), then separated and dried (with anhydrous sodium sulfate and the like). The extract is filtered and concentrated in vacuo to yield an optionally substituted oxo-(2-oxo-cyclohexyl)-acetic acid alkyl ester Compound A3 as a crude product used without further purification in the next step.

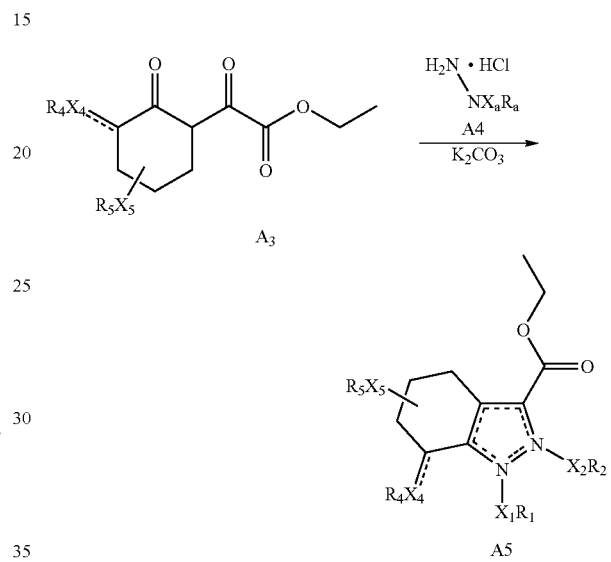

A substituted hydrazine hydrochloride Compound A4 and $K_2CO_3$ (potassium carbonate) are added to Compound A3 in solution (with one or more of MeOH, EtOH, $CH_2Cl_2$ and the like) at room temperature under an inert atmosphere. The reaction mixture is stirred overnight, then concentrated and diluted (with one or more of water, EtOAc (ethyl acetate) and the like). The organic layer is washed, separated and dried, then filtered and concentrated in vacuo to yield a crude product Compound A5 as a mixture of isomers, wherein a mixture of $X_1R_1$ and $X_2R_2$ isomers are present. The $X_aR_a$ substituent moiety on Compound A4 represents the possibility that, after separation, the substituted amine group may be found either on the $N^1$ position as $X_1R_1$ or on the $N^2$ position as $X_2R_2$.

The hydrazine hydrochloride or dihydrochloride Compound A4 may be converted to the free base by methods known to those skilled in the art. In the examples of the present invention, the free base is prepared either in situ (as shown for illustrative purposes in this Scheme) or separately (then added to the reaction mixture) by reaction with $K_2CO_3$.

As illustrated in this Scheme, Compound A4 may also be further substituted with a variety of $X_aR_a$ substituents (as previously defined herein). In many instances, the substituted hydrazine Compound A4 is commercially available. When not commercially available, a particularly substituted Compound A4 may be prepared by methods known to those skilled in the art. More specifically, a halogenated $X_aR_a$ substituent moiety is reacted with a hydrazine hydrate solution at reflux and used without further purification as Compound A4 (as described more completely in Example 3).

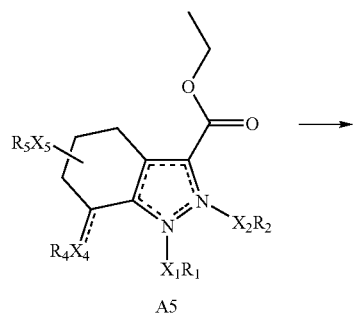

A5

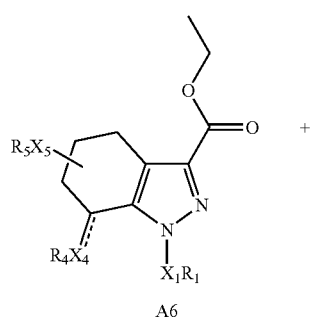

A6

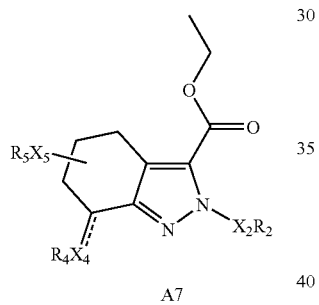

A7

The Compound A5 isomeric mixture is separated via flash chromatography (eluted with a suitable solvent mixture such as 20% or 30% EtOAc:hexane and the like) to provide a purified major isomer Compound A6 and a minor isomer Compound A7. The major isomer Compound A6 is substituted on the $N^1$ position with $X_1R_1$ ($X_2R_2$ is necessarily absent). The minor isomer Compound A7 is substituted on the $N^2$ position with $X_2R_2$ (wherein $X_1R_1$ is absent).

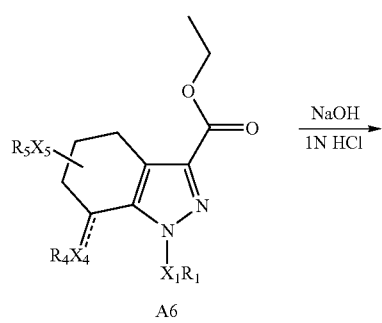

A6

-continued

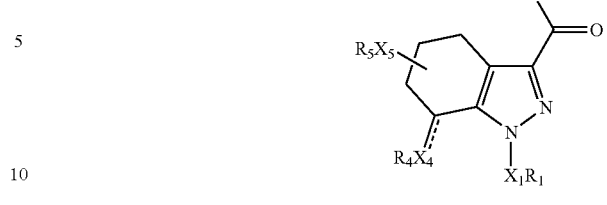

A8

The separated major isomer Compound A6 is treated with a reagent solution (such as a mixture of NaOH in a solvent such as THF or water and the like) and stirred overnight. The reaction is quenched and extracted with a solvent (such as $CH_2Cl_2$, EtOAc and the like). The organic layer is dried, filtered and concentrated in vacuo to yield Compound A8.

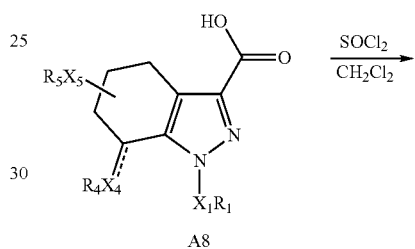

A8

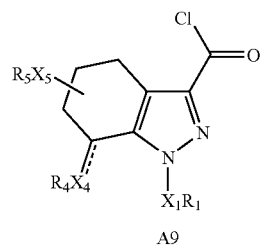

A9

A reagent (such as $SOCl_2$ (thionyl chloride) and the like) in a solvent (such as $CH_2Cl_2$ and the like) is added to Compound A8 at ambient temperature under an inert nitrogen atmosphere. The reaction mixture is stirred at reflux temperature for about 15 min, then concentrated in vacuo to afford the corresponding acid chloride intermediate Compound A9.

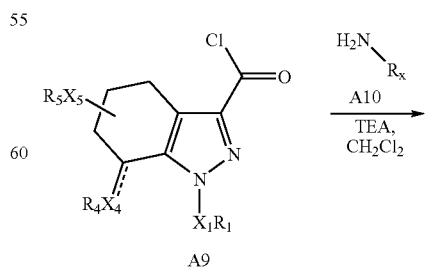

A9

-continued

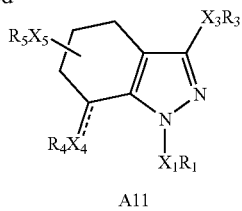

A11

Compound A9 (optionally in solution with TEA (triethylamine) and the like) is added to a solution of a substituted amine Compound A10 (in a solvent such as $CH_2Cl_2$ and the like) at ambient temperature under an inert nitrogen atmosphere.

In general, Compound A10 is a commercially available substituted amine. When not commercially available, a particularly substituted amine Compound A10 may be prepared by methods known to those skilled in the art.

The Compound A9/A10 mixture is stirred at about r.t. for a period of time, then diluted (with a mixture of water and $CH_2Cl_2$ and the like). The organic layer is separated and dried, then filtered and concentrated in vacuo to yield a crude product. The product is purified via flash chromatography (eluted with a solvent mixture such as 20% or 30% EtOAc in hexane) to provide a target Compound A11.

For purposes of illustration in this Scheme, the Compound A11 $X_3R_3$ substituent moiety incorporates the C(O) portion of the $C^3$ substituent from Compound A9 and the —NH— portion from Compound A10, wherein $X_3$ is absent and $R_3$ is either —$(R_6)C(O)Z_1R_7$ or —$(R_6)C(O)N(R_{9a})Z_2R_9$, and wherein $R_6$ is absent.

Scheme B

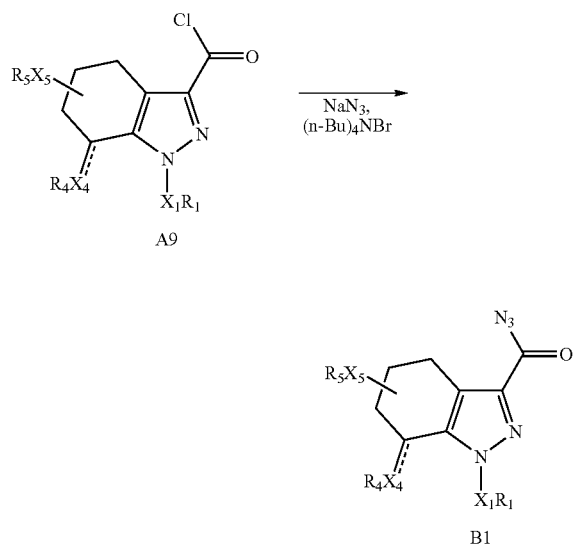

A catalytic amount of tetrabutylammonium bromide ((n-Bu)$_4$NBr) is added to a solution of Compound A9 (in a solvent such as DCE (dichloroethane) and the like) at 0° C. A saturated solution of NaN$_3$ (sodium azide) (in water) is added dropwise at 0° C. The reaction mixture is stirred for about 0.5 hrs, then diluted (with one or more of cold water, $CH_2Cl_2$ and the like). The organic layer is washed (with one or more of water, brine and the like) and dried (using sodium sulfate), then filtered and concentrated to give an azide Compound B1.

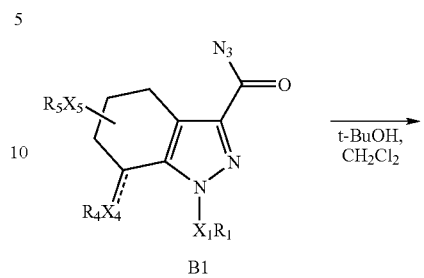

B1

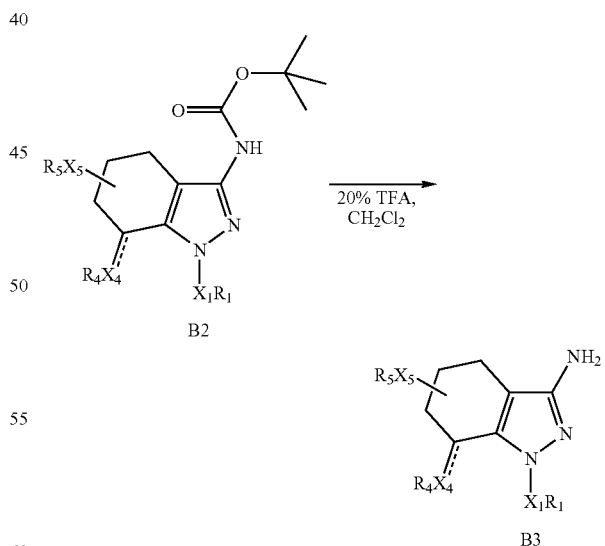

t-BuOH (tert-butanol) is added to a solution of Compound B1 (in a solvent such as $CH_2Cl_2$ and the like) and the mixture is refluxed for about 48 hrs. The reaction product is concentrated and purified via silica gel column (eluted with a solvent mixture such as 10% EtOAc in hexane) to give a Boc-protected amine Compound B2.

TFA is added to a solution of Compound B2 (in a solvent such as $CH_2Cl_2$ and the like) and the mixture is stirred overnight. The reaction product is concentrated and the residue is dissolved (in a solvent such as $CH_2Cl_2$ and the like) and washed (with one or more of 1N NaOH, water and the like)

and dried (using sodium sulfate), then filtered and concentrated to give an amine Compound B3.

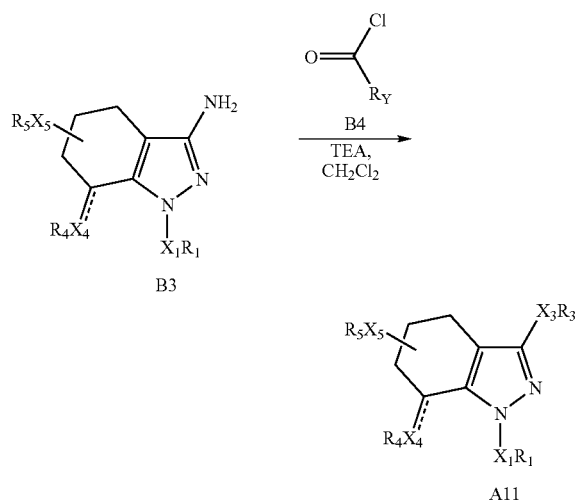

Compound B3 (optionally in solution with TEA and the like) is added to a solution of a substituted amine Compound B4 (in a solvent such as $CH_2Cl_2$ and the like) at ambient temperature under an inert nitrogen atmosphere. The mixture is stirred at r.t. for about 4 hrs, then concentrated and purified via silica gel column (eluted with a solvent mixture such as 15%, 20% or 30% EtOAc in hexane) to provide the target Compound A11.

For purposes of illustration in this Scheme, the Compound A11 $X_3R_3$ substituent moiety incorporates the NH portion of the $C^3$ substituent from Compound B3 and the $R_3C(O)$— portion from Compound B4, wherein $X_3$ is a —NH— and $R_3$ is either —$(R_6)C(O)Z_1R_7$, —$SO_2N(R_8)R_{8a}$, or —$(R_6)C(O)N(R_{9a})Z_2R_9$, and wherein $R_6$ is absent.

The synthetic examples that follow herein describe more completely the preparation of particular compounds included within the scope of the present invention.

EXAMPLE 1

(5S)-3-(adamantan-2-ylcarbamoyl)-1-cyclohexyl-4,5,6,7-tetrahydro-1H-indazole-5-carboxylic acid ethyl ester (Cpd 208)

(5R)-3-(adamantan-2-ylcarbamoyl)-1-cyclohexyl-4,5,6,7-tetrahydro-1H-indazole-5-carboxylic acid ethyl ester (Cpd 209)

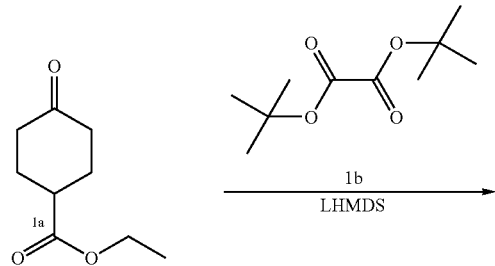

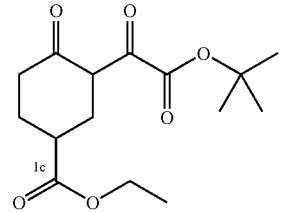

4-oxo-cyclohexanecarboxylic acid ethyl ester Compound 1a (3.4 g, 0.02 mol) was added to LHMDS (20 mL, 1M in THF, 0.02 mol) in THF (15 mL) at about −78° C. under $N_2$ and stirred at −78° C. for 40 min. Then oxalic acid di-tert-butyl ester Compound 1b (4.04 g, 0.02 mol) in THF (15 mL) was transferred into the mixture via cannula. The mixture was stirred for 1 hr at −78° C. and 2 hrs at r.t. The reaction was quenched with saturated $NH_4Cl$ and the product was concentrated in vacuo, then extracted using EtOAc (30 mL). The EtOAc was evaporated to provide a crude 3-tert-butoxyoxalyl-4-oxo-cyclohexanecarboxylic acid ethyl ester Compound 1c (5.0 g) which was used in the next step without further purification.

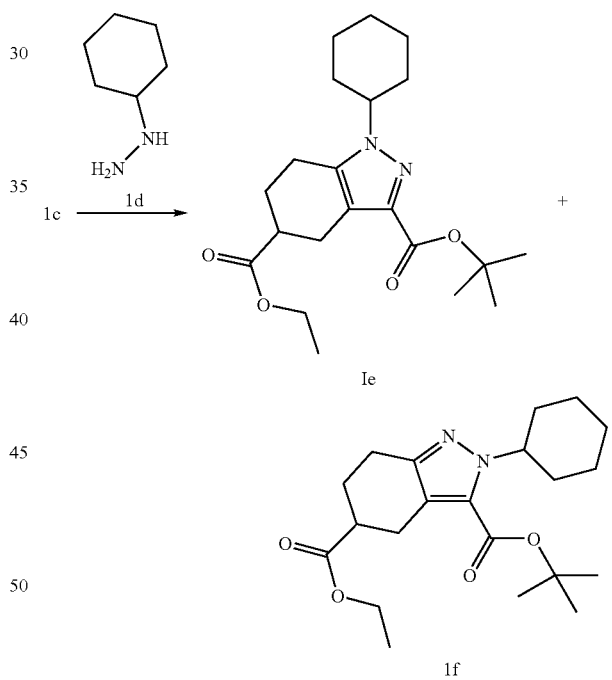

The crude Compound 1c (2.98 g) was stirred with cyclohexyl hydrazine hydrochloride Compound 1d (1.51 g, 0.01 mol) and $K_2CO_3$ (0.69 g, 0.005 mol) in $CH_2Cl_2$ (30 mL) under $N_2$ at r.t. overnight and then washed with water. The crude product was chromatographically purified (eluted with 30% EtOAc in hexane) to afford a mixture of a major isomer Compound 1e (2.5 g, 66.5% yield from Compound 1a) and a minor isomer Compound 1f (0.3 g, 8.0% yield from Compound 1a).

Compound 1e: MS m/z 377 (M+H)$^+$; $^1H$ NMR (CDCl$_3$, 300 MHz) δ: 4.18 (2H, q, J=7.1 Hz), 3.95 (1H, m), 3.14 (1H, m), 2.82 (2H, m), 2.63 (2H, m), 2.21 (1H, m), 1.89 (6H, m), 1.66 (1H, m), 1.58 (9H, s), 1.29 (4H, m), 1.28 (3H, t, J=7.1 Hz).

Compound 1f: MS m/z 377 (M+H)⁺; ¹H NMR (CDCl₃, 300 MHz) δ: 5.02 (1H, m), 4.16 (2H, q, J=7.2 Hz), 3.09 (1H, m), 2.82 (2H, m), 2.62 (2H, m), 2.21 (1H, m), 1.91 (6H, m), 1.69 (1H, m), 1.58 (9H, s), 1.25-1.45 (4H, m), 1.26 (3H, t, J=7.2 Hz).

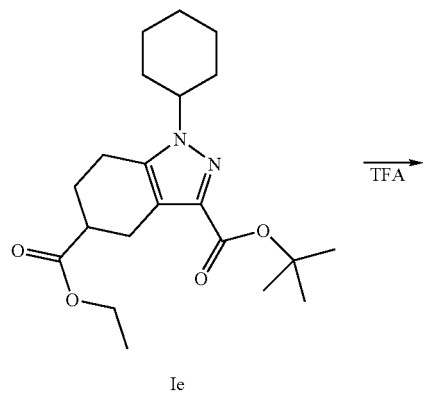

Ie

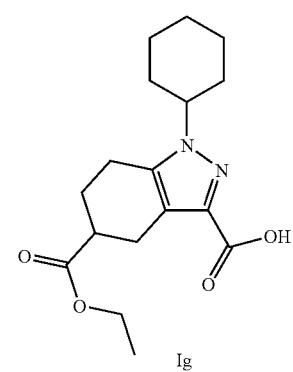

Ig

The separated major isomer Compound 1e (4.2 g, 11.16 mMol) was treated with a 50% TFA/CH₂Cl₂ solution (20 mL) over about an 8 hr period (overnight). The solvent was evaporated and the residue was washed with CH₂Cl₂ to give 1-cyclohexyl-4,5,6,7-tetrahydro-1H-indazole-3,5-dicarboxylic acid 5-ethyl ester Compound 1g (3.6 g, 100% yield) as a solid.

Compound 1g: MS m/z 321 (M+H)⁺, 343 (M+Na)⁺; ¹H NMR (CDCl₃, 300 MHz) δ: 4.23 (2H, q, J=7.1 Hz), 4.13 (1H, m), 3.19 (1H, m), 2.85 (4H, m), 2.3 (1H, m), 1.92 (6H, m), 1.72 (1H, m), 1.32 (7H, m).

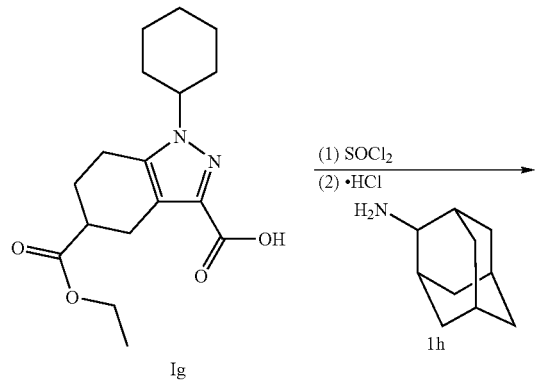

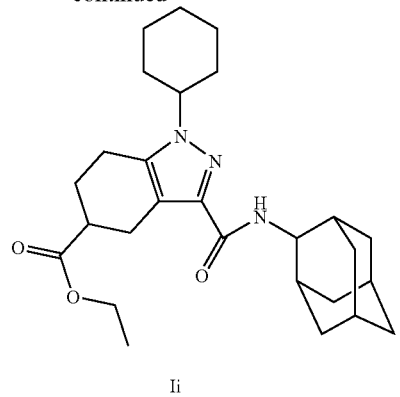

Ii

Compound 1g (3.6 g, 11.2 mMol) was reacted with thionyl chloride (14 mL, 190 mMol) and refluxed for about 15 min to form an acid chloride intermediate. The intermediate was further reacted with a 2-adamantanamine hydrochloride Compound 1h (2.09 gms, 11.16 mMol) in CH₂Cl₂. The crude product afforded was chromatographically purified (eluted with 30% EtOAc in hexane) to provide a 3-(adamantan-2-ylcarbamoyl)-1-cyclohexyl-4,5,6,7-tetrahydro-1H-indazole-5-carboxylic acid ethyl ester Compound 1i (3.2 g, 63% yield) as a white solid racemate.

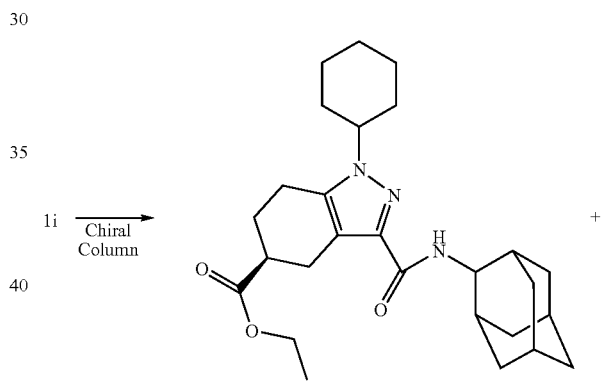

Cpd 208

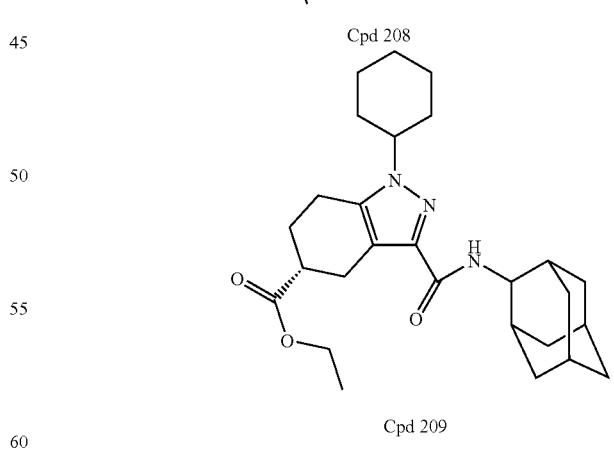

Cpd 209

The racemic Compound 1i was enantiomerically separated via chiral column chromatography (eluted with 90% hexane in IPA) to provide an (S)-enantiomer Compound 208 and an (R)-enantiomer Compound 209.

MS m/z 454 (M+H)⁺, 476 (M+Na)⁺; IR (KBr): 3419, 2908, 1732, 1668 cm⁻¹; ¹H NMR (CDCl₃, 300 MHz) δ: 7.25 (1H, d,

J=8.3 Hz), 4.22 (1H, m), 4.14 (2H, q, J=7.1 Hz), 3.91 (1H, m), 3.32 (1H, dd, J=16.4, 5.3 Hz), 2.83 (2H, m), 2.63 (2H, m), 2.20 (1H, m), 1.88 (23H, m), 1.32 (2H, m), 1.25 (3H, t, J=7.1 Hz); $^{13}$C NMR (CDCl$_3$, 75 MHz) δ: 175.5, 162.8, 141.5, 138.3, 116.6, 60.8, 58.7, 52.9, 40.4, 38.0, 37.6, 33.0, 32.9, 32.54, 32.51, 32.47, 27.7, 27.6, 25.9, 25.5, 25.3, 24.9, 21.1, 14.6; Anal. Calcd for C$_{27}$H$_{39}$N$_3$O$_3$: C, 71.49; H, 8.67; N, 9.26. Found: C, 71.32; H, 8.77; N, 9.07.

EXAMPLE 2

1-benzyl-4,5,6,7-tetrahydro-1H-indazole-3-carboxylic acid (1,3,3-trimethyl-bicyclo[2.2.1]hept-2-yl)-amide (Cpd 194)

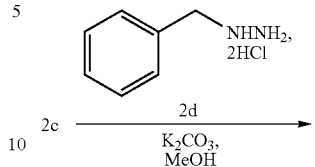

Cyclohexanone Compound 2a (20.54 g, 0.25 mol) in Et$_2$O (100 mL) was added to a solution of LHMDS (250 mL, 0.25 mol) in Et$_2$O (400 mL) at −78° C. under a N$_2$ atmosphere. The mixture was maintained at −78° C. and stirred for 60 min. A diethyloxylate Compound 2b (36.53 g, 0.25 mMol) in Et$_2$O (100 mL) was added to the mixture, which was stirred at −78° C. for 1 hr. The reaction mixture was allowed to warm to r.t. over 3 hrs and the reaction was quenched with 1N HCl (150 mL), The organic layer was extracted with Et$_2$O (200 mL), washed with brine and separated, then dried with anhydrous sodium sulfate, filtered and concentrated in vacuo to yield 48.50 g, 95% of oxo-(2-oxo-cyclohexyl)-acetic acid ethyl ester Compound 2c as a yellow oil. Compound 2c was used in the next step without further purification.

Benzylhydrazine dihydrochloride Compound 2d (1.75 g, 9.0 mMol) and K$_2$CO$_3$ (2.77 g, 19.5 mMol) were added to a solution of Compound 2c (1.88 g, 8.85 mMol) in MeOH (50 mL) at ambient temperature under a N$_2$ atmosphere. The resultant heterogeneous mixture was stirred overnight. The reaction mixture was concentrated to dryness and diluted with H$_2$O (100 mL) and EtOAc (500 mL). The organic layer was washed with brine, separated, dried with anhydrous sodium sulfate, filtered and concentrated in vacuo to yield a product as a crude oil. Purification by flash chromatography (eluted with 20% EtOAc in hexane) afforded a major isomer 1-benzyl-4,5,6,7-tetrahydro-1H-indazole-3-carboxylic acid ethyl ester Compound 2e (1.51 g, 60%) and a minor isomer 2-benzyl-4,5,6,7-tetrahydro-2H-indazole-3-carboxylic acid ethyl ester Compound 2f as a colorless oil.

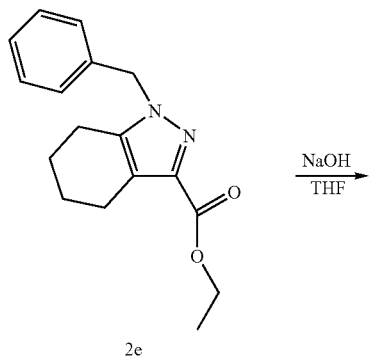

2e

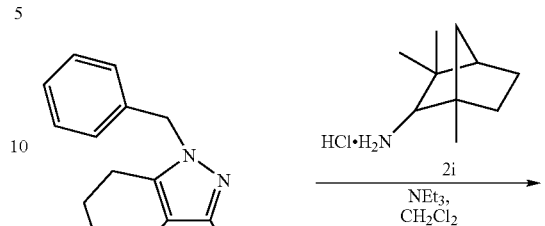

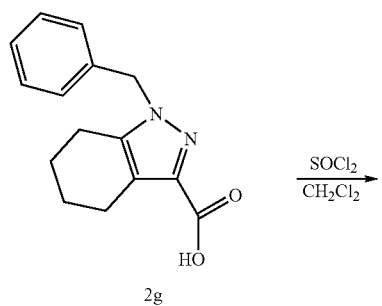

2g

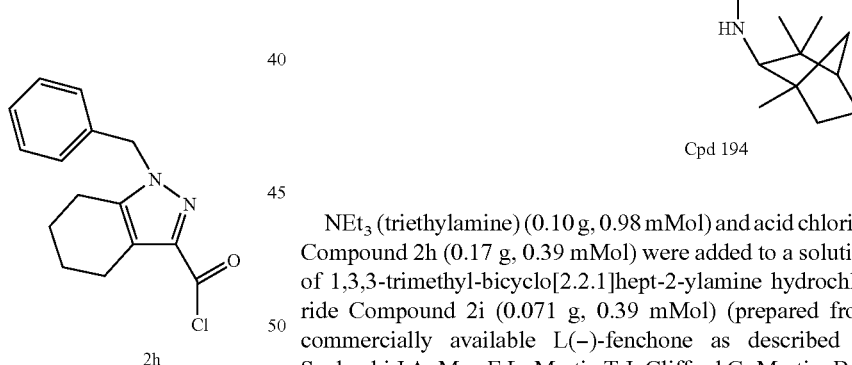

1N NaOH (10 mL) was added to Compound 2e (0.30 g, 1.05 mMol) in THF (10 mL). The mixture was stirred for 30 hours, acidified to pH 2 with 1N HCl and extracted with EtOAc (100 mL). The organic layer was washed with brine, dried over sodium sulfate, then filtered and concentrated in vacuo to yield 1-benzyl-4,5,6,7-tetrahydro-1H-indazole-3-carboxylic acid Compound 2g (0.190 g, 70%) as a white solid. Thionyl chloride (0.17 g, 0.39 mMol) was added to a solution of the carboxylic acid Compound 2g (0.15 g, 0.55 mMol) in CH$_2$Cl$_2$ (10 mL) at ambient temperature under a N$_2$ atmosphere. The reaction was stirred for 3 hrs and concentrated in vacuo to afford the corresponding acid chloride Compound 2h in quantitative yield.

NEt$_3$ (triethylamine) (0.10 g, 0.98 mMol) and acid chloride Compound 2h (0.17 g, 0.39 mMol) were added to a solution of 1,3,3-trimethyl-bicyclo[2.2.1]hept-2-ylamine hydrochloride Compound 2i (0.071 g, 0.39 mMol) (prepared from commercially available L(−)-fenchone as described in Suchocki J A; May E L; Martin T J; Clifford G; Martin, B R, J. Med. Chem., 1991, 34, 1003) in CH$_2$Cl$_2$ (10 mL) at ambient temperature under a N$_2$ atmosphere.

The reaction was stirred at r.t. for 3 hrs, then diluted with water (10 mL) and CH$_2$Cl$_2$ (50 mL). The organic layer was separated, dried with anhydrous sodium sulfate, filtered and concentrated in vacuo to yield a crude oil. Purification by flash chromatography (eluted with 20% EtOAc in hexane) afforded Compound 194 (0.09 g, 41%), as a white solid.

$^1$H NMR (CDCl$_3$, 400 MHz) δ 7.37-7.27 (m, 3H), 7.14-7.09 (m, 2H), 7.03-6.99 (d,J=12 Hz, 2H), 5.23 (s, 2H), 3.76-3.72(m, 1H), 2.85-2.80 (m, 1H), 2.44-2.40 (m, 1H), 1.80-1.70 (m, 7H), 1.55-1.42 (m, 2H), 1.24-1.28 (m, 1H), 1.17 (s, 3H), 1.12 (s, 3H), 0.86 (s, 3H). MS m/z 392 (M$^+$).

EXAMPLE 3

1-(1-phenyl-ethyl)-4,5,6,7-tetrahydro-1H-indazole-3-carboxylic acid [(1S)-1-cyclohexyl-ethyl]-amide (Cpd 249)

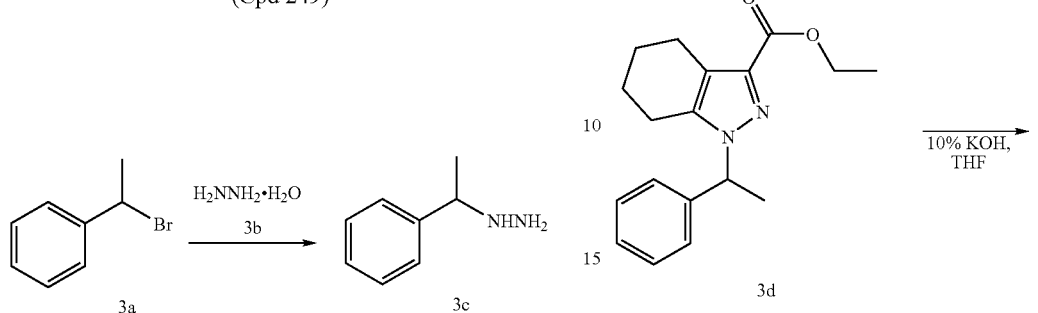

1-bromoethylbenzene Compound 3a (8.0 mL, 58.0 mMol) was added to a solution of hydrazine hydrate Compound 3b (20 mL) in THF (80 mL) which was then heated to reflux for 8 hrs. The solvent was removed in vacito and Et$_2$O (100 mL) was added. The organic layer was washed with brine, separated and dried over Na$_2$SO$_4$. The solvent was removed in vacuo to yield (1-phenyl-ethyl)-hydrazine Compound 3c as a pale yellow oil (5.8 g), used in the next step without purification. MS m/z 137 (M+H, 70%), 105 (M-NHNH$_2$, 100%).

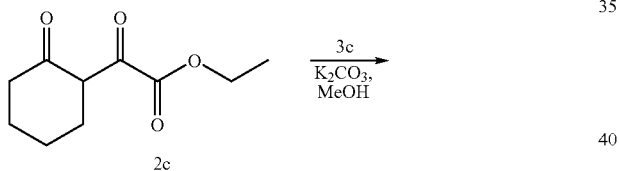

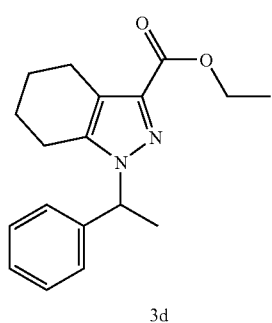

Oxo-(2-oxo-cyclohexyl)-acetic acid ethyl ester Compound 2c (3.97 g, 20.0 mMol) was added to a solution containing crude Compound 3c (5.8 g, 29.0 mMol) and K$_2$CO$_3$ (0.2 g) in MeOH (40 mL). The suspension was stirred at r.t. for 48 hrs. The solvent was removed in vacuo and the residue was extracted with CH$_2$Cl$_2$. The organic layer was washed with water and brine, then separated and dried over Na$_2$SO$_4$ to provide Compound 3d as a red oil (4.6 g), used in the next step without further purification. MS m/z 321 (M+Na, 100%).

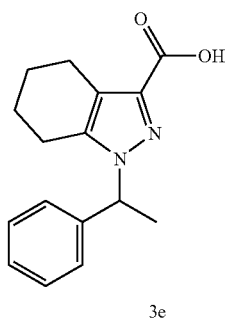

Compound 3d was dissolved in a solution of KOH (5.6 g, 100 mMol) in THF (40 mL) and water (60 mL). The resulting solution was stirred at r.t. for 12 hrs, followed by removal of the THF in vacuo. The aqueous solution was extracted with Et$_2$O to remove impurities. The aqueous layer was then acidified with 6 N HCl and was extracted with Et$_2$O (2×50 mL). The organic layer was separated and dried over Na$_2$SO$_4$. The solvent was removed in vacuo to yield 1-(1-phenyl-ethyl)-4,5,6,7-tetrahydro-1H-indazole-3-carboxylic acid Compound 3e as pale yellow solid. MS m/z (+ve mode) 293 (M+Na, 100%), MS m/z (−ve mode) 269 (M−H, 100%).

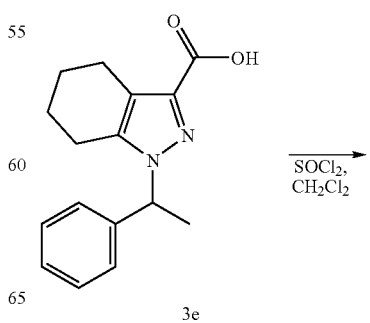

-continued

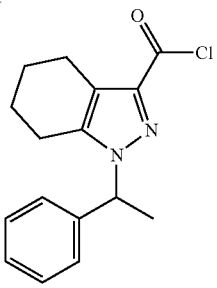

3f

Compound 3e (2.0 g, 7.4 mMol) was dissolved in CH₂Cl₂ (15 mL) and treated with SOCl₂ (8.0 g). The resulting solution was heated to reflux for 3 hrs followed by removal of the solvent in vacuo to provide 1-(1-phenyl-ethyl)-4,5,6,7-tetrahydro-1H-indazole-3-carbonyl chloride Compound 3f as a brownish yellow oil.

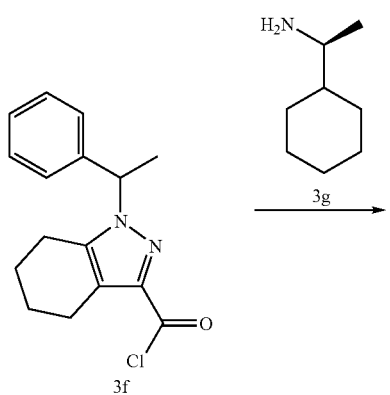

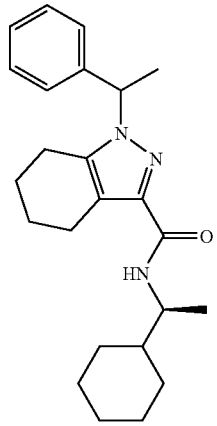

Cpd 249

A solution of Compound 3f (0.06 g, 0.2 mMol) in CH₂Cl₂ (1 mL) was added to a solution of commercially available (S)-1-cyclohexyl-ethylamine Compound 3g (0.03 mL, 0.18 mMol) in CH₂Cl₂ (2 mL) and triethylamine (0.1 mL, 0.8 mMol) at 0° C. The resulting suspension was stirred for 2 hrs, then the reaction was quenched with water (5 mL) and the mixture was extracted with Et₂O. The organic layer was washed with 10% NaOH and brine, then separated and dried over Na₂SO₄. The solvent was removed in vacuo and the crude product was purified by preparative TLC (1:1 hexane/EtOAc) to provide Compound 249 as a mixture of diastereomers in a brown oil. MS m/z 380 (M+H, 100%).

¹H NMR (300 MHZ, CDCl₃) δ 7.12-7.29 (m, 3H), 6.95-7.06 (m, 2H), 6.70 (br d, J=6.0 Hz, 1H), 5.27 (q, J=3.0 Hz, 1H), 3.84-4.01 (m, 1H), 2.72 (br t, 2H), 2.30-2.45 (br m, 1H), 2.12-2.26 (br m, 1H), 1.82 (d, J=6.0 Hz, 3H), 1.48-1.86 (br m, 8H), 1.27-1.42 (m, 1H), 1.12 (d, J=6.0 Hz, 3H), 0.90-1.25 (br m, 6H).

EXAMPLE 4

1-cyclohexyl-4,5,6,7-tetrahydro-1H-indazole-3-carboxylic acid [2-hydroxy-2-(4-methoxy-phenyl)-ethyl]-amide (Cpd 241)

Cpd 176

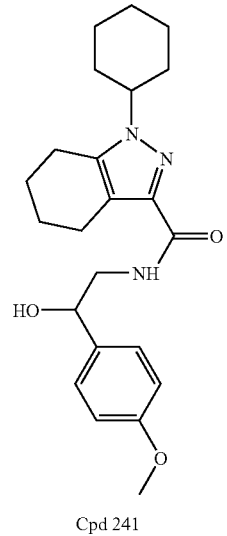

Cpd 241

Compound 176 was prepared according to the procedure of Example 2; replacing Compound 2d with cyclohexyl-hydrazine Compound 5a and using 2-amino-1-(4-methoxy-phenyl)-ethanone as Compound 2i). NaBH₄ (sodium borohydride) (0.05 g, 1.25 mMol) was added in one portion to a solution of Compound 176 (0.08 g, 0.2 mMol) in MeOH (2 mL) and THF (8 mL) at r.t. The mixture was stirred at r.t. for 4 hrs and the solvent was removed in vacuo. The residue was extracted with CH$_2$Cl$_2$ and the organic layer was washed successively with water, saturated aqueous NaHCO$_3$ and brine. The organic layer was separated, then dried with anhydrous sodium sulfate and filtered. The solvent was evaporated to provide a crude product which was then purified by preparative TLC on silica gel (3:2 hexane/EtOAc, Rf=0.35) to provide Compound 241 (29.8 mg, 75%) as a sticky solid.

MS m/z 420 (M+Na, 30%), 380 (M–H$_2$O, 100%); $^1$H NMR (300 MHZ, CDCl$_3$) δ 7.25 (br s, 1H), 7.21 (d, J=6.0 Hz, 2H), 6.78 (d, J=6.0 Hz, 2H), 4.75-4.83 (m, 1H), 3.82-3.98 (m, 1H), 3.71 (s, 3H), 3.55-3.68 (m, 1H), 3.33-3.47 (m, 1H), 2.70 (br t, 2H), 2.48 (br t, 2H), 1.58-1.90 (m, 10H), 1.18-1.39 (m, 4H).

EXAMPLE 5

1-cyclohexyl-4,5,6,7-tetrahydro-1H-indazole-3-carboxylic acid cyclohexylmethylamide (Cpd 304)

For this example, Compound 2c was prepared as follows: LHMDS (100 mL of 1.0 M solution in THF) was added to a 500 mL round bottom flask and cooled to –78° C. Cyclohexanone Compound 2a (10.36 mL, 100 mMol) in 20 mL THF was added dropwise and the mixture was stirred at –78° C. for 1 hr. Diethyl oxalate Compound 2b (13.6 mL, 100 mMol) was added slowly at –78° C. and the mixture was stirred at the same temperature for 1 hr. The reaction mixture was stirred and allowed to warm to r.t. overnight. The mixture was then concentrated and taken up in EtOAc (500 mL) and washed with 1N HCl (2×200 mL) followed by water (2×200 mL). The organic layer was separated, then dried with anhydrous sodium sulfate and filtered. The organic layer was separated, then dried with anhydrous sodium sulfate and filtered. The solvent was evaporated to provide an ester Compound 2c (15 g, 75.7%) as an orange oil.

Compound 2c (1.98 g, 10 mMol) was taken up in EtOH (40 mL) and anhydrous cyclohexyl hydrazine hydrochloride Compound 1d (1.5 g, 10 mMol) and K$_2$CO$_3$ (1.38 g, 10 mMol) were added. The mixture was stirred at r.t. overnight, then filtered and washed with EtOH (20 mL). The combined filtrate was concentrated and purified on a silica gel column (eluted with 20% EtOAc in hexane) to give of a mixture of a major isomer Compound 5b and a minor isomer Compound 5c (2.3 g, 83%).

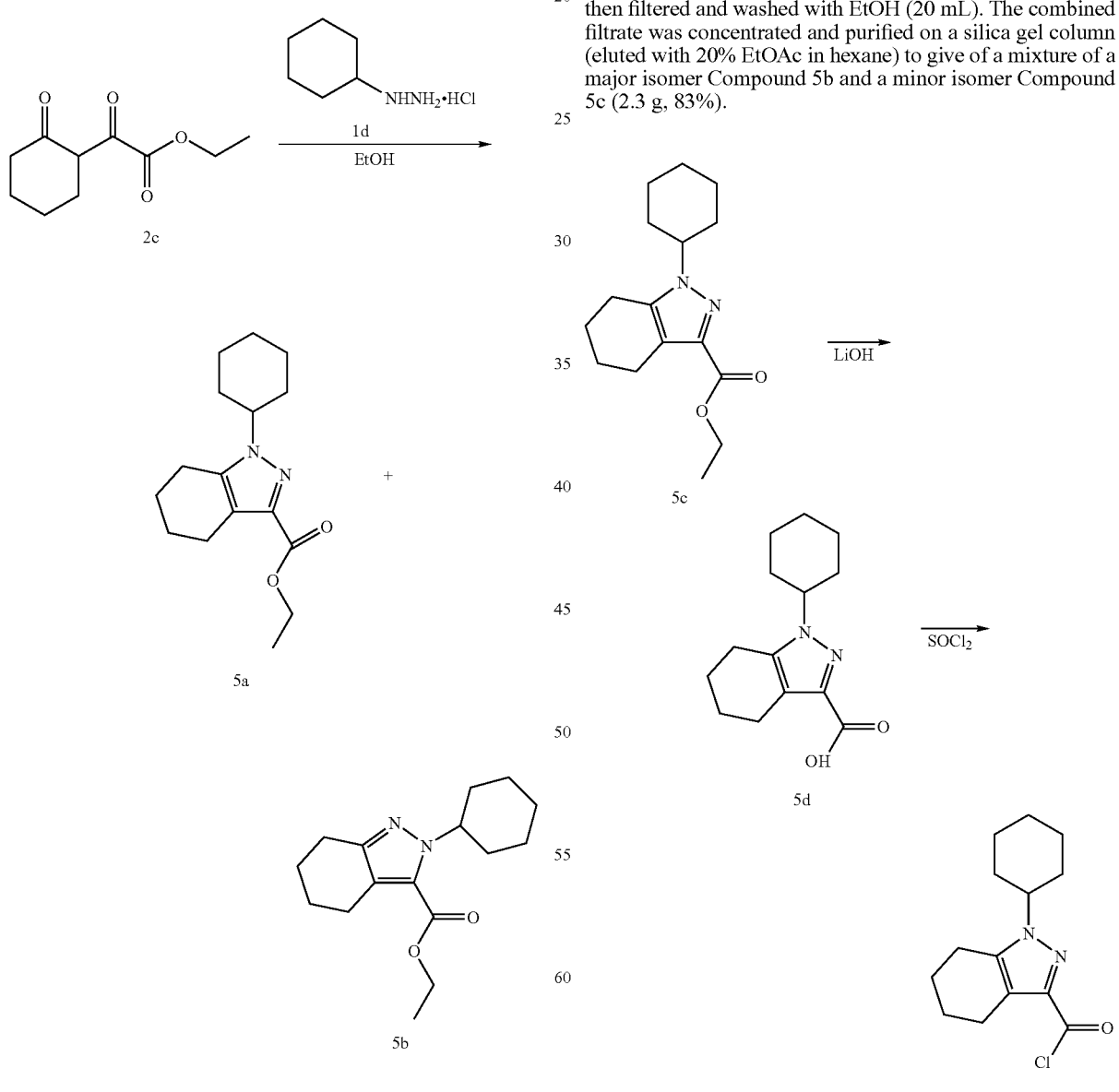

The major isomer Compound 5b (0.81 g, 2.92 mMol) was dissolved in a solution of MeOH (24 mL) and THF (8 mL) and aqueous LiOH (0.52 g LiOH in 8 mL H₂O) was added. The mixture was stirred at r.t. for 4 hrs, then concentrated and diluted with water (100 mL). The resulting aqueous solution was washed with EtOAc in hexane (1:1 in 50 mL). The aqueous layer was acidified to pH 4 using 1N HCl and extracted with EtOAc (100 mL). The organic layer was separated, then dried over magnesium sulfate and filtered. The solvent was evaporated to provide an acid Compound 5d (0.7 g, 96%).

Compound 5d (0.4 g, 1.6 mMol) was dissolved in 10 mL CH₂Cl₂ (methylene chloride) and was treated with SOCl₂ (thionyl chloride) (0.3 mL). The resulting solution was heated to reflux for 3 hrs and the solvent was removed in vacuo to provide 0.36 g (84%) of the acid chloride Compound 5e.

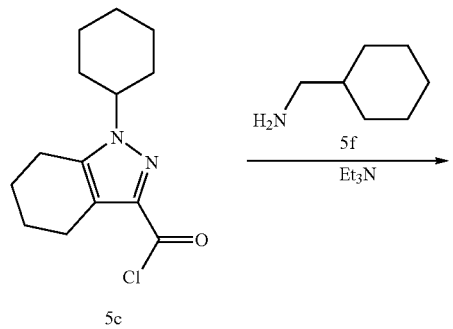

5c

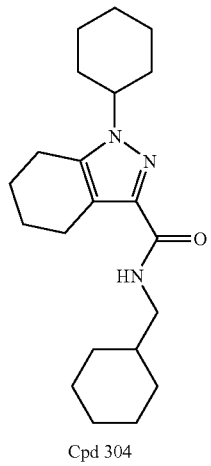

Cpd 304

The acid chloride Compound 5e (0.08 g, 0.3 mMol) was added to a solution of cyclohexylmethylamine Compound 5f (0.08 mL, 0.6 mMol) in 2 mL of CH₂Cl₂ and triethylamine (0.125 mL, 0.9 mMol). The resulting suspension was stirred at r.t. for 2 hrs and then diluted with 10 mL CH₂Cl₂. The resulting mixture was washed with 1N HCl (2×10 mL) and water (2×10 mL). The organic layer was dried over sodium sulfate, then concentrated and purified on a silica gel column (eluted with 20% EtOAc in hexane) to provide an amide Compound 304 (90 mg, 88%). MS m/z 344 (MH⁺).

EXAMPLE 6 naphthalene-2-carboxylic acid (1-cyclohexyl-4,5,6,7-tetrahydro-1H-indazol-3-yl)-amide (Cpd 178)

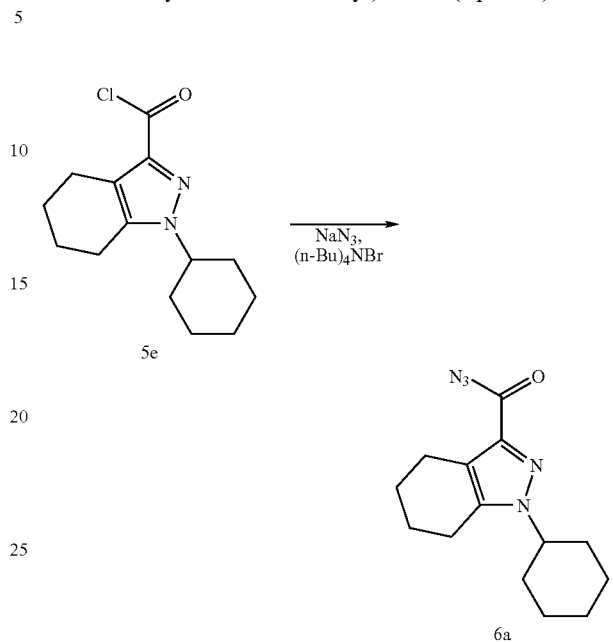

Tetrabutylammonium bromide ((n-Bu)₄NBr)(10 mg) in a catalytic amount was added to a solution of 1-cyclohexyl-4,5,6,7-tetrahydro-1H-indazole-3-carbonyl chloride Compound 5e (0.134 g, 0.5 mMol) in DCE (dichloroethane) (5 mL) at 0° C. NaN₃ (sodium azide) (0.5 mL saturated solution in water) was then added dropwise at 0° C. The resulting reaction mixture was stirred for 0.5 hrs before being diluted with cold water and CH₂Cl₂. The organic layer was washed with water (2×10 mL), brine (2×10 mL), dried over sodium sulfate, filtered and concentrated to give an azide Compound 6a (0.11 g, 80%).

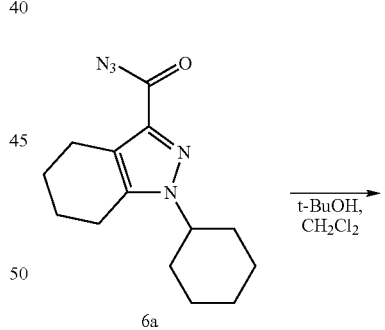

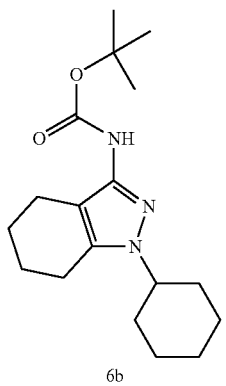

6b

To a solution of azide Compound 6a (0.2 g, 0.73 mMol) in 5 mL CH$_2$Cl$_2$ was added t-BuOH (tert-butanol) (1 g, 13.5 mMol). The resulting mixture was refluxed for 48 hrs before being concentrated. The crude product was purified on a silica gel column (eluted with 10% EtOAc in hexane) to give a Boc-protected amine Compound 6b (0.15 g, 64%).

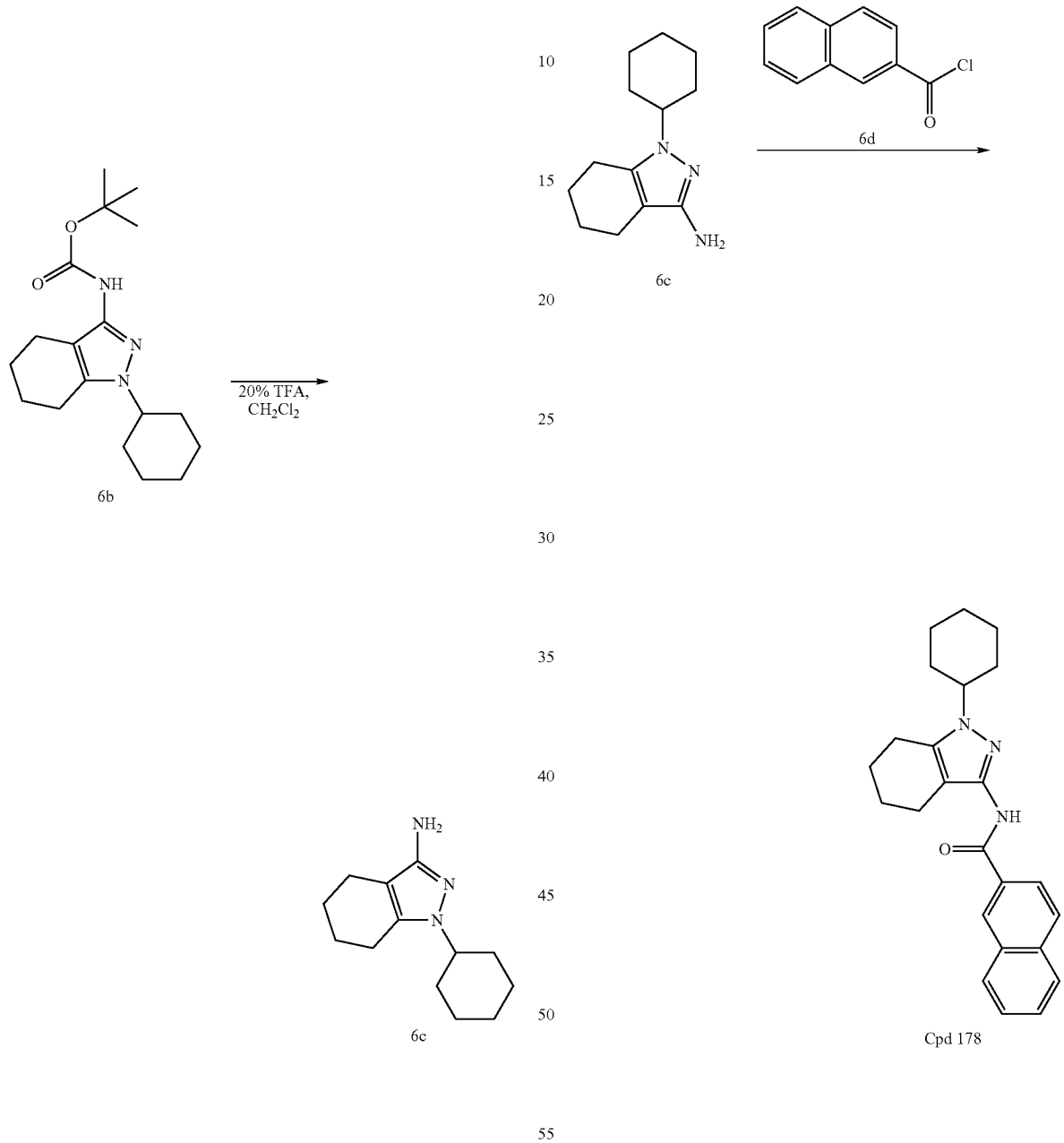

To a solution of Compound 6b (0.15 g, 0.47 mMol) in 8 mL CH$_2$Cl$_2$ was added 2 mL TFA. The reaction mixture was stirred overnight and then concentrated. The crude product was dissolved in CH$_2$Cl$_2$ and washed with 1N NaOH (2×20 mL) and water (2×20 mL). The organic layer was dried over sodium sulfate, filtered and concentrated to give Compound 6c (0.127 g, 93%).

Naphthalene-2-carbonyl chloride Compound 6d (5 mg, 0.026 mMol) and TEA (0.01 mL, 0.072 mMol) were added to a solution of Compound 6c (5 mg, 0.023 mMol). The reaction mixture was stirred at r.t. for 4 hrs, then concentrated and purified on a silica gel column (eluted with 15% EtOAc in hexane) to give Compound 178 (5.1 mg, 60%). MS m/z 374 (MH$^+$)

EXAMPLE 7

3-(adamantan-2-ylcarbamoyl)-1-cyclohexyl-4,5,6,7-tetrahydro-1H-indazole-5-carboxylic acid (Cpd 223)

1-cyclohexyl-4,5,6,7-tetrahydro-1H-indazole-3,5-dicarboxylic acid 3-adamantan-2-ylamide 5-[(1,1,3,3-tetramethyl-butyl)-amide] (Cpd 228)

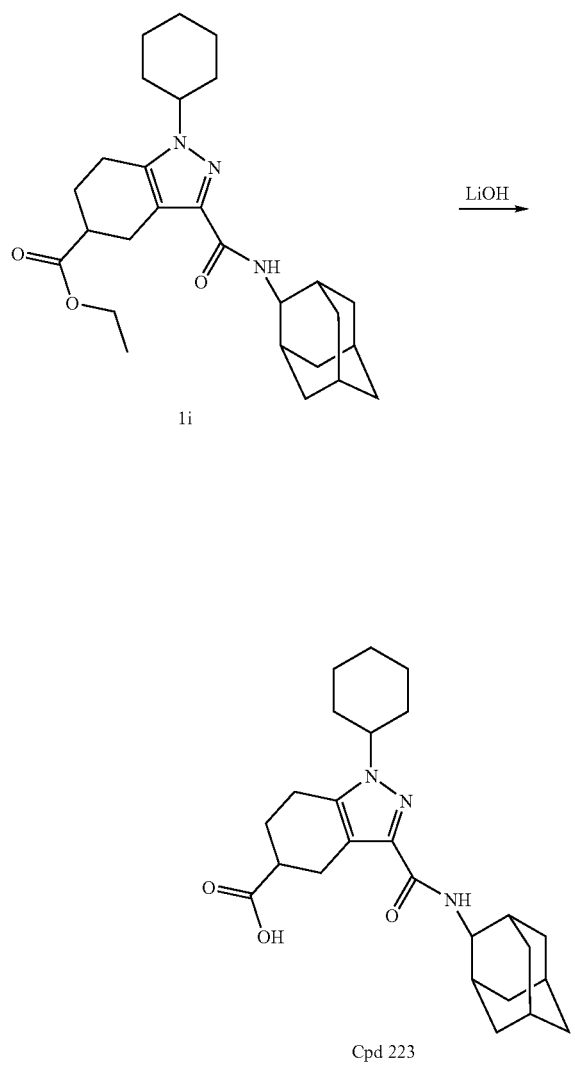

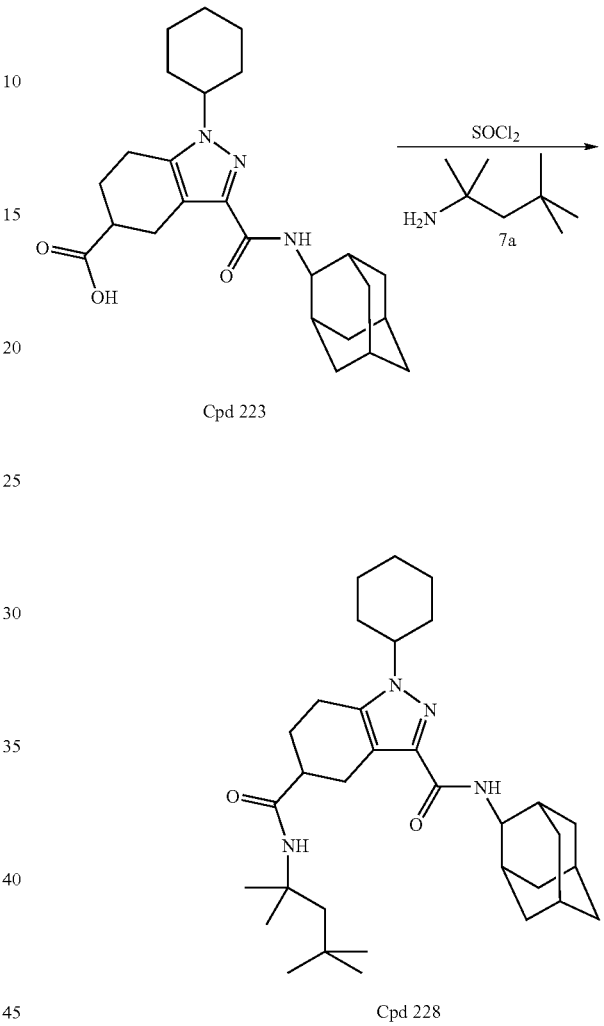

The 3-(adamantan-2-ylcarbamoyl)-1-cyclohexyl-4,5,6,7-tetrahydro-1H-indazole-5-carboxylic acid ethyl ester Compound 1i (100 mg, 0.22 mMol) was added to a solution of LiOH (lithium hydroxide) monohydrate (46 mg) in a 3:1:1 ratio of THF:MeOH:water (10 mL). The mixture was stirred overnight at r.t. and then concentrated in vacuo. The residue was neutralized with 1N HCl to give Compound 223 (87 mg, 93%) as a white precipitate. MS m/z 426 (M+H)$^+$, 448 (M+Na)$^+$; $^1$H NMR (CDCl$_3$, 300 MHz) δ: 7.26 (1H, b), 4.21 (1H, m), 3.91 (1H, m), 3.31 (1H, m), 2.93 (1H, m), 2.75 (3H, m), 2.21 (1H, m), 1.88 (23H, m), 1.35 (2H, m).

Thionyl chloride (1 mL) was added to Compound 223 (10 mg, 0.023 mMol) and the mixture was refluxed for 10 min. The excess thionyl chloride was evaporated and the residue was washed with CH$_2$Cl$_2$. 1,1,3,3-tetramethyl-butylamine Compound 7a (6 mg, 0.046 mMol) was added to the residue in CH$_2$Cl$_2$ and the mixture was stirred for 70 min, washed with 1N HCl and brine, then dried over sodium sulfate. The crude product was purified by preparative TLC (50% EtOAc in hexane) to give Compound 228 (8 mg, 63.5%) as a white solid.

MS m/z 537 (M+H)$^+$, 559 (M+Na)$^+$; $^1$H NMR (CDCl$_3$, 300 MHz) δ: 7.26 (1H, b), 5.42 (1H, b), 4.19 (1H, m), 3.90 (1H, m), 3.21 (1H, m), 2.79 (2H, m), 2.56 (2H, m), 2.21 (1H, m), 1.7-2.1 (23H, m), 1.42 (4H, m), 1.19 (3H, s), 1.02 (9H, s), 0.97 (3H, s).

EXAMPLE 8

[1-cyclohexyl-3-(1,3,3-trimethyl-bicyclo[2.2.1]hept-2-ylcarbamoyl)-4,5,6,7-tetrahydro-1H-indazol-5-yl]-carbamic acid tert-butyl ester (Cpd 86)

5-amino-1-cyclohexyl-4,5,6,7-tetrahydro-1H-indazole-3-carboxylic acid (1,3,3-trimethyl-bicyclo[2.2.1]hept-2-yl)-amide (Cpd 92)

1-cyclohexyl-5-hydroxy-4,5,6,7-tetrahydro-1H-indazole-3-carboxylic acid (1,3,3-trimethyl-bicyclo[2.2.1]hept-2-yl)-amide (Cpd 93)

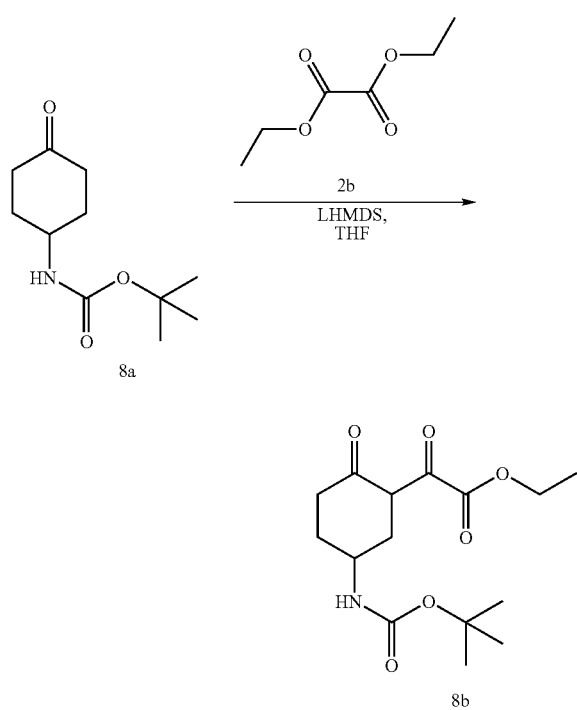

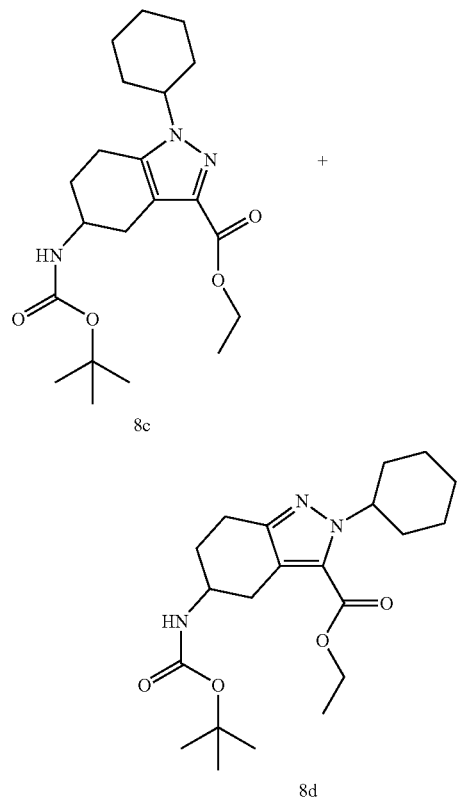

According to the procedure of Example 2, a solution of (4-oxo-cyclohexyl)-carbamic acid tert-butyl ester Compound 8a in ether was used in place of cyclohexanone Compound 2a and carried forward to produce (5-tert-butoxycarbonylamino-2-oxo-cyclohexyl)-oxo-acetic acid ethyl ester Compound 8b.

Using the procedure of Example 2, Compound 8b was used in place of oxo-(2-oxo-cyclohexyl)-acetic acid ethyl ester Compound 2c and cyclohexyl-hydrazine Compound 1d was used in place of benzylhydrazine dihydrochloride Compound 2d to produce a major isomer 5-tert-butoxycarbonylamino-1-cyclohexyl-4,5,6,7-tetrahydro-1H-indazole-3-carboxylic acid ethyl ester Compound 8c and a minor isomer 5-tert-butoxycarbonylamino-2-cyclohexyl-4,5,6,7-tetrahydro-2H-indazole-3-carboxylic acid ethyl ester Compound 8d.

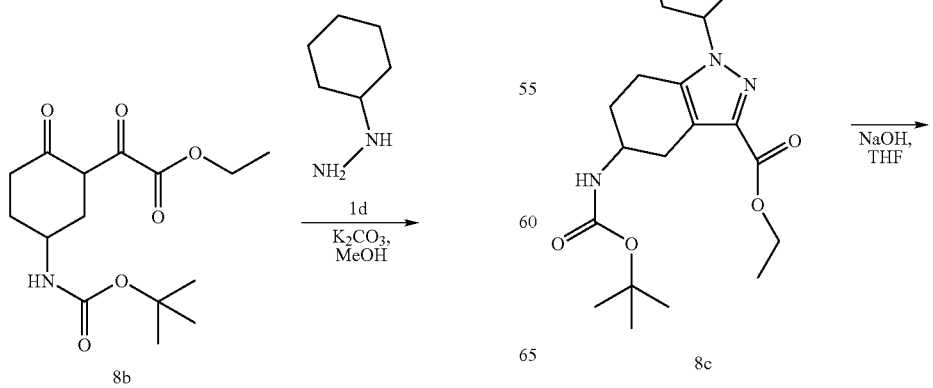

-continued

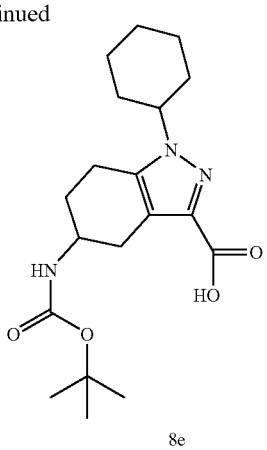

8e

Using the procedure of Example 2, Compound 8c was used in place of 1-benzyl-4,5,6,7-tetrahydro-1H-indazole-3-carboxylic acid ethyl ester Compound 2e to produce 5-tert-butoxycarbonylamino-1-cyclohexyl-4,5,6,7-tetrahydro-1H-indazole-3-carboxylic acid Compound 8e.

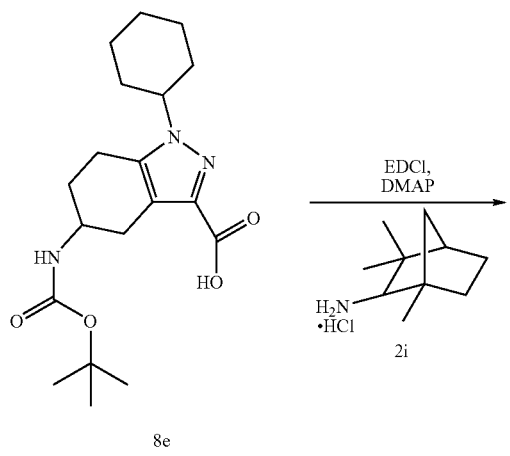

Using the procedure of Example 24, Compound 8e was used in place of 1-cyclohexyl-7-hydroxy-4,5,6,7-tetrahydro-1H-indazole-3-carboxylic acid Compound 24a and 1,3,3-trimethyl-bicyclo[2.2.1]hept-2-ylamine hydrochloride Compound 2i was used in place of (2S,3R)-3-amino-bicyclo[2.2.1]heptane-2-carboxylic acid ethyl ester Compound 24b to produce Compound 86.

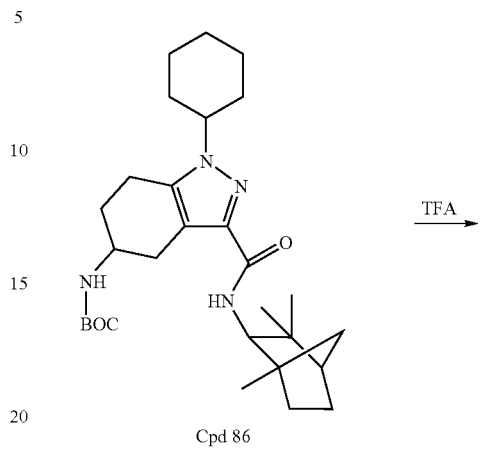

Ester Compound 86 (0.1 g, 0.2 mMol) was added to a solution of 50% TFA in $CH_2Cl_2$ (2 mL). The mixture was stirred for 3 hrs and the solvent was evaporated to give Compound 92 (0.1 g, yield 98%) as a TFA salt.

MS m/z 399 (M+H)+, 421 (M+Na)+. $^1$H NMR (CDCl$_3$, 300 MHz) δ: 7.05 (1H, b), 6.03 (3H, b), 3.86 (1H, m), 3.64 (1H, m), 3.42 (1H, m), 2.89 (2H, m), 2.69 (1H, m), 2.36 (1H, m), 1.65-1.95 (11H, m), 1.18-1.41 (8H, m), 1.05 (3H, s), 1.02 (3H, s), 0.82 (3H, s).

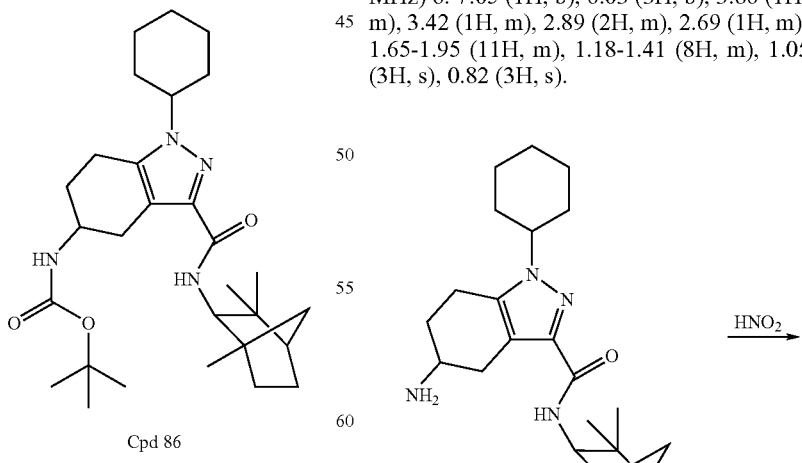

-continued

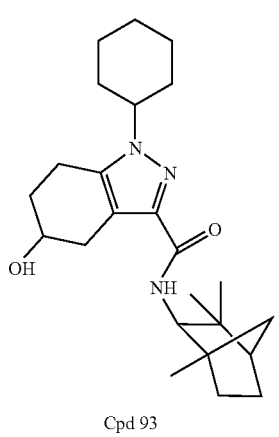

Cpd 93

-continued

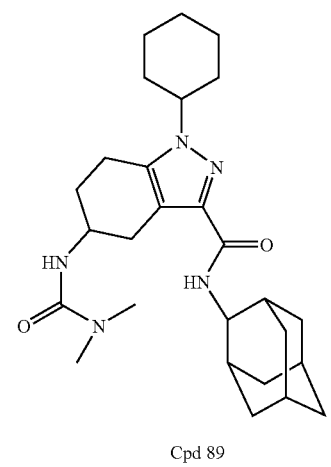

Cpd 89

Compound 92 (0.1 g, 0.2 mMol) was added to a solution of NaNO₂ (27 mg, 0.4 mMol) in acetic acid (3 mL) at 0° C. The mixture was stirred for 2 hrs and the product was run on prep TLC (30% EtOAc in hexane) to give Compound 93 (22 mg, yield 28%).

MS m/z 400 (M+H)⁺, 422 (M+Na)⁺. ¹H NMR (CDCl₃, 300 MHz) δ: 7.02 (1H, b), 4.19 (1H, m), 3.90 (1H, m), 3.72 (1H, m), 3.19 (1H, m), 2.81 (3H, m), 2.61 (1H, m), 1.89 (7H, m), 1.70 (4H, m), 1.34 (4H, m), 1.21 (3H, m), 1.13 (3H, s), 1.09 (3H, s), 0.82 (3H, s).

EXAMPLE 9

1-cyclohexyl-5-(3,3-dimethyl-ureido)-4,5,6,7-tetrahydro-1H-indazole-3-carboxylic acid adamantan-2-ylamide (Cpd 89)

Dimethylcarbamyl chloride Compound 9b (0.56 mL, 6 mMol) was added dropwise to a solution of Compound 9a (0.8 g, 2 mMol) (prepared similarly to Compound 92 using the procedure of Example 8) and TEA (0.3 g, 3 mMol) in CH₂Cl₂ (10 mL). The mixture was stirred for 2 hrs and the reaction was quenched with 1N NaOH. The organic layer was dried over Na₂SO₄ and the CH₂Cl₂ was evaporated. The crude product was purified via column chromatography (using EtOAc as the eluent) to give Compound 89 (0.8 g, yield 86%) as a white solid.

MS m/z 468 (M+H)⁺, 490 (M+Na)⁺. ¹H NMR (CDCl₃, 300 MHz) δ: 7.26 (1H, b), 4.32 (1H, d, J=6.6 Hz), 4.19 (1H, m), 4.07 (1H, m), 3.92 (1H, m), 3.21 (1H, dd, J=16.0, 5.2 Hz), 2.88 (6H, s), 2.65 (2H, m), 2.15 (1H, m), 2.02 (2H, m), 1.90 (16H, m), 1.75 (6H, m), 1.32 (2H, m).

EXAMPLE 10

1-(2,4-dichloro-phenyl)-7-(4-fluoro-benzylidene)-4,5,6,7-tetrahydro-1H-indazole-3-carboxylic acid piperidin-1-ylamide (Cpd 297)

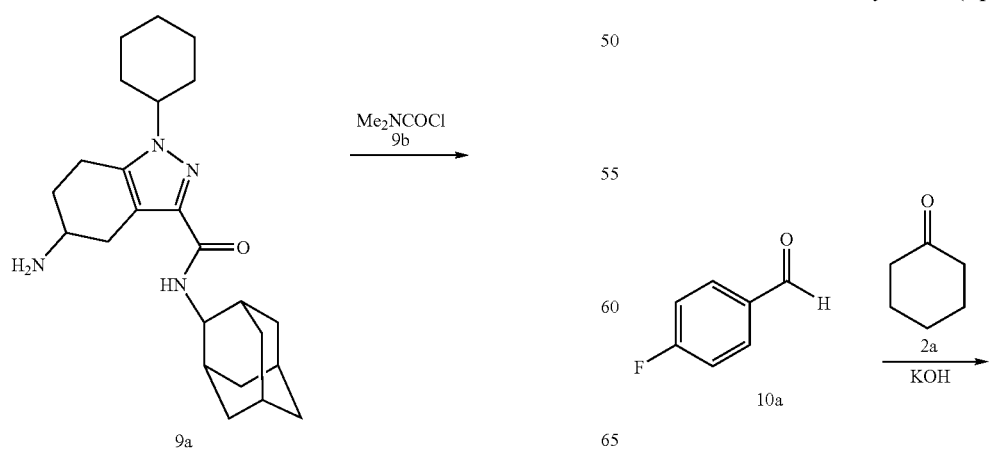

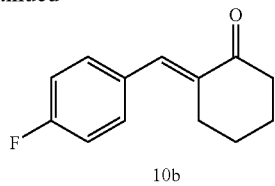

10b

An aqueous KOH (0.25 g in 4.4 mL water) solution was added to p-fluorobenzaldehyde Compound 10a (1.04 mL, 10 mMol) and the mixture was heated to 65° C. Cyclohexanone Compound 2a (1.03 mL, 10 mMol) was added dropwise over 10 min and the reaction mixture was refluxed for 5 hrs, then cooled to r.t. and stirred at r.t. overnight. The reaction mixture was acidified with 1N HCl (26 mL) and diluted with EtOAc. The organic layer was separated and washed with brine, then dried with anhydrous sodium sulfate and filtered. The solvent was evaporated to provide a crude product which was then purified by silica gel column (eluted with 6% EtOAc in hexane) to give 2-(4-fluoro-benzylidene)-cyclohexanone Compound 10b (1.1 g, 54%).

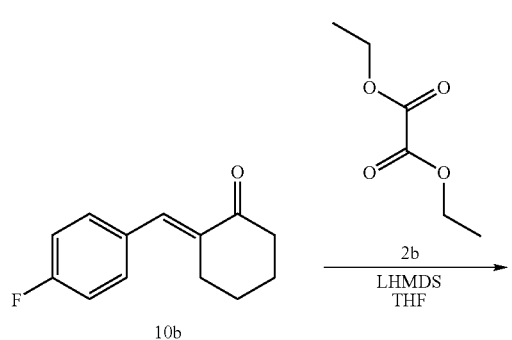

10c

Cyclohexanone Compound 10b (1.1 g, 5.4 mMol) in THF (5 mL) was added dropwise to a solution of lithium bis(trimethylsilyl)amide (5.4 mL of 1.0M solution in THF) in THF (10 mL) at −78° C. The mixture was stirred at −78° C. for 1 hr, then diethyl oxalate Compound 2b (0.732 mL, 5.4 mMol) in THF (5 mL) was added slowly at −78° C. The mixture was stirred at −78° C. for 1 hr, then stirred and allowed to warm to r.t. overnight. The mixture was concentrated, taken up in EtOAc (100 mL) and washed with 1N HCl (2×50 mL) and water (2×50 mL). The organic layer was separated, then dried with anhydrous sodium sulfate and filtered. The solvent was evaporated to provide a [3-(4-fluoro-benzylidene)-2-oxo-cyclohexyl]-oxo-acetic acid ethyl ester Compound 10c (1.4 g, 85%) as an orange oil which was used in the next step without further purification.

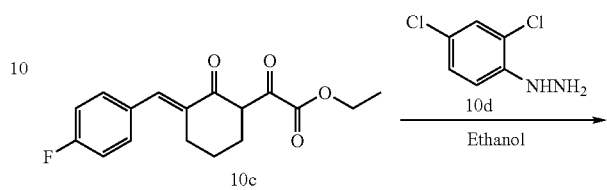

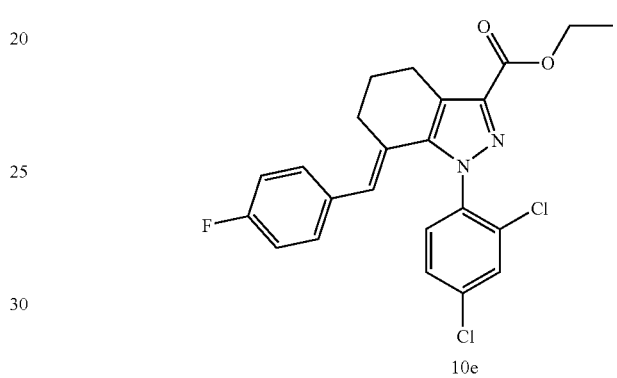

10e

Compound 10c (1.4 g, 4.62 mmol) was taken up in ethanol (30 mL), then anhydrous (2,4-dichloro-phenyl)-hydrazine hydrochloride Compound 10d (0.99 g, 4.62 mMol) and $K_2CO_3$ (1.28 g, 9.24 mMol) were added. The reaction mixture was stirred at r.t. overnight, then filtered and washed with ethanol (20 mL). The combined filtrate was concentrated and purified on a silica gel column (eluted with 20% EtOAc in hexane) to give 1-(2,4-Dichloro-phenyl)-7-(4-fluoro-benzylidene)-4,5,6,7-tetrahydro-1H-indazole-3-carboxylic acid ethyl ester Compound 10e (0.8 g, 39%).

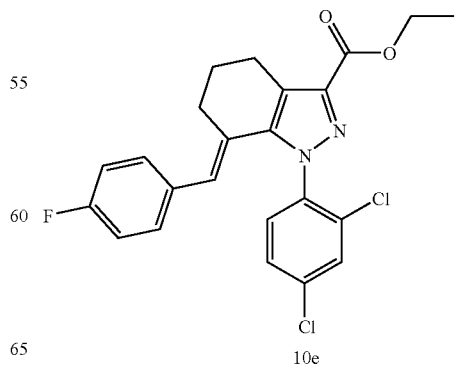

10e

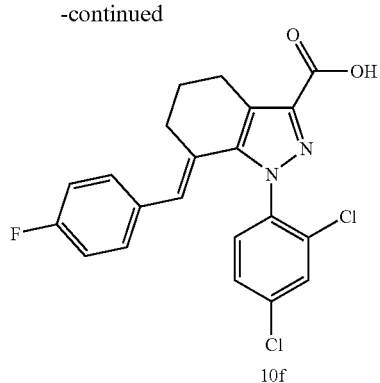

10f

Ethyl ester Compound 10e (0.8 g, 1.8 mMol) was dissolved in THF (18 mL). Aqueous LiOH (lithium hydroxide) (0.26 g in 6 mL), then ethanol (2 mL) were added and the mixture was stirred at r.t. for 24 hrs, then concentrated, diluted with water (25 mL) and acidified to pH 4 using 1N HCl. The aqueous suspension was extracted with EtOAc (100 mL).

The organic layer was separated and washed with brine, then dried over magnesium sulfate and filtered. The solvent was evaporated to provide an acid Compound 10f (0.74 g, 98%).

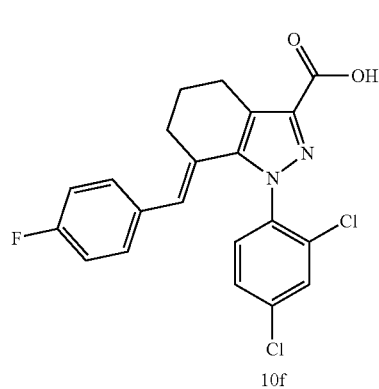

10f $\xrightarrow{SOCl_2}$

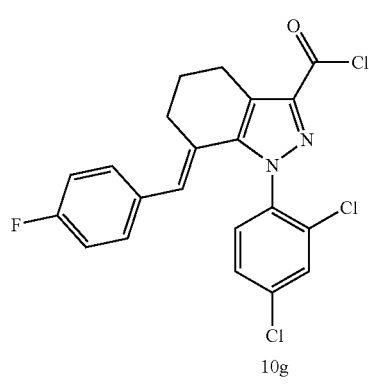

10g

The acid Compound 10f (0.74 g, 1.77 mMol) was taken up in $CH_2Cl_2$ (5 mL), then treated with thionyl chloride (1 mL, 14.1 mMol). The solution was heated to reflux for 3 hrs, the solvent was removed in vacuo to obtain the acid chloride Compound 10g (0.76 g, 99%).

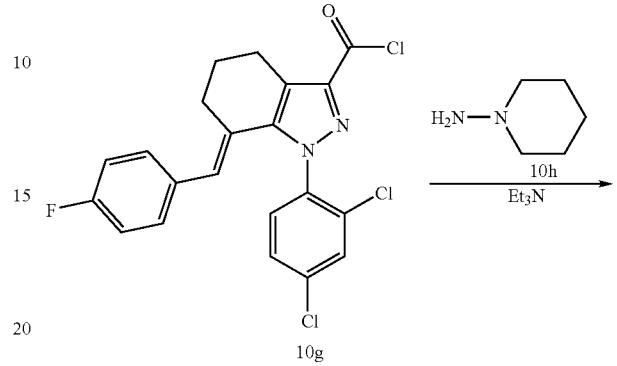

10g

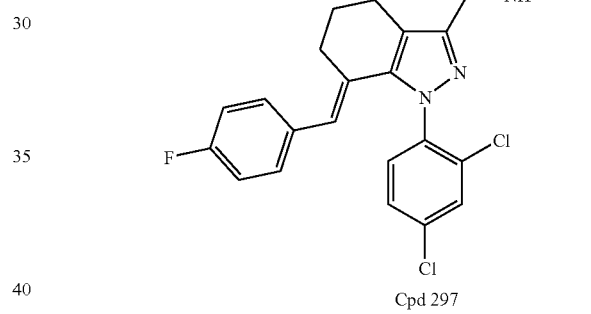

Cpd 297

Compound 10g (0.044 g, 0.1 mMol) was added to a solution of commercially available 1-aminopiperidine Compound 10h (0.021 mL, 0.2 mMol) in $CH_2Cl_2$ (2 mL) and triethylamine (0.055 mL, 0.4 mMol). The suspension was stirred, then diluted and washed. The organic layer was dried, concentrated and purified on a silica gel column (eluted with 40% EtOAc in hexane) to provide Compound 297 (40 mg, 80.2%). MS m/z 499 (MH+); $^1$H NMR (CDCl$_3$, 400 MHz) δ 7.57-7.41 (m, 4H), 7.07-6.92 (m, 4H), 5.89 (s, 1H), 3.09-3.00 (m, 2H), 2.87-2.79 (m, 4H), 2.71-2.54 (m, 2H), 1.93-1.68 (m, 6H), 1.45-1.36 (m, 2H).

Compound 297 (100 mg, 0.2 mMol) was dissolved in $CH_2Cl_2$ (2 mL) and a solution of 1N HCl in ether (1 mL) was added slowly. The mixture was stirred at r.t. for 1 hr, then concentrated and washed with ether (3×). The remaining ether was removed in vacuo to provide Compound 297 (95 mg, 89%) as a hydrochloride salt.

MS m/z 499 (MH+); $^1$H NMR (CDCl$_3$, 400 MHz) δ 9.33(s, 1H), 7.57(s, 1H), 7.46(s, 2H), 7.06-6.93 (m, 4H), 5.93 (s, 1H), 4.20-3.61(broad peak, 4H), 3.02-2.88 (m, 2H), 2.78-2.52 (m, 2H), 2.21-1.55 (m, 8H).

EXAMPLE 11

2-(1-benzyl-4,5,6,7-tetrahydro-1H-indazol-3-yl)-ethenesulfonic acid [(1R)-1-phenyl-ethyl]-amide (Cpd 260)

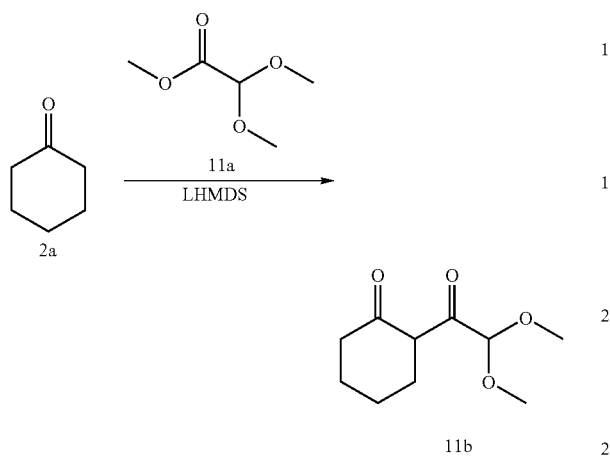

Cyclohexanone Compound 2a (1.37 g, 14.0 mMol) in THF (5 mL) was added dropwise to a solution of LHMDS (16.0 mL, 16.0 mMol) in anhydrous THF (25 mL) at −78° C. under a $N_2$ atmosphere. The solution was stirred at −78° C. for about 1 hr. Methyl dimethoxyacetate Compound 11a (1.88 g, 14.0 mMol) in anhydrous THF (5 mL) was then added dropwise. The reaction mixture was stirred while warming to r.t. over a period of about 15 hrs, then the reaction was quenched with water (5 mL). The organic layer was diluted with EtOAc (100 mL) and washed with water and brine. The organic layer was separated and dried with anhydrous sodium sulfate, then filtered and concentrated in vacuo to yield a crude product as an oil. The oil was purified by flash chromatography (eluted with 10% EtOAc in hexane) to afford 2-(2,2-dimethoxy-acetyl)-cyclohexanone Compound 11b (1.82 g, 65%).

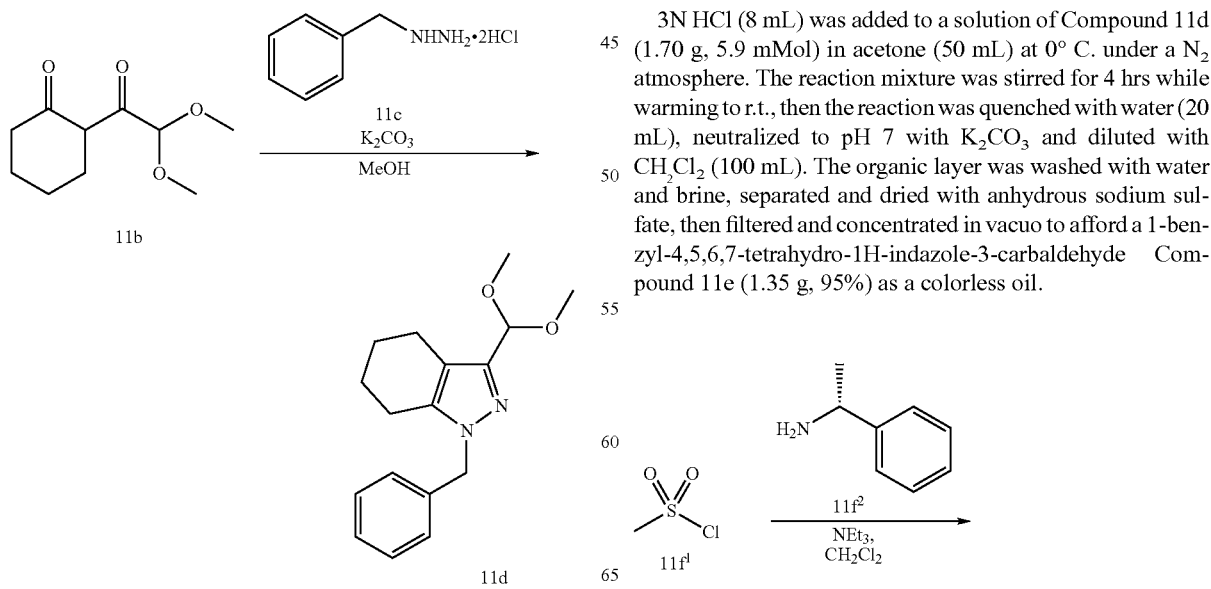

Benzylhydrazine dihydrochloride Compound 11c (1.75 g, 9.00 mMol) and $K_2CO_3$ (1.51 g, 10.92 mMol) were added to a solution of Compound 11b (1.80 g, 9.10 mMol) in MeOH (50 mL) at 0° C. under a $N_2$ atmosphere. The reaction mixture was stirred overnight while warming to r.t., then the reaction was quenched with water (20 mL). The organic layer was diluted with EtOAc (200 mL) and washed with water and brine. The organic layer was separated and dried with anhydrous sodium sulfate, then filtered and concentrated in vacuo to yield a crude product as an oil. The oil was purified by flash chromatography (eluted with 20% EtOAc in hexane) to afford 1-benzyl-3-dimethoxymethyl-4,5,6,7-tetrahydro-1H-indazole Compound 11d (1.80 g, 70%) as a colorless oil.

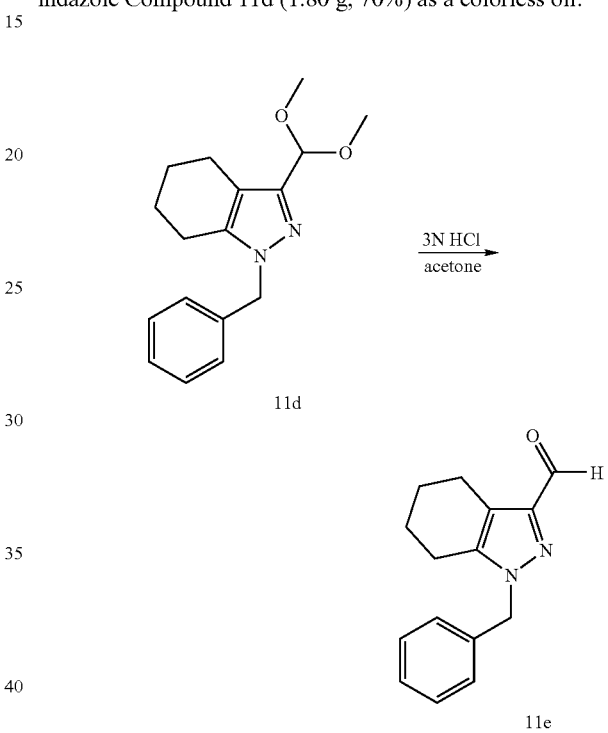

3N HCl (8 mL) was added to a solution of Compound 11d (1.70 g, 5.9 mMol) in acetone (50 mL) at 0° C. under a $N_2$ atmosphere. The reaction mixture was stirred for 4 hrs while warming to r.t., then the reaction was quenched with water (20 mL), neutralized to pH 7 with $K_2CO_3$ and diluted with $CH_2Cl_2$ (100 mL). The organic layer was washed with water and brine, separated and dried with anhydrous sodium sulfate, then filtered and concentrated in vacuo to afford a 1-benzyl-4,5,6,7-tetrahydro-1H-indazole-3-carbaldehyde Compound 11e (1.35 g, 95%) as a colorless oil.

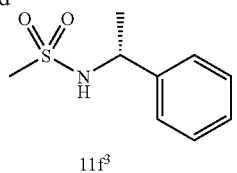

11f³

Methanesulfonyl chloride Compound 11f¹ (2.0 g, 17 mMol) and TEA (2.43 mL, 17.46 mMol) were added to a solution of (1R)-1-phenyl-ethylamine Compound 11f² (1.75 g, 17.5 mMol) in CH₂Cl₂ (50 mL) at 0° C. under a N₂ atmosphere. The mixture was stirred for 3 hrs while warming to r.t., then the reaction was quenched with water (5 mL). The organic layer was diluted with CH₂Cl₂ (100 mL) and then washed with water and brine. The organic layer was separated, dried with anhydrous sodium sulfate, then filtered and concentrated in vacuo to afford the corresponding N-(1-phenyl-ethyl)-methanesulfonamide Compound 11f³ as an oil.

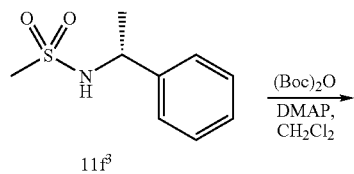

11f³

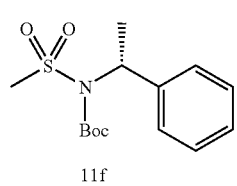

11f (Boc)₂O (di-tert-butyldicarbonate) (4.57 g, 21.0 mMol) and DMAP (8 mg) were added to a solution of the methanesulfonamide Compound 11f³ in CH₂Cl₂ (10 mL) at 0° C. under a N₂ atmosphere. The mixture was stirred overnight while warming to r.t., then the reaction was quenched with a saturated solution of NaHCO₃ (sodium bicarbonate) (10 mL). The organic layer was diluted with CH₂Cl₂ (100 mL) and then washed with water and brine. The organic layer was separated, dried with anhydrous sodium sulfate, then filtered and concentrated in vacuo to yield a crude Boc-protected methanesulfonamide product. The product was purified by flash chromatography (eluted with 10% EtOAc in hexane) to afford (methylsulfonyl)[(1R)-1-phenyl-ethyl]-carbamic acid tert-butyl ester Compound 11f (3.89 g, 80%) as a colorless oil.

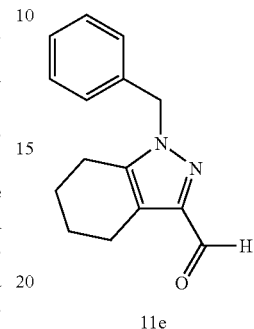

11e

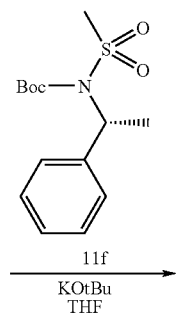

11f

KOtBu
THF

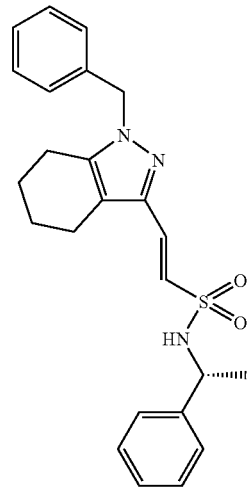

Cpd 260

Adapting a published procedure (Tozer M J, Woolford A J A and Linney I A, *Synlett*, 1998, 2, 186-188) to obtain the target compound, a 1M solution of KOtBu (potassium tert-butoxide) in THF (0.75 mL, 0.75 mMol) was added dropwise to a solution of the ester Compound 11f (0.070 g, 0.250 mMol) in anhydrous THF (5 mL) at −78° C. under a N₂ atmosphere. After 45 min, Compound 11e (0.060 g, 0.250 mMol) diluted in THF (3 mL) was added dropwise. The solution was reacted over a 15 hr period while warming to ambient temperature. The reaction was quenched with water (5 mL). The organic layer was diluted with EtOAc (100 mL)

and then washed with water and brine. The organic layer was separated and dried with anhydrous sodium sulfate, then filtered and concentrated in vacuo to yield a crude product. The product was purified by flash chromatography (eluted with 20% EtOAc in hexane) to give Compound 260 (0.079 g (75%), as a white solid.

MS m/z 422 (MH+); $^1$H NMR (CDCl$_3$, 400 MHz) δ 7.56 (d, J=15.5 Hz, 1H), 7.35-7.19 (m, 8H), 7.11-7.09 (m, 2H), 6.42 (d, J=15.5 Hz, 1H), 5.21 (s, 2H), 4.61-4.11 (m, 2H), 2.45-2.41 (m, 2H), 2.36-2.33 (m, 2H), 1.75-1.67 (m, 4H), 1.55 (d, J=6.5 Hz, 3H).

EXAMPLE 12

3-(1-benzyl-4,5,6,7-tetrahydro-1H-indazol-3-yl)-N-[(1R)-1-phenyl-ethyl]-acrylamide (Cpd 306)

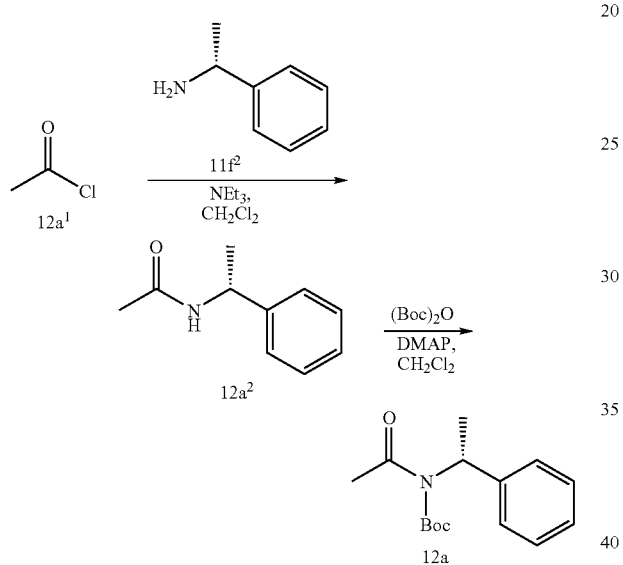

Acetyl-(1-phenyl-ethyl)-carbamic acid tert-butyl ester Compound 12a was synthesized using the procedure of Example 12, replacing mesyl chloride Compound 11f$^1$ with acetyl chloride Compound 12a$^1$.

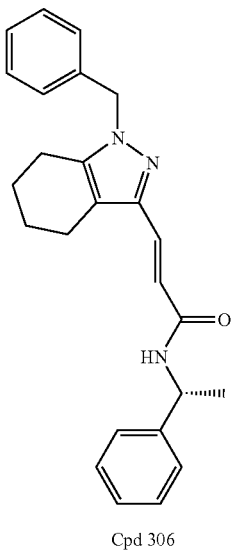

Acetyl-(1-phenyl-ethyl)-carbamic acid tert-butyl ester Compound 11e was reacted with Compound 12a, using the procedure of Example 12, to afford Compound 306 (0.067 g, 70%) as a white solid.

MS m/z 386 (MH+) $^1$H NMR (CDCl$_3$, 400 MHz) δ 7.56 (d, J=15.8 Hz, 1H), 7.35-7.23 (m, 8H), 7.11-7.09 (m, 2H), 6.42 (d, J=15.8 Hz, 1H), 5.77-5.11 (d, J=7.4 Hz, 1H), 5.30-5.23 (m, 1H), 5.21 (s, 2H), 2.59-2.56 (m, 2H), 2.44-2.42 (m, 2H), 1.74-1.71 (m, 4H), 1.54 (d, J=6.9 Hz, 3H).

EXAMPLE 13

3-(1-cyclohexyl-4,5,6,7-tetrahydro-1H-indazol-3-yl)-2-(2-methoxy-phenyl)-propionic acid ethyl ester (Cpd 332)

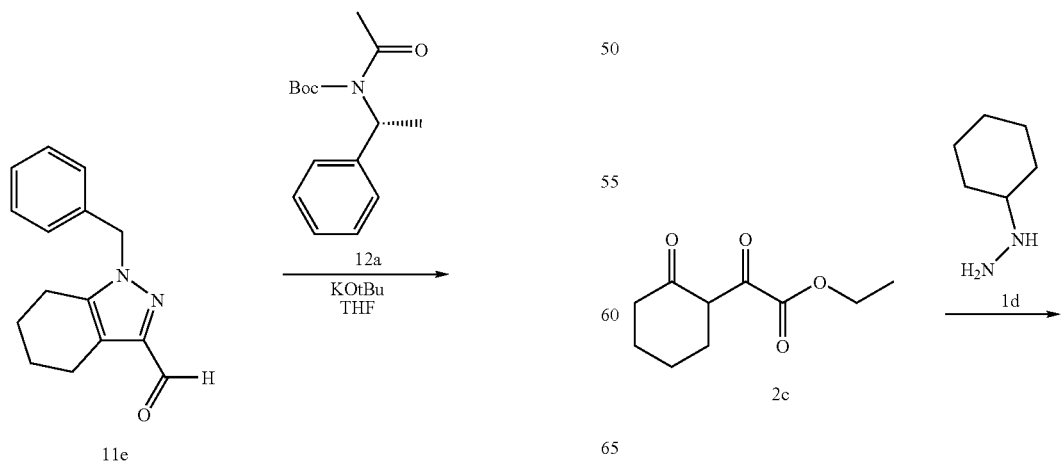

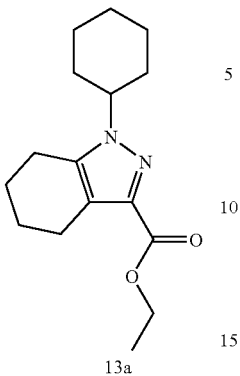

13a

Cyclohexylhydrazine hydrochloride Compound 1d (6.0 g, 46.5 mMol) and K₂CO₃ (9.0 g, 65.0 mMol) were added to a solution of Compound 2c (10.10 g, 50.95 mMol) in EtOH (50 mL) at ambient temperature under a N₂ atmosphere. The mixture was stirred overnight, concentrated to dryness, then diluted with water (100 mL) and EtOAc (500 mL). The organic layer was washed with brine, separated, dried with anhydrous sodium sulfate, then filtered and concentrated in vacuo to yield a crude oil. Purification by flash chromatography (eluted with 10% EtOAc in hexane) afforded 1cyclohexyl-4,5,6,7-tetrahydro-1H-indazole-3-carboxylic acid ethyl ester Compound 13a (12.2 g, 44.14 mMol, 95%) as a yellow oil.

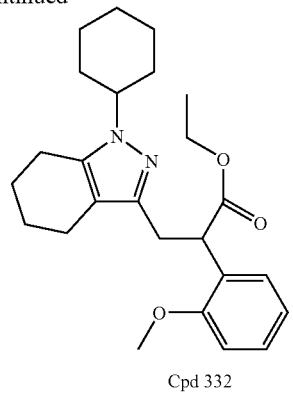

Cpd 332

The scheme above, wherein Compound 13a is taken to Compound 332 using the conditions and reagents indicated, describes the use of a published procedure (Murray W. Va., Hadden S K, Wachter M P, *J. Het. Chem.*, 1990, 27, 1933-40; U.S. Pat. Nos. 4,826,868; 4,898,952; 5,051,518; 5,164,381 and 5,242,940) to produce the target Compound 332. MS m/z 411 (MH⁺).

EXAMPLE 14

3-(1-cyclohexyl-4,5,6,7-tetrahydro-1H-indazol-3-yl)-2-(2-methoxy-phenyl)-N-(1,3,3-trimethyl-bicyclo[2.2.1]hept-2-yl)-propionamide (Cpd 333)

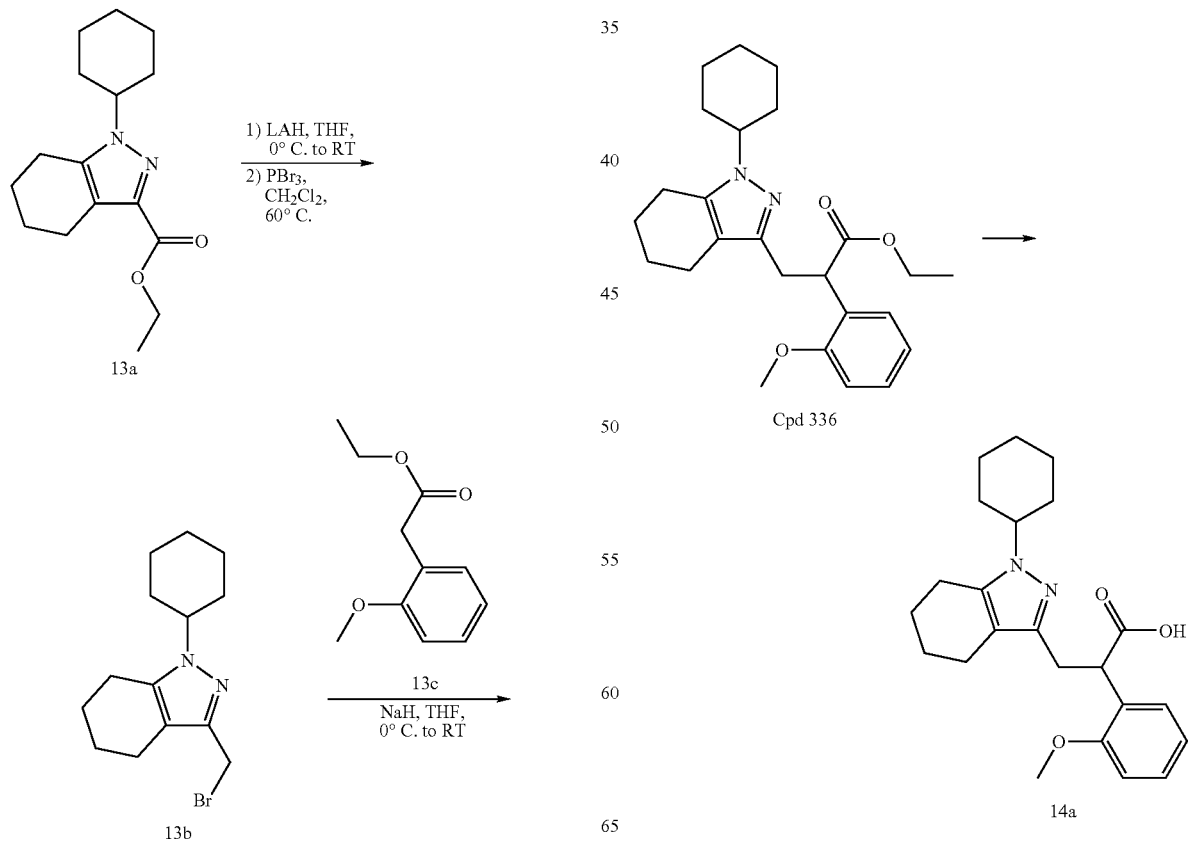

Using the procedure of Example 2, 1N NaOH (10 mL) was added to a solution of ester Compound 336 (0.295 g, 0.72 mMol) in THF (10 mL). The mixture was stirred for 30 hrs, acidified to pH 2 with 1N HCl and extracted with EtOAc (50 mL). The organic layer was washed with brine, dried over sodium sulfate, then filtered and concentrated in vacuo to yield a carboxylic acid Compound 14a (0.150 g, 54%) as a white solid.

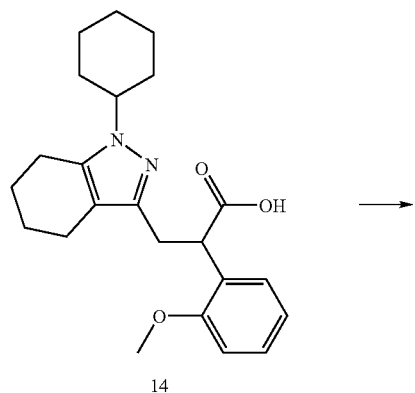

Thionyl chloride (0.25 g, 2.16 mMol) was added to a solution of Compound 14a (0.15 g, 0.39 mMol) in CH₂Cl₂ (10 mL) at ambient temperature under a N₂ atmosphere. The mixture was stirred for 3 hrs and concentrated in vacuo to afford Compound 14b.

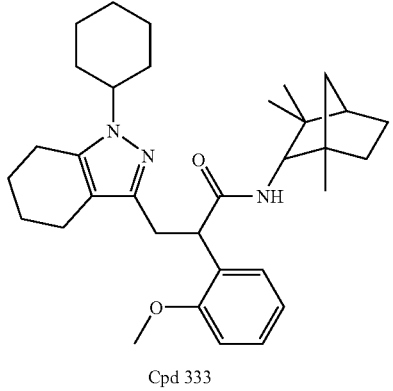

Triethylamine (0.16 g, 1.58 mMol) and Compound 14b (0.075 g, 0.63 mMol) were added to a solution of Compound 2i (0.12 g, 0.63 mMol) in CH₂Cl₂ (10 mL) at ambient temperature under a N₂ atmosphere. The mixture was stirred at r.t. for 3 hrs, then diluted with water (10 mL) and CH₂Cl₂ (50 mL). The organic layer was separated, dried with anhydrous sodium sulfate, then filtered and concentrated in vacuo to yield a crude oil. Purification by flash chromatography (eluted with 20% EtOAc in hexane) afforded Compound 333 (0.039 g, 33%) as a white solid. MS m/z 518 (MH⁺).

EXAMPLE 15

3-(1-cyclohexyl-4,5,6,7-tetrahydro-1H-indazol-3-yl)-N-(1,3,3-trimethyl-bicyclo[2.2.1]hept-2-yl)-propionamide (Cpd 50)

Carboxylic acid Compound 15a was derived using a published procedure (as described in Murray W V, Wachter M P, Barton D and Forero-Kelly Y, *Synthesis*, 1991, 01, 18-20)

using cyclohexanone as the starting material and carried forward using the procedure of Example 2 to provide 3-(1-cyclohexyl-4,5,6,7-tetrahydro-1H-indazol-3-yl)-propionic acid Compound 15b. MS m/z 277 (MH⁺).

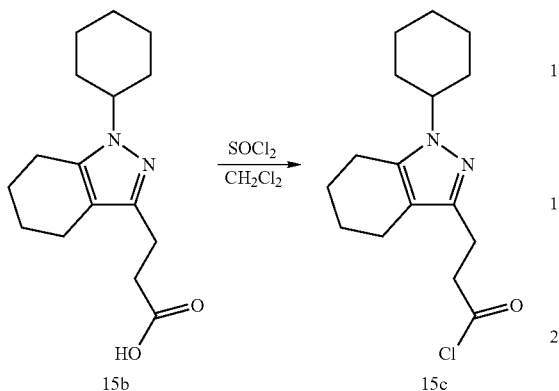

Thionyl chloride (1.94 g, 16.41 mMol) was added to a solution of Compound 15b (1.51 g, 5.47 mMol) in CH₂Cl₂ (10 mL) at ambient temperature under a N₂ atmosphere. The mixture was stirred for 3 hrs and concentrated in vacuo to afford the corresponding acid chloride Compound 15c.

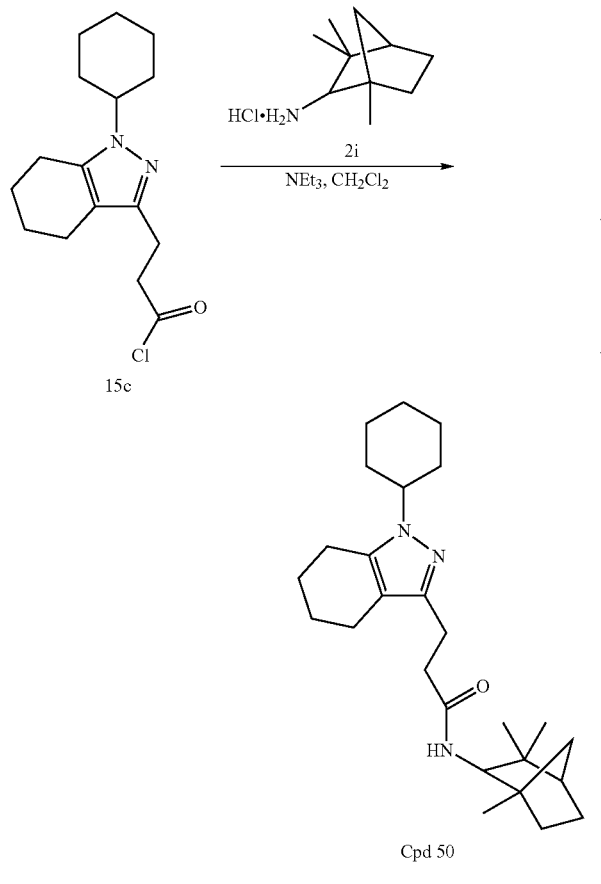

Triethylamine (0.16 g, 1.58 mMol) and acid chloride Compound 15c (0.15 g, 0.50 mMol) were added to a solution of Compound 2i (0.08 g, 0.50 mMol) in CH₂Cl₂ (10 mL) at ambient temperature under a N₂ atmosphere. The mixture was stirred at r.t. for 3 hrs, then diluted with water (10 mL) and CH₂Cl₂ (50 mL). The organic layer was separated, dried with anhydrous sodium sulfate, then filtered and concentrated in vacuo to yield a crude oil. Purification by flash chromatography (eluted with 20% EtOAc in hexane) afforded Compound 50 (0.05 g, 24%) as a white solid. MS m/z 412 (MH⁺).

EXAMPLE 16

N-adamantan-2-yl-3-(1-cyclohexyl-4,5,6,7-tetrahydro-1H-indazol-3-yl)-2,2-dimethyl-propionamide (Cpd 66)

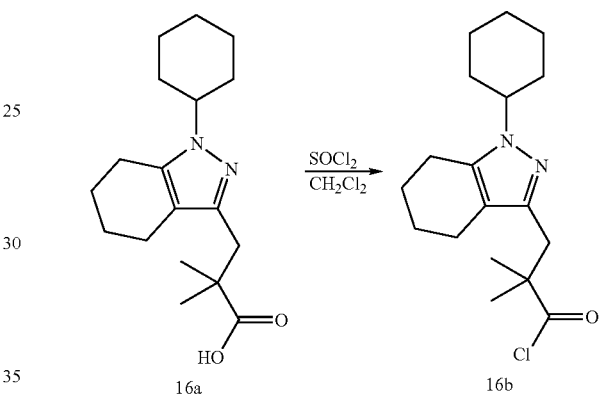

3-(1-cyclohexyl-4,5,6,7-tetrahydro-1H-indazol-3-yl)-2,2-dimethyl-propionic acid Compound 16a was derived by the procedure described in U.S. Pat. No. 5,051,518 whereby cyclohexanone Compound 2a was used as the starting material and carried forward. MS m/z 305 (MH⁺). Thionyl chloride (0.28 g, 2.40 mMol) was added to a solution of the acid Compound 16a (0.24 g, 0.80 mMol) in CH₂Cl₂ (5 mL) at ambient temperature under a N₂ atmosphere. The mixture was stirred for 3 hrs and concentrated in vacuo to afford the corresponding acid chloride Compound 16b.

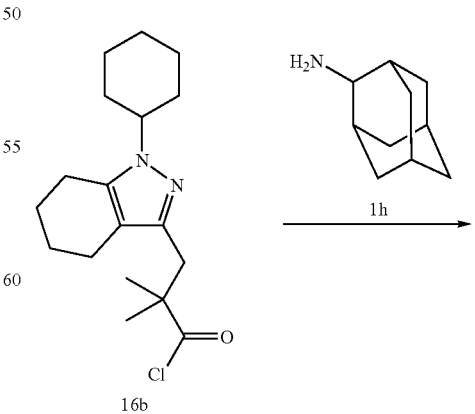

-continued

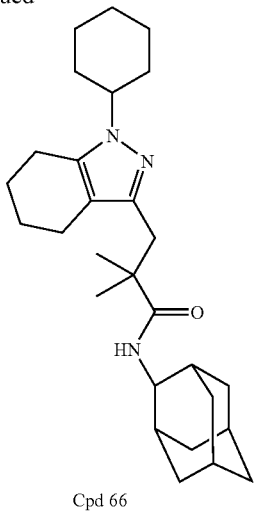

Cpd 66

Triethylamine (0.05 g, 0.50 mMol) and acid chloride Compound 16b (0.70 g, 0.60 mMol) were added to a solution of 2-adamantanamine Compound 1h (0.03 g, 0.20 mMol) in CH$_2$Cl$_2$ (5 mL) at ambient temperature under a N$_2$ atmosphere. The mixture was stirred at r.t. for 3 hrs, then diluted with water (10 mL) and CH$_2$Cl$_2$ (50 mL). The organic layer was separated, dried with anhydrous sodium sulfate, then filtered and concentrated in vacuo to yield a crude oil. Purification by flash chromatography (eluted with 20% EtOAc in hexane) afforded Compound 66 (0.032 g, 37%) as a white solid. MS m/z 438 (MH$^+$).

EXAMPLE 17

1-cyclohexyl-4,5,6,7-tetrahydro-1H-indazole-3-carboxylic acid [(1R)-1-cyclohexyl-ethyl]-methylamide (Cpd 328)

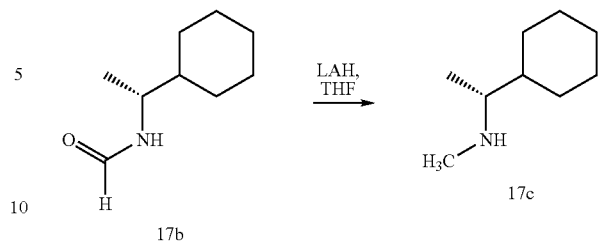

A solution of LAH in THF (1.0 M, 15 mL, 15 mMol) was added dropwise via syringe to a solution of Compound 17b (1.55 g, 10 mMol) in anhydrous THF at 0° C. The mixture was heated to reflux for 8 hrs and provided a grayish suspension. The suspension was cooled to 0° C. and the reaction was quenched carefully by a sequential addition of water (0.6 mL), 2N NaOH (0.6 mL) and water (2.0 mL). A white residue was produced, then filtered through a sintered glass funnel and washed with Et$_2$O (20 mL). The solvent from the combined filtrate was removed in vacuo to provide [(1R)-1-cyclohexyl-ethyl]-methylamine Compound 17c (1.1 g, 72%) as a pale yellow oil, which was used in the next step without purification. MS m/z 142 (MH$^+$).

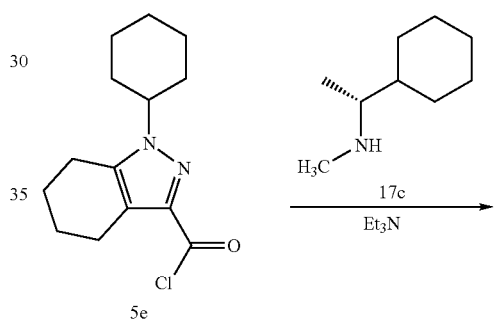

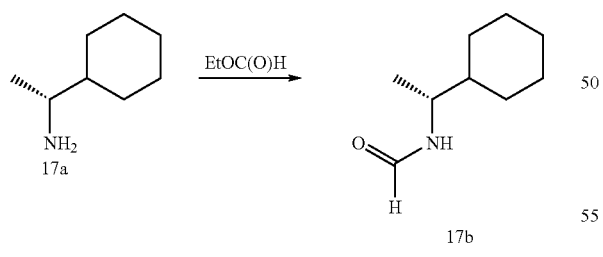

Ethyl formate (1.2 mL, 15.0 mMol) was added to a round bottom flask containing (1R)-1-cyclohexyl-ethylamine Compound 17a (1.27 g, 10 mMol) at 0° C. and the mixture was stirred at r.t. for 15 hrs. Excess ethyl formate was removed in vacuo to obtain N-[(1R)-1-cyclohexyl-ethyl]-formamide Compound 17b (1.55 g) as a white solid, which was used in the next step without purification. MS m/z 156 (MH$^+$).

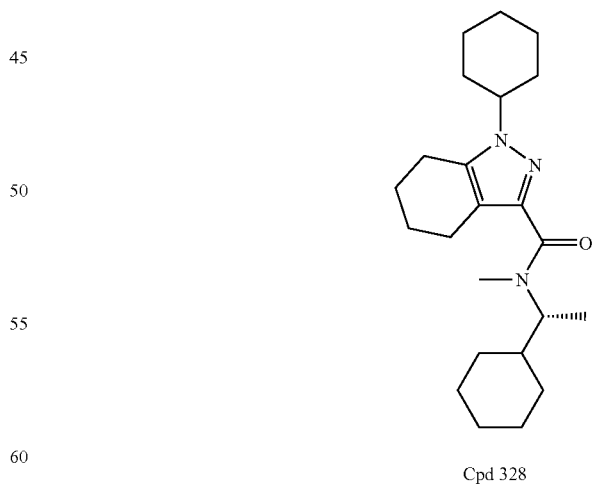

Cpd 328

The acid chloride Compound 5e (0.04 g, 0.15 mMol) was added to a solution of the methylamine Compound 17c (0.05 g, 0.035 mMol) in CH$_2$Cl$_2$ (2 mL) and triethylamine (0.06 mL, 0.5 mMol). The resulting suspension was stirred at r.t. for 2 hrs, diluted with CH$_2$Cl$_2$ (10 mL), then washed with 1N HCl (2×10 mL) and water (2×10 mL). The organic layer was dried over sodium sulfate, then concentrated and purified on a silica gel column (eluted with 20% EtOAc in hexane) to provide Compound 328 (44 mg, 80%). MS m/z 372 (MH$^+$).

EXAMPLE 18

1-cyclohexyl-4,5,6,7-tetrahydro-1H-indazole-3-carboxylic acid (cyclohexyl-phenyl)methylamide (Cpd 331)

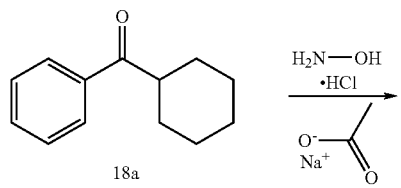

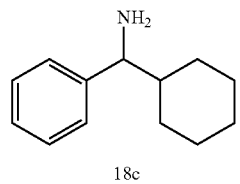

18c

A solution of Compound 18b (0.45 g, 0.22 mMol) in anhydrous THF (10 mL) added dropwise via syringe to a suspension of LAH (0.5 g, 1.3 mMol) in THF (20 mL) at 0° C. The mixture was heated to reflux for 8 hrs and provided a grayish suspension. The suspension was cooled to 0° C. and the reaction was quenched carefully by sequential addition of water (0.5 mL), 2N NaOH (0.5 mL) and water (1.5 mL). A white residue was produced, then filtered through a sintered glass funnel and washed with Et$_2$O (20 mL). The solvent from the combined filtrate was removed in vacuo to provide C-cyclohexyl-C-phenyl-methylamine Compound 18c (0.38 g, 91%) as a pale yellow oil, which was used in the next step without purification. MS m/z 190 (MH$^+$).

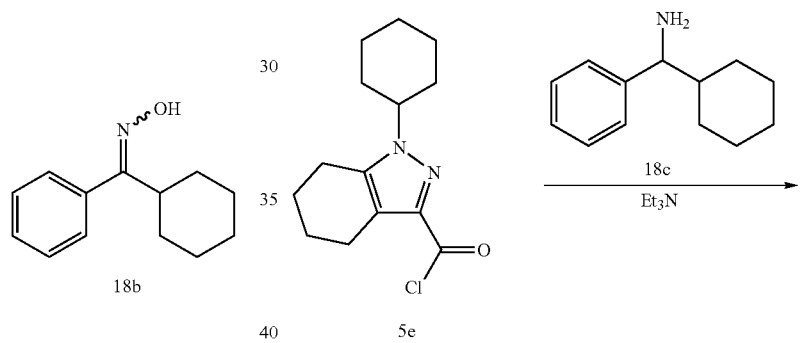

Hydroxylamine hydrochloride (0.48 g, 6.7 mMol) and sodium acetate (1.4 g, 10.2 mMol) were added to a round bottom flask containing cyclohexyl-phenyl-methanone Compound 18a (0.97 g, 5.1 mMol) in MeOH (30 mL) at r.t. The mixture was stirred at r.t. for 15 hrs. The solvent was removed in vacuo and the residue was extracted with CH$_2$Cl$_2$. The organic layer was sequentially washed with a saturated solution of NaHCO$_3$, then brine. The organic layer was dried over Na$_2$SO$_4$, decanted and the solvent removed in vacuo to provide cyclohexyl-phenyl-methanone oxime Compound 18b (1.0 g) as a white solid, which was used in the next step without purification. MS m/z 204 (MH$^+$).

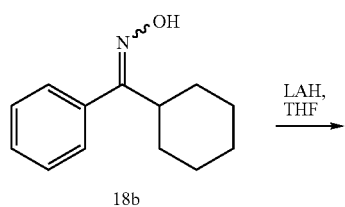

Cpd 331

Using the procedure of Example 5, Compound 18c was reacted with acid chloride Compound 5e to provide Compound 331.

EXAMPLE 19

1-cyclohexyl-5-hydroxymethyl-4,5,6,7-tetrahydro-1H-indazole-3-carboxylic acid (1-adamantan-1-yl-ethyl)-amide (Cpd 143)

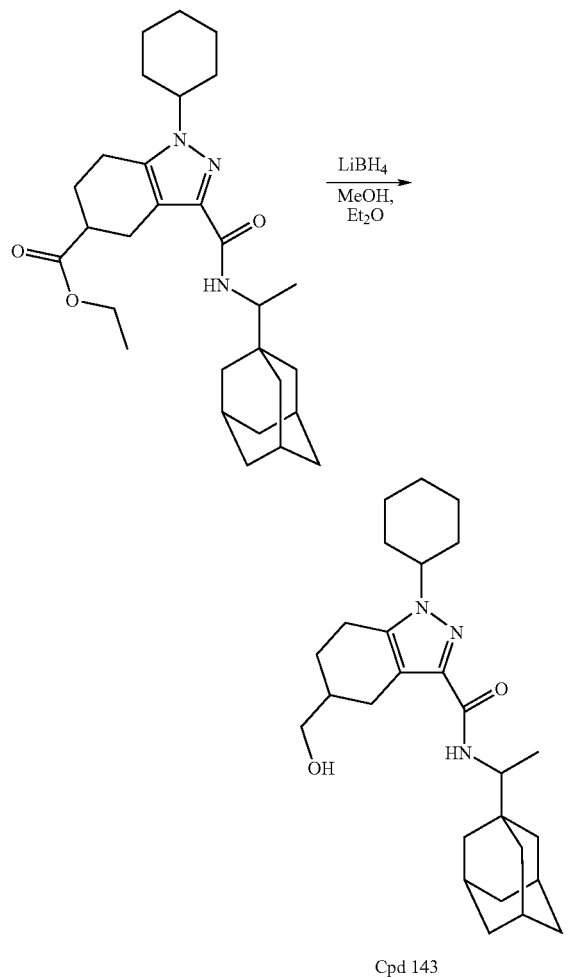

Cpd 143

Compound 132 (prepared according to the procedure of Example 1, replacing Compound 1h with 1-adamantan-1-yl-ethylamine) (25.0 mg, 0.052 mMol), LiBH$_4$ (lithium borohydride) (2.0 mg, 0.092 mMol) and methanol (0.01 mL) in ether (3.0 mL) were refluxed for 0.5 hr. The reaction was quenched with 1N HCl (2.0 mL). The organic layer was concentrated, extracted with DCM (dichloromethane) (2×5.0 mL) and dried over Na$_2$SO$_4$. The solvent was evaporated to give Compound 143 (22.0 mg, 96%) as a white solid.

MS m/z 440 (MH$^+$), 462 (MNa$^+$); $^1$H NMR (CDCl$_3$, 300 MHz) δ: 6.71 (1H, d, J=10.1 Hz), 3.82 (2H, m), 3.62 (1H, m), 3.41 (1H, m), 2.99 (1H, dd, J=16.4, 5.0 Hz), 2.65 (1H, m), 2.47 (1H, m), 2.24 (1H, m), 2.03 (1H, m), 1.83 (10H, m), 1.52 (14H; m), 1.25 (4H, m), 1.03 (3H, d, J=6.8 Hz).

EXAMPLE 20

2-[1-(4-fluoro-phenyl)-7-phenethyl-4,5,6,7-tetrahydro-1H-indazol-3-yl]-ethenesulfonic acid (1-phenyl-ethyl)-amide (Cpd 258)

2-[1-(4-fluoro-phenyl)-7-phenethyl-4,5,6,7-tetrahydro-1H-indazol-3-yl]-ethenesulfonic acid (1-cyclohexyl-ethyl)-amide (Cpd 259)

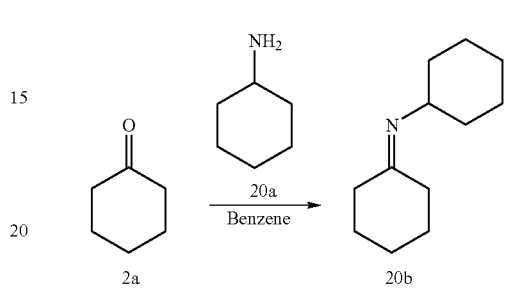

Cyclohexylamine Compound 20a (4.64 g, 46.50 mmol) was added to a solution of cyclohexanone Compound 2a (4.0 g, 46.50 mmol) in benzene (100 mL) at ambient temperature under a N$_2$ atmosphere. The mixture was refluxed at 80° C. for 5 hours, using a Dean Stark apparatus for the removal of water, and concentrated to dryness. The crude product was purified by distillation at aspirator pressure to afford cyclohexyl-cyclohexylidene-amine Compound 20b (7.33 g, 88%) as a clear oil.

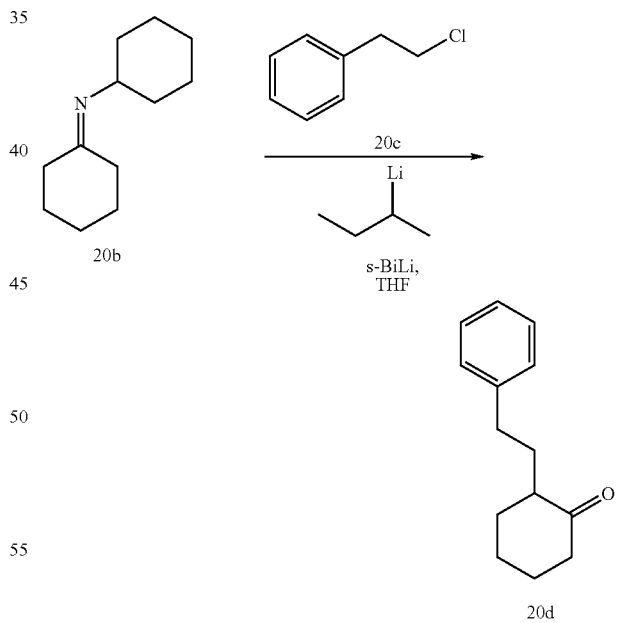

s-BuLi (28.0 mL, 1.3 M) was added slowly to a solution of Compound 20b (7.0 g) in THF (50 mL) at −78° C. The mixture stirred for 1 hr at −78° C. and then (2-chloro-ethyl)-benzene Compound 20c (5.11 g, 36.4 mmol) in THF (10 mL) was added dropwise. The reaction mixture was stirred for 24 hrs while warming to r.t. The reaction was quenched with 1N HCl (5 mL), then diluted with water (100 mL) and EtOAc (500 mL). The organic layer was washed with brine, separated and dried with anhydrous sodium sulfate, then filtered and concentrated in vacuo to yield a crude product. Purification by flash chromatography (eluted with 10% EtOAc in Hexane) afforded 2-phenethyl-cyclohexanone Compound 20d (4.05 g, 20.0 mMol, 58%) as a yellow oil.

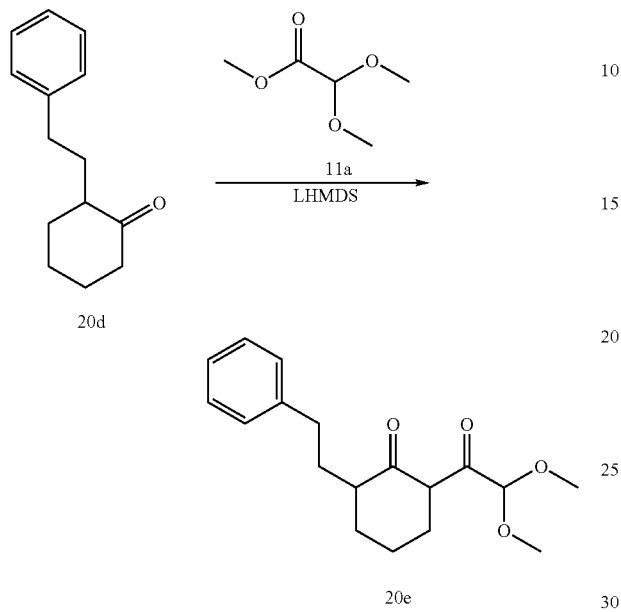

Compound 20d was carried forward in place of Compound 2a using the procedure of Example 11 to provide 2-(2,2-dimethoxy-acetyl)-6-phenethyl-cyclohexanone Compound 20e.

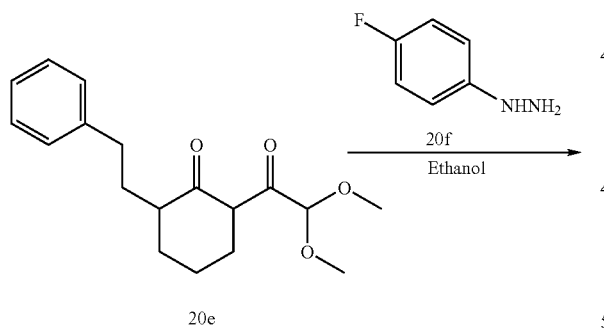

Using the procedure of Example 10, Compound 20e was used in place of [3-(4-fluoro-benzylidene)-2-oxo-cyclohexyl]-oxo-acetic acid ethyl ester Compound 10c and (4-fluoro-phenyl)-hydrazine Compound 20f was used in place of (2,4-dichloro-phenyl)-hydrazine Compound 10d to provide 1-[1-(4-fluoro-phenyl)-7-phenethyl-4,5,6,7-tetrahydro-1H-indazol-3-yl]-2,2-dimethoxy-ethanone Compound 20g.

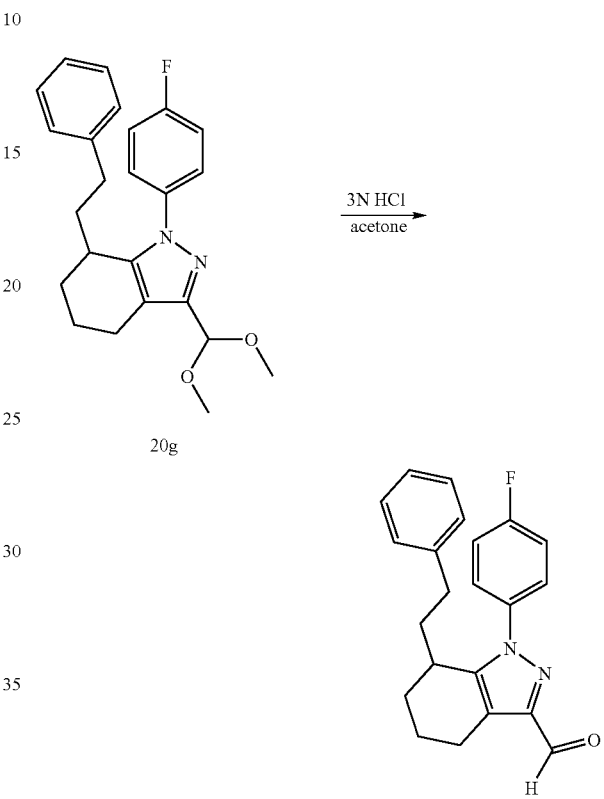

Using the procedure of Example 11, Compound 20g was used in place of [3-(4-fluoro-benzylidene)-2-oxo-cyclohexyl]-oxo-acetic acid ethyl ester Compound 11d to provide 1-(4-fluoro-phenyl)-7-phenethyl-4,5,6,7-tetrahydro-1H-indazole-3-carbaldehyde Compound 20h.

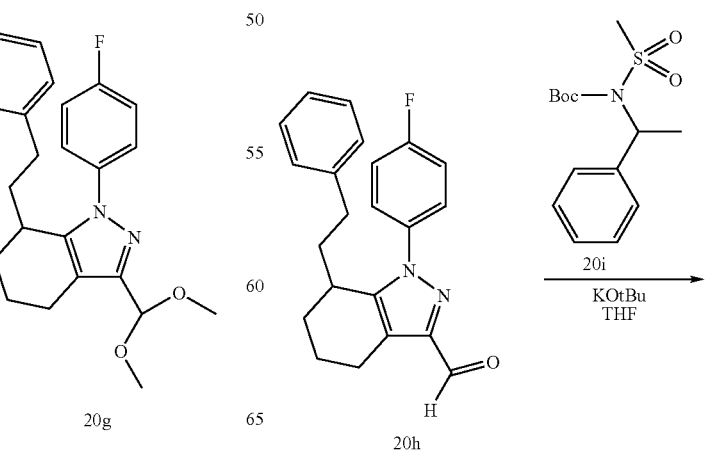

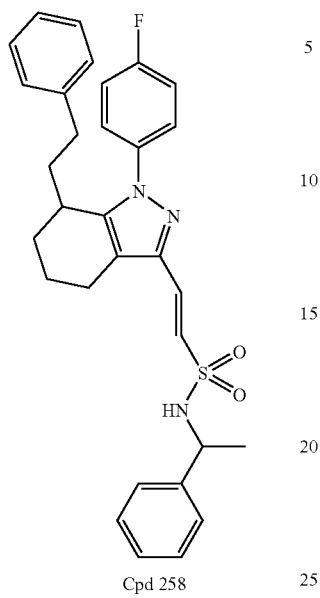

Cpd 258

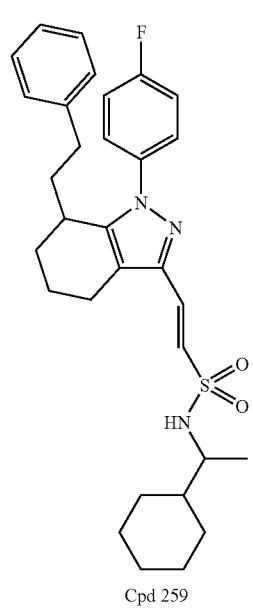

Cpd 259

Using the procedure of Example 11, Compound 20h was used in place of 1-benzyl-4,5,6,7-tetrahydro-1H-indazole-3-carbaldehyde Compound 11e and (methylsulfonyl)(1-phenyl-ethyl)-carbamic acid tert-butyl ester Compound 20i was used in place of (methylsulfonyl)[(1R)-1-phenyl-ethyl]-carbamic acid tert-butyl ester Compound 11f to provide Compound 258.

Using the procedure of Example 11, Compound 20h was used in place of 1-benzyl-4,5,6,7-tetrahydro-1H-indazole-3-carbaldehyde Compound 11e and (methylsulfonyl)(1-cyclohexyl-ethyl)-carbamic acid tert-butyl ester Compound 20j was used in place of (methylsulfonyl)[(1R)-1-phenyl-ethyl]-carbamic acid tert-butyl ester Compound 11f to provide Compound 259.

EXAMPLE 21

1-cyclohexyl-4,5,6,7-tetrahydro-1H-indazole-3-carboxylic acid N'-cyclooctyl-hydrazide (Cpd 300)

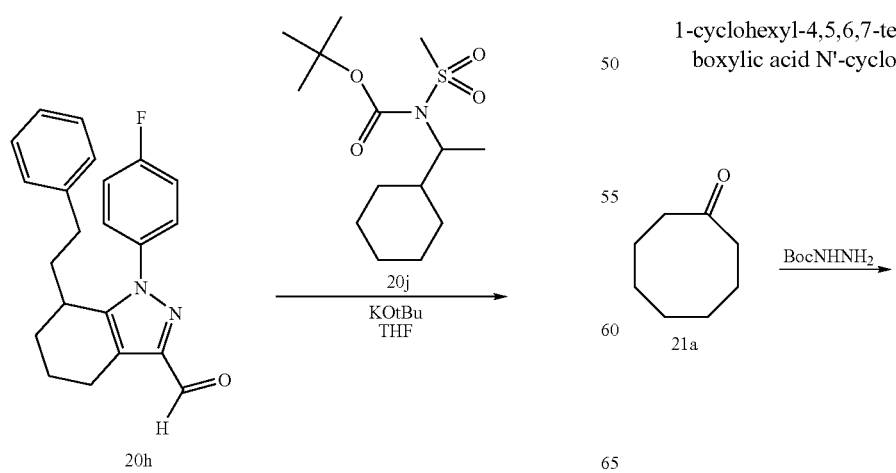

283

-continued

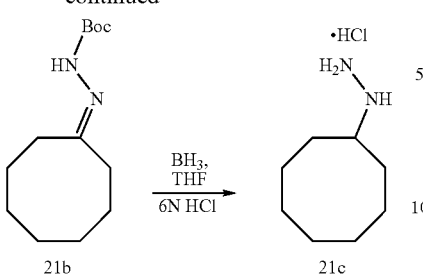

According to a published procedure, cyclooctanone Compound 21a was reacted with hydrazinecarboxylic acid tert-butyl ester to produce an intermediate N'-cyclooctylidene-hydrazinecarboxylic acid tert-butyl ester Compound 21b (as described in Ghali N K and Venton D L, *J. Org. Chem.*, 1981, 46, 5413). According to the published procedure, Compound 21b was carried forward to provide cyclooctyl-hydrazine hydrochloride Compound 21c.

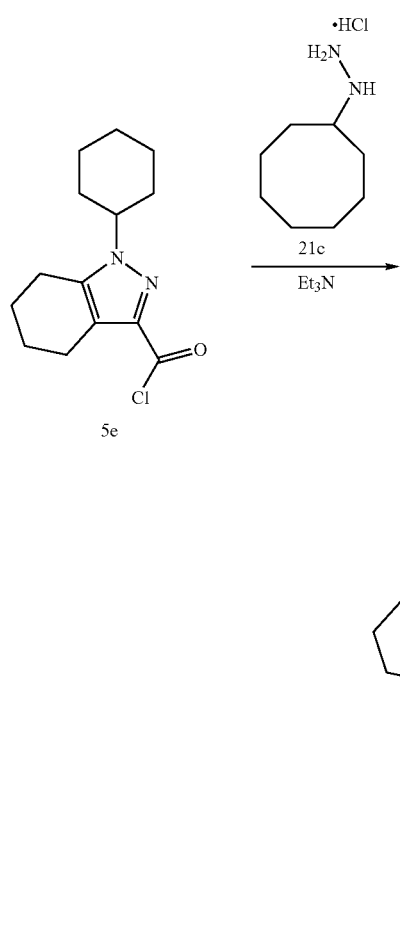

According to the procedure of Example 5, the acid chloride Compound 5e was reacted with Compound 21c in a solution of $CH_2Cl_2$ and triethylamine to provide an amide Compound 300. MS m/z 345.1 ($MH^+$).

284

EXAMPLE 22

1-cyclohexyl-5-oxo-4,5,6,7-tetrahydro-1H-indazole-3-carboxylic acid (1,3,3-trimethyl-bicyclo[2.2.1]hept-2-yl)-amide (Cpd 96)

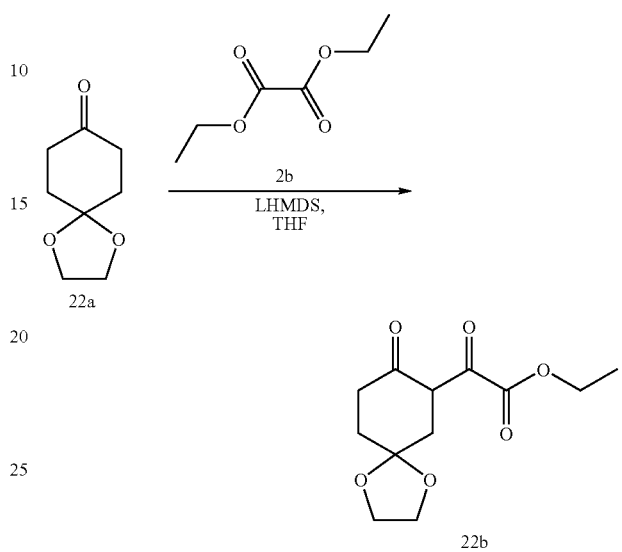

According to the procedure of Example 2, a solution of 1,4-dioxaspiro[4.5]decane-8-one Compound 22a in ether was added to a solution of LHMDS in ether at −78° C. The diethyloxalate Compound 2b was added to the mixture and reacted to produce an oxo-(8-oxo-1,4-dioxa-spiro[4.5]dec-7-yl)-acetic acid ethyl ester Compound 22b.

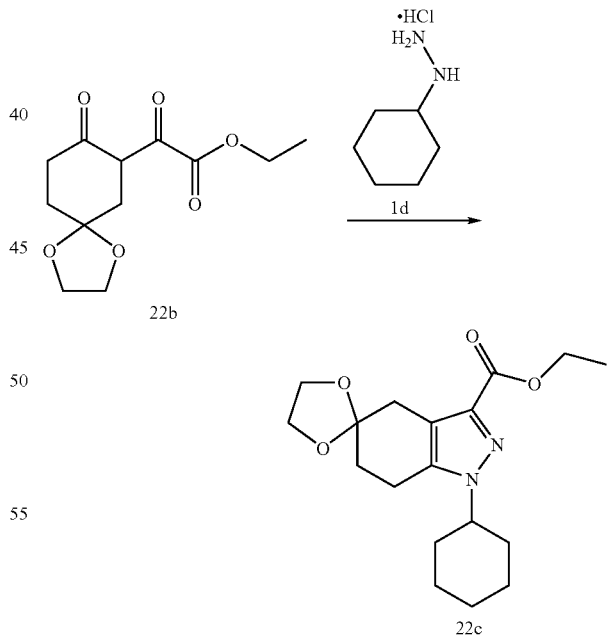

According to the procedure of Example 1, Compound 22b was reacted with a solution of cyclohexyl hydrazine hydrochloride Compound 1d and $K_2CO_3$ in $CH_2Cl_2$ to produce (N-8-cyclohexyl-1,4-dioxa-spiro[4.6]-4,5,6,7-tetrahydro-1H-indazol-10-yl) carboxylic acid ethyl ester Compound 22c.

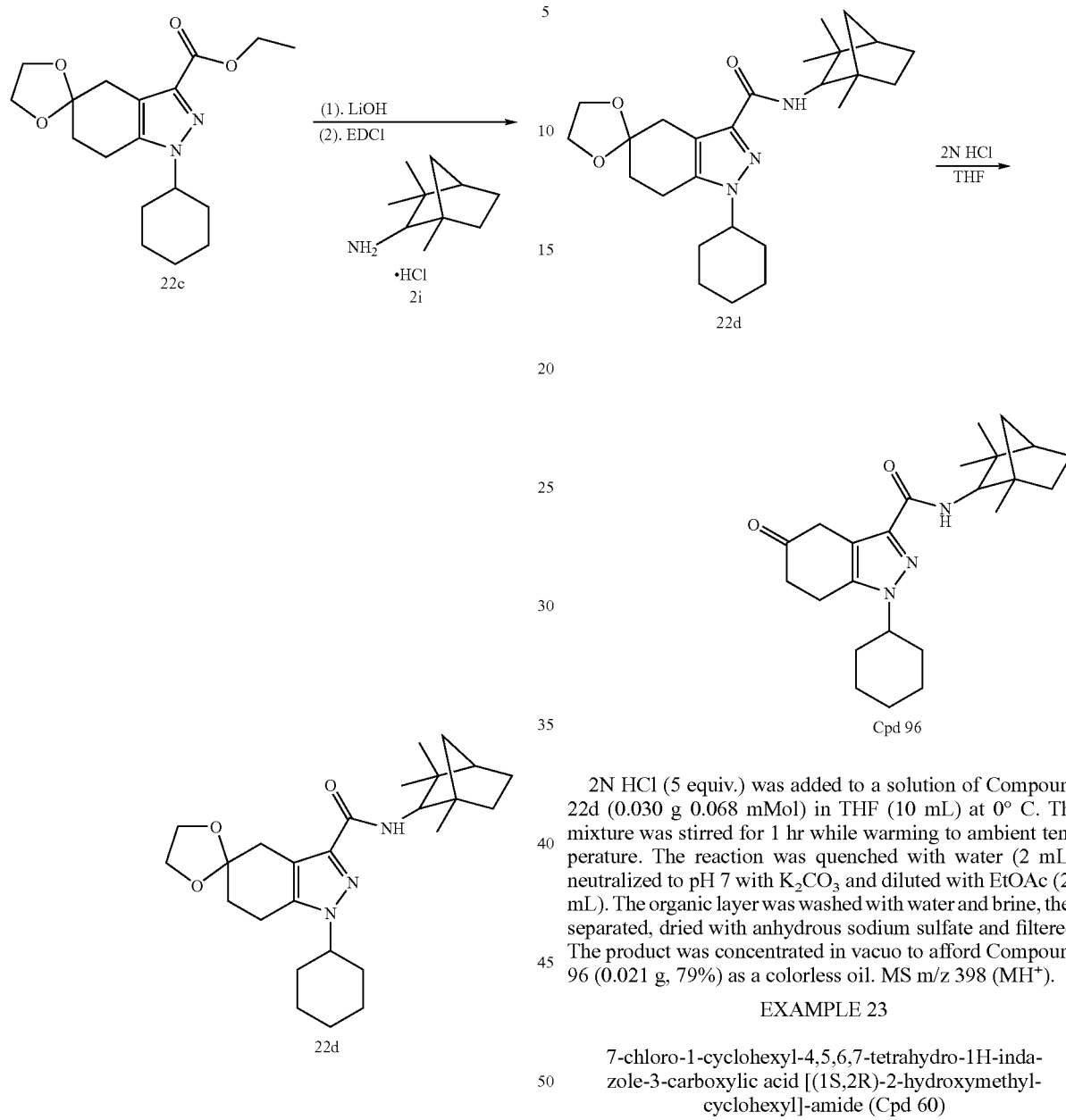

2N HCl (5 equiv.) was added to a solution of Compound 22d (0.030 g 0.068 mMol) in THF (10 mL) at 0° C. The mixture was stirred for 1 hr while warming to ambient temperature. The reaction was quenched with water (2 mL), neutralized to pH 7 with $K_2CO_3$ and diluted with EtOAc (20 mL). The organic layer was washed with water and brine, then separated, dried with anhydrous sodium sulfate and filtered. The product was concentrated in vacuo to afford Compound 96 (0.021 g, 79%) as a colorless oil. MS m/z 398 ($MH^+$).

EXAMPLE 23

7-chloro-1-cyclohexyl-4,5,6,7-tetrahydro-1H-indazole-3-carboxylic acid [(1S,2R)-2-hydroxymethyl-cyclohexyl]-amide (Cpd 60)

According to the procedure of Example 8, Compound 22c was used in place of 5-tert-butoxycarbonylamino-cyclohexyl-4,5,6,7-tetrahydro-1H-indazole-3-carboxylic acid ethyl ester Compound 8c and carried forward to provide (N-8-cyclohexyl-1,4-dioxa-spiro[4.6]-4,5,6,7-tetrahydro-1H-indazol-10-yl) carboxylic acid (1,3,3-trimethyl-bicyclo[2.2.1]hept-2-yl)-amide Compound 22d.

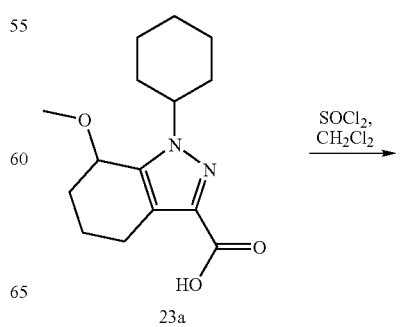

-continued

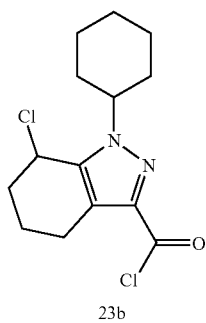
23b 1-cyclohexyl-7-methoxy-4,5,6,7-tetrahydro-1H-indazole-3-carboxylic acid Compound 23a was prepared according to the procedure of Example 2, wherein 2-methoxy-cyclohexanone was used in place of Compound 2a as the starting material.

Thionyl chloride (0.20 g, 1.7 mmol) was added to a solution of Compound 23a (0.15 g, 0.55 mmol) in CH$_2$Cl$_2$ (10 mL) at ambient temperature under a N$_2$ atmosphere. The mixture was stirred for 3 hrs at 35° C., cooled to ambient temperature, then concentrated in vacuo to afford the corresponding 7-chloro-1-cyclohexyl-4,5,6,7-tetrahydro-1H-indazole-3-carbonyl chloride Compound 23b.

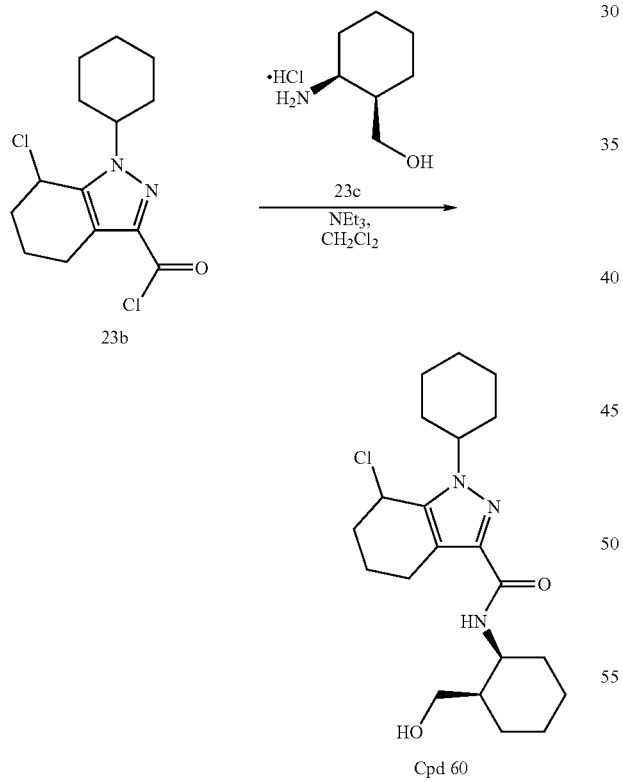
Cpd 60

NEt$_3$ (triethylamine) (0.10 g, 0.98 mMol) and Compound 23b (0.06, 0.20 mMol) were added to a solution of (1R,2S)-(2-amino-cyclohexyl)-methanol hydrochloride Compound 23c (0.064 g, 0.39 mMol) in CH$_2$Cl$_2$ (10 mL) at ambient temperature under a N$_2$ atmosphere. The mixture was stirred at r.t. for 3 hrs, then diluted with water (10 mL) and CH$_2$Cl$_2$ (50 mL). The organic layer was separated, dried with anhydrous sodium sulfate, then filtered and concentrated in vacuo to yield a crude product. Purification by flash chromatography (eluted with 20% EtOAc in hexane) afforded Compound 60 (0.034 g, 45%) as a white solid. MS m/z 394 (MH$^+$).

EXAMPLE 24

(2S,3R)-3-[(1-cyclohexyl-7-hydroxy-4,5,6,7-tetrahydro-1H-indazole-3-carbonyl)-amino]-bicyclo[2.2.1]heptane-2-carboxylic acid ethyl ester (Cpd 164)

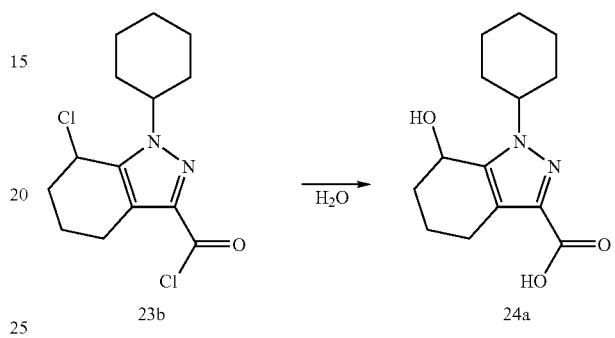

7-chloro-1-cyclohexyl-4,5,6,7-tetrahydro-1H-indazole-3-carbonyl chloride Compound 23b was hydrolyzed to provide 1-cyclohexyl-7-hydroxy-4,5,6,7-tetrahydro-1H-indazole-3-carboxylic acid Compound 24a.

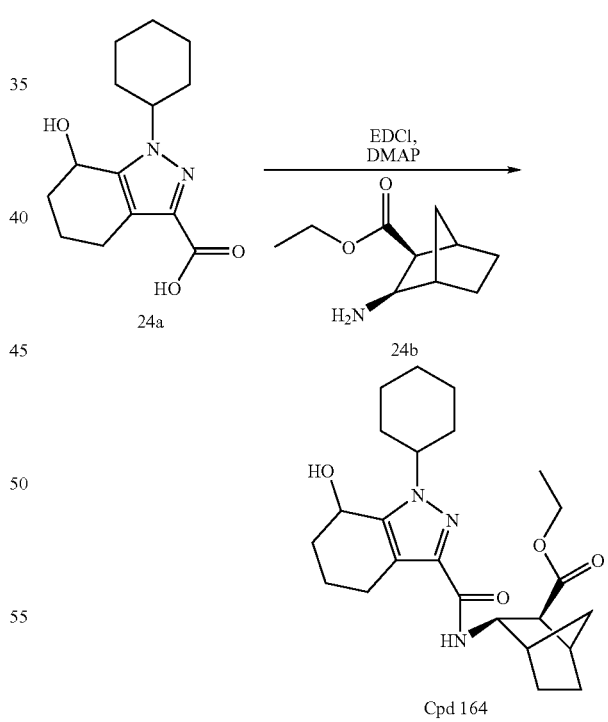
Cpd 164

1-(3-dimethylaminopropyl)-3-ethylcarbodiimide hydrochloride (EDCI) (0.15 g, 0.81 mmol), dimethylaminopyridine (DMAP) (8 mg) and (2S,3R)-3-amino-bicyclo[2.2.1]heptane-2-carboxylic acid ethyl ester Compound 24b (0.059 g, 0.27 mmol) were added to a solution of 1-cyclohexyl-7-hydroxy-4,5,6,7-tetrahydro-1H-indazole-3-carboxylic acid Compound 24a (0.071 g, 0.27 mmol) in 5 mL CH$_2$Cl$_2$ at 0° C.

EXAMPLE 25

1-(2,4-dichloro-phenyl)-7-(3-methoxy-phenyl)-4,5,6,7-tetrahydro-1H-indazole-3-carboxylic acid [(1S)-2-hydroxy-1-phenyl-ethyl]-amide (Cpd 313)

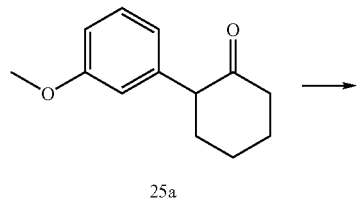

25a

According to the procedure of Example 2, a solution of 2-(3-methoxy-phenyl)-cyclohexanone Compound 25a (commercially available) in ether was carried forward in place of Compound 2a to produce 1-(2,4-dichloro-phenyl)-7-(3-methoxy-phenyl)-4,5,6,7-tetrahydro-1H-indazole-3-carbonyl chloride Compound 25b.

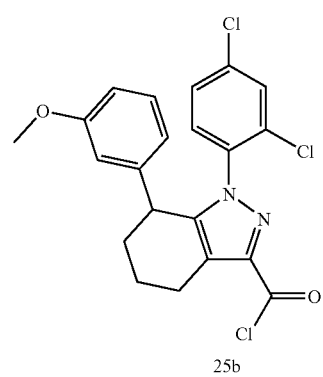

25b

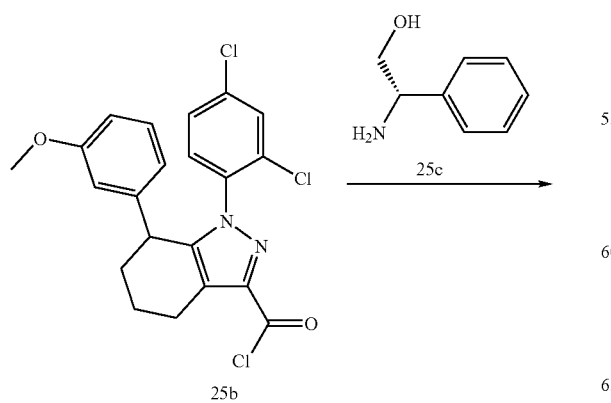

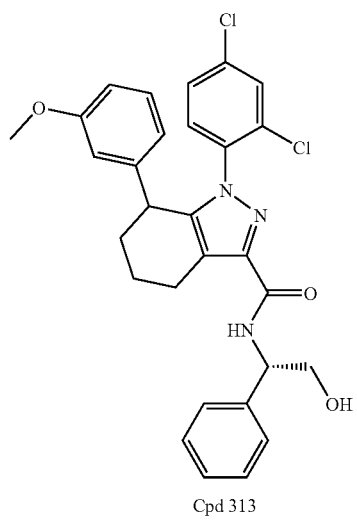

Cpd 313

According to the procedure of Example 2, triethylamine and Compound 25b were reacted with (1S)-2-amino-2-phenyl-ethanol Compound 25c in $CH_2Cl_2$ to provide amide Compound 313.

EXAMPLE 26

1-(2,4-dichloro-phenyl)-7-(3-methoxy-phenyl)-4,5,6,7-tetrahydro-1H-indazole-3-carboxylic acid [(1S)-2-chloro-1-phenyl-ethyl]-amide (Cpd 316)

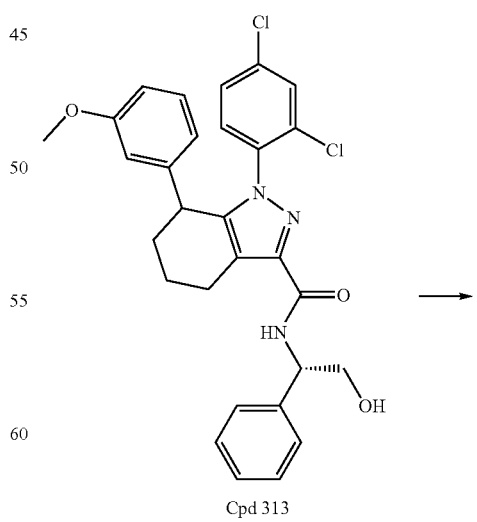

Cpd 313 under a $N_2$ atmosphere. The mixture was stirred for 6 hrs while warming to r.t., then concentrated in vacuo and purified by flash chromatography (eluted with 15% EtOAc in hexane) to afford Compound 164 (0.075 g, 65%) as a white solid.

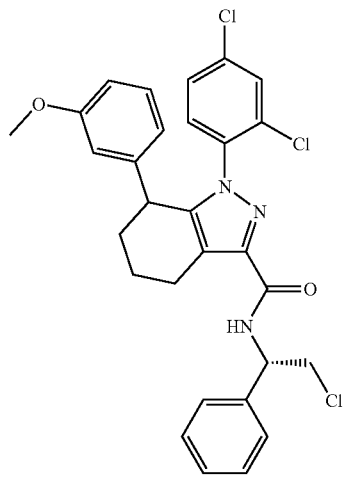

Cpd 316

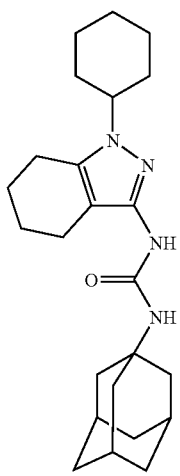

Cpd 182

Thionyl chloride (0.01 g, 0.08 mmol) was added to a solution of Compound 313 (0.02 g, 0.04 mmol) in 5 mL $CH_2Cl_2$ at 0° C. under a $N_2$ atmosphere. The mixture was stirred for 2 hrs while warming to ambient temperature, then concentrated in vacuo to afford the corresponding acid chloride. Purification by flash chromatography (eluted with 20% EtOAc in hexane) afforded Compound 316 (0.036 g, 95%) as a white solid. MS m/z 554 ($MH^+$).

EXAMPLE 27

1-adamantan-1-yl-3-(1-cyclohexyl-4,5,6,7-tetrahydro-1H-indazol-3-yl)-urea (Cpd 182)

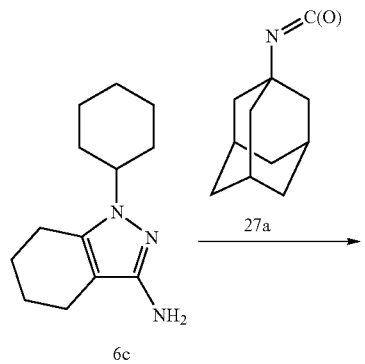

1-isocyanato-adamantane Compound 27a (4.6 mg, 0.026 mMol) and triethyl amine (0.01 mL, 0.072 mMol) were added to a solution of 1-cyclohexyl-4,5,6,7-tetrahydro-1H-indazol-3-ylamine Compound 6c (5 mg, 0.023 mMol) (Prepared using the procedure of Example 6). The mixture was stirred at r.t. for 4 hrs. The mixture was then concentrated and purified on a silica gel column (eluted with 15% EtOAc/hexane) to give Compound 182 (5.5 mg, 60%). MS m/z 397 ($MH^+$).

Additional compounds may be made according to the synthetic methods of the present invention by one skilled in the art, differing only in possible starting materials, reagents and conditions used in the instant methods.

BIOLOGICAL EXAMPLES

The following examples illustrate that the compounds of the present invention are CB receptor modulators useful for treating, ameliorating or preventing a cannabinoid receptor mediated syndrome, disorder or disease in a subject in need thereof.

Example 1

Binding Assay for CB1 or CB2 Agonists or Inverse Agonists

The human CB1 and CB2 receptors were stably expressed in SK-N-MC cells transfected with pcDNA3 CB-1 (human) or pcDNA3 CB-2 (human). The cells were grown in T-180 cell culture flasks under standard cell culture conditions at 37° C. in a 5% $CO_2$ atmosphere. The cells were harvested by trysinization and homogenized in a homogenization buffer (10 mM Tris, 0.2 mM MgCl$_2$, 5 mM KCl, with protease inhibitors aprotinin, leupeptin, pepstatin A and bacitracin) and centrifuged (2000 g). The supernatant was then centrifuged in 2M sucrose (31,300 g) to produce a semi-purified membrane pellet. The pellet was resuspended in homogenization and store at –80° C.

On the day of the assay, the pellet was thawed on ice and diluted in assay buffer (50 mM Tris-HCl, 5 mM MgCl$_2$, 2.5 mM EDTA, 0.5 mg/mL fatty acid free bovine serum albumin, pH 7.5). The diluted membrane was added with buffer, test compound or standard and the radioligand [H]$^{3+}$-CP-55,940_ (0.2 nM) to the wells of a 96-well polypropylene plate. Non-specific binding was measured in wells containing 10 uM WIN 55,212. The plate was covered and incubated for 90 minutes at 30° C. The contents were then aspirated onto a Packard UNIFILTER GF/C filter bottom plate prewet with 0.5% polyethyleneimine. The wells of the polypropylene plate were rinsed and aspirated seven times with a 0.9% saline-0.5% TWEEN 20 solution. The UNIFILTER plate was dried, a scintillation cocktail was added to each well and the counts representing binding were quantitated in a TOP-COUNT scintillation counter.

CB1 and CB2 Receptor Binding Results

The IC$_{50}$ binding values for compounds tested were calculated by linear regression and were obtained from studies in which varying compound concentrations were used.

TABLE 1a

Cannabinoid CB1 Receptor Binding IC$_{50}$ (μM)

| Cpd | IC$_{50}$ | Cpd | IC$_{50}$ | Cpd | IC$_{50}$ | Cpd | IC$_{50}$ |
|---|---|---|---|---|---|---|---|
| 1 | 0.3767 | 5 | 6.8 | 6 | 6.75 | 7 | 3.1 |
| 9 | 0.3383 | 10 | 0.045 | 11 | 0.2854 | 12 | 0.1485 |
| 13 | 0.1084 | 14 | 0.216 | 15 | 0.2413 | 16 | 0.1851 |
| 17 | 0.1682 | 18 | 0.0918 | 19 | 0.114 | 20 | 0.169 |
| 21 | 0.044 | 22 | 1.03 | 23 | 1.8 | 24 | 3.81 |
| 25 | 0.0753 | 26 | 0.7233 | 27 | 0.108 | 28 | 0.85 |
| 29 | 0.7897 | 30 | 7.885 | 31 | 1.694 | 32 | 0.02 |
| 33 | 0.058 | 34 | 0.1356 | 35 | 0.7 | 36 | 0.1053 |
| 37 | 0.0693 | 38 | 0.006 | 39 | 0.009 | 40 | 1.44 |
| 41 | 0.049 | 42 | 10.7 | 43 | 0.014 | 44 | 0.079 |
| 45 | 0.04 | 47 | 22.6 | 48 | 0.249 | 49 | 0.15 |
| 50 | 0.255 | 51 | 15.2 | 52 | 6.26 | 53 | 6.12 |
| 54 | 11.4 | 57 | 10.897 | 58 | 0.736 | 59 | 0.34 |
| 60 | 5.235 | 61 | 2.195 | 62 | 0.28 | 63 | 13.655 |
| 64 | 0.41 | 66 | 3.59 | 67 | 0.3 | 68 | 0.4633 |
| 69 | 0.22 | 70 | 0.125 | 71 | 0.53 | 72 | 8.4 |
| 73 | 0.76 | 74 | 0.015 | 75 | 0.0237 | 76 | 1.96 |
| 77 | 0.052 | 78 | 4.6 | 79 | 0.03 | 80 | 0.23 |
| 81 | 0.49 | 82 | 0.7 | 83 | 0.038 | 84 | 0.4 |
| 85 | 0.6 | 87 | 0.855 | 88 | 2.4 | 89 | 3.7 |
| 90 | 1.84 | 92 | 1.6 | 93 | 1.15 | 94 | 1.78 |
| 95 | 6.4 | 96 | 9.5 | 97 | 9.7 | 98 | 20.5 |
| 99 | 0.96 | 102 | 30.9 | 103 | 2 | 104 | 17.1 |
| 105 | 8.5 | 106 | 12.7 | 107 | 0.91 | 108 | 2.4 |
| 119 | 0.006 | 120 | 2.46 | 122 | 0.004 | 123 | 0.0075 |
| 124 | 0.007 | 125 | 0.026 | 126 | 0.597 | 127 | 0.0099 |
| 128 | 0.01 | 129 | 0.0057 | 130 | 0.4 | 131 | 0.03 |
| 132 | 2.9 | 133 | 12 | 134 | 0.4 | 135 | 0.67 |
| 136 | 0.0008 | 137 | 3.95 | 139 | 0.16 | 140 | 0.89 |
| 141 | 0.3 | 142 | 0.6 | 143 | 2.4 | 144 | 0.22 |
| 145 | 0.95 | 147 | 2.075 | 148 | 0.013 | 149 | 0.067 |
| 150 | 0.13 | 151 | 0.59 | 152 | 0.34 | 153 | 1.39 |
| 154 | 0.06 | 156 | 0.097 | 157 | 0.03 | 158 | 0.013 |
| 159 | 0.74 | 161 | 5.235 | 162 | 0.635 | 163 | 4.77 |
| 164 | 6.01 | 167 | 1.66 | 169 | 0.43 | 171 | 0.64 |
| 173 | 0.444 | 175 | 2.16 | 177 | 10.45 | 179 | 7.3 |
| 180 | 0.7 | 181 | 0.3 | 183 | 0.05 | 184 | 0.05 |
| 185 | 0.9 | 187 | 3.69 | 189 | 0.01 | 190 | 1.62 |
| 192 | 0.06 | 193 | 0.12 | 194 | 0.0001 | 195 | 0.1 |
| 196 | 0.125 | 197 | 0.98 | 198 | 0.1 | 199 | 0.019 |
| 200 | 0.008 | 201 | 0.0017 | 202 | 0.1147 | 203 | 0.59 |
| 204 | 0.8 | 205 | 1.58 | 206 | 0.097 | 207 | 0.0824 |
| 208 | 0.66 | 209 | 0.26 | 210 | 0.335 | 211 | 0.005 |

TABLE 1a-continued

Cannabinoid CB1 Receptor Binding IC$_{50}$ (μM)

| Cpd | IC$_{50}$ | Cpd | IC$_{50}$ | Cpd | IC$_{50}$ | Cpd | IC$_{50}$ |
|---|---|---|---|---|---|---|---|
| 212 | 0.26 | 213 | 0.95 | 214 | 1.23 | 216 | 2.8 |
| 217 | 0.0026 | 218 | 0.4 | 219 | 0.1 | 221 | 3.29 |
| 222 | 0.28 | 223 | 169.9 | 224 | 1.5 | 226 | 0.0079 |
| 227 | 2.77 | 230 | 0.01 | 231 | 0.6375 | 232 | 2.4 |
| 233 | 1.6 | 234 | 0.23 | 235 | 3.6 | 236 | 25.35 |
| 237 | 0.89 | 238 | 25.1 | 241 | 3.4 | 242 | 0.3 |
| 243 | 0.13 | 244 | 0.3 | 245 | 0.02 | 246 | 2.27 |
| 247 | 0.26 | 248 | 0.16 | 249 | 0.05 | 250 | 0.07 |
| 252 | 0.04 | 253 | 0.025 | 256 | 0.26 | 265 | 0.096 |
| 267 | 0.15 | 269 | 0.191 | 270 | 3.1 | 271 | 6.2 |
| 272 | 0.086 | 273 | 1.59 | 274 | 0.0187 | 275 | 0.323 |
| 276 | 0.135 | 277 | 1.3 | 278 | 0.4025 | 279 | 3.8 |
| 280 | 3.6 | 281 | 19.66 | 282 | 11.805 | 283 | 0.1 |
| 284 | 0.35 | 285 | 2.9 | 287 | 2.5 | 289 | 0.88 |
| 290 | 0.025 | 291 | 0.18 | 292 | 0.033 | 293 | 0.006 |
| 294 | 0.11 | 295 | 0.003 | 296 | 0.005 | 297 | 0.013 |
| 298 | 0.064 | 301 | 0.024 | 304 | 0.16 | 305 | 9.8 |
| 308 | 0.019 | 309 | 0.047 | 320 | 0.014 | 321 | 0.23 |
| 328 | 5.1 | 329 | 1.7 | 330 | 1.9 | 331 | 3 |
| 332 | 3.9 | 333 | 5.7 | 334 | 12.5 | 336 | 45 |
| 338 | 1.35 | 339 | 0.008 | 340 | 0.016 | 341 | 0.02 |
| 342 | 0.041 | 343 | 0.037 | 344 | 0.053 | 345 | 0.07 |
| 346 | 0.033 | 347 | 0.018 | 348 | 0.011 | 349 | 0.04 |
| 350 | 0.017 | 351 | 0.012 | 353 | 0.016 | 356 | 0.077 |
| 357 | 0.021 | 358 | 0.013 | 360 | 0.012 | 362 | 0.038 |
| 363 | 0.013 | 364 | 0.016 | 365 | 0.016 | 368 | 0.039 |
| 369 | 0.042 | 371 | 0.039 | 373 | 0.02 | 374 | 0.019 |
| 376 | 0.016 | 377 | 0.043 | 380 | 0.032 | 381 | 0.015 |
| 382 | 0.005 | 383 | 0.01 | 384 | 0.021 | 385 | 0.007 |
| 386 | 0.011 | 387 | 0.033 | 388 | 0.015 | 389 | 0.014 |
| 390 | 0.02 | 393 | 0.043 | 394 | 0.077 | 395 | 0.071 |
| 396 | 0.052 | 397 | 0.059 | 398 | 0.048 | | |

TABLE 1b

Cannabinoid CB2 Receptor Binding IC$_{50}$ (μM)

| Cpd | IC$_{50}$ | Cpd | IC$_{50}$ | Cpd | IC$_{50}$ | Cpd | IC$_{50}$ |
|---|---|---|---|---|---|---|---|
| 1 | 0.0135 | 2 | 1.57 | 3 | 0.4285 | 4 | 3.69 |
| 5 | 0.2915 | 6 | 0.3665 | 7 | 3.575 | 8 | 21.22 |
| 9 | 0.0119 | 10 | 0.006 | 11 | 0.0406 | 12 | 0.0214 |
| 13 | 0.0065 | 14 | 0.0309 | 15 | 0.0538 | 16 | 0.0054 |
| 17 | 0.0045 | 18 | 0.0036 | 19 | 0.013 | 20 | 0.0352 |
| 21 | 0.011 | 22 | 0.143 | 23 | 0.1 | 24 | 6.82 |
| 25 | 0.0016 | 26 | 0.015 | 27 | 0.003 | 28 | 0.0075 |
| 29 | 0.1146 | 30 | 1.465 | 31 | 0.195 | 32 | 0.0069 |
| 33 | 0.008 | 34 | 0.0409 | 35 | 0.094 | 36 | 0.0128 |
| 37 | 0.112 | 38 | 0.0033 | 39 | 0.006 | 40 | 0.2147 |
| 41 | 0.0348 | 42 | 0.64 | 43 | 0.001 | 44 | 0.0024 |
| 45 | 0.0056 | 46 | 9.2 | 47 | 4.885 | 48 | 0.0553 |
| 49 | 0.0728 | 50 | 0.013 | 51 | 8.4177 | 52 | 4.9 |
| 53 | 0.23 | 54 | 6.05 | 55 | 7.9 | 56 | 20 |
| 57 | 2.2 | 58 | 0.1705 | 59 | 0.07 | 60 | 0.515 |
| 61 | 0.19 | 62 | 0.005 | 63 | 3.295 | 64 | 0.03 |
| 66 | 1.4 | 67 | 0.0155 | 68 | 0.057 | 69 | 0.0027 |
| 70 | 0.016 | 71 | 0.5 | 72 | 4.1 | 73 | 0.295 |
| 74 | 0.0014 | 75 | 0.0007 | 77 | 0.003 | 78 | 1.21 |
| 79 | 0.01 | 80 | 0.17 | 81 | 0.02 | 82 | 0.2 |
| 83 | 0.02 | 85 | 0.082 | 86 | 0.275 | 87 | 0.0266 |
| 88 | 0.087 | 89 | 0.0014 | 90 | 1.12 | 92 | 0.09 |
| 93 | 0.02 | 94 | 0.02 | 97 | 0.03 | 99 | 0.25 |
| 104 | 0.2 | 107 | 1.4 | 111 | 0.17 | 113 | 0.77 |
| 114 | 0.53 | 115 | 0.18 | 116 | 0.99 | 117 | 0.37 |
| 118 | 0.4 | 119 | 0.01 | 120 | 0.875 | 121 | 6.27 |
| 122 | 0.0015 | 123 | 0.0046 | 124 | 0.016 | 125 | 0.0022 |
| 126 | 0.593 | 127 | 0.0039 | 129 | 0.0017 | 130 | 0.005 |
| 131 | 0.01 | 132 | 0.0255 | 133 | 1.34 | 134 | 0.3 |
| 135 | 0.02 | 136 | 0.0005 | 137 | 1.55 | 138 | 11.8 |
| 139 | 0.3 | 140 | 3.4 | 141 | 0.14 | 142 | 0.4 |
| 143 | 1.26 | 144 | 0.04 | 145 | 1.1 | 147 | 1.79 |
| 148 | 0.03 | 149 | 0.008 | 150 | 0.04 | 151 | 0.03 |

TABLE 1b-continued

Cannabinoid CB2 Receptor Binding $IC_{50}$ (μM)

| Cpd | $IC_{50}$ | Cpd | $IC_{50}$ | Cpd | $IC_{50}$ | Cpd | $IC_{50}$ |
|---|---|---|---|---|---|---|---|
| 152 | 0.2 | 153 | 0.06 | 154 | 0.37 | 156 | 0.002 |
| 157 | 0.002 | 158 | 0.009 | 159 | 0.13 | 160 | 3.5 |
| 161 | 0.775 | 162 | 0.11 | 163 | 0.21 | 164 | 0.49 |
| 165 | 0.8 | 166 | 1.7 | 167 | 0.028 | 169 | 0.017 |
| 170 | 0.3 | 171 | 0.3 | 173 | 0.526 | 174 | 16 |
| 175 | 1.56 | 176 | 4 | 177 | 2.4 | 178 | 2.9 |
| 179 | 0.7 | 180 | 1.7 | 181 | 1.6 | 182 | 0.028 |
| 183 | 0.0069 | 184 | 0.02 | 185 | 0.12 | 186 | 2.29 |
| 187 | 1.6 | 188 | 5.1 | 189 | 0.01 | 190 | 4.5 |
| 191 | 0.19 | 192 | 0.002 | 193 | 0.005 | 194 | 0.0002 |
| 195 | 0.02 | 196 | 0.12 | 197 | 0.8 | 198 | 0.0057 |
| 199 | 0.01 | 200 | 0.001 | 201 | 0.002 | 202 | 0.0045 |
| 203 | 0.24 | 204 | 0.01 | 205 | 0.07 | 206 | 0.0141 |
| 207 | 0.0016 | 208 | 0.014 | 209 | 0.2 | 210 | 0.008 |
| 211 | 0.0007 | 212 | 0.074 | 213 | 0.2 | 214 | 0.0153 |
| 215 | 0.2 | 216 | 0.07 | 217 | 0.0001 | 218 | 0.003 |
| 219 | 0.004 | 220 | 0.23 | 221 | 0.46 | 222 | 0.0049 |
| 223 | 2.9 | 224 | 1.2 | 225 | 0.65 | 226 | 0.0055 |
| 227 | 1.1535 | 228 | 0.25 | 229 | 1.3 | 230 | 0.001 |
| 232 | 0.03 | 233 | 0.88 | 234 | 0.01 | 235 | 1.4 |
| 236 | 0.94 | 237 | 0.1513 | 238 | 3.7225 | 239 | 0.3 |
| 240 | 1.7 | 241 | 0.5 | 242 | 1.6 | 243 | 0.004 |
| 244 | 0.079 | 245 | 0.002 | 246 | 0.09 | 247 | 0.047 |
| 248 | 0.02 | 250 | 0.0056 | 251 | 0.0028 | 252 | 0.048 |
| 253 | 0.3 | 256 | 0.3 | 265 | 0.041 | 267 | 0.27 |
| 269 | 0.0386 | 270 | 1.8 | 271 | 2.6 | 272 | 0.07 |
| 273 | 0.414 | 274 | 0.0016 | 275 | 1.3 | 276 | 0.25 |
| 277 | 3.3 | 278 | 0.0375 | 279 | 0.83 | 280 | 0.679 |
| 281 | 16.5 | 282 | 3.805 | 283 | 0.1 | 284 | 0.045 |
| 285 | 2.4 | 286 | 2.7 | 287 | 2.1 | 289 | 0.4 |
| 290 | 1 | 291 | 1.7 | 292 | 0.06 | 293 | 0.6 |
| 294 | 0.7 | 299 | 5.5167 | 301 | 0.033 | 302 | 9.41 |
| 304 | 0.02 | 305 | 7.2 | 306 | 1.8 | 321 | 0.6 |
| 328 | 1.6 | 329 | 0.02 | 330 | 0.03 | 331 | 0.098 |
| 332 | 1.9 | 333 | 2.9 | 334 | 0.98 | 336 | 2.7 |
| 337 | 0.08 | 338 | 0.027 | | | | |

Example 2

Functional Cell-Based Assay for CB1 or CB2 Agonist and Inverse Agonist Effects on Intra-Cellular Adenylate Cyclase Activity The CB1 and CB2 receptors are G-protein coupled receptors (GPCR) which influence cell function via the Gi-protein. These receptors modulate the activity of intracellular adenylate cyclase which in turn produces the intracellular signal messenger cyclic-AMP (cAMP).

At baseline, or during non-ligand bound conditions, these receptors are constitutively active and tonically suppress adenylate cyclase activity. The binding of an agonists causes further receptor activation and produces additional suppression of adenylate cyclase activity. The binding of an inverse agonist inhibits the constitutive activity of the receptors and results in an increase in adenylate cyclase activity.

By monitoring intracellular adenylate cyclase activity, the ability of compounds to act as agonists or inverse agonists can be determined.

Assay

Test compounds were evaluated in SK-N-MC cells which, using standard transfection procedures, were stably transfected with human cDNA for pcDNA3-CRE β-gal and pcDNA3 CB1 receptor (human) or pcDNA3 CB2 receptor (human). By expressing CRE β-gal, the cells produced β-galactosidase in response to CRE promoter activation by cAMP. Cells expressing CRE β-gal and either the human CB1 or CB2 receptor will produce less β-galactosidase when treated with a CB1/CB2 agonist and will produce more β-galactosidase when treated with a CB1/CB2 inverse agonist.

Cell Growth

The cells were grown in 96-well plates under standard cell culture conditions at 37° C. in a 5% $CO_2$ atmosphere. After 3 days, the media was removed and a test compound in media (wherein the media was supplemented with 2 mM L-glutamine, 1M sodium pyruvate, 0.1% low fatty acid FBS (fetal bovine serum) and antibiotics) was added to the cell. The plates were incubated for 30 minutes at 37° C. and the plate cells were then treated with forskolin over a 4-6 hour period, then washed and lysed. The β-galactosidase activity was quantitated using commercially available kit reagents (Promega Corp. Madison, Wis.) and a VMAX Plate Reader (Molecular Devices, Inc).

CB1 Receptor Mediated Change in CRE β-GAL Expression (Table 2A & 2B)

For cells expressing CRE β-gal and the CB1 receptor, CB1 agonists reduced β-galactosidase activity in a dose-dependent manner and CB1 inverse agonists increased β-galactosidase activity in a dose-dependent manner.

The change in β-galactosidase activity was determined by setting a vehicle treated cell's activity value at 100% and expressing the β-galactosidase activity measured in a corresponding compound treated cell as a percent of the vehicle treated cell activity.

CB1 Receptor Results

The $EC_{50}$ values for compounds tested were calculated by linear regression and were obtained from studies in which varying compound concentrations were used.

TABLE 2a

CB1 Receptor Functional Inverse Agonist $EC_{50}$ (μM)

| Cpd | $EC_{50}$ | Cpd | $EC_{50}$ | Cpd | $EC_{50}$ | Cpd | $EC_{50}$ |
|---|---|---|---|---|---|---|---|
| 2 | 1.51 | 7 | 3.876 | 9 | 2.755 | 28 | 2.03 |
| 43 | 0.2947 | 67 | 0.5242 | 70 | 1 | 73 | 1.742 |
| 91 | 3.371 | 144 | 0.1759 | 146 | 1.515 | 147 | 0.1525 |
| 151 | 0.8008 | 165 | 1.034 | 167 | 3.36 | 169 | 0.05 |
| 220 | 0.399 | 253 | 1.94 | 256 | 0.25 | 258 | 0.48 |
| 259 | 0.61 | 290 | 0.044 | 291 | 0.01 | 292 | 0.009 |
| 293 | 0.025 | 294 | 0.14 | 295 | <0.03 | 296 | 0.013 |
| 297 | 0.005 | 298 | 0.004 | 305 | 0.63 | 307 | 0.1 |
| 309 | 0.081 | 312 | 0.036 | 316 | 0.046 | 319 | 0.05 |
| 320 | 0.001 | 321 | 0.133 | | | | |

TABLE 2b

CB1 Receptor Functional Agonist $EC_{50}$ (μM)

| Cpd | $EC_{50}$ |
|---|---|
| 33 | 0.135 |
| 38 | 0.103 |
| 222 | 0.1945 |
| 226 | 0.52 |
| 338 | 0.0060 |

CB2 Receptor Mediated Change in CRE β-GAL Expression (Table 2C & 2D)

For cells expressing CRE β-gal and the CB2 receptor, CB2 agonists reduced β-galactosidase activity in a dose-dependent manner and CB2 inverse agonists increased β-galactosidase activity in a dose-dependent manner.

The change in β-galactosidase activity was determined by setting a vehicle treated cell's activity value at 100% and expressing the β-galactosidase activity measured in a corresponding compound treated cell as a percent of the vehicle treated cell activity.

CB2 Receptor Binding Results

The $EC_{50}$ values for compounds tested were calculated by linear regression and were obtained from studies in which varying compound concentrations were used.

TABLE 2c

CB2 Receptor Functional Inverse Agonist $EC_{50}$ (µM)

| Cpd | $EC_{50}$ | Cpd | $EC_{50}$ | Cpd | $EC_{50}$ |
|---|---|---|---|---|---|
| 3 | 0.19 | 67 | 0.023 | 70 | 0.0459 |
| 116 | 0.5 | 149 | 0.0079 | 156 | 0.035 |
| 157 | 0.0015 | 208 | 0.0086 | 209 | 0.074 |
| 211 | 0.016 | 214 | 0.12 | 215 | 0.22 |
| 218 | 0.006 | 219 | 0.32 | 220 | 0.22 |
| 222 | 0.033 | 226 | 0.065 | 231 | 0.035 |
| 232 | 0.36 | 251 | 0.023 | 284 | 0.36 |

TABLE 2d

CB2 Receptor Functional Agonist $EC_{50}$ (µM)

| Cpd | $EC_{50}$ | Cpd | $EC_{50}$ | Cpd | $EC_{50}$ |
|---|---|---|---|---|---|
| 1 | 0.015 | 10 | 0.0019 | 13 | 0.0041 |
| 18 | 0.0027 | 26 | 0.011 | 28 | 0.33 |
| 32 | 0.047 | 35 | 0.035 | 36 | 0.005 |
| 37 | 0.01 | 40 | 0.031 | 44 | 0.029 |
| 62 | 0.00057 | 75 | 0.0001 | 87 | 0.25 |
| 94 | 0.025 | 122 | 0.037 | 123 | 0.0075 |
| 154 | 0.009 | 184 | 0.1 | 195 | 0.0055 |
| 207 | 0.01 | 212 | 0.0037 | 217 | 0.000052 |
| 278 | 0.00078 | 338 | 0.00000082 | | |

Example 3

Effect of Sub-Chronic Treatment on Food Consumption and Body Weight Gain in Sprague-Dawley Rats The effect of daily administration of a compound of the present invention was tested in male Sprague-Dawley rats. Animals in each dose group (n=6/group) were orally administered a daily dose of either a test compound (at a 3, 10 or 30 mg/Kg dose) or vehicle (50% PEG-400 in distilled water) in a volume of 2 mL/Kg of body weight immediately prior to the beginning of the dark phase each day for a period of 7 days.

Food consumption was electronically monitored during the dark and light phase that followed dosing (24 hrs total). The effect on food intake was expressed as the percent change of total food consumed in the 24 hr period after dosing to total food consumed in the 24 hr period prior to dosing.

Effect on Total Food Consumption

Animals at all three test compound dose levels had a relatively dose-dependent decrease in total food consumed compared to animals dosed with vehicle at the end of the treatment period.

Effect on Body Weight Gain

Animals at all three test compound dose levels had a dose-dependent decrease in body weight gain compared to animals in the vehicle chow group over the treatment period.

Example 4

Effect of Acute Treatment on Food Consumption in Sprague-Dawley Rats

The effect of acute, single-dose administration of a compound of the present invention was tested in male Sprague-Dawley rats. Animals in each dose group (n=6/group) were orally administered a single dose of either a test compound (at a 3, 10 or 30 mg/Kg dose) or vehicle (50% PEG-400 in distilled water) in a volume of 2 mL/Kg of body weight immediately prior to the beginning of the dark phase.

Food consumption was electronically monitored during the dark and light phase prior to dosing and the dark and light phase that followed dosing (48 hrs total). The effect on food intake was expressed as the percent change of total food consumed in the 24 hr period after dosing to total food consumed in the 24 hr period prior to dosing.

Effect on Total Food Consumption

Animals administered a single dose of the test compound at all three dose levels had a dose-dependent decrease in total food consumed compared to animals administered a single vehicle dose (p value <0.05 for 30 mg/Kg dose level).

Example 5

Effect of Chronic Treatment on Body and Epididymal Fat Pad Weight in Sprague-Dawley Rats The effect of daily administration of a compound of the present invention was tested in male Sprague-Dawley rats. Animals were fed chow (10% Kcal) containing either a test compound (test chow) or vehicle (vehicle chow) over a 28 day treatment period. The test chow was formulated based upon the estimated daily consumption needed to achieve a 1, 3, 10 or 30 mg/kg dose level.

Effect on Body Weight Gain

Animals in the test chow groups had a dose-dependent decrease in body weight gain compared to animals in the vehicle chow group over the treatment period.

Effect on Epididymal Fat Pad Weight

Animals in the test chow groups had a relatively dose-dependent decrease in epididymal fat pad weight compared to animals in the vehicle chow group over the treatment period (p value <0.01 for 30 mg/Kg dose level).

Example 6

Effect of Acute Treatment on Food Consumption and Meal Count in Ob/Ob Mice

The effect of acute, single-dose administration of a compound of the present invention was tested in hyperphagic obese ob/ob mice. Animals in each dose group (n=8/group) were orally administered a single dose of either a test compound (at a 3, 10 or 30 mg/Kg dose) or vehicle (50% PEG400 in distilled water) in a volume of 2 mL/Kg of body weight immediately prior to the beginning of the dark phase.

Food consumption was electronically monitored during the dark and light phase prior to dosing and the dark and light phase that followed dosing (48 hrs total). The effect on food intake was expressed as the percent change of total food consumed in the 24 hr period after dosing to total food consumed in the 24 hr period prior to dosing.

Effect on Total Food Consumption

Animals administered a single dose of the test compound at all three dose levels had a relatively dose-dependent decrease in total food consumed compared to animals administered a single vehicle dose (one-way ANOVA p value <0.05) and a downward trend in total meal count.

Example 7

Effect of Chronic Treatment on Body Weight Gain, Adipose Distribution, Energy Expenditure and Locomotor Activity in Ob/Ob Mice The effect of daily administration of a compound of the present invention was tested in ob/ob mice. The mice were fed chow containing either a test compound (test chow) or vehicle (vehicle chow) over a 26 day treatment period. The test chow was formulated based upon the estimated daily consumption needed to achieve a 3, 10 or 30 mg/kg dose level.

Effect on Body Weight Gain

Animals in the 10 or 30 mg/kg test chow groups had a dose-dependent decrease in body weight gain compared to animals in the vehicle chow group over the treatment period.

Effect on Adipose Distribution

Adipose distribution was measured by quantitative computerized tomography for mice in the 30 mg/kg test chow group.

Animals in the test chow group had a lower total mass (as measured by abdominal cross-section), a lower adipose mass and reduced visceral adipose compartments compared to animals in the vehicle chow group over the treatment period (one-way ANOVA p value <0.05). Lean mass for test chow animals was relatively unaffected.

Effect on Energy Expenditure and Locomotor Activity

Energy expenditure was measured by indirect calorimetry measurements during both light and dark phases for mice in the 30 mg/kg test chow group.

Animals in the test chow group had a decreased respiratory quotient ($CO_2/O_2$), suggesting a shift in the primary fuel source from carbohydrates to fatty acids, an increased energy metabolism ($O_2$) and slightly increased spontaneous motor activity (as determined by summation of movement along the X, Y and Z axes) compared to animals in the vehicle chow group over the treatment period (one-way ANOVA p value <0.05).

Example 8

Effect of Chronic Treatment on Body, Epididymal Fat Pad and Liver Weight, Adipose Distribution, Energy Expenditure and Locomotor Activity and Plasma Triglyceride and Cholesterol Levels in Mice with Diet-Induced Obesity The effect of daily administration of a compound of the present invention was tested in mice with diet-induced obesity (DIO). Obesity was induced by feeding "high-fat" (60% Kcal) chow to non-leptin-deficient mice over a 4 month period. The mice with DIO thus produced were then fed "high-fat" chow containing either a test compound (test chow) or vehicle (vehicle chow) over a 28 day treatment period. The test chow was formulated based upon the estimated daily consumption needed to achieve a 1, 3, 10 or 30 mg/kg dose level.

Effect on Body Weight Gain

Animals in all four test chow groups had a dose-dependent decrease in body weight gain compared to animals in the vehicle chow group over the treatment period.

Effect on Epididymal Fat Pad Weight

Animals in all four test chow groups had either maintained epididymal fat pad weight or lost weight compared to animals in the vehicle chow group over the treatment period (one-way ANOVA p value <0.05).

Effect on Liver Weight and Fat Content

Animals in all four test chow groups either maintained relatively the same liver weight or lost weight compared to animals in the vehicle chow group over the treatment period (one-way ANOVA p value <0.05).

Animals in the 10 and 30 mg/kg test chow groups tested for liver fat content also had a decrease in fat content (as a percent of total liver area) compared to animals in the vehicle chow group over the treatment period (one-way ANOVA p value <0.05).

Effect on Adipose Distribution

Adipose distribution was measured by quantitative computerized tomography for mice in the 30 mg/kg test chow group.

Animals in the test chow group had a lower total mass (as measured by abdominal cross-section), a lower adipose mass and reduced visceral adipose compartments compared to animals in the vehicle chow group over the treatment period (one-way ANOVA p value <0.05). Lean mass for test chow animals was relatively unaffected.

Effect on Energy Expenditure and Locomotor Activity

Energy expenditure was measured by indirect calorimetry measurements during both light and dark phases for mice in the 30 mg/kg test chow group.

Animals in the test chow group had a decreased respiratory quotient ($CO_2/O_2$), suggesting a shift in the primary fuel source from carbohydrates to fatty acids, an increased energy metabolism ($O_2$) and relatively no increase in spontaneous motor activity (as determined by summation of movement along the X, Y and Z axes) compared to animals in the vehicle chow group over the treatment period (one-way ANOVA p value <0.05).

Effect on Plasma Triglyceride and Cholesterol Levels

Animals in all four test chow groups had a decreased plasma triglyceride level compared to animals in the vehicle chow group over the treatment period (one-way ANOVA p value <0.05) and a downward trend in total cholesterol.

It is to be understood that the preceding description of the invention and various examples thereof have emphasized certain aspects. Numerous other equivalents not specifically elaborated on or discussed may nevertheless fall within the spirit and scope of the present invention or the following claims and are intended to be included.

What is claimed is:

1. A compound having a structure according to formula I:

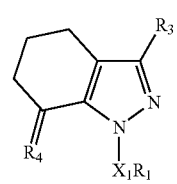

wherein $X_1$ is absent, or is lower alkylene;

$R_1$ is selected from the group consisting of aryl, $C_3$-$C_{12}$ cycloalkyl, or heterocyclyl, any of which are optionally substituted at one or more positions by halogen, lower alkyl, hydroxy or lower alkoxy;

$R_3$ is
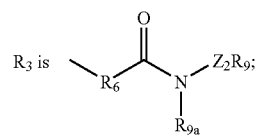

$R_4$ is CH-aryl wherein aryl is optionally substituted at one or more positions by hydroxy, lower alkyl, lower alkoxy or halogen; or CH-heterocyclyl wherein heterocyclyl is optionally substituted at one or more positions by hydroxy, lower alkyl, lower alkoxy or halogen;

$R_6$ is absent;

$R_{6a}$ is hydrogen; lower alkyl; or aryl optionally substituted by one or more of halogen, hydroxy, lower alkoxy, carboxy or alkoxycarbonyl;

$R_9$ is aryl optionally substituted by one or more hydroxy, halogen, —NH($R_{6a}$), —SO$_2$—NH($R_{6a}$), lower alkyl, carboxy, alkoxycarbonyl, lower alkoxy, hydroxy-alkylene-, aryloxy or arylalkoxy; $C_3$-$C_{12}$ cycloalkyl optionally substituted by one or more hydroxy, halogen, amino, lower alkyl, carboxy, alkoxycarbonyl, lower alkoxy, hydroxy-alkylene-, aryloxy, arylalkoxy, or lower alkylene; or heterocyclyl optionally substituted by one or more hydroxy, halogen, amino, lower alkyl, carboxy, alkoxycarbonyl, lower alkoxy, hydroxy-alkylene-, aryloxy or arylalkoxy $R_{9a}$ is hydrogen or lower alkyl;

$Z_2$ is absent; or is lower alkylene optionally substituted at one or more positions by aryl, cycloalkyl, halogen, hydroxy, lower alkyl, lower alkoxy, carboxy, alkoxycarbonyl or aryl;

or a pharmaceutically acceptable salt or polymorph thereof.

2. The compound of claim 1 wherein $X_1$ is absent and $R_1$ is aryl optionally substituted at one or more positions by lower alkyl, lower alkoxy or halogen.

3. The compound of claim 1 selected from the group consisting of:

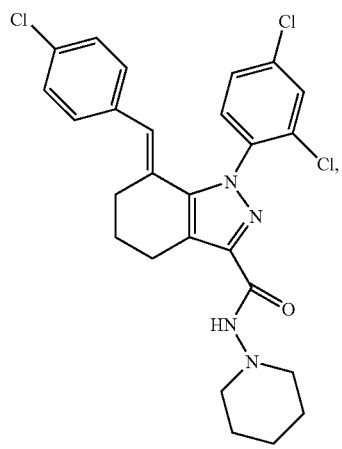

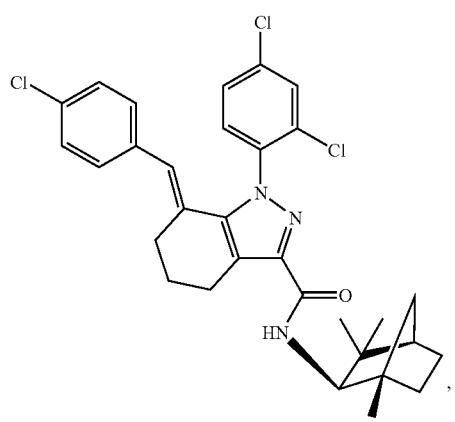

-continued

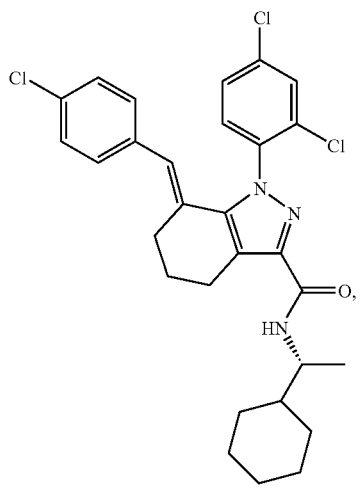

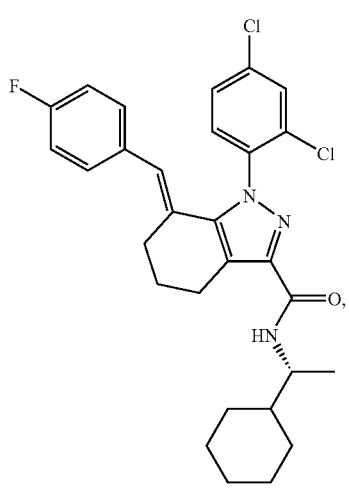

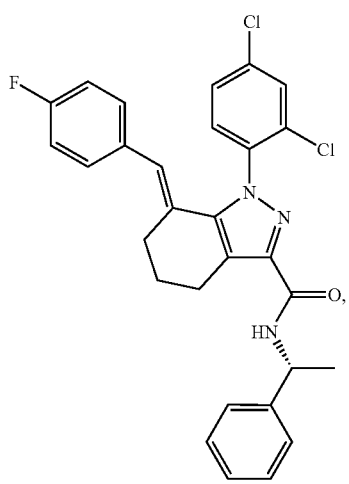

303
-continued
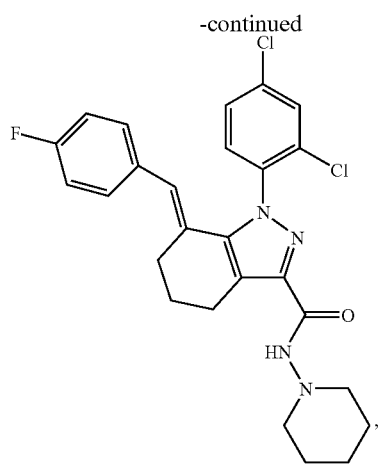
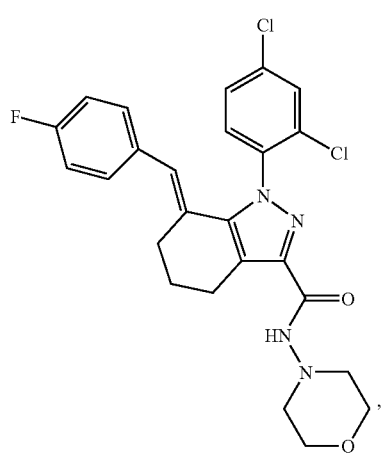
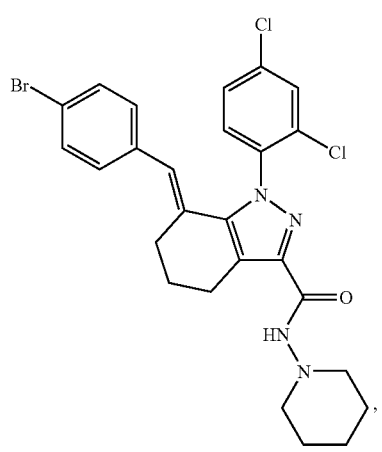
304
-continued
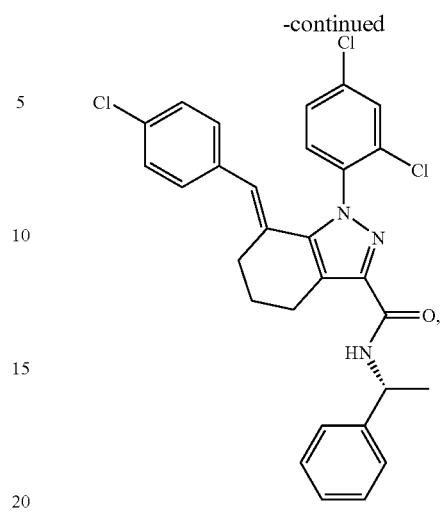
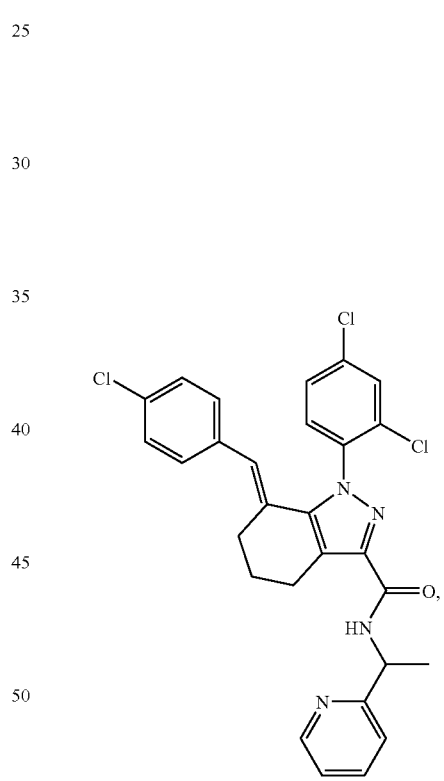
and pharmaceutically acceptable forms thereof.
4. The compound of claim 1 selected from the group consisting of:

305
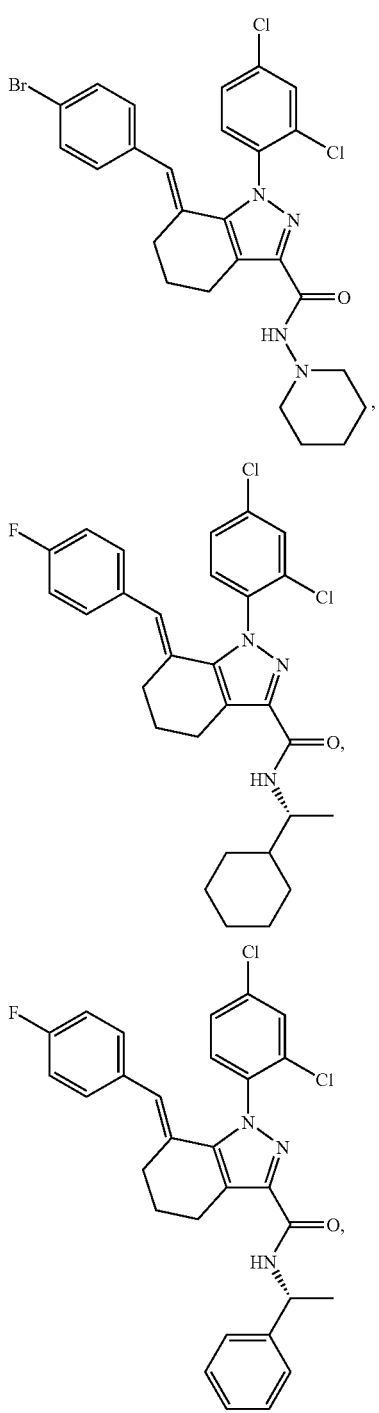
306
-continued
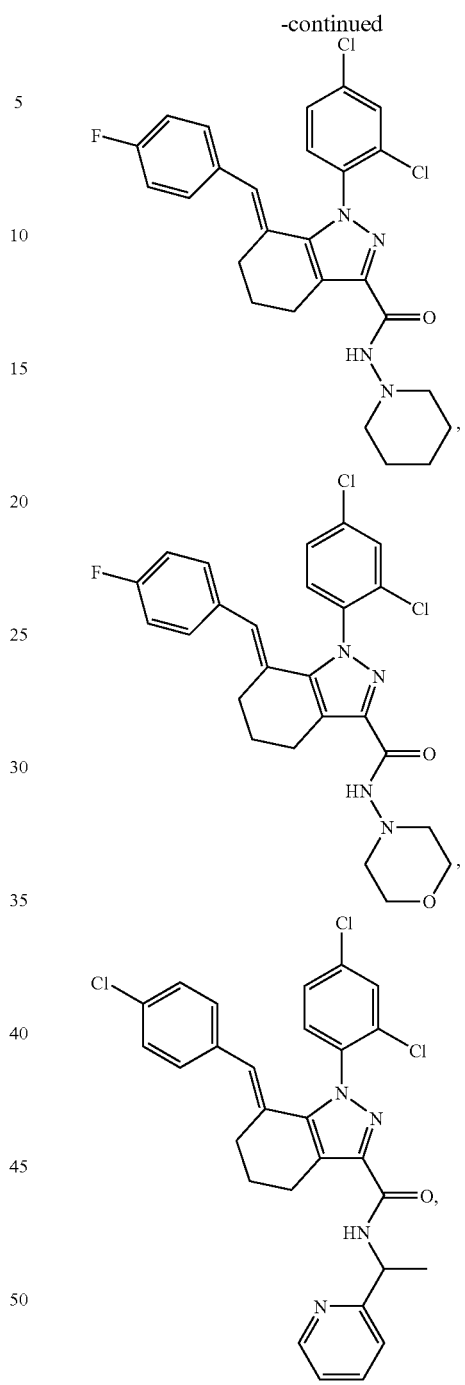
and pharmaceutically acceptable forms thereof.
* * * * *